(12) United States Patent
Daniloff et al.

(10) Patent No.: US 8,303,973 B2
(45) Date of Patent: Nov. 6, 2012

(54) MULTIFUNCTIONAL COMPOUNDS FOR FORMING CROSSLINKED BIOMATERIALS AND METHODS OF PREPARATION AND USE

(75) Inventors: George Y. Daniloff, Mountain View, CA (US); Michael Huy Ngo, Santa Clara, CA (US); Olof Mikael Trollsas, San Jose, CA (US); David M. Gravett, Vancouver (CA); Philip M. Toleikis, Vancouver (CA)

(73) Assignee: Angiotech Pharmaceuticals (US), Inc., Seattle, WA (US)

( * ) Notice: Subject to any disclaimer, the term of this patent is extended or adjusted under 35 U.S.C. 154(b) by 1574 days.

(21) Appl. No.: 11/575,484

(22) PCT Filed: Sep. 19, 2005

(86) PCT No.: PCT/US2005/033367
§ 371 (c)(1),
(2), (4) Date: Mar. 16, 2007

(87) PCT Pub. No.: WO2006/034128
PCT Pub. Date: Mar. 30, 2006

(65) Prior Publication Data
US 2008/0312315 A1    Dec. 18, 2008

Related U.S. Application Data

(60) Provisional application No. 60/611,077, filed on Sep. 17, 2004.

(51) Int. Cl.
*A61F 2/02* (2006.01)
(52) U.S. Cl. ...................................................... 424/423
(58) Field of Classification Search .................. None
See application file for complete search history.

(56) References Cited

U.S. PATENT DOCUMENTS
6,908,963 B2    6/2005    Roberts et al. ............... 525/54.1

*Primary Examiner* — Carlos Azpuru
(74) *Attorney, Agent, or Firm* — Seed IP Law Group PLLC

(57) ABSTRACT

Multifunctional compounds are provided that readily crosslink in situ to provide crosslinked biomaterials. The multifunctional compounds contain a single component having at least three reactive functional groups thereon, with the functional groups selected so as to be non-reactive in an initial environment and inter-reactive in a modified environment. Reaction of a plurality of the multifunctional compounds results in a three-dimensional crosslinked matrix. In one embodiment, a first functional group is nucleophilic, a second functional group is electrophilic, and at least one additional functional group is nucleophilic or electrophilic. Methods for preparing and using the multifunctional compounds, and kits including the multifunctional compounds are also provided. Exemplary uses for the multifunctional compounds include tissue augmentation, biologically active agent delivery, bioadhesion, and prevention of adhesions following surgery or injury.

18 Claims, 2 Drawing Sheets

MULTIFUNCTIONAL COMPOUNDS FOR FORMING CROSSLINKED BIOMATERIALS AND METHODS OF PREPARATION AND USE

CROSS-REFERENCE TO RELATED APPLICATION

This application claims priority to PCT Application No. PCT/US2005/033367, filed on Sep. 19, 2005 (Sep. 17, 2005, being a Saturday), and published as PCT Publication No. WO 2006/034128), which claims priority to U.S. Provisional Patent Application No. 60/611,077, filed on Sep. 17, 2004, the disclosures of which are incorporated by reference in their entireties herein.

TECHNICAL FIELD

This invention relates generally to multifunctional compounds, systems for forming crosslinked biomaterials, the crosslinked biomaterials prepared thereby, and to methods of using such compositions. Such methods include the use of the crosslinked biomaterials as bioadhesives and for tissue augmentation; for prevention of surgical adhesions; for coating surfaces of synthetic implants; as drug delivery matrices; for ophthalmic applications; and for other applications, as discussed herein and/or as appreciated by one of ordinary skill in the art.

BACKGROUND OF THE INVENTION

Much work has been done in developing bioadhesive materials. U.S. Pat. No. 5,162,430 to Rhee et al. describes the use of collagen-synthetic polymer conjugates prepared by covalently binding collagen to synthetic hydrophilic polymers such as various derivatives of polyethylene glycol. In a related patent, U.S. Pat. No. 5,328,955 to Rhee et al., various activated forms of polyethylene glycol and various linkages are described, which can be used to produce collagen-synthetic polymer conjugates having a range of physical and chemical properties. U.S. Pat. No. 5,324,775 to Rhee et al. also describes synthetic hydrophilic polyethylene glycol conjugates, but the conjugates involve naturally occurring polymers such as polysaccharides.

EP 0 732 109 A1 to Rhee discloses a crosslinked biomaterial composition that is prepared using a hydrophobic crosslinking agent, or a mixture of hydrophilic and hydrophobic crosslinking agents, where the preferred hydrophobic crosslinking agents include hydrophobic polymers that contain, or can be chemically derivatized to contain, two or more succinimidyl groups.

U.S. Pat. No. 5,580,923 to Yeung et al. discloses surgical adhesive material that comprises a substrate material and an anti-adhesion binding agent. The substrate material is preferably collagen and the binding agent preferably comprises at least one tissue-reactive functional group and at least one substrate-reactive functional group.

U.S. Pat. No. 5,614,587 to Rhee et al. describes bioadhesives that comprise collagen that is crosslinked using a multifunctionally activated synthetic hydrophilic polymer.

U.S. Pat. No. 5,874,500 to Rhee et al. describes a crosslinked polymer composition that comprises one component having multiple nucleophilic groups and another component having multiple electrophilic groups. Covalently bonding of the nucleophilic and electrophilic groups forms a three dimensional matrix that has a variety of medical uses including tissue adhesion, surface coatings for synthetic implants, and drug delivery. More recent developments include the addition of a third component having either nucleophilic or electrophilic groups, as is described in U.S. Pat. No. 6,458,889 to Trollsas et al.

However, in spite of the advances in the art, there remains a need for improved crosslinked biomaterials that are easy to use and store. This need, as well as others, are met by the instant invention, which is a multifunctional compound having a core substituted with at least three reactive groups, wherein each reactive group is capable of reacting with at least one other reactive group, and wherein the compound is essentially non-reactive in an initial environment. Upon reaction, a three-dimensional matrix is formed.

SUMMARY OF THE INVENTION

One aspect of the invention relates to a multifunctional compound comprising a core substituted with at least three reactive groups. The compound is essentially non-reactive in an initial environment but is rendered reactive upon exposure to a modification in the initial environment that provides a modified environment such that a plurality of the multifunctional compounds inter-react in the modified environment to form a three-dimensional matrix. The multifunctional compound is particularly suitable for application involving contact between a biological system and the multifunctional compound and the three-dimensional matrix formed therefrom.

Still another aspect of the invention pertains to a multifunctional compound having the formula (I):

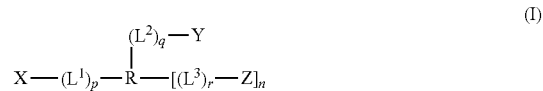

wherein n is an integer from 1-12, and when n is 2-12, each Z component may be different; R is selected from hydrophilic polymers, hydrophobic polymers, amphiphilic polymers, $C_{2-14}$ hydrocarbyls, and heteroatom-containing $C_{2-14}$ hydrocarbyls; X, Y, and Z are reactive groups and can be the same or different, each one of which is capable of reacting with at least one other reactive group; $L^1$, $L^2$, and $L^3$ are linking groups; and p, q and r are integers from 0-1. The compound is essentially non-reactive in an initial environment but is rendered reactive upon exposure to a modification in the initial environment that provides a modified environment such that a plurality of the multifunctional compounds inter-react in the modified environment to form a three-dimensional matrix.

Another aspect of the invention pertains to a multifunctional compound having the formula (II):

wherein a and b are integers from 0-1; c is an integer from 3-12; R' is selected from hydrophilic polymers, hydrophobic polymers, amphiphilic polymers, $C_{2-14}$ hydrocarbyls, and heteroatom-containing $C_{2-14}$ hydrocarbyls; X' and Y' are reactive groups and can be the same or different; and $L^4$ and $L^5$ are linking groups.

In a preferred embodiment of formula (I), X is a nucleophilic group, Y, is an electrophilic group, and Z is an electrophilic or a nucleophilic group.

In a preferred embodiment of formula (II), X' is a nucleophilic group and Y' is an electrophilic group.

With formulas (I) and (II), the reactive groups may be selected from nucleophilic groups, electrophilic groups, redox groups, oxidative coupling reactive groups, photoinitiated reactive groups, and temperature-sensitive groups. In one embodiment, the reactive groups are nucleophilic and electrophilic groups that undergo a nucleophilic substitution reaction, a nucleophilic addition reaction, or both. The nucleophilic groups may be selected from —$NH_2$, —$NHR^1$, —$N(R^1)_2$, —SH, —OH, —COOH, —$C_6H_4$—OH, —H, —$PH_2$, —$PHR^1$, —$P(R^1)_2$, —NH—$NH_2$, —CO—NH—$NH_2$, and —$C_5H_4N$, where $R^1$ is a hydrocarbyl group, and each $R^1$ may be the same or different. The electrophilic groups may be selected from —CO—Cl, —(CO)—O—(CO)—R (where R is an alkyl group), —CH=CH—CH=O and —CH=CH—C(CH$_3$)=O, halo, —N=C=O, —N=C=S, —SO$_2$CH=CH$_2$, —O(CO)—C=CH$_2$, —O(CO)—C(CH$_3$)=CH$_2$, —S—S—(C$_5$H$_4$N), —O(CO)—C(CH$_2$CH$_3$)=CH$_2$, —CH=CH—C=NH, —COOH, —(CO)O—N(COCH$_2$)$_2$, —CHO, —(CO)O—N(COCH$_2$)$_2$—S(O)$_2$OH, and —N(COCH)$_2$.

In one embodiment of formulas (I) and (II), the nucleophilic groups are amino groups and the electrophilic groups are amine-reactive groups. The amine-reactive groups may contain an electrophilically reactive carbonyl group susceptible to nucleophilic attack by a primary or secondary amine. The amine-reactive groups may be selected from carboxylic acid esters, acid chloride groups, anhydrides, ketones, aldehydes, halo, isocyanato, thioisocyanato, epoxides, activated hydroxyl groups, olefins, carboxyl, succinimidyl ester, sulfosuccinimidyl ester, maleimido, epoxy, and ethenesulfonyl.

In another embodiment of formulas (I) and (II), the nucleophilic groups are sulfhydryl groups and the electrophilic groups are sulfhydryl-reactive groups. The sulfhydryl-reactive groups may be selected from mixed anhydrides; ester derivatives of phosphorus; ester derivatives of p-nitrophenol, p-nitrothiophenol and pentafluorophenol; esters of substituted hydroxylamines, including N-hydroxyphthalimide esters, N-hydroxysuccinimide esters, N-hydroxysulfosuccinimide esters, and N-hydroxyglutarimide esters; esters of 1-hydroxybenzotriazole; 3-hydroxy-3,4-dihydro-benzotriazin-4-one; 3-hydroxy-3,4-dihydro-quinazoline-4-one; carbonylimidazole derivatives; acid chlorides; ketenes; and isocyanates. The sulfhydryl-reactive groups may be selected so as to form a thioester, imido-thioester, thioether, or disulfide linkage upon reaction with the sulfhydryl groups. Where the sulfhydryl-reactive groups form a disulfide linkage, they may have the structure —S—S—Ar where Ar is a substituted or unsubstituted nitrogen-containing heteroaromatic moiety or a non-heterocyclic aromatic group substituted with an electron-withdrawing moiety. Where the sulfhydryl-reactive groups form a thioether linkage, they may be selected from maleimido, substituted maleimido, haloalkyl, epoxy, imino, aziridino, olefins, and α,β-unsaturated aldehydes and ketones.

In another embodiment of formulas (I) and (II), the reactive groups undergo an oxidation-reduction reaction and are vinyl groups.

In a further embodiment of formulas (I) and (II), the reactive groups are oxidative coupling reactive groups and are halo groups, with an adjacent electron-withdrawing group on the halogen-bearing carbon.

In still another embodiment of formulas (I) and (II), the reactive groups are photoinitiated reactive groups and are selected from azide, alkyl, and benzophenone.

In yet another embodiment of formulas (I) and (II), the reactive groups are temperature sensitive groups and are vinyl groups.

In the embodiment of formulas (I) and (II), where R is a hydrophilic polymer, the hydrophilic polymer may be linear, branched, dendrimeric, hyperbranched, or star polymer.

In a preferred embodiment, the R group of formulas (I) and (II) is a hydrophilic polymer selected from polyalkylene oxides; polyols; poly(oxyalkylene)-substituted diols and polyols; polyoxyethylated sorbitol; polyoxyethylated glucose; poly(acrylic acids) and analogs and copolymers thereof; polymaleic acids; polyacrylamides; poly(olefinic alcohols); poly(N-vinyl lactams); polyoxazolines; polyvinylamines; and copolymers thereof. The polyalkylene oxide or polyol may be selected from polyethylene glycol and poly (ethylene oxide)-poly(propylene oxide) copolymers. The polyol may be selected from glycerol, polyglycerol, and propylene glycol. The poly(oxyalkylene)-substituted polyol may be selected from mono-, di- and tri-polyoxyethylated glycerol, mono- and di-polyoxyethylated propylene glycol, and mono- and di-polyoxyethylated trimethylene glycol. The poly(acrylic acid), analog or copolymer thereof may be selected from poly(acrylic acid), poly(methacrylic acid), poly (hydroxyethylmethacry late), poly(hydroxyethylacrylate), poly(methylalkylsulfoxide acrylates), and poly(methylalkylsulfoxide methacrylates). The polyacrylamide may be selected from polyacrylamide, poly(methacrylamide), poly (dimethylacrylamide), poly(N-isopropylacrylamide), and copolymers thereof. The poly(olefinic alcohol) may be selected from poly (vinyl alcohols) and copolymers thereof. The poly(N-vinyl lactam) may be selected from poly(vinyl pyrrolidones), poly(vinyl caprolactams), and copolymers thereof. The polyoxazoline may be selected from poly(m-ethyloxazoline) and poly(ethyloxazoline).

In another embodiment of formulas (I) and (II), the R group is a hydrophilic polymer selected from proteins, carboxylated polysaccharides, aminated polysaccharides, and activated polysaccharides. In a preferred embodiment, the hydrophilic polymer is selected from collagen and glycosaminoglycans.

Where the R group of formulas (I) and (II) is a hydrophobic polymer, the hydrophobic polymer may contain repeating monomer units. In a preferred embodiment, the hydrophobic polymer selected from polylactic acid and polyglycolic acid.

Where the R group of formulas (I) and (II) is an amphiphilic polymer, the amphiphilic polymer may contain repeating monomer units.

Where the R group of formulas (I) and (II) is a $C_{2-14}$ hydrocarbyl, the $C_{2-14}$ hydrocarbyl may be selected from alkanes, diols, polyols, and polyacids.

Where the R group of formulas (I) and (II) is a heteroatom-containing $C_{2-14}$ hydrocarbyl, heteroatom-containing $C_{2-14}$ hydrocarbyl may be selected from di- and poly-electrophiles.

In another embodiment of formulas (I) and (II), the inter-reaction comprises formation of covalent bonds, noncovalent bonds, or both. The noncovalent bonds may be ionic bonds, hydrogen bonds, or association of hydrophobic molecular segments. In a preferred embodiment, all of the molecular segments are the same.

In a further embodiment of formulas (I) and (II), the linking groups provide hydrolyzable linkages selected from ester linkages, anhydride linkages, ortho ester linkages, ortho carbonate linkages, amide linkages, phosphoester linkages, α-hydroxy acid linkages, lactone-based linkages, and amide linkages. In another embodiment, the linking groups provide non-degradable linkages selected from succinimide, propionic acid, and carboxymethylate linkages. In still another embodiment, the linking groups provide enzymatically degradable linkages selected from Leu-Gly-Pro-Ala, which is degraded by collagenase, and Gly-Pro-Lys, which is degraded by plasmin.

Another aspect of the invention pertains to a pharmaceutical composition comprising the multifunctional compound. A pharmaceutically acceptable carrier may also be included.

The multifunctional compound may further comprise a biologically active agent with or without a pharmaceutically acceptable carrier. The pharmaceutically acceptable carrier may be a micelle, a microsphere, or a nanosphere.

Where the pharmaceutically acceptable carrier is a microsphere or a nanosphere, the pharmaceutically acceptable carrier may be a degradable polymer, such as a polyester, and the polyester may be a glycolide/lactide copolymer. The degradable polymer may also be comprised of residues of one or more monomers selected from the group consisting of lactide, lactic acid, glycolide, glycolic acid, e-caprolactone, gamma-caprolactone, hydroxyvaleric acid, hydroxybutyric acid, beta-butyrolactone, gamma-butyrolactone, gamma-valerolactone, γ-decanolactone, 5-decanolactone, trimethylene carbonate, 1,4-dioxane-2-one or 1,5-dioxepan-Zone).

The multifunctional compound may further comprise a biologically active agent.

In one embodiment of the invention, the multifunctional compound further comprises a biologically active agent that is an anti-fibrotic agent. As used in the multifunctional compound, the anti-fibrotic agent may be used to inhibit any of the following: cell regeneration, angiogenesis, fibroblast migration, fibroblast proliferation, deposition of extracellular matrix, tissue remodeling, adenosine deaminase, purine ring synthesis, dihydrofolate reduction, ribonucleotide synthesis or function, thymidine monophosphate synthesis or function, DNA synthesis, protein synthesis, and microtubule function. The anti-fibrotic agent may also be used to block thymidine monophosphate, to cause DNA damage, and to cause DNA adduct formation.

Any of the following anti-fibrotic agents may be used in the multifunctional compound: an angiogenesis inhibitor; a 5-lipoxygenase inhibitor or antagonist; a chemokine receptor antagonist; a cell cycle inhibitor; a taxane; an anti-microtubule agent; paclitaxel; an analogue or derivative of paclitaxel; a vinca alkaloid; camptothecin or an analogue or derivative thereof; a podophyllotoxin, wherein the podophyllotoxin may be an etoposide or an analogue or derivative thereof; an anthracycline, wherein the anthracycline may be doxorubicin or an analogue or derivative thereof or the anthracycline may be mitoxantrone or an analogue or derivative thereof; a platinum compound; a nitrosourea; a nitroimidazole; a folic acid antagonist; a cytidine analogue; a pyrimidine analogue; a fluoropyrimidine analogue; a purine analogue; a nitrogen mustard or an analogue or derivative thereof; a hydroxyurea; a mytomicin or an analogue or derivative thereof; an alkyl sulfonate; a benzamide or an analogue or derivative thereof; a nicotinamide or an analogue or derivative thereof; a halogenated sugar or an analogue or derivative thereof; a DNA alkylating agent; an anti-microtubule agent; a topoisomerase inhibitor; a DNA cleaving agent; an antimetabolite; a nucleotide interconversion inhibitor; a hydroorotate dehydrogenase inhibitor; a DNA intercalation agent; an RNA synthesis inhibitor; a pyrimidine synthesis inhibitor; a cyan dependent protein kinase inhibitor; an epidermal growth factor kinase inhibitor; an elastase inhibitor; a factor Xa inhibitor; a farnesyltransferase inhibitor; a fibrinogen antagonist; a guanylate cyclase stimulant; a heat shock protein 90 antagonist; which may be a geldanamycin or an analogue or derivative thereof; a guanylate cyclase stimulant; a HMGCoA reductase inhibitor, which may be simvastatin or an analogue or derivative thereof; an IKK2 inhibitor; an IL-1 antagonist; an ICE antagonist; an IRAK antagonist; an IL-4 agonist; an immunomodulatory agent; sirolimus or an analogue or derivative thereof; everolimus or an analogue or derivative thereof; tacrolimus or an analogue or derivative thereof; biolmus or an analogue or derivative thereof; tresperimus or an analogue or derivative thereof; auranofin or an analogue or derivative thereof; 27-0-demethylrapamycin or an analogue or derivative thereof; gusperimus or an analogue or derivative thereof; pimecrolimus or an analogue or derivative thereof; ABT-578 or an analogue or derivative thereof; an inosine monophosphate dehydrogenase (IMPDH) inhibitor, which may be mycophenolic acid or an analogue or derivative thereof or 1-alpha-25 dihydroxy vitamin $D_3$ or an analogue or derivative thereof; a leukotriene inhibitor; an MCP-1 antagonist; an MMP inhibitor; an NF kappa B inhibitor, which may be Bay 11-7082; an NO antagonist; a p38 MAP kinase inhibitor, which may be SB 202190; a phosphodiesterase inhibitor; a TGF beta inhibitor; a thromboxane A2 antagonist; a TNF alpha antagonist; a TACE inhibitor; a tyrosine kinase inhibitor; vitronectin inhibitor; a fibroblast growth factor inhibitor; a protein kinase inhibitor; a PDGF receptor kinase inhibitor; an endothelial growth factor receptor kinase inhibitor; a retinoic acid receptor antagonist; a platelet derived growth factor receptor kinase inhibitor; a fibrinogen antagonist; an antimycotic agent; sulconizole; a bisphosphonate; a phospholipase A1 inhibitor; a histamine H1/H2/H3 receptor antagonist; a macrolide antibiotic; a GPIIb/IIIa receptor antagonist; an endothelin receptor antagonist; a peroxisome proliferator-activated receptor agonist; an estrogen receptor agent; a somastostatin analogue; a neurokinin 1 antagonist; a neurokinin 3 antagonist; a VLA-4 antagonist; an osteoclast inhibitor; a DNA topoisomerase ATP hydrolyzing inhibitor; an angiotensin 1 converting enzyme inhibitor; an angiotensin II antagonist; an enkephalinase inhibitor; a peroxisome proliferator-activated receptor gamma agonist insulin sensitizer; a protein kinase C inhibitor; a ROCK (rho-associated kinase) inhibitor; a CXCR3 inhibitor; Itk inhibitor; a cytosolic phospholipase $A_2$-alpha inhibitor; a PPAR agonist; an immunosuppressant; an Erb inhibitor; an apoptosis agonist; a lipocortin agonist; a VCAM-1 antagonist; a collagen antagonist; an alpha 2 integrin antagonist; a TNF alpha inhibitor; a nitric oxide inhibitor; and a cathepsin inhibitor.

In another embodiment of the invention, the multifunctional compound further comprises a biologically active agent that is a fibrosing agent. As used in the multifunctional compound, the anti-fibrotic agent may be used to promote any of the following: regeneration; angiogenesis; fibroblast migration; fibroblast proliferation; deposition of extracellular matrix (ECM); and tissue remodeling. The fibrosing agent may also be used as an arterial vessel wall irritant.

Fibrosing agents that may be used in the multifunctional compound may be or may be comprised of silk; silkworm silk; spider silk; recombinant silk; raw silk; hydrolyzed silk; acid-treated silk; acylated silk; mineral particles; talc; chitosan; polylysine; fibronectin; bleomycin; or CTGF. The fibrosing agent may also be in the form of a particulate, which may be a biodegradable particulate or a non-biodegradable particulate. Biodegradable particulates may be comprised of a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester. Non-biodegradable particulates may be comprised of a material selected from the group consisting of polyester, polyurethane, silicone, polyethylene, polypropylene, polystyrene, polyacrylate, polymethacrylate, and silk. Examples of preferred particulates may be a particulate form of a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic, and other inorganic particles.

In a further embodiment of the multifunctional compound, the biologically active agent promotes bone growth. Within this embodiment, the fibrosing agent may promote the bone growth. Fibrosing agents that may promote bone growth may include a bone morphogenic protein and an osteogenic growth factor, the latter which may be selected from transforming growth factor, platelet-derived growth factor, and fibroblast growth factor.

In another embodiment of the invention, the multifunctional compound with a fibrosing agent further comprises a pharmaceutical agent that induces sclerosis (a sclerosant), wherein the sclerosant may be a surfactant or it may be selected from the group consisting of ethanol, dimethyl sulfoxide, sucrose, sodium chloride, dextrose, glycerin, minocycline, tetracycline, doxycycline, polidocanol, sodium tetradecyl sulfate, sodium morrhuate, and sotradecol.

In a further embodiment of the invention, the multifunctional compound with a fibrosing agent further comprises an inflammatory cytokine, which may be selected from the group consisting of TGFβ, PDGF, VEGF, bFGF, TNFα, NGF, GM-CSF, IGF-a, IL-1, IL-1-β, IL-8, IL-6, and growth hormone.

In still another embodiment of the invention, the multifunctional compound with a fibrosing agent further comprises an agent that stimulates cell proliferation, which may be selected from the group consisting of dexamethasone, isotretinoin (13-cis retinoic acid), 17-β-estradiol, estradiol, 1-α-25 dihydroxyvitamin $D_3$, diethylstibesterol, cyclosporine A, L-NAME, all-trans retinoic acid (ATRA), and analogues and derivatives thereof.

In a further embodiment of the multifunctional compound, the biologically active agent is mixed with the multifunctional compound to form a mixture.

In another embodiment of the multifunctional compound, the biologically active agent is chemically coupled to the multifunctional compound.

Yet another aspect of the invention relates to a method of forming a three-dimensional matrix comprising the steps of: (a) providing a plurality of multifunctional compounds each comprising a core substituted with at least three reactive groups, as described above, and (b) activating the plurality of multifunctional compounds to effect inter-reaction in the modified environment to form a three-dimensional matrix.

Still another aspect of the invention pertains to a method of adhering tissue of a patient comprising the steps of: (a) placing into contact with tissue an adhesive composition comprising a plurality of multifunctional compounds, as described above, and (b) activating the plurality of multifunctional compounds to effect inter-reaction in the modified environment to form a three-dimensional matrix to adhere the tissue.

Another aspect of the invention relates to a method of forming a three-dimensional matrix comprising the steps of: (a) providing a multifunctional compound of the invention; and (b) rendering the nucleophilic and electrophilic groups reactive by exposing the composition to an aqueous environment to effect inter-reaction; wherein said exposure comprises: (i) dissolving the composition in a first buffer solution having a pH within the range of about 1.0 to 5.5 to form a homogeneous solution, and (ii) adding a second buffer solution having a pH within the range of about 6.0 to 11.0 to the homogeneous solution; and (c) allowing a three-dimensional matrix to form. A preferred composition for use in this method is the multifunctional compound. The three-dimensional matrix of the invention may be formed without input of any external energy or by polymerization.

In a preferred embodiment, the pH of the first buffer solution is selected to retard the reactivity of the nucleophilic groups on the multifunctional compound by rendering the nucleophilic groups relatively non-nucleophilic. In this preferred embodiment, the second buffer solution neutralizes the effect of the first buffer solution, so that the nucleophilic groups of the multifunctional compound regain their nucleophilic character and inter-react with the electrophilic groups of the second component.

In another preferred embodiment, the multifunctional compound, first buffer solution and second buffer solution are housed separately in a multiple-compartment syringe system having a multiple barrels, a mixing head, and an exit orifice; step (b)(i) comprises adding the first buffer solution to the barrel housing the multifunctional compound to dissolve the composition and form a homogeneous solution, and extruding the homogeneous solution into the mixing head; step (b)(ii) comprises simultaneously extruding the second buffer solution into the mixing head; and step (c) further comprises extruding the resulting composition through the orifice onto a surface.

Yet another aspect of the invention relates to a method of sealing tissue of a patient comprising the steps of: (a) providing a plurality of a multifunctional compound of the invention; (b) rendering the nucleophilic and electrophilic groups reactive by exposing the multifunctional compound to an aqueous environment to effect inter-reaction; wherein said exposure comprises: (i) dissolving the multifunctional compound in a first buffer solution having a pH within the range of about 1.0 to 5.5 to form a homogeneous solution, and (ii) adding a second buffer solution having a pH within the range of about 6.0 to 11.0 to the homogeneous solution to form a mixture; and (c) placing the mixture into contact with tissue and allowing a three-dimensional matrix to form and seal the tissue. A preferred composition for use in this method is the multifunctional compound.

Still another aspect of the invention relates to a method of preventing adhesions between tissues of a patient comprising the steps of: (a) providing a plurality of a multifunctional compound of the invention; (b) rendering the nucleophilic and electrophilic groups reactive by exposing the multifunctional compound to an aqueous environment to effect inter-reaction; wherein said exposure comprises: (i) dissolving the multifunctional compound in a first buffer solution having a pH within the range of about 1.0 to 5.5 to form a homogeneous solution, and (ii) adding a second buffer solution having a pH within the range of about 6.0 to 11.0 to the homogeneous solution to form a mixture; and (c) placing the mixture into contact with tissue and allowing a three-dimensional matrix to form on the tissue. A preferred composition for use in this method is the multifunctional compound.

A further aspect of the invention relates to a method of forming a three-dimensional matrix on a surface of a device comprising the steps of: (a) providing a plurality of a multifunctional compound of the invention; and (b) rendering the nucleophilic and electrophilic groups reactive by exposing the multifunctional compound to an aqueous environment to effect inter-reaction; wherein said exposure comprises: (i) dissolving the multifunctional compound in a first buffer solution having a pH within the range of about 1.0 to 5.5 to form a homogeneous solution, and (ii) adding a second buffer solution having a pH within the range of about 6.0 to 11.0 to the homogeneous solution; and (c) applying the homogeneous solution to a surface of a device and allowing the three-dimensional matrix to form. A preferred composition for use in this method is the multifunctional compound.

Another aspect of the invention relates to a method of preventing scarring in the vicinity of a medical implant comprising the steps of: (a) providing a plurality of a multifunctional compound of the invention, wherein the multifunctional compound further comprises an anti-fibrotic agent; (b) rendering the nucleophilic and electrophilic groups reactive by exposing the multifunctional compound to an aqueous environment to effect inter-reaction; wherein said exposure comprises: (i) dissolving the multifunctional compound in a first buffer solution having a pH within the range of about 1.0 to 5.5 to form a homogeneous solution, and (ii) adding a second buffer solution having a pH within the range of about 6.0 to 11.0 to the homogeneous solution to form a mixture; (c) applying the mixture to a surface of a medical implant and allowing a three-dimensional matrix to form on the surface of the medical implant; and (d) placing the medical implant into an animal host, wherein release of the anti-fibrotic agent from the composition inhibits scarring in the animal host. In one embodiment, the anti-fibrotic agent is released into tissue in the vicinity of the implant after deployment of the implant. A preferred composition for use in this method is the multifunctional compound with an anti-fibrotic agent.

Yet another aspect of the invention relates to a method of promoting scarring in the vicinity of a medical implant comprising the steps of: (a) providing a plurality of a multifunctional compound of the invention, where the multifunctional compound further comprises a fibrosing agent; (b) rendering the nucleophilic and electrophilic groups reactive by exposing the multifunctional compound to an aqueous environment to effect inter-reaction; wherein said exposure comprises: (i) dissolving the multifunctional compound in a first buffer solution having a pH within the range of about 1.0 to 5.5 to form a homogeneous solution, and (ii) adding a second buffer solution having a pH within the range of about 6.0 to 11.0 to the homogeneous solution; and (c) applying the mixture to a surface of a medical implant and allowing a three-dimensional matrix to form on the surface of the medical implant; and (d) placing the medical implant into an animal host, wherein release of the fibrotic agent from the matrix inhibits scarring in the animal host. In a preferred embodiment, the fibrosing agent is released into tissue in the vicinity of the implant after deployment of the implant. A preferred composition for use in this method is the multifunctional compound with a fibrosing agent.

Still another aspect of the invention relates to a kit for use in for use in medical applications, comprising: (a) a plurality of a multifunctional compound of the invention; (b) a first buffer solution having a pH within the range of about 1.0 to 5.5; and (c) a second buffer solution having a pH within the range of about 6.0 to 11.0, wherein the nucleophilic and electrophilic groups are non-reactive in a dry environment but are rendered reactive upon exposure to an aqueous environment such that the plurality of multifunctional compounds inter-react in the aqueous environment to form a three-dimensional matrix and further wherein each component is packaged separately and admixed immediately prior to use.

Another aspect of the invention relates to a kit for use in medical applications, comprising: (a) a plurality of a multifunctional compound of the invention; (b) a first buffer solution having a pH within the range of about 1.0 to 5.5; and (c) a second buffer solution having a pH within the range of about 6.0 to 11.0, wherein each component is packaged separately and admixed immediately prior to use. A preferred composition of the invention for use in this kit is the multifunctional compound. It is preferred that each component of the kit is in a separate sterile package.

The kit may further comprise a delivery device, which in one embodiment, may be a multi-compartment device. A preferred multi-compartment device of the invention is a multiple-compartment syringe system having multiple barrels, a mixing head, and an exit orifice. Where the kit is a multiple-compartment syringe system, the multifunctional compound, the first buffer solution, and the second buffer solution are housed separately in the multiple-compartment syringe system.

In another embodiment of the invention, the delivery device is a pressurized delivery system. A preferred pressurized delivery system comprises: a plurality of fluid component inlets each adapted to communicate with a source of different fluid components; at least one carrier fluid inlet adapted to communicate with a source of a pressurized carrier fluid; a diffuser surface located downstream from the plurality of fluid component inlets and the at least one carrier fluid inlet; and an outlet extending through the diffuser surface, wherein the diffuser surface is adapted to receive fluid components thereon and has a shape effective to direct and maintain each received fluid component in a different flow path toward the outlet for mixing and dispensing therethrough by the pressurized carrier fluid from the at least one carrier fluid inlet. Within this embodiment, a preferred pressurized carrier fluid is pressurized air and the preferred fluid components are the first buffer solution and the second buffer solution of the invention.

Another embodiment of the kit for use in medical applications further comprises a biologically active agent and the medical application involves delivering the biologically active agent. The biologically active agent may be packaged with the multifunctional compound and may further comprise a pharmaceutically acceptable carrier packaged with the biologically active agent and the multifunctional compound. The biologically active agent may also be packaged as a solution with the first buffer or as a solution with the second buffer. The kit may further comprise a pharmaceutically acceptable carrier as a fourth component. The biologically active agent is packaged with the pharmaceutically acceptable carrier.

Yet another embodiment of the kit for use in medical applications further comprises living cells or genes, and the medical application involves delivering the living cells or genes.

Other medical applications that the kit may be used for include adhering or sealing biological tissue, bioadhesion, ophthalmic applications, tissue augmentation, adhesion prevention, forming a synthetic implant or coating a synthetic implant, treatment of aneurysms, and laparoscopic procedures.

These and other aspects of the present invention are described in detail below.

BRIEF DESCRIPTION OF THE DRAWINGS

FIG. 1 depicts the device in exploded view and FIG. 2 depicts the interior diffuser surface of the cap.

DETAILED DESCRIPTION OF THE INVENTION

Definitions and Nomenclature

Figure 1:
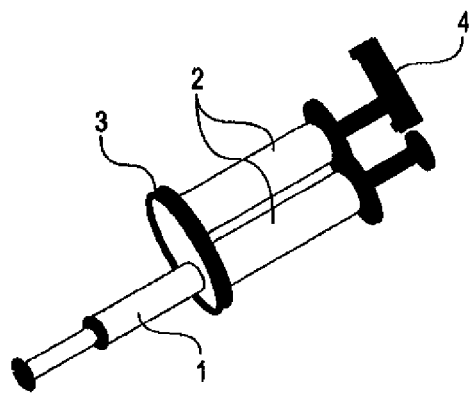
FIG. 1 depicts a preferred multi-compartment syringe device of the present invention.

Before describing the present invention in detail, it is to be understood that unless otherwise indicated this invention is not limited to particular compositional forms, crosslinkable components, crosslinking techniques, or methods of use, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, "a multifunctional compound" refers not only to a single multifunctional compound but also to a combination of two or more of the same or different multifunctional compounds, "a reactive group" refers to a combination of reactive groups as well as to a single reactive group, and the like.

Unless defined otherwise, all technical and scientific terms used herein have the meaning commonly understood by one of ordinary skill in the art to which the invention pertains. Although any methods and materials similar or equivalent to those described herein may be useful in the practice or testing of the present invention, preferred methods and materials are described below. All patents, patent applications and other publications mentioned herein are incorporated herein by reference. Specific terminology of particular importance to the description of the present invention is defined below.

The term "inter-react" and "inter-reaction" as used herein refers to the formulation of covalent bonds, noncovalent bonds, or both. The term thus includes crosslinking, which involves both intermolecular crosslinks and optionally intramolecular crosslinks as well, arising from the formation of covalent bonds. Covalent bonding between two reactive groups may be direct, in which case an atom in reactive group is directly bound to an atom in the other reactive group, or it may be indirect, through a linking group. Noncovalent bonds include ionic (electrostatic) bonds, hydrogen bonds, or the association of hydrophobic molecular segments, which may be the same or different. A crosslinked matrix may, in addition to covalent bonds, also include such intermolecular and/or intramolecular noncovalent bonds.

When referring to polymers, the terms "hydrophilic" and "hydrophobic" are generally defined in terms of an HLB value, i.e., a hydrophilic lipophilic balance. A high HLB value indicates a hydrophilic compound, while a low HLB value characterizes a hydrophobic compound. HLB values are well known in the art, and generally range from 1 to 18. Preferred multifunctional compound cores are hydrophilic, although as long as the multifunctional compound as a whole contains at least one hydrophilic component, crosslinkable hydrophobic components may also be present.

The term "polymer" is used not only in the conventional sense to refer to molecules composed of repeating monomer units, including homopolymers, block copolymers, random copolymers, and graft copolymers, but also refers to polyfunctional small molecules that do not contain repeating monomer units but are "polymeric" in the sense of being "polyfunctional," i.e., containing two or more functional groups. Accordingly, it will be appreciated that when the term "polymer" is used, difunctional and polyfunctional small molecules are included. Such moieties include, by way of example: the difunctional electrophiles disuccinimidyl suberate (DSS), bis(sulfosuccinimidyl) suberate ($BS^3$), dithiobis (succinimidylpropionate) (DSP), bis(2-succinimidooxy-carbonyloxy)ethyl sulfone (BSOCOES), 3,3'-dithiobis (sulfosuccinimidylpropionate) (DTSSP); and the di- and polyfunctional nucleophiles ethylenediamine ($H_2N-CH_2-CH_2-NH_2$), tetramethylene diamine ($H_2N-[CH_2]_4-NH_2$), pentamethylene diamine (cadaverine) ($H_2N-[CH_2]_5-NH_2$), hexamethylene diamine ($H_2N-[CH_2]_6-NH_2$), bos(2-aminoethyl)amine ($HN-[CH_2-CH_2-NH_2]_2$), and tris(2-aminoethyl)amine ($N-[CH_2-CH_2-NH_2]_3$). All suitable polymers herein are nontoxic, non-inflammatory, and nonimmunogenic, and will preferably be essentially non-degradable in vivo over a period of at least several months.

The term "synthetic" is used to refer to polymers, compounds and other such materials that are "chemically synthesized." For example, a synthetic material in the present compositions may have a molecular structure that is identical to a naturally occurring material, but the material per se, as incorporated in the compositions of the invention, has been chemically synthesized in the laboratory or industrially. "Synthetic" materials also include semi-synthetic materials, i.e., naturally occurring materials, obtained from a natural source, that have been chemically modified in some way. Generally, however, the synthetic materials herein are purely synthetic, i.e., they are neither semi-synthetic nor have a structure that is identical to that of a naturally occurring material.

The term "effective amount" refers to the amount of composition required in order to obtain the effect desired. For example, a "tissue growth-promoting amount" of a composition refers to the amount needed in order to stimulate tissue growth to a detectable degree. Tissue, in this context, includes connective tissue, bone, cartilage, epidermis and dermis, blood, and other tissues. The actual amount that is determined to be an effective amount will vary depending on factors such as the size, condition, sex, and age of the patient and can be more readily determined by the caregiver.

The term "in situ" as used herein means at the site of administration. Thus, compositions of the invention can be injected or otherwise applied to a specific site within a patient's body, e.g., a site in need of augmentation, and allowed to crosslink at the site of injection. Suitable sites will generally be intradermal or subcutaneous regions for augmenting dermal support, at a bone fracture site for bone repair, within sphincter tissue for sphincter augmentation (e.g., for restoration of continence), within a wound or suture to promote tissue regrowth, and within or adjacent to vessel anastomoses to promote vessel regrowth.

The term "aqueous medium" includes solutions, suspensions, dispersions, colloids, and the like containing water. The term "aqueous environment" means an environment containing an aqueous medium. Similarly, the term "dry environment" means an environment that does not contain an aqueous medium.

The term "biologically active agent" refers to an organic molecule that exerts biological effects in vivo. Examples of biologically active agents include, by way of example and not limitation, enzymes, receptor antagonists or agonists, hormones, growth factors, autogenous bone marrow, antibiotics, antimicrobial agents, and antibodies. The term "biologically active agent" is also intended to encompass various cell types and genes that can be incorporated into the compositions of the invention.

The terms "active agent," "biologically active agent," and "drug" are used interchangeably herein to refer to a chemical material or compound suitable for administration to a patient and that induces a desired effect. The terms include agents that are therapeutically effective as well as prophylactically effective. Also included are derivatives and analogs of those compounds or classes of compounds specifically mentioned that also induce the desired effect.

As used herein the terms "active agent," "biologically active agent," "therapeutic agent," "pharmacologically active agent," and "drug" refer to an organic molecule that exerts biological effects in vivo. For purposes of this discussion, the term "biologically active agent" is used, with the understanding that the use of this term does not exclude the application to the remaining terms. Examples of biologically active agents include, by way of example and not limitation, enzymes, receptor antagonists or agonists, hormones, growth factors, autogenous bone marrow, antibiotics, antimicrobial agents and antibodies. The term biologically active agent is also intended to encompass various cell types and genes that can be incorporated into the compositions of the invention. Other examples of biologically active agents include those that inhibit fibrosis and those that promote fibrosis. In certain embodiments, a biologically active agent may promote adhesion between a tissue and a substrate (e.g., a surface of a medical device).

"Fibrosis," "scarring," or "fibrotic response" refers to the formation of fibrous tissue in response to injury or medical intervention. Therapeutic agents which promote (also referred to interchangeably herein as "induce," "stimulate," "cause," and the like) fibrosis or scarring are referred to interchangeably herein as "fibrosis-inducing agents," "scarring agents," "fibrosing agents," "adhesion-inducing agents," and the like, where these agents do so through one or more mechanisms including: inducing or promoting angiogenesis, stimulating migration or proliferation of connective tissue cells (such as fibroblasts, smooth muscle cells, vascular smooth muscle cells), inducing ECM production, and/or promoting tissue remodeling. Therapeutic agents which inhibit fibrosis or scarring are referred to herein as "fibrosis-inhibiting agents," "anti-scarring agents," and the like, where these agents inhibit fibrosis through one or more mechanisms including: inhibiting angiogenesis, inhibiting migration or proliferation of connective tissue cells (such as fibroblasts, smooth muscle cells, vascular smooth muscle cells), reducing ECM production, and/or inhibiting tissue remodeling.

"Sclerosing" refers to a tissue reaction in which an irritant is applied locally to a tissue which results in an inflammatory reaction and is followed by scar tissue formation at the site of irritation. A pharmaceutical agent that induces or promotes sclerosis is referred to as a "sclerosant," or a "sclerosing agent." Representative examples of sclerosants include ethanol, dimethyl sulfoxide, surfactants (e.g., TRITON X, sorbitan monolaurate, sorbitan sesquioleate, glycerol monostearate, and polyoxyethylene, polyoxyethylene cetyl ether, and the like), sucrose, sodium chloride, dextrose, glycerin, minocycline, tetracycline, doxycycline, polidocanol, sodium tetradecyl sulfate, sodium morrhuate, ethanolamine, phenol, sarapin and sotradecol.

"Anti-microtubule agents" should be understood to include any protein, peptide, chemical, or other molecule which impairs the function of microtubules, for example, through the prevention or stabilization of polymerization. Compounds that stabilize polymerization of microtubules are referred to herein as "microtubule stabilizing agents." A wide variety of methods may be utilized to determine the anti-microtubule activity of a particular compound, including for example, assays described by Smith et al. (*Cancer Lett* 79(2): 213-219 (1994)) and Mooberry et al., (*Cancer Lett.* 96(2): 261-266 (1995)). The terms "medical device," "implant," "medical implant," and the like are used synonymously to refer to any object that is designed to be placed partially or wholly within a patient's body for one or more therapeutic or prophylactic purposes such as for restoring physiological function, alleviating symptoms associated with disease, delivering therapeutic agents, and/or repairing or replacing or augmenting damaged or diseased organs and tissues. While normally composed of biologically compatible synthetic materials (e.g., medical-grade stainless steel, titanium and other metals; polymers such as polyurethane, silicon, PLA, PLGA and other materials) that are exogenous, some medical devices and implants include materials derived from animals (e.g., "xenografts" such as whole animal organs; animal tissues such as heart valves; naturally occurring or chemically-modified molecules such as collagen, hyaluronic acid, proteins, carbohydrates and others), human donors (e.g., "allografts" such as whole organs; tissues such as bone grafts, skin grafts and others), or from the patients themselves (e.g., "autografts" such as saphenous vein grafts, skin grafts, tendon/ligament/muscle transplants).

With regard to nomenclature pertinent to molecular structures, the following definitions apply:

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of one to six carbon atoms, preferably one to four carbon atoms. "Substituted alkyl" refers to alkyl substituted with one or more substituent groups. "Alkylene," "lower alkylene" and "substituted alkylene" refer to divalent alkyl, lower alkyl, and substituted alkyl groups, respectively.

The term "aryl" as used herein, and unless otherwise specified, refers to an aromatic substituent containing a single aromatic ring (monocyclic) or multiple aromatic rings that are fused together, linked covalently, or linked to a common group such as a methylene or ethylene moiety. The common linking group may also be a carbonyl as in benzophenone, an oxygen atom as in diphenylether, or a nitrogen atom as in diphenylamine. Preferred aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl in which at least one carbon atom is replaced with a heteroatom. The terms "arylene" and "substituted arylene" refer to divalent aryl and substituted aryl groups as just defined.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus or silicon.

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, preferably one to four carbon atoms. The term "hydrocarbylene" intends a divalent hydrocarbyl moiety containing 1 to about 30 carbon atoms, preferably 1 to about 24 carbon atoms, most preferably 1 to about 12 carbon atoms, including branched or unbranched, saturated or unsaturated species, or the like. The term "lower hydrocarbylene" intends a hydrocarbylene group of one to six carbon atoms, preferably one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. If not otherwise indicated, "hydrocarbyl" indicates unsubstituted hydrocarbyl, substituted hydrocarbyl, heteroatom-containing hydrocarbyl, and substituted heteroatom-containing hydrocarbyl. Unless otherwise indicated, the terms "hydrocarbyl" and "hydrocarbylene" include substituted hydrocarbyl and substituted hydrocarbylene, heteroatom-containing hydrocarbyl and heteroatom-containing hydrocarbylene, and substituted heteroatom-containing hydrocarbyl and substituted heteroatom-containing hydrocarbylene, respectively.

By "substituted" as in "substituted hydrocarbyl," "substituted alkyl," and the like, as alluded to in some of the aforementioned definitions, is meant that in the hydrocarbyl, alkyl, or other moiety, at least one hydrogen atom bound to a carbon atom is replaced with one or more substituents that are functional groups such as alkoxy, hydroxy, halo, nitro, and the like. Unless otherwise indicated, it is to be understood that specified molecular segments can be substituted with one or more substituents that do not compromise a compound's utility. For example, "succinimidyl" is intended to include unsubstituted succinimidyl as well as sulfosuccinimidyl and other succinimidyl groups substituted on a ring carbon atom, e.g., with alkoxy substituents, polyether substituents, or the like.

The Multifunctional Compound

In accordance with the present invention, a multifunctional compound is provided that contains a core substituted with a minimum of three reactive groups, each of which participates in a reaction, i.e., inter-reacts, to form a three-dimensional matrix. The reactive groups may be directed attached to the core, or the reactive groups may further comprise a linking group through which they are attached to the core.

The reactive groups are selected so that the compound is essentially non-reactive in an initial environment. Upon exposure to a specific modification in the initial environment, providing a modified environment, the compound is rendered reactive and a plurality of multifunctional compounds are then able to inter-react in the modified environment to form a three-dimensional matrix.

Examples of modification in the initial environment include the addition of an aqueous medium, a change in pH, exposure to ultraviolet radiation, a change in temperature, or contact with a redox initiator. These are detailed below.

The multifunctional compound is particularly suitable for application involving contact between a biological system and the multifunctional compound and the three-dimensional matrix formed therefrom. The biological system can be a biological tissue, and in a preferred embodiment, is living tissue.

The resulting three-dimensional matrix is useful in a variety of contexts, and is particularly useful as a biomaterial for medical applications, such as for bioadhesion, delivery of biologically active agents, tissue augmentation, tissue sealing, hemostasis, the prevention of adhesions following a surgical procedure or injury, and so forth.

The core and reactive groups can also be selected so as to provide a compound that has one of more of the following features: are biocompatible, are non-immunogenic, and do not leave any toxic, inflammatory or immunogenic reaction products at the site of administration. Similarly, the core and reactive groups can also be selected so as to provide a resulting matrix that has one or more of these features.

In one embodiment of the invention, substantially immediately or immediately upon exposure to the modified environment, the multifunctional compounds inter-react form a three-dimensional matrix. The term "substantially immediately" is intended to mean within less than five minutes, preferably within less than two minutes, and the term "immediately" is intended to mean within less than one minute, preferably within less than 30 seconds.

In one embodiment, the multifunctional compound and resulting matrix are not subject to enzymatic cleavage by matrix metalloproteinases such as collagenase, and are therefore not readily degradable in vivo. Further, the multifunctional compound may be readily tailored, in terms of the selection and quantity of each component, to enhance certain properties, e.g., compression strength, swellability, tack, hydrophilicity, optical clarity, and the like.

The multifunctional compound of the invention is comprised of at least four components: a core and a minimum of three reactive groups. In one embodiment, the multifunctional compound can be described as having the formula (I), where R is the core and the reactive groups are represented by, for example, the reactive group X having an optional linker, $L^1$:

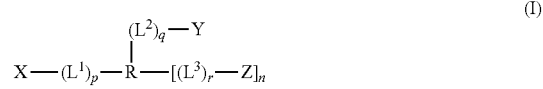

(I)

wherein n is an integer from 1-12, and when n is 2-12, each Z component may be different; R is selected from hydrophilic polymers, hydrophobic polymers, amphiphilic polymers, $C_{2-14}$ hydrocarbyls, and heteroatom-containing $C_{2-14}$ hydrocarbyls; X, Y, and Z are reactive groups and can be the same or different; $L^1$, $L^2$, and $L^3$ are linking groups; and p, q and r are integers from 0-1.

Each of these reactive groups inter-reacts with at least one other reactive group to form a three-dimensional matrix. Therefore X can inter-react with Y and/or Z, Y can inter-react with X and/or Z, Z can inter-react with X and/or Y and so forth. When n is greater than 1, the individual Z components may be the same or different, and therefore each Z group may be the same or different. When the Z groups are different, they can inter-react with each other.

In one preferred embodiment, R is a hydrophilic polymer. In another preferred embodiment, X is a nucleophilic group, Y is an electrophilic group, and Z is either an electrophilic or a nucleophilic group. Additional embodiments are detailed below.

A higher degree of inter-reaction, e.g., crosslinking, may be useful when a less swellable matrix is desired or increased compressive strength is desired. In those embodiments, it may be desirable to have n be an integer from 2-12. In addition, when a plurality of multifunctional compounds are utilized, the compounds may be the same or different.

In the compound of formula (I), each side chain typically has one reactive group. However, the invention also encompasses multifunctional compounds where the side chains can contain more than one reactive group. Thus, in another embodiment of the invention, the multifunctional compound has the formula (II):

(II)

wherein a and b are integers from 0-1; c is an integer from 3-12; R' is selected from hydrophilic polymers, hydrophobic polymers, amphiphilic polymers, $C_{2-14}$ hydrocarbyls, and heteroatom-containing $C_{2-14}$ hydrocarbyls; X' and Y' are reactive groups and can be the same or different; and $L^4$ and $L^5$ are linking groups. Each reactive group inter-reacts with the other reactive group to form a three-dimensional matrix. The compound is essentially non-reactive in an initial environment but is rendered reactive upon exposure to a modification in the initial environment that provides a modified environment such that a plurality of the multifunctional compounds inter-react in the modified environment to form a three-dimensional matrix. In one preferred embodiment, R is a hydrophilic polymer. In another preferred embodiment, X' is a nucleophilic group and Y' is an electrophilic group.

The following multifunctional compound shown in the structure of formula (III) is one example of a compound of formula (II):

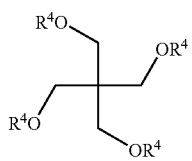
(III)

wherein $R^4$ has the formula:

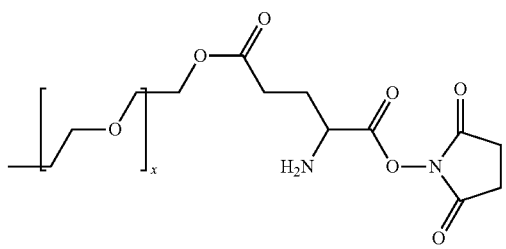

Thus, in formula (III), a and b are 1; c is 4; the core R' is the hydrophilic polymer, tetrafunctionally activated polyethylene glycol, $(C(CH_2—O—)_4$; X' is the electrophilic reactive group, succinimidyl; Y' is the nucleophilic reactive group —CH—NH$_2$; $L^4$ is —C(O)—O—; and $L^5$ is —(CH$_2$—CH$_2$—O—CH$_2$)$_x$—CH$_2$—O—C(O)—(CH$_2$)$_2$—.

The multifunctional compounds of the invention are readily synthesized by techniques that are well known in the art. An exemplary synthesis is set forth below:

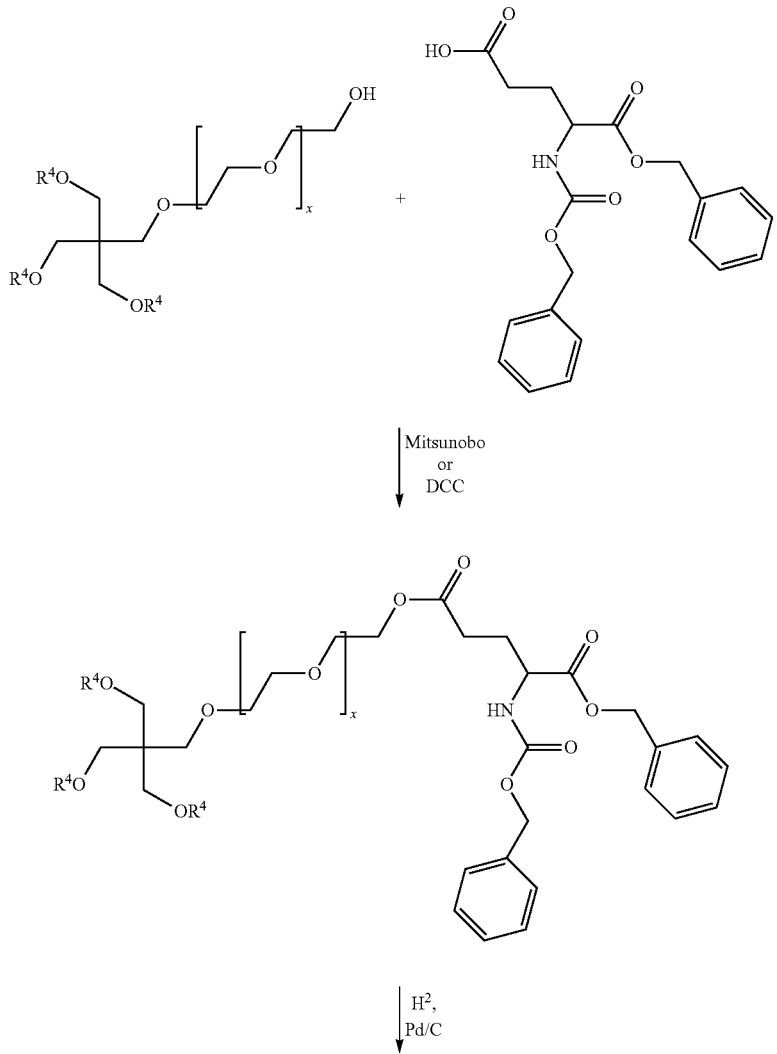

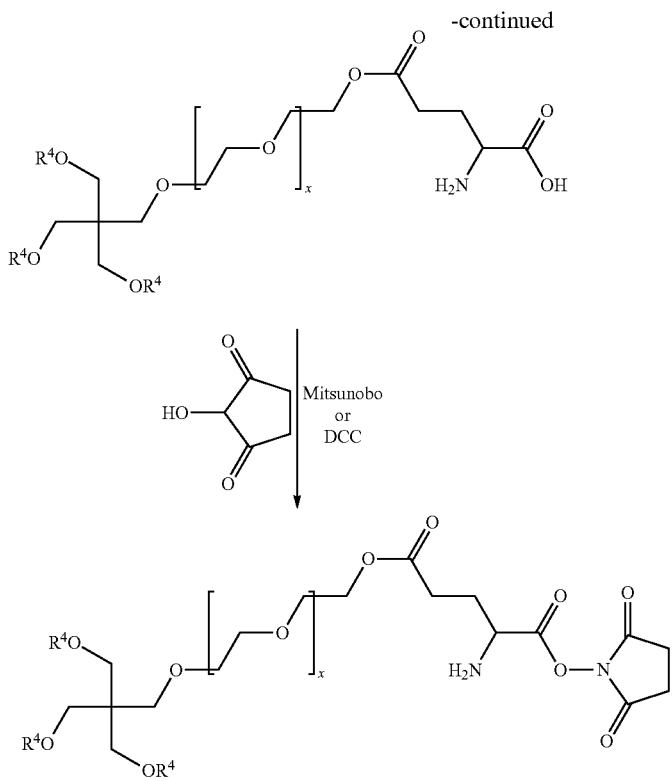

Reactive Groups

Prior to use, the multifunctional compound is stored in an initial environment that insures that the compound remain essentially non-reactive until use. Upon modification of this environment, the compound is rendered reactive and a plurality of compounds will then inter-react to form the desired matrix. The initial environment, as well as the modified environment, is thus determined by the nature of the reactive groups involved.

The number of reactive groups can be the same or different. However, in one embodiment of the invention, the number of X, Y, and Z reactive groups are approximately equal. As used in this context, the term "approximately" refers to a 2:1 to 1:2 ratio of moles of one reactive group to moles of a different reactive groups. A 1:1:1 molar ratio of reactive groups is generally preferred.

In general, the concentration of the multifunctional compounds in the modified environment, when liquid in nature, will be in the range of about 1 to 50 wt %, generally about 2 to 40 wt %. The preferred concentration of the compound in the liquid will depend on a number of factors, including the type of compound (i.e., type of molecular core and reactive groups), its molecular weight, and the end use of the resulting three-dimensional matrix. For example, use of higher concentrations of the compounds, or using highly functionalized compounds, will result in the formation of a more tightly crosslinked network, producing a stiffer, more robust gel As such, compositions intended for use in tissue augmentation will generally employ concentrations of multifunctional compounds that fall toward the higher end of the preferred concentration range. Compositions intended for use as bioadhesives or in adhesion prevention do not need to be as firm and may therefore contain lower concentrations of the multifunctional compounds.

Electrophilic and Nucleophilic Reactive Groups

In one embodiment of the invention, the reactive groups are electrophilic and nucleophilic groups, which undergo a nucleophilic substitution reaction, a nucleophilic addition reaction, or both. The term "electrophilic" refers to a reactive group that is susceptible to nucleophilic attack, i.e., susceptible to reaction with an incoming nucleophilic group. Electrophilic groups herein are positively charged or electron-deficient, typically electron-deficient. The term "nucleophilic" refers to a reactive group that is electron rich, has an unshared pair of electrons acting as a reactive site, and reacts with a positively charged or electron-deficient site. For such reactive groups, the modification in the initial environment comprises the addition of an aqueous medium and/or a change in pH.

In one embodiment of the invention, X can be a nucleophilic group and Y can be an electrophilic group or vice versa, and Z can be either an electrophilic or a nucleophilic group.

X may be virtually any nucleophilic group, so long as reaction can occur with the electrophilic group Y and also with Z, when Z is electrophilic ($Z_{EL}$). Analogously, Y may be virtually any electrophilic group, so long as reaction can take place with X and also with Z when Z is nucleophilic ($Z_{NU}$). The only limitation is a practical one, in that reaction between X and Y, and X and $Z_{EL}$, or Y and $Z_{NU}$ should be fairly rapid and take place automatically upon admixture with an aqueous medium, without need for heat or potentially toxic or non-biodegradable reaction catalysts or other chemical reagents. It is also preferred although not essential that reaction occur without need for ultraviolet or other radiation. In one embodiment, the reactions between X and Y, and between either X and $Z_{EL}$ or Y and $Z_{NU}$, are complete in under 60 minutes, preferably under 30 minutes. Most preferably, the reaction occurs in about 5 to 15 minutes or less.

Examples of nucleophilic groups suitable as X or $Fn_N$ include, but are not limited to, $-NH_2$, $-NHR^1$, $-N(R^1)_2$, $-SH$, $-OH$, $-COOH$, $-C_6H_4-OH$, $-H$, $-PH_2$, $-PHR^1$, $-P(R^1)_2$, $-NH-NH_2$, $-CO-NH-NH_2$, $-C_5H_4N$, etc. wherein $R^1$ is a hydrocarbyl group and each R1 may be the same or different. $R^1$ is typically alkyl or monocyclic aryl, preferably alkyl, and most preferably lower alkyl. Organometallic moieties are also useful nucleophilic groups for the purposes of the invention, particularly those that act as carbanion donors. Examples of organometallic moieties include: Grignard functionalities $-R^2MgHal$ wherein $R^2$ is a carbon atom (substituted or unsubstituted), and Hal is halo, typically bromo, iodo or chloro, preferably bromo; and lithium-containing functionalities, typically alkyllithium groups; sodium-containing functionalities.

It will be appreciated by those of ordinary skill in the art that certain nucleophilic groups must be activated with a base so as to be capable of reaction with an electrophilic group. For example, when there are nucleophilic sulfhydryl and hydroxyl groups in the multifunctional compound, the compound must be admixed with an aqueous base in order to remove a proton and provide an $-S^-$ or $-O^-$ species to enable reaction with the electrophilic group. Unless it is desirable for the base to participate in the reaction, a non-nucleophilic base is preferred. In some embodiments, the base may be present as a component of a buffer solution. Suitable bases and corresponding crosslinking reactions are described herein.

The selection of electrophilic groups provided on the multifunctional compound, must be made so that reaction is possible with the specific nucleophilic groups. Thus, when the X reactive groups are amino groups, the Y and any $Z_{EL}$ groups are selected so as to react with amino groups. Analogously, when the X reactive groups are sulfhydryl moieties, the corresponding electrophilic groups are sulfhydryl-reactive groups, and the like. In general, examples of electrophilic groups suitable as Y or $Z_{EL}$ include, but are not limited to, $-CO-Cl$, $-(CO)-O-(CO)-R$ (where R is an alkyl group), $-CH=CH-CH=O$ and $-CH=CH-C(CH_3)=O$, halo, $-N=C=O$, $-N=C=S$, $-SO_2CH=CH_2$, $-O(CO)-C=CH_2$, $-O(CO)-C(CH_3)=CH_2$, $-S-S-(C_5H_4N)$, $-O(CO)-C(CH_2CH_3)=CH_2$, $-CH=CH-C=NH$, $-COOH$, $-(CO)O-N(COCH_2)_2$, $-CHO$, $-(CO)O-N(COCH_2)_2-S(O)_2OH$, and $-N(COCH)_2$.

When X is amino (generally although not necessarily primary amino), the electrophilic groups present on Y and $Z_{EL}$ are amine-reactive groups. Exemplary amine-reactive groups include, by way of example and not limitation, the following groups, or radicals thereof: (1) carboxylic acid esters, including cyclic esters and "activated" esters; (2) acid chloride groups ($-CO-Cl$); (3) anhydrides ($-(CO)-O-(CO)-R$, where R is an alkyl group); (4) ketones and aldehydes, including α,β-unsaturated aldehydes and ketones such as $-CH=CH-CH=O$ and $-CH=CH-C(CH_3)=O$; (5) halo groups; (6) isocyanate group ($-N=C=O$); (7) thioisocyanato group ($-N=C=S$); (8) epoxides; (9) activated hydroxyl groups (e.g., activated with conventional activating agents such as carbonyldiimidazole or sulfonyl chloride); and (10) olefins, including conjugated olefins, such as ethenesulfonyl ($-SO_2CH=CH_2$) and analogous functional groups, including acrylate ($-O(CO)-C=CH_2$), methacrylate ($-O(CO)-C(CH_3)=CH_2$), ethyl acrylate ($-O(CO)-C(CH_2CH_3)=CH_2$), and ethyleneimino ($-CH=CH-C=NH$).

In one embodiment the amine-reactive groups contain an electrophilically reactive carbonyl group susceptible to nucleophilic attack by a primary or secondary amine, for example the carboxylic acid esters and aldehydes noted above, as well as carboxyl groups ($-COOH$).

Since a carboxylic acid group per se is not susceptible to reaction with a nucleophilic amine, components containing carboxylic acid groups must be activated so as to be amine-reactive. Activation may be accomplished in a variety of ways, but often involves reaction with a suitable hydroxyl-containing compound in the presence of a dehydrating agent such as dicyclohexylcarbodiimide (DCC) or dicyclohexylurea (DHU). For example, a carboxylic acid can be reacted with an alkoxy-substituted N-hydroxy-succinimide or N-hydroxysulfosuccinimide in the presence of DCC to form reactive electrophilic groups, the N-hydroxysuccinimide ester and the N-hydroxysulfosuccinimide ester, respectively. Carboxylic acids may also be activated by reaction with an acyl halide such as an acyl chloride (e.g., acetyl chloride), to provide a reactive anhydride group. In a further example, a carboxylic acid may be converted to an acid chloride group using, e.g., thionyl chloride or an acyl chloride capable of an exchange reaction. Specific reagents and procedures used to carry out such activation reactions will be known to those of ordinary skill in the art and are described in the pertinent texts and literature.

Accordingly, in one embodiment, the amine-reactive groups are selected from succinimidyl ester ($-O(CO)-N(COCH_2)_2$), sulfosuccinimidyl ester ($-O(CO)-N(COCH_2)_2-S(O)_2OH$), maleimido ($-N(COCH)_2$), epoxy, isocyanato, thioisocyanato, and ethenesulfonyl.

Analogously, when X is sulfhydryl, the electrophilic groups present on Y and $Z_{EL}$ are groups that react with a sulfhydryl moiety. Such reactive groups include those that form thioester linkages upon reaction with a sulfhydryl group, such as those described in WO 00/62827 to Wallace et al. As explained in detail therein, sulfhydryl reactive groups include, but are not limited to: mixed anhydrides; ester derivatives of phosphorus; ester derivatives of p-nitrophenol, p-nitrothiophenol and pentafluorophenol; esters of substituted hydroxylamines, including N-hydroxyphthalimide esters, N-hydroxysuccinimide esters, N-hydroxysulfosuccinimide esters, and N-hydroxyglutarimide esters; esters of 1-hydroxybenzotriazole; 3-hydroxy-3,4-dihydro-benzotriazin-4-one; 3-hydroxy-3,4-dihydro-quinazoline-4-one; carbonylimidazole derivatives; acid chlorides; ketenes; and isocyanates. With these sulfhydryl reactive groups, auxiliary reagents can also be used to facilitate bond formation, e.g., 1-ethyl-3-[3-dimethylaminopropyl]carbodiimide, can be used to facilitate coupling of sulfhydryl groups to carboxyl-containing groups.

In addition to the sulfhydryl reactive groups that form thioester linkages, various other sulfhydryl reactive functionalities can be utilized that form other types of linkages. For example, compounds that contain methyl imidate derivatives form imido-thioester linkages with sulfhydryl groups. Alternatively, sulfhydryl reactive groups can be employed that form disulfide bonds with sulfhydryl groups; such groups generally have the structure $-S-S-Ar$ where Ar is a substituted or unsubstituted nitrogen-containing heteroaromatic moiety or a non-heterocyclic aromatic group substituted with an electron-withdrawing moiety, such that Ar may be, for example, 4-pyridinyl, o-nitrophenyl, m-nitrophenyl, p-nitrophenyl, 2,4-dinitrophenyl, 2-nitro-4-benzoic acid, 2-nitro-4-pyridinyl, etc. In such instances, auxiliary reagents, i.e., mild oxidizing agents such as hydrogen peroxide, can be used to facilitate disulfide bond formation.

Yet another class of sulfhydryl reactive groups forms thioether bonds with sulfhydryl groups. Such groups include, inter alia, maleimido, substituted maleimido, haloalkyl, epoxy, imino, and aziridino, as well as olefins (including conjugated olefins) such as ethenesulfonyl, etheneimino, acrylate, methacrylate, and α,β-unsaturated aldehydes and ketones.

When X is —OH, the electrophilic functional groups on the remaining component(s) must react with hydroxyl groups. The hydroxyl group may be activated as described above with respect to carboxylic acid groups, or it may react directly in the presence of base with a sufficiently reactive electrophilic group such as an epoxide group, an aziridine group, an acyl halide, an anhydride, and so forth.

When X is an organometallic nucleophilic group such as a Grignard functionality or an alkyllithium group, suitable electrophilic functional groups for reaction therewith are those containing carbonyl groups, including, by way of example, ketones, and aldehydes.

It will also be appreciated that certain functional groups can react as nucleophilic or as electrophilic groups, depending on the selected reaction partner and/or the reaction conditions. For example, a carboxylic acid group can act as a nucleophilic group in the presence of a fairly strong base, but generally acts as an electrophilic group allowing nucleophilic attack at the carbonyl carbon and concomitant replacement of the hydroxyl group with the incoming nucleophilic group.

These, as well as other embodiments are illustrated below, where the covalent linkages in the matrix that result upon covalent binding of specific nucleophilic reactive groups to specific electrophilic reactive groups on the multifunctional compound include, solely by way of example, the following:

For multifunctional compounds containing electrophilic and nucleophilic reactive groups, the initial environment typically can be dry and sterile. Since electrophilic groups react with water, storage in sterile, dry form will prevent hydrolysis. The dry synthetic polymer may be compression molded into a thin sheet or membrane, which can then be sterilized using gamma or e-beam irradiation. The resulting dry membrane or sheet can be cut to the desired size or chopped into smaller size particulates. The modification of a dry initial environment will typically comprise the addition of an aqueous medium.

In one embodiment, the initial environment can be an aqueous medium such as in a low pH buffer, i.e., having a pH less than about 6.0, in which both electrophilic and nucleophilic groups are non-reactive. Suitable liquid media for storage of such compounds include aqueous buffer solutions such as monobasic sodium phosphate/dibasic sodium phosphate, sodium carbonate/sodium bicarbonate, glutamate or acetate, at a concentration of 0.5 to 300 mM. Modification of an initial low pH aqueous environment will typically comprise increasing the pH to at least pH 7.0, more preferably increasing the pH to at least pH 9.5.

In another embodiment the modification of a dry initial environment comprises dissolving the multifunctional compound in a first buffer solution having a pH within the range of about 1.0 to 5.5 to form a homogeneous solution, and (ii) adding a second buffer solution having a pH within the range of about 6.0 to 11.0 to the homogeneous solution. The buffer solutions are aqueous and can be any pharmaceutically acceptable basic or acid composition. The term "buffer" is used in a general sense to refer to an acidic or basic aqueous solution, where the solution may or may not be functioning to

TABLE 1

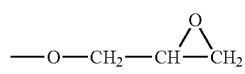

| Representative Nucleophilic Group ($X, Z_{NU}$) | Representative Electrophilic Group ($Y, Z_{EL}$) | Resulting Linkage |
|---|---|---|
| —NH$_2$ | —O—(CO)—O—N(COCH$_2$)$_2$ succinimidyl carbonate terminus | —NH—(CO)—O— |
| —SH | —O—(CO)—O—N(COCH$_2$)$_2$ | —S—(CO)—O— |
| —OH | —O—(CO)—O—N(COCH$_2$)$_2$ | —O—(CO)— |
| —NH$_2$ | —O(CO)—CH=CH$_2$ acrylate terminus | —NH—CH$_2$CH$_2$—(CO)—O— |
| —SH | —O—(CO)—CH=CH$_2$ | —S—CH$_2$CH$_2$—(CO)—O— |
| —OH | —O—(CO)—CH=CH$_2$ | —O—CH$_2$CH$_2$—(CO)—O— |
| —NH$_2$ | —O(CO)—(CH$_2$)$_3$—CO$_2$—N(COCH$_2$)$_2$ succinimidyl glutarate terminus | —NH—(CO)—(CH$_2$)$_3$—(CO)—O— |
| —SH | —O(CO)—(CH$_2$)$_3$—CO$_2$—N(COCH$_2$)$_2$ | —S—(CO)—(CH$_2$)$_3$—(CO)—O— |
| —OH | —O(CO)—(CH$_2$)$_3$—CO$_2$—N(COCH$_2$)$_2$ | —O—(CO)—(CH$_2$)$_3$—(CO)—O— |
| —NH$_2$ | —O—CH$_2$—CO$_2$—N(COCH$_2$)$_2$ succinimidyl acetate terminus | —NH—(CO)—CH$_2$—O— |
| —SH | —O—CH$_2$—CO$_2$—N(COCH$_2$)$_2$ | —S—(CO)—CH$_2$—O— |
| —OH | —O—CH$_2$—CO$_2$—N(COCH$_2$)$_2$ | —O—(CO)—CH$_2$—O— |
| —NH$_2$ | —O—NH(CO)—(CH$_2$)$_2$—CO$_2$—N(COCH$_2$)$_2$ succinimidyl succinamide terminus | —NH—(CO)—(CH$_2$)$_2$—(CO)—NH—O— |
| —SH | —O—NH(CO)—(CH$_2$)$_2$—CO$_2$—N(COCH$_2$)$_2$ | —S—(CO)—(CH$_2$)$_2$—(CO)—NH—O— |
| —OH | —O—NH(CO)—(CH$_2$)$_2$—CO$_2$—N(COCH$_2$)$_2$ | —O—(CO)—(CH$_2$)$_2$—(CO)—NH—O— |
| —NH$_2$ | —O—(CH$_2$)$_2$—CHO propionaldehyde terminus | —NH—(CO)—(CH$_2$)$_2$—O— |
| —NH$_2$ | —O—CH$_2$—CH—CH$_2$ (epoxide) glycidyl ether terminus | —NH—CH$_2$—CH(OH)—CH$_2$—O— and —N[CH$_2$—CH(OH)—CH$_2$—O—]$_2$ |
| —NH$_2$ | —O—(CH$_2$)$_2$—N=C=O (isocyanate terminus) | —NH—(CO)—NH—CH$_2$—O— |
| —NH$_2$ | —SO$_2$—CH=CH$_2$ vinyl sulfone terminus | —NH—CH$_2$CH$_2$—SO$_2$— |
| —SH | —SO$_2$—CH=CH$_2$ | —S—CH$_2$CH$_2$—SO$_2$— | provide a buffering effect (i.e., resistance to change in pH upon addition of acid or base) in the compositions of the present invention. For example, the multifunctional compound can be in the form of a homogeneous dry powder. This powder is then combined with a buffer solution having a pH within the range of about 1.0 to 5.5 to form a homogeneous acidic aqueous solution, and this solution is then combined with a buffer solution having a pH within the range of about 6.0 to 11.0 to form a reactive solution. For example, 0.375 grams of the dry powder can be combined with 0.75 grams of the acid buffer to provide, after mixing, a homogeneous solution, where this solution is combined with 1.1 grams of the basic buffer to provide a reactive mixture that substantially immediately forms a three-dimensional matrix.

Acidic buffer solutions having a pH within the range of about 1.0 to 5.5, include by way of illustration and not limitation, solutions of: citric acid, hydrochloric acid, phosphoric acid, sulfuric acid, AMPSO (3-[(1,1-dimethyl-2-hydroxyethyl)amino]2-hydroxy-propane-sulfonic acid), acetic acid, lactic acid, and combinations thereof. In a preferred embodiment, the acidic buffer solution is a solution of citric acid, hydrochloric acid, phosphoric acid, sulfuric acid, and combinations thereof. Regardless of the precise acidifying agent, the acidic buffer preferably has a pH such that it retards the reactivity of the nucleophilic groups on the core. For example, a pH of 2.1 is generally sufficient to retard the nucleophilicity of thiol groups. A lower pH is typically preferred when the core contains amine groups as the nucleophilic groups. In general, the acidic buffer is an acidic solution that, when contacted with nucleophilic groups, renders those nucleophilic groups relatively non-nucleophilic.

An exemplary acidic buffer is a solution of hydrochloric acid, having a concentration of about 6.3 mM and a pH in the range of 2.1 to 2.3. This buffer may be prepared by combining concentrated hydrochloric acid with water, i.e., by diluting concentrated hydrochloric acid with water. Similarly, this buffer A may also be conveniently prepared by diluting 1.23 grams of concentrated hydrochloric acid to a volume of 2 liters, or diluting 1.84 grams of concentrated hydrochloric acid to a volume to 3 liters, or diluting 2.45 grams of concentrated hydrochloric acid to a volume of 4 liters, or diluting 3.07 grams concentrated hydrochloric acid to a volume of 5 liters, or diluting 3.68 grams of concentrated hydrochloric acid to a volume to 6 liters. For safety reasons, the concentrated acid is preferably added to water.

Basic buffer solutions having a pH within the range of about 6.0 to 11.0, include by way of illustration and not limitation, solutions of: glutamate, acetate, carbonate and carbonate salts (e.g., sodium carbonate, sodium carbonate monohydrate and sodium bicarbonate), borate, phosphate and phosphate salts (e.g., monobasic sodium phosphate monohydrate and dibasic sodium phosphate), and combinations thereof. In a preferred embodiment, the basic buffer solution is a solution of carbonate salts, phosphate salts, and combinations thereof.

In general, the basic buffer is an aqueous solution that neutralizes the effect of the acidic buffer, when it is added to the homogeneous solution of the compound and first buffer, so that the nucleophilic groups on the core regain their nucleophilic character (that has been masked by the action of the acidic buffer), thus allowing the nucleophilic groups to inter-react with the electrophilic groups on the core.

An exemplary basic buffer is an aqueous solution of carbonate and phosphate salts. This buffer may be prepared by combining a base solution with a salt solution. The salt solution may be prepared by combining 34.7 g of monobasic sodium phosphate monohydrate, 49.3 g of sodium carbonate monohydrate, and sufficient water to provide a solution volume of 2 liter. Similarly, a 6 liter solution may be prepared by combining 104.0 g of monobasic sodium phosphate monohydrate, 147.94 g of sodium carbonate monohydrate, and sufficient water to provide 6 liter of the salt solution. The basic buffer may be prepared by combining 7.2 g of sodium hydroxide with 180.0 g of water. The basic buffer is typically prepared by adding the base solution as needed to the salt solution, ultimately to provide a mixture having the desired pH, e.g., a pH of 9.65 to 9.75.

In general, the basic species present in the basic buffer should be sufficiently basic to neutralize the acidity provided by the acidic buffer, but should not be so nucleophilic itself that it will react substantially with the electrophilic groups on the core. For this reason, relatively "soft" bases such as carbonate and phosphate are preferred in this embodiment of the invention.

To illustrate the preparation of a three-dimensional matrix of the present invention, one may combine an admixture of the multifunctional compound with a first, acidic, buffer (e.g., an acid solution, e.g., a dilute hydrochloric acid solution) to form a homogeneous solution. This homogeneous solution is mixed with a second, basic, buffer (e.g., a basic solution, e.g., an aqueous solution containing phosphate and carbonate salts) whereupon the reactive groups on the core of the multifunctional compound substantially immediately inter-react with one another to form a three-dimensional matrix.

Redox Reactive Groups

In one embodiment of the invention, the reactive groups are vinyl groups such as styrene derivatives, which undergo a radical polymerization upon initiation with a redox initiator. The term "redox" refers to a reactive group that is susceptible to oxidation-reduction activation. The term "vinyl" refers to a reactive group that is activated by a redox initiator, and forms a radical upon reaction. X, Y, and Z can be the same or different vinyl groups, for example, methacrylic groups.

For multifunctional compounds containing vinyl reactive groups, the initial environment typically will be an aqueous environment. The modification of the initial environment involves the addition of a redox initiator.

Oxidative Coupling Reactive Groups

In one embodiment of the invention, the reactive groups undergo an oxidative coupling reaction. For example, X, Y, and Z can be a halo group such as chloro, with an adjacent electron-withdrawing group on the halogen-bearing carbon (e.g., on the "L" linking group). Exemplary electron-withdrawing groups include nitro, aryl, and so forth.

For such reactive groups, the modification in the initial environment comprises a change in pH. For example, in the presence of a base such as KOH, the multifunctional compounds then undergo a de-hydro, chloro coupling reaction, forming a double bond between the carbon atoms, as illustrated below:

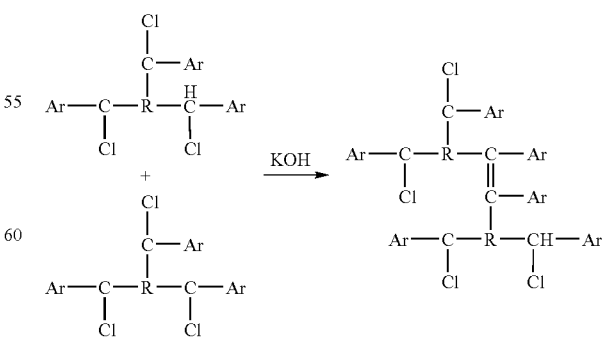

For multifunctional compounds containing oxidative coupling reactive groups, the initial environment typically can be can be dry and sterile, or a non-basic medium. The modification of the initial environment will typically comprise the addition of a base.

Photoinitiated Reactive Groups

In one embodiment of the invention, the reactive groups are photoinitiated groups. For such reactive groups, the modification in the initial environment comprises exposure to ultraviolet radiation.

In one embodiment of the invention, X can be an azide (—$N_3$) group and Y can be an alkyl group such as —CH($CH_3$)$_2$ or vice versa. Exposure to ultraviolet radiation will then form a bond between the groups to provide for the following linkage: —NH—C($CH_3$)$_2$—$CH_2$—. In another embodiment of the invention, X can be a benzophenone (—($C_6H_4$)—C(O)—($C_6H_5$)) group and Y can be an alkyl group such as —CH($CH_3$)$_2$ or vice versa. Exposure to ultraviolet radiation will then form a bond between the groups to provide for the following linkage:

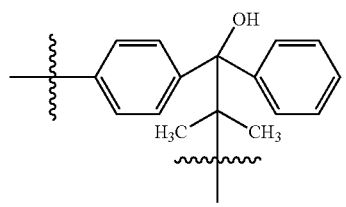

For multifunctional compounds containing photoinitiated reactive groups, the initial environment typically will be in an ultraviolet radiation-shielded environment. This can be for example, storage within a container that is impermeable to ultraviolet radiation.

The modification of the initial environment will typically comprise exposure to ultraviolet radiation.

Temperature-Sensitive Reactive Groups

In one embodiment of the invention, the reactive groups are temperature-sensitive groups, which undergo a thermochemical reaction. For such reactive groups, the modification in the initial environment thus comprises a change in temperature. The term "temperature-sensitive" refers to a reactive group that is chemically inert at one temperature or temperature range and reactive at a different temperature or temperature range.

In one embodiment of the invention, X, Y, and Z are the same or different vinyl groups.

For multifunctional compounds containing reactive groups that are temperature-sensitive, the initial environment typically will be within the range of about 10 to 30° C.

The modification of the initial environment will typically comprise changing the temperature to within the range of about 20 to 40° C.

Linking Groups

The reactive groups may be directly attached to the core, or they may be indirectly attached through a linking group, with longer linking groups also termed "chain extenders." In the formula (I) shown above, the optional linker groups are represented by $L^1$, $L^2$, and $L^3$, wherein the linking groups are present when p, q and r are equal to 1.

Suitable linking groups are well known in the art. See, for example, WO 97/22371 to Rhee et al. Linking groups are useful to avoid steric hindrance problems that can sometimes be associated with the formation of direct linkages between molecules. Linking groups may additionally be used to link several multifunctional compounds together to make larger molecules. In one embodiment, a linking group can be used to alter the degradative properties of the compositions after administration and resultant gel formation. For example, linking groups can be used to promote hydrolysis, to discourage hydrolysis, or to provide a site for enzymatic degradation.

Examples of linking groups that provide hydrolyzable sites, include, inter alia: ester linkages; anhydride linkages, such as those obtained by incorporation of glutarate and succinate; ortho ester linkages; ortho carbonate linkages such as trimethylene carbonate; amide linkages; phosphoester linkages; α-hydroxy acid linkages, such as those obtained by incorporation of lactic acid and glycolic acid; lactone-based linkages, such as those obtained by incorporation of caprolactone, valerolactone, γ-butyrolactone and p-dioxanone; and amide linkages such as in a dimeric, oligomeric, or poly (amino acid) segment. Examples of non-degradable linking groups include succinimide, propionic acid, and carboxymethylate linkages. See, for example, WO 99/07417 to Coury et al. Examples of enzymatically degradable linkages include Leu-Gly-Pro-Ala, which is degraded by collagenase; and Gly-Pro-Lys, which is degraded by plasmin.

Linking groups can also be included to enhance or suppress the reactivity of the various reactive groups. For example, electron-withdrawing groups within one or two carbons of a sulfhydryl group would be expected to diminish its effectiveness in coupling, due to a lowering of nucleophilicity. Carbon-carbon double bonds and carbonyl groups will also have such an effect. Conversely, electron-withdrawing groups adjacent to a carbonyl group (e.g., the reactive carbonyl of glutaryl-N-hydroxysuccinimidyl) would increase the reactivity of the carbonyl carbon with respect to an incoming nucleophilic group. By contrast, sterically bulky groups in the vicinity of a reactive group can be used to diminish reactivity and thus reduce the coupling rate as a result of steric hindrance.

By way of example, particular linking groups and corresponding formulas are indicated in Table 2:

TABLE 2

| Linking group | Component structure |
|---|---|
| —O—(CH$_2$)$_x$— | —O—(CH$_2$)$_x$—X |
| | —O—(CH$_2$)$_x$—Y |
| | —O—(CH$_2$)$_x$—Z |
| —S—(CH$_2$)$_x$— | —S—(CH$_2$)$_x$—X |
| | —S—(CH$_2$)$_x$—Y |
| | —S—(CH$_2$)$_x$—Z |
| —NH—(CH$_2$)$_x$— | —NH—(CH$_2$)$_x$—X |
| | —NH—(CH$_2$)$_x$—Y |
| | —NH—(CH$_2$)$_x$—Z |
| —O—(CO)—NH—(CH$_2$)$_x$— | —O—(CO)—NH—(CH$_2$)$_x$—X |
| | —O—(CO)—NH—(CH$_2$)$_x$—Y |
| | —O—(CO)—NH—(CH$_2$)$_x$—Z |
| —NH—(CO)—O(CH$_2$)$_x$— | —NH—(CO)—O(CH$_2$)$_x$—X |
| | —NH—(CO)—O(CH$_2$)$_x$—Y |
| | —NH—(CO)—O(CH$_2$)$_x$—Z |
| —O—(CO)—(CH$_2$)$_x$— | —O—(CO)—(CH$_2$)$_x$—X |
| | —O—(CO)—(CH$_2$)$_x$—Y |
| | —O—(CO)—(CH$_2$)$_x$—Z |
| —(CO)—O—(CH$_2$)$_x$— | —(CO)—O—(CH$_2$)$_x$—X |
| | —(CO)—O—(CH$_2$)$_x$—Y |
| | —(CO)—O—(CH$_2$)$_x$—Z |
| —O—(CO)—O—(CH$_2$)$_x$— | —O—(CO)—O—(CH$_2$)$_x$—X |
| | —O—(CO)—O—(CH$_2$)$_x$—Y |
| | —O—(CO)—O—(CH$_2$)$_x$—Z |
| —O—(CO)—CHR$^2$— | —O—(CO)—CHR$^2$—X |
| | —O—(CO)—CHR$^2$—Y |
| | —O—(CO)—CHR$^2$—Z |
| —O—R$^3$—(CO)—NH— | —O—R$^3$—(CO)—NH—X |
| | —O—R$^3$—(CO)—NH—Y |
| | —O—R$^3$—(CO)—NH—Z |

In Table 2, x is generally in the range of 1 to about 10; R$^2$ is generally hydrocarbyl, typically alkyl or aryl, preferably alkyl, and most preferably lower alkyl; and $R^3$ is hydrocarbylene, heteroatom-containing hydrocarbylene, substituted hydrocarbylene, or substituted heteroatom-containing hydrocarbylene) typically alkylene or arylene (again, optionally substituted and/or containing a heteroatom), preferably lower alkylene (e.g., methylene, ethylene, n-propylene, n-butylene, etc.), phenylene, or amidoalkylene (e.g., —(CO)—NH—$CH_2$).

Other general principles that should be considered with respect to linking groups are as follows. If a higher molecular weight multifunctional compound is to be used, it will preferably have biodegradable linkages as described above, so that fragments larger than 20,000 mol. wt. are not generated during resorption in the body. In addition, to promote water miscibility and/or solubility, it may be desired to add sufficient electric charge or hydrophilicity. Hydrophilic groups can be easily introduced using known chemical synthesis, so long as they do not give rise to unwanted swelling or an undesirable decrease in compressive strength. In particular, polyalkoxy segments may weaken gel strength.

The Core

The "core" of each multifunctional compound is comprised of the molecular structure to which the reactive groups are bound. The molecular core can be a polymer, which includes synthetic polymers and naturally occurring polymers. In one embodiment, the core is a polymer containing repeating monomer units. The polymers can be hydrophilic, hydrophobic, or amphiphilic. The molecular core can also be a low molecular weight component such as a $C_{2-14}$ hydrocarbyl or a heteroatom-containing $C_{2-14}$ hydrocarbyl. The heteroatom-containing $C_{2-14}$ hydrocarbyl can have 1 or 2 heteroatoms selected from N, O, and S. In a preferred embodiment, the multifunctional compound comprises a molecular core of a synthetic hydrophilic polymer.

Hydrophilic Polymers

The term "hydrophilic polymer" as used herein refers to a polymer having an average molecular weight and composition that naturally renders, or is selected to render the polymer as a whole "hydrophilic." Preferred polymers are highly pure or are purified to a highly pure state such that the polymer is or is treated to become pharmaceutically pure. Most hydrophilic polymers can be rendered water-soluble by incorporating a sufficient number of oxygen (or less frequently nitrogen) atoms available for forming hydrogen bonds in aqueous solutions.

Synthetic hydrophilic polymers may be homopolymers, block copolymers including di-block and tri-block copolymers, random copolymers, or graft copolymers. In addition, the polymer may be linear or branched, and if branched, may be minimally to highly branched, dendrimeric, hyperbranched, or a star polymer. The polymer may include biodegradable segments and blocks, either distributed throughout the polymer's molecular structure or present as a single block, as in a block copolymer. Biodegradable segments preferably degrade so as to break covalent bonds. Typically, biodegradable segments are segments that are hydrolyzed in the presence of water and/or enzymatically cleaved in situ. Biodegradable segments may be composed of small molecular segments such as ester linkages, anhydride linkages, ortho ester linkages, ortho carbonate linkages, amide linkages, phosphonate linkages, etc. Larger biodegradable "blocks" will generally be composed of oligomeric or polymeric segments incorporated within the hydrophilic polymer. Illustrative oligomeric and polymeric segments that are biodegradable include, by way of example, poly(amino acid) segments, poly(orthoester) segments, poly(orthocarbonate) segments, and the like. Other biodegradable segments that may form part of the hydrophilic polymer core include polyesters such as polylactide, polyethers such as polyalkylene oxide, polyamides such as a protein, and polyurethanes. For example, the core of the multifunctional compound can be a diblock copolymer of tetrafunctionally activated polyethylene glycol and polylactide.

Synthetic hydrophilic polymers that are useful herein include, but are not limited to: polyalkylene oxides, particularly polyethylene glycol (PEG) and poly(ethylene oxide)-poly(propylene oxide) copolymers, including block and random copolymers; polyols such as glycerol, polyglycerol (PG) and particularly highly branched polyglycerol, propylene glycol; poly(oxyalkylene)-substituted diols, and poly(oxyalkylene)-substituted polyols such as mono-, di- and tri-polyoxyethylated glycerol, mono- and di-polyoxyethylated propylene glycol, and mono- and di-polyoxyethylated trimethylene glycol; polyoxyethylated sorbitol, polyoxyethylated glucose; poly(acrylic acids) and analogs and copolymers thereof, such as polyacrylic acid per se, polymethacrylic acid, poly(hydroxyethylmethacrylate), poly(hydroxyethylacrylate), poly(methylalkylsulfoxide methacrylates), poly(methylalkylsulfoxide acrylates) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly(methacrylamide), poly(dimethylacrylamide), poly(N-isopropyl-acrylamide), and copolymers thereof; poly (olefinic alcohols) such as poly(vinyl alcohols) and copolymers thereof; poly(N-vinyl lactams) such as poly(vinyl pyrrolidones), poly(N-vinyl caprolactams), and copolymers thereof; polyoxazolines, including poly(methyloxazoline) and poly(ethyloxazoline); and polyvinylamines; as well as copolymers of any of the foregoing. It must be emphasized that the aforementioned list of polymers is not exhaustive, and a variety of other synthetic hydrophilic polymers may be used, as will be appreciated by those skilled in the art.

Those of ordinary skill in the art will appreciate that synthetic polymers such as polyethylene glycol cannot be prepared practically to have exact molecular weights, and that the term "molecular weight" as used herein refers to the weight average molecular weight of a number of molecules in any given sample, as commonly used in the art. Thus, a sample of PEG 2,000 might contain a statistical mixture of polymer molecules ranging in weight from, for example, 1,500 to 2,500 daltons with one molecule differing slightly from the next over a range. Specification of a range of molecular weights indicates that the average molecular weight may be any value between the limits specified, and may include molecules outside those limits. Thus, a molecular weight range of about 800 to about 20,000 indicates an average molecular weight of at least about 800, ranging up to about 20 kDa.

Other suitable synthetic hydrophilic polymers include chemically synthesized polypeptides, particularly polynucleophilic polypeptides that have been synthesized to incorporate amino acids containing primary amino groups (such as lysine) and/or amino acids containing thiol groups (such as cysteine). Poly(lysine), a synthetically produced polymer of the amino acid lysine (145 MW), is particularly preferred. Poly(lysine)s have been prepared having anywhere from 6 to about 4,000 primary amino groups, corresponding to molecular weights of about 870 to about 580,000. Poly(lysine)s for use in the present invention preferably have a molecular weight within the range of about 1,000 to about 300,000, more preferably within the range of about 5,000 to about 100,000, and most preferably, within the range of about 8,000 to about 15,000. Poly(lysine)s of varying molecular weights are commercially available from Peninsula Laboratories, Inc. (Belmont, Calif.).

Although a variety of different synthetic hydrophilic polymers can be used in the present compounds, preferred synthetic hydrophilic polymers are PEG and PG, particularly highly branched PG. Various forms of PEG are extensively used in the modification of biologically active molecules because PEG lacks toxicity, antigenicity, and immunogenicity (i.e., is biocompatible), can be formulated so as to have a wide range of solubilities, and do not typically interfere with the enzymatic activities and/or conformations of peptides. A particularly preferred synthetic hydrophilic polymer for certain applications is a PEG having a molecular weight within the range of about 100 to about 100,000, although for highly branched PEG, far higher molecular weight polymers can be employed, up to 1,000,000 or more, providing that biodegradable sites are incorporated ensuring that all degradation products will have a molecular weight of less than about 30,000. For most PEGs, however, the preferred molecular weight is about 1,000 to about 20,000, more preferably within the range of about 7,500 to about 20,000. Most preferably, the polyethylene glycol has a molecular weight of approximately 10,000.

Naturally occurring hydrophilic polymers include, but are not limited to: proteins such as collagen, fibronectin, albumins, globulins, fibrinogen, fibrin and thrombin, with collagen particularly preferred; carboxylated polysaccharides such as polymannuronic acid and polygalacturonic acid; aminated polysaccharides, particularly the glycosaminoglycans, e.g., hyaluronic acid, chitin, chondroitin sulfate A, B, or C, keratin sulfate, keratosulfate and heparin; and activated polysaccharides such as dextran and starch derivatives. Collagen and glycosaminoglycans are preferred naturally occurring hydrophilic polymers for use herein.

The term "collagen" as used herein refers to all forms of collagen, including those, which have been processed or otherwise modified. Thus, collagen from any source may be used in the compounds of the invention; for example, collagen may be extracted and purified from human or other mammalian source, such as bovine or porcine corium and human placenta, or may be recombinantly or otherwise produced. The preparation of purified, substantially non-antigenic collagen in solution from bovine skin is well known in the art. For example, U.S. Pat. No. 5,428,022 to Palefsky et al. discloses methods of extracting and purifying collagen from the human placenta, and U.S. Pat. No. 5,667,839 to Berg discloses methods of producing recombinant human collagen in the milk of transgenic animals, including transgenic cows. Non-transgenic, recombinant collagen expression in yeast and other cell lines) is described in U.S. Pat. Nos. 6,413,742 to Olsen et al.; 6,428,978 to Olsen et al.; and 6,653,450 to Berg et al.

Collagen of any type, including, but not limited to, types I, II, III, IV, or any combination thereof, may be used in the compounds of the invention, although type I is generally preferred. Either atelopeptide or telopeptide-containing collagen may be used; however, when collagen from a natural source, such as bovine collagen, is used, atelopeptide collagen is generally preferred, because of its reduced immunogenicity compared to telopeptide-containing collagen.

Collagen that has not been previously crosslinked by methods such as heat, irradiation, or chemical crosslinking agents is preferred for use in the invention, although previously crosslinked collagen may be used.

Collagens for use in the present invention are generally, although not necessarily, in aqueous suspension at a concentration between about 20 mg/mL to about 120 mg/mL, preferably between about mg/mL to about 90 mg/mL. Although intact collagen is preferred, denatured collagen, commonly known as gelatin, can also be used. Gelatin may have the added benefit of being degradable faster than collagen.

Nonfibrillar collagen is generally preferred for use in compounds of the invention, although fibrillar collagens may also be used. The term "nonfibrillar collagen" refers to any modified or unmodified collagen material that is in substantially nonfibrillar form, i.e., molecular collagen that is not tightly associated with other collagen molecules so as to form fibers. Typically, a solution of nonfibrillar collagen is more transparent than is a solution of fibrillar collagen. Collagen types that are nonfibrillar (or microfibrillar) in native form include types IV, VI, and VII.

Chemically modified collagens that are in nonfibrillar form at neutral pH include succinylated collagen and methylated collagen, both of which can be prepared according to the methods described in U.S. Pat. No. 4,164,559 to Miyata et al. Methylated collagen, which contains reactive amine groups, is a preferred nucleophile-containing component in the compositions of the present invention. In another aspect, methylated collagen is a component that is present in addition to first and second components in the matrix-forming reaction of the present invention. Methylated collagen is described in, for example, in U.S. Pat. No. 5,614,587 to Rhee et al.

Collagens for use in the compositions of the present invention may start out in fibrillar form and can then be rendered nonfibrillar by the addition of one or more fiber disassembly agent. The fiber disassembly agent must be present in an amount sufficient to render the collagen substantially nonfibrillar at pH 7, as described above. Fiber disassembly agents for use in the present invention include, without limitation, various biocompatible alcohols, amino acids, inorganic salts, and carbohydrates, with biocompatible alcohols being particularly preferred. Preferred biocompatible alcohols include glycerol and propylene glycol. Non-biocompatible alcohols, such as ethanol, methanol, and isopropanol, are not preferred for use in the present invention, due to their potentially deleterious effects on the body of the patient receiving them. Preferred amino acids include arginine. Preferred inorganic salts include sodium chloride and potassium chloride. Although carbohydrates, such as various sugars including sucrose, may be used in the practice of the present invention, they are not as preferred as other types of fiber disassembly agents because they can have cytotoxic effects in vivo.

Fibrillar collagen is less preferred for use in the compounds of the invention. However, as disclosed in U.S. Pat. No. 5,614,587 to Rhee et al., fibrillar collagen, or mixtures of nonfibrillar and fibrillar collagen, may be preferred for use in compounds intended for long-term persistence in vivo.

Hydrophobic Polymers

The core of the multifunctional compound may also comprise a hydrophobic polymer, including low molecular weight polyfunctional species; although for most uses hydrophilic polymers are preferred. Generally, "hydrophobic polymers" herein contain a relatively small proportion of oxygen and/or nitrogen atoms. Preferred hydrophobic polymers for use in the invention generally have a carbon chain that is no longer than about 14 carbons. Polymers having carbon chains substantially longer than 14 carbons generally have very poor solubility in aqueous solutions and, as such, have very long reaction times when mixed with aqueous solutions of synthetic polymers containing, for example, multiple nucleophilic groups. Thus, use of short-chain oligomers can avoid solubility-related problems during reaction. Polylactic acid and polyglycolic acid are examples of two particularly suitable hydrophobic polymers. While collagen is hydrophobic at neutral pH, it may be made more or less hydrophilic as through modification with the substituents described herein.

Amphiphilic Polymers

Generally, amphiphilic polymers have a hydrophilic portion and a hydrophobic (or lipophilic) portion. The hydrophilic portion can be at one end of the core and the hydrophobic portion at the opposite end, or the hydrophilic and hydrophobic portions may be distributed randomly (random copolymer) or in the form of sequences or grafts (block copolymer) to form the amphiphilic polymer core of the multifunctional compound. The hydrophilic and hydrophobic portions may include any of the aforementioned hydrophilic and hydrophobic polymers.

Alternately, the amphiphilic polymer core can be a hydrophilic polymer that has been modified with hydrophobic moieties (e.g., alkylated PEG or a hydrophilic polymer modified with one or more fatty chains), or a hydrophobic polymer that has been modified with hydrophilic moieties (e.g., "PEGylated" phospholipids such as polyethylene glycolated phospholipids).

Low Molecular Weight Components

As indicated above, the molecular core of the multifunctional compound can also be a low molecular weight compound, defined herein as being a $C_{2-14}$ hydrocarbyl or a heteroatom-containing $C_{2-14}$ hydrocarbyl, which contains 1 to 2 heteroatoms selected from N, O, S, and combinations thereof. Such a molecular core can be substituted with any of the reactive groups described herein.

Alkanes are suitable $C_{2-14}$ hydrocarbyl molecular cores. Exemplary alkanes, for substituted with a nucleophilic primary amino group and a Y electrophilic group, include, ethyleneamine ($H_2N$—$CH_2CH_2$—Y), tetramethyleneamine ($H_2N$—$(CH_4)$—Y), pentamethyleneamine ($H_2N$—$(CH_5)$—Y), and hexamethyleneamine ($H_2N$—$(CH_6)$—Y).

Low molecular weight diols and polyols are also suitable $C_{2-14}$ hydrocarbyls and include trimethylolpropane, di(trimethylol propane), pentaerythritol, and diglycerol. Polyacids are also suitable $C_{2-14}$ hydrocarbyls, and include trimethylolpropane-based tricarboxylic acid, di(trimethylol propane)-based tetracarboxylic acid, heptanedioic acid, octanedioic acid (suberic acid), and hexadecanedioic acid (thapsic acid).

Low molecular weight di- and poly-electrophiles are suitable heteroatom-containing $C_{2-14}$ hydrocarbyl molecular cores. These include, for example, disuccinimidyl suberate (DSS), bis(sulfosuccinimidyl)suberate ($BS_3$), dithiobis(succinimidylpropionate) (DSP), bis(2-succinimidooxycarbonyloxy)ethyl sulfone (BSOCOES), and 3,3'-dithiobis(sulfosuccinimidylpropionate) (DTSPP), and their analogs and derivatives.

In one embodiment of the invention, the multifunctional compound of the invention comprises a low-molecular weight material core, with a plurality of acrylate moieties and a plurality of thiol groups.

Preparation

The multifunctional compounds are readily synthesized to contain a hydrophilic, hydrophobic or amphiphilic polymer core or a low molecular weight core, functionalized with the desired functional groups, i.e., nucleophilic and electrophilic groups, which enable crosslinking. For example, preparation of a multifunctional compound having a polyethylene glycol (PEG) core is discussed below. However, it is to be understood that the following discussion is for purposes of illustration and analogous techniques may be employed with other polymers.

With respect to PEG, first of all, various functionalized PEGs have been used effectively in fields such as protein modification (see Abuchowski et al., Enzymes as Drugs, pp. 367-383 John Wiley & Sons: New York, N.Y. (1981); and Dreborg et al., Crit. Rev. Therap. Drug Carrier Syst. 6:315 (1990)), peptide chemistry (see, Mutter et al., The Peptides, Academic: New York, N.Y. 2:285-332; and Zalipsky et al., Int. J. Peptide Protein Res. 30:740 (1987)), and the synthesis of polymeric drugs (see Zalipsky et al., Eur. Polym. J. 19:1177 (1983); and Ouchi et al., J. Macromol. Sci. Chem. A24:1011 (1987)).

Functionalized forms of PEG, including multi-functionalized PEG, are commercially available, and are also easily prepared using known methods. For example, see Chapter 22 of Poly(ethylene Glycol) Chemistry: Biotechnical and Biomedical Applications, J. Milton Harris, ed., Plenum Press, NY (1992).

Multi-functionalized forms of PEG are of particular interest and include, PEG succinimidyl glutarate, PEG succinimidyl propionate, succinimidyl butylate, PEG succinimidyl acetate, PEG succinimidyl succinamide, PEG succinimidyl carbonate, PEG propionaldehyde, PEG glycidyl ether, PEG-isocyanate, and PEG-vinylsulfone. Many such forms of PEG are described in U.S. Pat. Nos. 5,328,955 and 6,534,591, both to Rhee et al. Similarly, various forms of multi-amino PEG are commercially available from sources such as PEG Shop, a division of SunBio of South Korea (www.sunbio.com), Nippon Oil and Fats (Yebisu Garden Place Tower, 20-3 Ebisu 4-chome, Shibuya-ku, Tokyo), Nektar Therapeutics (San Carlos, Calif.) and from Huntsman's Performance Chemicals Group (Houston, Tex.) under the name JEFFAMINE® polyoxyalkyleneamines. Multi-amino PEGs useful in the present invention include the JEFFAMINE® diamines ("D" series) and triamines ("T" series), which contain two and three primary amino groups per molecule. Analogous poly(sulfhydryl) PEGs are also available from Nektar Therapeutics, e.g., in the form of pentaerythritol poly(ethylene glycol) ether tetra-sulfhydryl (molecular weight 10,000). These multi-functionalized forms of PEG can then be modified to include the other desired reactive groups.

Reaction with succinimidyl groups to convert terminal hydroxyl groups to reactive esters is one technique for preparing a core with electrophilic groups. This core can then be modified include nucleophilic groups such as primary amines, thiols, and hydroxyl groups. Other agents to convert hydroxyl groups include carbonyldiimidazole and sulfonyl chloride. However, as discussed herein, a wide variety of electrophilic groups may be advantageously employed for reaction with corresponding nucleophilic groups. Examples of such electrophilic groups include acid chloride groups; anhydrides, ketones, aldehydes, isocyanate, isothiocyanate, epoxides, and olefins, including conjugated olefins such as ethenesulfonyl (—$SO_2CH$=$CH_2$) and analogous functional groups.

Compositions of the Multifunctional Compound

The multifunctional compound of the invention can included in a pharmaceutical composition. A pharmaceutically acceptable carrier may also be included.

In order to enhance matrix strength, it may be generally desirable to add a "tensile strength enhancer" to the composition. Such tensile strength enhancers preferably comprise micron-size, preferably 5 to 40 microns in diameter and 20 to 5000 microns in length, high tensile strength fibers, usually with glass transition temperatures well above 37° C.

Suitable tensile strength enhancers for use with the multifunctional compound of the present invention include, inter alia, collagen fibers, polyglycolide and polylactide fibers, as well as other organic tensile strength enhancers and inorganic tensile strength enhancers. A particularly useful tensile strength enhancer is VICRYL® (polyglycolide:polylactide, 90:10) The use of tensile strength enhancers, which are part of the broader category of "fillers," are well known. For example, silicone gums, when cross-linked with peroxides, are weak gels with tensile strength on the order of only about 34 N/cm². When suitably compounded with reinforcing fillers, the tensile strength of these gums may increase as much as fifty-fold. Lichtenwalner et al., eds., *Encyclopedia of Polymer Science and Technology*, vol. 12, p. 535 (John Wiley, New York, 1970). Suitable tensile strength enhancers are those that have inherent high tensile strength and also can interact by covalent or non-covalent bonds with the three-dimensional matrix. The tensile strength enhancer should bond to the matrix, either mechanically or covalently, in order to provide tensile support. Tensile strengths of polyglycolide resorbable sutures are approximately 89,000 N/cm²; that of collagen fibers is 5000-10,000 N/cm². Tsuruta and Hayashi, eds., *Biomedical Applications of Polymeric Materials* (CRC Press, Boca Raton, Fla. 1993).

The multifunctional compound can also be prepared to contain various imaging agents such as iodine or barium sulfate, or fluorine, in order to aid visualization of the compositions after administration via X-ray or $^{19}$F-MRI, respectively.

For use in tissue adhesion as discussed below, it may also be desirable to incorporate proteins such as albumin, fibrin, or fibrinogen into the multifunctional compound to promote cellular adhesion.

In addition, the introduction of hydrocolloids such as carboxymethylcellulose may promote tissue adhesion and/or swellability.

The multifunctional compound may be comprised of a crosslinkable composition comprised of (a) a first crosslinkable component having m nucleophilic groups, wherein $m \geq 2$; and (b) a second crosslinkable component having n electrophilic groups capable of reaction with the m nucleophilic groups to form covalent bonds, wherein $n \geq 2$ and $m+n \geq 5$, the first component comprises two or more amino acid residues selected from the group consisting of amino acids comprising primary amine groups and amino acids comprising thiol groups, the second component comprises a polyethylene glycol moiety, and each of the first and second crosslinkable components is biocompatible, synthetic, and nonimmunogenic, and further wherein crosslinking of the composition results in a biocompatible, nonimmunogenic, crosslinked matrix.

Any of the following are preferred embodiments of the crosslinkable composition described immediately above: m>3, m=3, m=4, n=4, the electrophilic groups are succinimidyl moieties, all n are identical, and all m are identical.

In one preferred embodiment, the selected amino acid residues are lysine. Within this embodiment, any of the following is preferred: m>3, m=3, m=4, n=4, the electrophilic groups are succinimidyl moieties, all n are identical, and all m are identical.

In another preferred embodiment, the selected amino acid residues are cysteine. Within this embodiment, any of the following is preferred: m>3, m=3, m=4, n=4, the electrophilic groups are succinimidyl moieties, all n are identical, and all m are identical.

The multifunctional compound may also be comprised of a crosslinkable composition comprised of: (a) a first crosslinkable component having m nucleophilic groups, wherein $m \geq 2$; and (b) a second crosslinkable component having n electrophilic groups capable of reaction with the m nucleophilic groups to form covalent bonds, wherein $n \geq 2$ and $m+n \geq 5$, the first component comprises two or more amino acid residues selected from the group consisting of amino acids comprising primary amine groups and amino acids comprising thiol groups, the second component comprises a polyethylene glycol moiety, the electrophilic groups are succinimidyl moieties, and each of the first and second crosslinkable components is biocompatible, synthetic, and nonimmunogenic, and further wherein crosslinking of the composition results in a biocompatible, nonimmunogenic, crosslinked matrix.

Any of the following are preferred embodiments of the crosslinkable composition described immediately above: m>3, m=3, m=4, n=4, the electrophilic groups are succinimidyl moieties, all n are identical, and all m are identical.

In one preferred embodiment, the selected amino acid residues are lysine. Within this embodiment, any of the following is preferred: m>3, m=3, m=4, n=4, the electrophilic groups are succinimidyl moieties, all n are identical, and all m are identical.

In another preferred embodiment, the selected amino acid residues are cysteine. Within this embodiment, any of the following is preferred: m>3, m=3, m=4, n=4, the electrophilic groups are succinimidyl moieties, all n are identical, and all m are identical.

The multifunctional compound may also be comprised of a crosslinkable composition comprised of: (a) a first crosslinkable component having m nucleophilic groups, wherein $m \geq 2$; and (b) a second crosslinkable component having n electrophilic groups capable of reaction with the m nucleophilic groups to form covalent bonds, wherein n24 and $m+n \geq 5$, the first component comprises two or more amino acid residues selected from the group consisting of amino acids comprising primary amine groups and amino acids comprising thiol groups, the second component comprises a multifunctionally activated polyethylene glycol, and each of the first and second crosslinkable components is biocompatible, synthetic, and nonimmunogenic, and further wherein crosslinking of the composition results in a biocompatible, nonimmunogenic, crosslinked matrix.

Any of the following are preferred embodiments of the crosslinkable composition described immediately above: m>3, m=3, m=4, n=4, the electrophilic groups are succinimidyl moieties, all n are identical, all m are identical, the multifunctionally activated polyethylene glycol is tetrafunctionally activated polyethylene glycol, and the multifunctionally activated polyethylene glycol is a star-branched polyethylene glycol.

In one preferred embodiment, the selected amino acid residues are lysine. Within this embodiment, any of the following is preferred: m>3, m=3, m=4, n=4, the electrophilic groups are succinimidyl moieties, all n are identical, all m are identical, and the multifunctionally activated polyethylene glycol is tetrafunctionally activated polyethylene glycol or the multifunctionally activated polyethylene glycol is a star-branched polyethylene glycol.

In another preferred embodiment, the selected amino acid residues are cysteine. Within this embodiment, any of the following is preferred: m>3, m=3, m=4, n=4, the electrophilic groups are succinimidyl moieties, all n are identical, all m are identical, and the multifunctionally activated polyethylene glycol is tetrafunctionally activated polyethylene glycol or the multifunctionally activated polyethylene glycol is a star-branched polyethylene glycol.

The multifunctional compound may also be comprised of a crosslinkable composition comprised of: (a) a first crosslinkable component having m nucleophilic groups, wherein m≧2; and (b) a second crosslinkable component having n electrophilic groups capable of reaction with the m nucleophilic groups to form covalent bonds, wherein n≧2 and m+n≧5, the first component comprises two or more amino acid residues selected from the group consisting of lysine and cysteine, the second component comprises a polyethylene glycol moiety, and each of the first and second crosslinkable components is biocompatible, synthetic, and nonimmunogenic, and crosslinking of the composition results in a biocompatible, nonimmunogenic, crosslinked matrix.

Any of the following are preferred embodiments of the crosslinkable composition described immediately above: m>3, m=3, m=4, n=4, the electrophilic groups are succinimidyl moieties, all n are identical, all m are identical, the first component consists of three lysine residues, and the first component consists of three cysteine residues.

The multifunctional compound may also be comprised of a crosslinkable composition comprised of: (a) a first crosslinkable component having m nucleophilic groups, wherein m>2; and (b) a second crosslinkable component having n electrophilic groups capable of reaction with the m nucleophilic groups to form covalent bonds, wherein n≧2 and m+n≧5, the first component comprises two or more lysine residues, the second component comprises a polyethylene glycol moiety, and each of the first and second crosslinkable components is biocompatible, synthetic, and nonimmunogenic, and crosslinking of the composition results in a biocompatible, nonimmunogenic, crosslinked matrix.

Any of the following are preferred embodiments of the crosslinkable composition described immediately above: m>3, m=3, m=4, n=4, the electrophilic groups are succinimidyl moieties, all n are identical, all m are identical, and the first component consists of three lysine residues.

The multifunctional compound may also be comprised of a crosslinkable composition comprised of: (a) a first crosslinkable component having m nucleophilic groups, wherein m≧2; and (b) a second crosslinkable component having n electrophilic groups capable of reaction with the m nucleophilic groups to form covalent bonds, wherein n≧2 and m+n≧5, the first component consists of lysine residues, the second component comprises a polyethylene glycol moiety, and each of the first and second crosslinkable components is biocompatible, synthetic, and nonimmunogenic, and crosslinking of the composition results in a biocompatible, nonimmunogenic, crosslinked matrix.

Any of the following are preferred embodiments of the crosslinkable composition described immediately above: m>3, m=3, m=4, n=4, the electrophilic groups are succinimidyl moieties, all n are identical, all m are identical, and the first component consists of three lysine residues.

The multifunctional compound may also be comprised of a crosslinkable composition comprised of: (a) a first crosslinkable component having m nucleophilic groups, wherein m≧2; and (b) a second crosslinkable component having n electrophilic groups capable of reaction with the m nucleophilic groups to form covalent bonds, wherein n≧2 and m+n≧5, the first component comprises two or more cysteine residues, the second component comprises a polyethylene glycol moiety, and each of the first and second crosslinkable components is biocompatible, synthetic, and nonimmunogenic, and crosslinking of the composition results in a biocompatible, nonimmunogenic, crosslinked matrix.

Any of the following are preferred embodiments of the crosslinkable composition described immediately above: m>3, m=3, m=4, n=4, the electrophilic groups are succinimidyl moieties, all n are identical, all m are identical, the first component consists of three cysteine residues.

The multifunctional compound may also be comprised of a crosslinkable composition comprised of: (a) a first crosslinkable component having m nucleophilic groups, wherein m≧2; and (b) a second crosslinkable component having n electrophilic groups capable of reaction with the m nucleophilic groups to form covalent bonds, wherein n≧2 and m+n≧5, wherein the first component consists of cysteine residues, the second component comprises a polyethylene glycol moiety, and each of the first and second crosslinkable components is biocompatible, synthetic, and nonimmunogenic, and crosslinking of the composition results in a biocompatible, nonimmunogenic, crosslinked matrix.

Any of the following are preferred embodiments of the crosslinkable composition described immediately above: m>3, m=3, m=4, n=4, the electrophilic groups are succinimidyl moieties, all n are identical, all m are identical, and the first component consists of three cysteine residues.

The crosslinkable composition may also be comprised of: (a) a first crosslinkable component having m nucleophilic groups, wherein m≧2; and (b) a second crosslinkable component having n electrophilic groups capable of reaction with the m nucleophilic groups to form covalent bonds, wherein n≧2 and m+n≧5, the first component comprises two or more amino acid residues selected from the group consisting of lysine and cysteine, the second component comprises a polyethylene glycol moiety, the electrophilic groups are succinimidyl moieties, and each of the first and second crosslinkable components is biocompatible, synthetic, and nonimmunogenic, and crosslinking of the composition results in a biocompatible, nonimmunogenic, crosslinked matrix.

Any of the following are preferred embodiments of the crosslinkable composition described immediately above: m>3, m=3, m=4, n=4, all n are identical, all m are identical, the first component consists of three lysine residues, and the first component consists of three cysteine residues.

The crosslinkable composition may also be comprised of: (a) a first crosslinkable component having m nucleophilic groups, wherein m≧2; and (b) a second crosslinkable component having n electrophilic groups capable of reaction with the m nucleophilic groups to form covalent bonds, wherein n≧2 and m+n≧5, the first component comprises two or more lysine residues, the second component comprises a polyethylene glycol moiety, the electrophilic groups are succinimidyl moieties, and each of the first and second crosslinkable components is biocompatible, synthetic, and nonimmunogenic, and crosslinking of the composition results in a biocompatible, nonimmunogenic, crosslinked matrix.

Any of the following are preferred embodiments of the crosslinkable composition described immediately above: m>3, m=3, m=4, n=4, all n are identical, all m are identical, and the first component consists of three lysine residues.

The crosslinkable composition may also be comprised of: (a) a first crosslinkable component having m nucleophilic groups, wherein m≧2; and (b) a second crosslinkable component having n electrophilic groups capable of reaction with the m nucleophilic groups to form covalent bonds, wherein n≧2 and m+n≧5, the first component consists of lysine residues, the second component comprises a polyethylene glycol moiety, the electrophilic groups are succinimidyl moieties, and each of the first and second crosslinkable components is biocompatible, synthetic, and nonimmunogenic, and crosslinking of the composition results in a biocompatible, nonimmunogenic, crosslinked matrix.

Any of the following are preferred embodiments of the crosslinkable composition described immediately above: m>3, m=3, m=4, n=4, all n are identical, all m are identical, and the first component consists of three lysine residues.

The crosslinkable composition may also be comprised of: (a) a first crosslinkable component having m nucleophilic groups, wherein $m \geq 2$; and (b) a second crosslinkable component having n electrophilic groups capable of reaction with the m nucleophilic groups to form covalent bonds, wherein $n \geq 2$ and $m+n \geq 5$, the first component comprises two or more cysteine residues, the second component comprises a polyethylene glycol moiety, the electrophilic groups are succinimidyl moieties, and each of the first and second crosslinkable components is biocompatible, synthetic, and nonimmunogenic, and crosslinking of the composition results in a biocompatible, nonimmunogenic, crosslinked matrix.

Any of the following are preferred embodiments of the crosslinkable composition described immediately above: $m>3$, $m=3$, $m=4$, $n=4$, all n are identical, all m are identical, and the first component consists of three cysteine residues.

The crosslinkable composition may also be comprised of: (a) a first crosslinkable component having m nucleophilic groups, wherein $m \geq 2$; (b) a second crosslinkable component having n electrophilic groups capable of reaction with the m nucleophilic groups to form covalent bonds, wherein $n \geq 2$ and $m+n \geq 5$, the first component consists of cysteine residues, the second component comprises a polyethylene glycol moiety, the electrophilic groups are succinimidyl moieties, and each of the first and second crosslinkable components is biocompatible, synthetic, and nonimmunogenic, and crosslinking of the composition results in a biocompatible, nonimmunogenic, crosslinked matrix.

Any of the following are preferred embodiments of the crosslinkable composition described immediately above: $m>3$, $m=3$, $m=4$, $n=4$, all n are identical, all m are identical, and the first component consists of three cysteine residues.

Formation of the Three-Dimensional Matrix

In one embodiment of the invention, a three-dimensional matrix is formed by the steps of: (a) providing a composition comprised of a multifunctional compound of the invention; (b) rendering the nucleophilic and electrophilic groups reactive by exposing the composition to an aqueous environment to effect inter-reaction; wherein said exposure comprises: (i) dissolving the composition in a first buffer solution having a pH within the range of about 1.0 to 5.5 to form a homogeneous solution, and (ii) adding a second buffer solution having a pH within the range of about 6.0 to 11.0 to the homogeneous solution; and (c) allowing a three-dimensional matrix to form. Typically, the matrix is formed, e.g., by polymerization, without input of any external energy.

The first and second components of the composition are typically combined in amounts such that the number of nucleophilic groups in the mixture is approximately equal to the number of electrophilic groups in the mixture. As used in this context, the term "approximately" refers to a 2:1 to 1:2 ratio of moles of nucleophilic groups to moles of electrophilic groups. A 1:1 molar ratio of nucleophilic to electrophilic groups is generally preferred.

The first and second components are blended together to form a homogeneous dry powder. This powder is then combined with a buffer solution having a pH within the range of about 1.0 to 5.5 to form a homogeneous acidic aqueous solution, and this solution is then combined with a buffer solution having a pH within the range of about 6.0 to 11.0 to form a reactive solution. For example, 0.375 grams of the dry powder can be combined with 0.75 grams of the acid buffer to provide, after mixing, a homogeneous solution, where this solution is combined with 1.1 grams of the basic buffer to provide a reactive mixture that substantially immediately forms a three-dimensional matrix.

The buffer solutions are aqueous and can be any pharmaceutically acceptable basic or acid composition. The term "buffer" is used in a general sense to refer to an acidic or basic aqueous solution, where the solution may or may not be functioning to provide a buffering effect (i.e., resistance to change in pH upon addition of acid or base) in the compositions of the present invention.

Acidic buffer solutions having a pH within the range of about 1.0 to 5.5, include by way of illustration and not limitation, solutions of: citric acid, hydrochloric acid, phosphoric acid, sulfuric acid, AMPSO (3-[(1,1-dimethyl-2-hydroxyethyl)amino]2-hydroxy-propane-sulfonic acid), acetic acid, lactic acid, and combinations thereof. In a preferred embodiment, the acidic buffer solution is a solution of citric acid, hydrochloric acid, phosphoric acid, sulfuric acid, and combinations thereof.

Regardless of the precise acidifying agent, the acidic buffer preferably has a pH such that it retards the reactivity of the nucleophilic groups on the first component. For example, a pH of 2.1 is generally sufficient to retard the nucleophilicity of thiol groups. A lower pH is typically preferred when the first component contains amine groups as the nucleophilic groups. In general, the acidic buffer is an acidic solution that, when contacted with nucleophilic groups that are present as part of the first component, renders those nucleophilic groups relatively non-nucleophilic.

An exemplary acidic buffer is a solution of hydrochloric acid, having a concentration of about 6.3 mM and a pH in the range of 2.1 to 2.3. This buffer may be prepared by combining concentrated hydrochloric acid with water, i.e., by diluting concentrated hydrochloric acid with water. Similarly, this buffer A may also be conveniently prepared by diluting 1.23 grams of concentrated hydrochloric acid to a volume of 2 liters, or diluting 1.84 grams of concentrated hydrochloric acid to a volume to 3 liters, or diluting 2.45 grams of concentrated hydrochloric acid to a volume of 4 liters, or diluting 3.07 grams concentrated hydrochloric acid to a volume of 5 liters, or diluting 3.68 grams of concentrated hydrochloric acid to a volume to 6 liters. For safety reasons, the concentrated acid is preferably added to water.

Basic buffer solutions having a pH within the range of about 6.0 to 11.0, include by way of illustration and not limitation, solutions of: glutamate, acetate, carbonate and carbonate salts (e.g., sodium carbonate, sodium carbonate monohydrate and sodium bicarbonate), borate, phosphate and phosphate salts (e.g., monobasic sodium phosphate monohydrate and dibasic sodium phosphate), and combinations thereof. In a preferred embodiment, the basic buffer solution is a solution of carbonate salts, phosphate salts, and combinations thereof.

In general, the basic buffer is an aqueous solution that neutralizes the effect of the acidic buffer, when it is added to the homogeneous solution of the first and second components and the acid buffer, so that the nucleophilic groups of the first component regain their nucleophilic character (that has been masked by the action of the acidic buffer), thus allowing the nucleophilic groups to inter-react with the electrophilic groups of the second component.

An exemplary basic buffer is an aqueous solution of carbonate and phosphate salts. This buffer may be prepared by combining a base solution with a salt solution. The salt solution may be prepared by combining 34.7 g of monobasic sodium phosphate monohydrate, 49.3 g of sodium carbonate monohydrate, and sufficient water to provide a solution volume of 2 liter. Similarly, a 6-liter solution may be prepared by combining 104.0 g of monobasic sodium phosphate monohydrate, 147.94 g of sodium carbonate monohydrate, and sufficient water to provide 6 liter of the salt solution. The basic buffer may be prepared by combining 7.2 g of sodium hydroxide with 180.0 g of water. The basic buffer is typically prepared by adding the base solution as needed to the salt solution, ultimately to provide a mixture having the desired pH, e.g., a pH of 9.65 to 9.75.

In general, the basic species present in the basic buffer should be sufficiently basic to neutralize the acidity provided by the acidic buffer, but should not be so nucleophilic itself that it will react substantially with the electrophilic groups of the second component. For this reason, relatively "soft" bases such as carbonate and phosphate are preferred in this embodiment of the invention.

To illustrate the preparation of a three-dimensional matrix of the present invention, one may combine an admixture of a first component (e.g., a polyethyleneglycol core with four nucleophilic thiol groups, such as pentaerythritol tetrakis [mercaptoethyl poly(oxyethylene)ether]("HS-PEG") available from Aldrich Chemical Co. (Milwaukee, Wis.), and a second component (e.g., a polyethyleneglycol core with four electrophilic N-hydroxysuccinimide groups, such as pentaerythritol tetrakis [1-(1'-oxo-5-succimidylpentanoate)-2-poly(oxyethylene)ether]("NHS-PEG," 10,000 MW, available from Aldrich Chemical Co.), with a first, acidic, buffer (e.g., an acid solution, e.g., a dilute hydrochloric acid solution) to form a homogeneous solution. This homogeneous solution is mixed with a second, basic, buffer (e.g., a basic solution, e.g., an aqueous solution containing phosphate and carbonate salts) whereupon the first and second components substantially immediately inter-react with one another to form a three-dimensional matrix.

Administration

The invention is also directed at a method of formulating an in-situ curing composition. This method involves a delayed activation/triggering/initiation of the reaction between the reactive groups, generating a cured composition with consistent and uniform strength.

The multifunctional compounds of the invention may be administered before, during or after they inter-react in the modified environment to form a three-dimensional matrix. Certain uses, which are discussed in greater detail below, such as tissue augmentation, may require the matrix to be formed before administration, whereas other applications, such as tissue adhesion, require the compositions to be administered before the inter-reaction has reached "equilibrium." The point at which inter-reaction has reached equilibrium is defined herein as the point at which the composition no longer feels tacky or sticky to the touch.

The multifunctional compounds of the present invention are generally delivered to the site of administration in such a way that the individual reactive groups of the compounds are exposed to the modified environment for the first time at the site of administration, or immediately preceding administration. Thus, the compounds are preferably delivered to the site of administration using an apparatus that allows the compounds to be delivered in an initial environment, where the compounds are essentially non-reactive. For example, a composition can be delivered to the site so that the individual reactive groups of the multifunctional compound are exposed to an aqueous environment for the first time at the site of administration, or immediately preceding administration. Thus, the composition is delivered using an apparatus that allows the composition to be delivered in an dry environment, where the compounds are essentially non-reactive.

Delivery Systems

Multi-Compartment Devices

Suitable delivery systems may involve a multi-compartment spray device, where one or more compartments contain the multifunctional compounds and one or more compartments contain materials needed to provide for the modified environment, so that the multifunctional compounds are exposed to the modified environment as they leave the compartment. Many devices that are adapted for delivery of multi-component tissue sealants/hemostatic agents are well known in the art and can also be used in the practice of the present invention. Alternatively, the compounds can be delivered using any type of controllable extrusion system, or they can be delivered manually in the form of pastes, liquids, or dry powders, and exposed to the modified environment at the site of administration.

The multifunctional compound and the material(s) needed to provide for the modified environment may be conveniently formed under aseptic conditions by placing each of the ingredients into separate syringe barrels. For example, the multifunctional compound and the material(s) needed to provide for the modified environment can be housed separately in a multiple-compartment syringe system having a multiple barrels, a mixing head, and an exit orifice. Material(s) can then be added to the barrel housing the multifunctional compound, which is then extruded into the mixing head. Additional materials can be simultaneously extruded into the mixing head, if needed. Finally, the resulting composition can then be extruded through the orifice onto a surface.

For example, the syringe barrels holding the multifunctional compound and other material(s) may be part of a dual-syringe system, e.g., a double barrel syringe as described in U.S. Pat. No. 4,359,049 to Redl et al. In this embodiment, the acid buffer can be added to the syringe barrel that also holds the multifunctional compound in e.g., a dry powder, so as to produce the homogeneous solution. In other words, the acid buffer may be added (e.g., injected) into the syringe barrel holding the dry powder to thereby produce a homogeneous solution of the first and second components. This homogeneous solution can then be extruded into a mixing head, while the basic buffer is simultaneously extruded into the mixing head. Within the mixing head, the homogeneous solution and the basic buffer are mixed together to thereby form a reactive mixture. Thereafter, the reactive mixture is extruded through an orifice and onto a surface (e.g., tissue), where a film is formed, which can function as a sealant or a barrier, or the like. The reactive mixture begins forming a three-dimensional matrix immediately upon being formed by the mixing of the homogeneous solution and the basic buffer in the mixing head. Accordingly, the reactive mixture is preferably extruded from the mixing head onto the tissue very quickly after it is formed so that the three-dimensional matrix forms on, and is able to adhere to, the tissue.

A preferred embodiment of the multi-compartment syringe system of the present invention is shown in FIG. 1. The device is comprised of three syringes, two housing each of the two buffers of the present invention with the third syringe housing the multifunctional compound in dry powder form 1. The two syringes housing the solutions 1 are pre-assembled into a syringe housing 2 with a transfer port closure 3 attached to the housing assembly 2 to allow mixing of the multifunctional compound into the correct syringe. A syringe clip 4 is attached to the plunger rod of the syringe that does not require mixing with the dry powder multifunctional compound.

Other systems for combining reactive materials are well known in the art, and include the systems described in U.S. Pat. Nos. 6,454,786 to Holm et al.; 6,461,325 to Delmotte et al.; 5,585,007 to Antanavich et al.; 5,116,315 to Capozzi et al.; 4,631,055 to Redl et al.; and U.S. Patent Application Publication No. 2004/0068266 to Delmotte.

Pressurized Delivery Devices

Other delivery systems for dispensing the multicomponent compositions of the invention may include pressurized delivery devices, examples of which are described in commonly owned co-pending U.S. patent application Ser. No. 10/957, 493, filed on Oct. 1, 2004, and entitled "Mixing and Dispensing Fluid Components of a Multicomponent Composition." Such a pressurized delivery device may include a diffuser surface having an outlet extending therethrough that is positioned downstream from a plurality of inlets. While at least one inlet is adapted to communicate with a source of a pressurized carrier fluid, each of a plurality of inlets is adapted to communicate with a source of a different fluid component. Using this device, the multifunctional compound in a dry powder form is premixed with the first buffer to form a homogeneous solution as previously described and this solution is subsequently communicated with a first fluid component. The second fluid component will communicate with the second buffer solution previously described. Once the diffuser surface receives fluid components from the inlets, each received fluid component is pushed toward the outlet for mixing and dispensing therethrough by the pressurized carrier fluid, typically a gas such as air, from the carrier fluid inlet. The diffuser surface and the inlets may represent components of a mixing nozzle.

In general, there are two categories of gas-enhanced nozzles for dispensing reactive components of a multicomponent composition—those that involve internal mixing and those that involve external mixing. When the diffuser surface is a part of a nozzle, the nozzle may be considered an internal-mixing nozzle. Unlike other internal-mixing technologies, the internal-mixing nozzle of the pressurized delivery device of the present invention provides several features that serve individually and collectively to eliminate clogging. For example, a diffuser surface typically has a shape effective to direct and maintain each received fluid component in a different flow path on the diffuser surface toward the outlet for mixing therein and dispensing therethrough. Due to the minimal residence time of the mixture within the nozzle, reactive components do not have time to set and clog the nozzle before the mixture is forced out of the nozzle by the pressurized carrier fluid. In addition, the outlet may be aligned with any or all of the carrier fluid inlets that may be present in the nozzle to direct the pressurized carrier fluid in a manner that enhances fluid component mixing and to expel the mixture in a jet like manner. As the orientation of the diffuser surface relative to the inlets affects the performance of the device, the diffuser surface may be permanently affixed or immobilized with respect to the inlets; however, when the diffuser surface is detachable from the inlets, the nozzle may be disassembled to facilitate cleaning and/or replacement of parts. For example, the diffuser surface may be replaceable/and or disposable. Nevertheless, when the pressurized delivery device of the present invention has diffuser surface that is detachable from the inlets, the device may be constructed to allow assembly of the components in only configurations that align the diffuser surface to the inlets such that the performance of the device is optimized.

Figure 2:
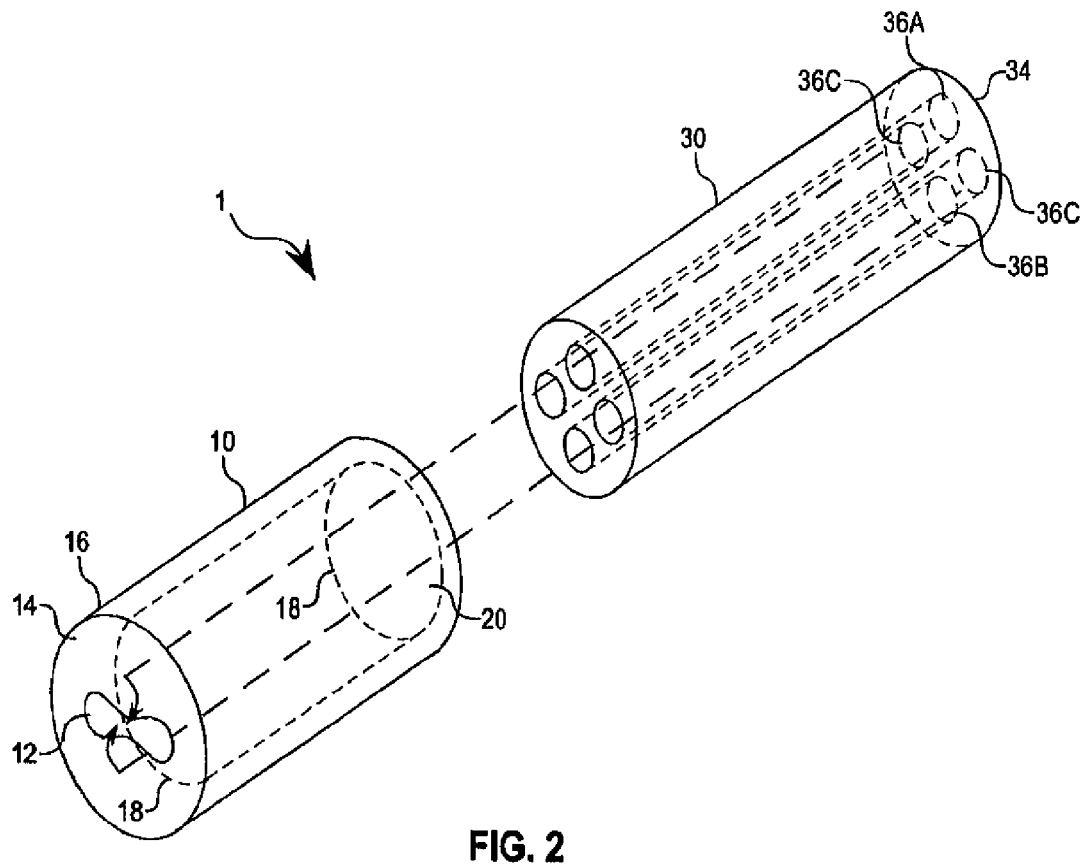
FIGS. 2 and 3 schematically illustrate an embodiment of the pressurized delivery device of the present invention that includes a cap having an interior diffuser surface and a lumen assembly for delivering fluid components and a pressurized carrier fluid to the diffuser surface.
Figure 3:
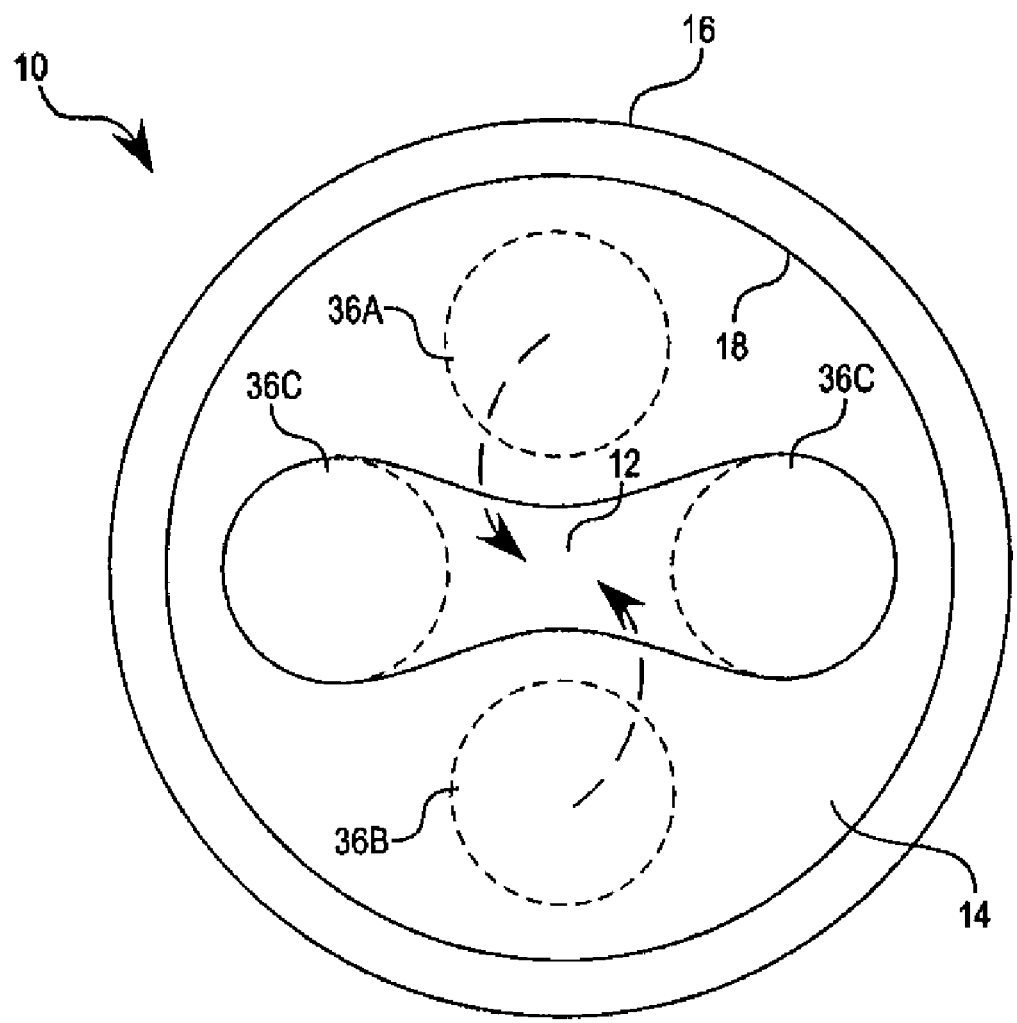

FIGS. 2 and 3 illustrate an example of the pressurized delivery device of the present invention in the form of a nozzle that includes all of the above-discussed features which serve eliminate the problems associated with nozzle clogging. As is the case with all figures referenced herein, in which like parts are referenced by like numerals, FIGS. 2 and 3 are not necessarily to scale, and certain dimensions may be exaggerated for clarity of presentation. As depicted in FIG. 2, the nozzle 1 includes a cap 10 having a slot-shaped outlet orifice 12 that extends through the center of the distal end 14 of the cap 10. The cap 10 is shown as having a cylindrical exterior surface 16 and an interior surface 18 that terminates at opening 20, but additional cap shapes are also suitable for use with the pressurized delivery device of the present invention. As shown in FIG. 3, the interior surface 18 of the cap 10 at end 14 serves to receive fluid components thereon.

Also provided is a generally elongate cylindrical connector 30 in the form of a unitary member having a first terminus 32 and a second terminus 34. A plurality of inlet lumens 36A, 36B, and 36C traversing the length of the connector defined by termini 32 and 34. As depicted, the connector 30 is detached from the cap 10. Inlet lumens 36A and 36B each communicate at the second terminus 34 with a different source of a fluid component, e.g., the first buffer mixed with the dry powder in one source and the second buffer in the other source (not shown). Similarly, inlet lumens 36C are provided fluid communication at the second terminus 34 with a source of pressurized carrier gas (not shown). The carrier fluid inlet lumens 36C define a plane that is perpendicular to a plane defined by the fluid component inlet lumens 36A and 36B. As depicted in FIGS. 2 and 3, the first terminus 32 of the connector 30 has dimensions suitable for forming a fluid-tight seal against the interior surface 18 of the cap 10 at its proximal end 20.

In operation, the cap 10 is placed over the first terminus 32 of the connector 30 such that the carrier fluid inlet lumens 36C are aligned with outlet orifice 12. In addition, each of a plurality of different fluid component sources is provided fluid communication with the fluid component inlet lumens 36A and 36B and at least one source of pressurized carrier gas is provided fluid communication with the carrier fluid inlet 36C.

As discussed above, the interior surface 18 of the cap 10 at distal end 14 serves as a diffuser surface 18 that is adapted to receive fluid components thereon. As depicted in FIG. 2, the diffuser surface 18 exhibits two-fold axial symmetry. The dotted lines indicate the position of lumens 36A, 36B, and 36C relative to the diffuser surface 18. Similarly, in FIG. 2, the dashed lines shown within the connector 30 indicate the separate flow paths of the fluid components emerging from the fluid component inlet lumens 36A and 36B, respectively, and directed by the diffuser surface 18 in a generally inward direction toward the center outlet orifice 12. Once the fluid components reach outlet orifice 12, pressurized gas from carrier fluid lumens 36C mix the fluid components and force the mixture out of the outlet orifice 12.

In the pressurized delivery device of the present invention, the geometries of, and spatial relationships between the various components of diffuser surface 18 represent an important aspect of the pressurized delivery device. For example, the pressurized delivery device may be used to carry out mixing of a plurality of reactive components. Typically, nozzles for mixing reactive components are of the external mixing category because previously known internal mixing designs are prone to clogging. Clogging results when reactive components are mixed prior to introduction to the gas stream. In contrast, the pressurized delivery device provides a high-pressure area between the inlets 36A-36C and the diffuser surface 18 that serves to mix reactive fluids while simultaneously forcing the mixture out of the orifice 12.

In addition, the diffuser surface 18 is located downstream from the inlets 36A-36C and is effective to direct fluid components toward the outlet for mixing and dispensing therethrough by a pressurized carrier fluid; thus, the diffuser surface 18 should exhibit an appropriate shape to carry out its desired function while minimizing the odds of device clogging. For example, while the diffuser surface 18 depicted in FIGS. 2 and 3 is located within a cylindrical cap 10 having a flat exterior circular end surface and contains a centrally located slot-shaped orifice 12, such geometry is not required.

As depicted in FIGS. 2 and 3, the exterior surface of the cap is parallel to the diffuser surface. While such a parallel configuration of the exterior surface of the cap is preferred, it is understood that it is merely exemplary and not a requirement of the pressurized delivery system of the present invention. Similarly, while both FIGS. 2 and 3 depict caps that exhibit axial symmetry, such axial symmetry is merely preferred and not required. Where the caps of the present invention are symmetrical, the symmetry may be axial or mirror symmetry. It is expected that variations on diffuser surface shapes and nozzle configurations may be developed through routine experimentation. With respect to the inlets, the pressurized delivery device of the present invention generally requires a plurality of fluid component inlets for communication with an equal or less number of sources of fluid components. While a single carrier fluid inlet may be provided, the pressurized delivery device typically provides a plurality of carrier fluid inlets. Often the carrier fluid inlets are provided communication with a single source of carrier fluid via a splitter or manifold, though a plurality of carrier fluid sources may be advantageously used as well in certain instances.

In addition, inlets are typically each located at the terminus of a corresponding lumen. In some instances, the lumens may coextend through an elongate cylindrical connector 30, as depicted in FIG. 2 (with 36A-36C depicting the lumens). Alternatively, the lumens may extend through separate tubes. Furthermore, tubes and/or tubing members may be constructed to form a lumen assembly. For example, various lengths of multilumen delivery tubing for use in specific surgical or non-surgical applications. Particularly in laparoscopic applications, it may be useful to employ flexible tubing. The tubing serves to maintain separation of the two fluid components and provide a pathway for the delivery of pressurized gas to the diffuser surface.

Additional features also serve to enhance the mixing and delivery performance of the pressurized delivery device of the present invention. As discussed above, two or more fluid components may be individually delivered through inlets to impinge upon the diffuser surface. Typically, the components first impinge upon the diffuser plate near the outlet to reduce the residence time of the components in the device. Any of a number of means may be used to provide motive force to introduce fluid components through the inlets and toward the outlet. Exemplary motive force means include pumps, compressors, pistons, and the like.

Then, as the diffuser plate directs the components toward the outlet 12, and the pressurized carrier fluid simultaneously provides a force to mix and expel the components through the outlet. Accordingly, one or more the carrier fluid inlets are positioned such that a high-pressure zone is created between the component inlets and the diffuser surface while a comparatively low-pressure zone is created downstream from the outlet. "Dead space" that serve to trap residue is generally avoided. As a result, a fluid mixture is forced through the outlet in a jet-like fashion, thereby reducing any potential or actual buildup of residue that serve to clog the pressurized delivery device.

In general, any of a number of carrier fluids may be employed with the pressurized delivery device of the present invention. For example, the carrier fluid may be gaseous and/or liquid in nature. Typically, however, the carrier fluid is chemically inert with respect to the fluid components. Suitable inert gases include, without limitation, air, carbon dioxide, nitrogen, argon, helium, gaseous perfluorinated alkanes and ethers, gaseous chlorofluorocarbons and the like. Suitable inert liquids include, without limitation, polysiloxanes, perfluoroinated polyethers, and the like. Pressurized air represents an economical and practical carrier fluid for use with the pressurized delivery device. Equipment associated with pressurized air is well known in the art and may include pressurized tanks or cylinders as well as compressors. In some instances, one or more check valves, e.g., one-way valves, may be provided to prevent back flow of fluid component resulting from pressure buildup associated with the use of the pressurized delivery device. Such check valves may be positioned upstream from the diffuser surface, e.g., within lumens associated with the inlets. Such check valves are particularly useful when inlet lumens are short, e.g., about 2 to about 5 centimeters in length, because the potential for back flow tends to be inversely proportional to the length of the lumens; however, check valves may be employed with longer lumens as well.

The portions of the device that contact multicomponent composition and the fluid components thereof should be inert and preferably repellant to the materials contacted. Thus, portions of the device that contact the fluids in operation should be selected according to the fluids themselves. For example, the device or components thereof may be made from a plastic such as polycarbonates, polyurethane, polyesters, acrylics, ABS polymers, polysulfone, and the like. Adhesion inhibiting coatings such as polysiloxanes, perfluorinated polymers, and the like may be used as well. Thus, the diffuser surface is typically inert and optionally repelling to the fluid components. Similar, lumen surfaces that may contact the fluid components or the carrier fluid are typically inert and optionally repelling to the corresponding fluid as well.

The pressurized delivery device of the present invention is particularly useful for dispensing multicomponent compositions. While some gaseous components may be used, the pressurized delivery device is particularly useful for liquids. Thus, at least one fluid component is usually a liquid. Often, each fluid component includes a liquid. For example, the pressurized delivery device is useful to dispense composition such as fluid mixtures, wherein the mixing of a plurality of fluids results in an increase in viscosity sufficient to impair mixture flow. Such compositions may be formed from fluid components that are chemically reactive with respect to each other. In some instances, a crosslinking agent may be provided.

In practice, then, a diffuser surface having an outlet extending therethrough such that the diffuser surface is downstream from a plurality of fluid component inlets and at least one carrier fluid inlet. A different fluid component is directed from each of the fluid component inlets toward the diffuser surface. In some instances, fluid components are directed at substantially the same flow rate toward the diffuser surface. Alternatively, the fluid components are directed at different flow rates toward the diffuser surface. Typically, the flow rate of the carrier fluid is higher than that for the fluid components. The diffuser surface maintains and directs each received fluid component in a different flow path toward the outlet. Pressurized carrier fluid from the at least one carrier fluid inlet is also directed through the outlet, thereby mixing the fluid components present at the outlet and dispensing the composition through the outlet.

Other Delivery Systems

Yet another way of delivering the multifunctional compounds of the present invention is to prepare the compounds in such a manner so that the individual reactive groups of the compounds are in an inactive form as either a liquid or powder. Such reactive groups can then be activated after application to the tissue site, or immediately beforehand, by applying an activator, which provides for the modified environment. For example, the activator can be a buffer solution having a pH that will activate the reactive groups on the compounds once mixed therewith. Still another way of delivering the compositions is to prepare preformed sheets, and apply the sheets as such to the site of administration.

Kits

The multifunctional compounds of the invention can also be packaged in kits and used in a variety of medical applications. The kit would include a plurality of multifunctional compounds, as well as whatever materials are needed to change the environement so as to render the compound reactive, e.g., buffer solutions, as well as written or otherwise illustrated instructions for use. For example a typical kit for use in medical applications, may include: (a) a multifunctional compound of the invention or a plurality of multifunctional compounds of the invention; (b) a first buffer solution having a pH within the range of about 1.0 to 5.5; and (c) a second buffer solution having a pH within the range of about 6.0 to 11.0; wherein each component is packaged separately and admixed immediately prior to use. As is evident to those of ordinary skill in the art, prior to use, each component should remain in a separate sterile package. As previously described where the reactive groups of the multifunctional compound are nucleophilic and electrophilic groups, the nucleophilic and electrophilic groups are non-reactive in a dry environment, but are rendered reactive upon exposure to an aqueous environment such that a plurality of the multifunctiona compounds interact in the aqueous environment to form a three-dimensional matrix.

In another embodiment, the kit can further comprise a delivery system that will allow the composition to be delivered as a spray. The spray can be generated by manually mixing the components and passing them through a spray nozzle. The spray generation can also be accomplished by using a flow of gas (for example, air, nitrogen, carbon dioxide).

Kits contemplated under the present invention will preferably include a delivery system for the compositions of the present invention. Delivery devices that may be included in the kits will preferably be one of the multi-component syringe device and/or the pressurized delivery devices described herein.

In one embodiment of the kit, a multi-component syringe device is included in the kit. As previously described, the multi-component spray device may be a multiple-compartment syringe system having multiple barrels, a mixing head, and an exit orifice, wherein the dry powder composition, the first buffer, and the second buffer are housed separately in the multiple-compartment syringe system.

FIG. 1 describes a preferred embodiment of the multi-compartment device. When provided in a kit, the device is provided with three pouches. The first pouch is a liquid components pouch, which consists of two syringes that are pre-assembled into a housing. A transfer port closure is attached to the housing assembly to allow mixing of the dry powders into the correct syringe. A clip is attached to the plunger rod of the syringe that does not require mixing with the dry powders. The second pouch is a powder component pouch, which consists of a syringe containing the dry powder(s) and a dessicant package. The third pouch is an applicator pouch, which contains two applicators.

To use the preferred kit of FIG. 1, each pouch is opened using aseptic techniques and the contents of each pouch are transferred into a sterile field. In the sterile field, the liquid and powder components are prepared as follows. Without removing the syringe clip, the luer cap on the transfer port closure is removed. The cap is removed from the powder syringe and the powder syringe is connected to the opening of the transfer port closure. The liquid is transferred into the powder by forcefully depressing the plunger. The contents between the two syringes are mixed back and forth between the two syringes until the solid is completely dissolved (e.g., 18-20 times). The entire content is then pushed into the syrnting contained in the syringe housing. The powder syringe is disengaged by detaching the transfer port closure by grasping the powder syringe barrel; pressing the levers on the syringe housing; and pulling both the empty powder syringe and transfer port closure from the housing. To expel all air from the syringe, the syringe tips are held up, the syringe plungers are leveled, the syringe clip is rotated to connect to the other plunger; and holding the syringe upright, all air is expelled from the syringe. As a final step, the applicator is snapped onto the end of the syringe housing making the composition ready to use. A clear gel should be seen approximately three minutes following the mixing of the components.

In another embodiment of the kit, a pressurized delivery device is included in the kit. As previously described, the pressurized delivery device of the present invention includes a plurality of fluid component inlets each adapted to communicate with a source of different fluid components; at least one carrier fluid inlet adapted to communicate with a source of a pressurized carrier fluid; a diffuser surface located downstream from the plurality of fluid component inlets and the at least one carrier fluid inlet; and an outlet extending through the diffuser surface, wherein the diffuser surface is adapted to receive fluid components thereon and has a shape effective to direct and maintain each received fluid component in a different flow path toward the outlet for mixing and dispensing therethrough by the pressurized carrier fluid from the at least one carrier fluid inlet.

Kits contemplated under the present invention are not limited to the devices described herein and may also include any other suitable delivery device known in the art of drug delivery.

Exemplary medical applications involve, by way of illustration and not limitation, adhering or sealing biological tissue, delivering a biologically active agent (in which case, the kit would further comprise a biologically active agent, for example, mixed with the components to form a homogeneous mixture or packaged separately), delivering cells and genes (in which case, the kit would further comprise the living cells or genes, for example, mixed with the components to form a homogeneous mixture or packaged separately), bioadhesion, in ophthalmic applications, for tissue augmentation, for adhesion prevention, forming synthetic implants and coating synthetic implants, and for the treatment of aneurysms. In a preferred embodiment, the mixture of the biologically active agents with the components is a homogeneous mixture; however, this feature is not required. Whether packaged together or separately, each of the components and the biological agent should be in sterile packages prior to use.

For purposes of description only, the surgical use of the multi-compartment syringe kit of FIG. 1 is described. As a preliminary step, blood circulation to the surgical site is restored to expand the graft by unclamping the site and after circulation is restored, the site is reclamped to stop circulation. Excess blood is aspirated and all surfaces are air dried prior to application of the composition. Holding the applicator approximately 3 cm from the site (touching the site or holding more than 6 cm from the site is not recommended), sealant is forcibly applied to the site. To enhance mixing, the applicator is moved quickly along the anastomotic site. If the composition is to be applied to more than one site, the applicator tip should be wiped with gauze and the device should be set upright to prevent clogging. If the composition does not gel within 30 seconds, i.e., the composition remains watery on the site, the site should be flushed with saline and the material aspirated. If the treated site fails to seal, the surface should be blotted dry; reclamping the vessel may be required to dry the field for reapplication of the composition. If the applicator becomes clogged, it should be replaced with a new applicator.

Uses

The multifunctional compounds of the present invention can be used in a variety of different applications. In general, the compounds can be adapted for use in any tissue engineering application where synthetic gel matrices are currently being utilized. For example, the compositions are useful as tissue sealants, vascular sealants, in tissue augmentation, in tissue repair, as hemostatic agents, in preventing tissue adhesions, in providing surface modifications, and in drug/cell/gene delivery applications and may be used in a variety of open, endocopic, and laparoscopic surgical procedures. One of skill in the art can easily determine the appropriate administration protocol to use with any particular composition having a known gel strength and gelation time. A more detailed description of several specific applications is given below.

Tissue Sealants and Adhesives

In one application, the multifunctional compounds described herein can be used for medical conditions that require a coating or sealing layer to prevent the leakage of gases, liquid, or solids. The method entails applying the multifunctional compounds to the damaged tissue or organ to seal 1) vascular and or other tissues or organs to stop or minimize the flow of blood; 2) thoracic tissue to stop or minimize the leakage of air; 3) gastrointestinal tract or pancreatic tissue to stop or minimize the leakage of fecal or tissue contents; 4) bladder or ureters to stop or minimize the leakage of urine; 5) dura to stop or minimize the leakage of CSF; and 6) skin or serosal tissue to stop the leakage of serosal fluid. These compounds may also be used to adhere biological tissues together such as small vessels, nerves, or dermal tissue. Such biological tissues will typically, but not necessarily, be living tissue. The compounds can be used 1) by applying them to the surface of one tissue and then a second tissue may be rapidly pressed against the first tissue or 2) by bringing the tissues in close juxtaposition and then applying the compounds. In addition, the compounds can be used to fill spaces in soft and hard tissues that are created by disease or surgery.

In one embodiment of the invention, there is provided a method of sealing tissue of a patient comprising the steps of: (a) providing a composition comprising a plurality of the multifunctional compounds in an initial environment; (b) rendering the reactive groups reactive by exposing the compound to a modified environment; and (c) placing the a plurality of the multifunctional compounds into contact with tissue and allowing a three-dimensional matrix to form and seal the tissue.

In another embodiment of the invention, there is provided a method of sealing tissue of a patient comprising the steps of: (a) providing a composition of the invention comprising a plurality of the multifunctional compounds of the invention; (b) rendering the nucleophilic and electrophilic groups reactive by exposing the composition to an aqueous environment to effect inter-reaction; wherein said exposure comprises: (i) dissolving the composition in a first buffer solution having a pH within the range of about 1.0 to 5.5 to form a homogeneous solution, and (ii) adding a second buffer solution having a pH within the range of about 6.0 to 11.0 to the homogeneous solution to form a mixture; and (c) placing the mixture into contact with tissue and allowing a three-dimensional matrix to form and seal the tissue.

In a further embodiment of the invention, the compositions can be applied in conjunction with an implanted medical device such that it prevents the leakage of gases, liquids or solids from the device or from the device-tissue interface. For example, following the implantation of a vascular graft (either synthetic or biological), there is often leakage of blood through the suture holes in the graft or at the interface between the graft and the tissue. The composition of the invention can be applied to this area to prevent further blood leakage.

In certain aspects of the invention, the composition may be further combined with a fibrosing agent to further enhance the properties of the sealant or adhesive. In one aspect of the present invention, a fibrosing (i.e., scarring) agent can be included in a polymeric sealant spray which solidifies into a film or coating to promote fibrosis and seal air leaks.

In one illustrative application, a fibrosing agent may be included with the polymer composition for use as a pulmonary sealant during open or endoscopic lung reduction surgeries, for example, to seal off pulmonary bullae in open and endoscopic lung destruction procedures. The addition of a fibrosis-inducing agent to a pulmonary sealant can induce the formation of a stable, fibrous scar that permanently seals the parietal surface of the lung at the surgical location (or the alveolar surface of the lung if delivered endoscopically during lung reduction surgery), reduces hospitalization time and prevents recurrence of the air leak. Clinically a fibrosis-inducing pulmonary sealant can be useful to improve the outcomes in open lung surgery, endoscopic lung reduction surgery for emphysema (severe COPD), esophageal leaks after endoscopy or resection, complications of treatment of other intra-thoracic malignancies, pleural effusion, haemothorax, pneumothorax, chylothorax, complications of aspiration, and tuberculosis.

It should be apparent to one of skill in the art that potentially any adhesion or fibrosis-inducing agents described above may be utilized alone, or in combination with the present composition, in the practice of this embodiment. Exemplary fibrosing agents for use in sealants and adhesive include talc, silk, wool, chitosan, polylysine, fibronectin, bleomycin, and connective tissue growth factor (CTGF), as well as analogues and derivatives of the aforementioned.

The exact dose administered can vary with the composition of the sealant or adhesive; however, certain principles can be applied in the application of this art. Drug dose can be calculated as a function of dose per unit area (of the amount of the sealant being applied), total drug dose administered can be measured, and appropriate surface concentrations of active drug can be determined. Regardless of the method of incorporation of the drug into the sealant or adhesive, the exemplary fibrosing agents, used alone or in combination, should be administered under the following dosing guidelines:

Utilizing talc as an exemplary fibrosis-inducing agent, the total dose of talc delivered from a sealant, or coated onto the surface of a lung, should not exceed 100 mg (range of 1 µg to 100 mg). In one embodiment, the total amount of talc released from the sealant should be in the range of 10 µg to 50 mg. The dose per unit area (i.e., the dosage of talc as a function of the surface area of the lung to which drug is applied) should fall within the range of 0.05 µg-10 µg per $mm^2$ of surface area coated. In another embodiment, talc should be applied to a lung surface at a dose of 0.05 µg/$mm^2$-10 µg/$mm^2$ of surface area coated.

Utilizing silk as an exemplary fibrosis-inducing agent, the total dose of silk delivered from a pulmonary sealant, or coated onto the surface of a lung, should not exceed 100 mg (range of 1 µg to 100 mg). In one embodiment, the total amount of silk released from the sealant should be in the range of 10 µg to 50 mg. The dose per unit area (i.e., the dosage of silk as a function of the surface area of the lung to which drug is applied) should fall within the range of 0.05 µg-10 µg per mm$^2$ of surface area coated. In another embodiment, silk should be applied to a lung surface at a dose of 0.05 µg/mm$^2$-10 µg/mm$^2$ of surface area coated. As specific (polymeric and non-polymeric) drug delivery vehicles and specific pulmonary sealants can release silk at differing rates, the above dosing parameters should be utilized in combination with the release rate of the drug from the sealant such that a minimum concentration of 0.01 nM to 1000 µM of silk is delivered to the tissue.

Utilizing chitosan as an exemplary fibrosis-inducing agent, the total dose of chitosan delivered from a pulmonary sealant, or coated onto the surface of a lung, should not exceed 100 mg (range of 1 µg to 100 mg). In one embodiment, the total amount of chitosan released from the sealant should be in the range of 10 µg to 50 mg. The dose per unit area (i.e., the dosage of chitosan as a function of the surface area of the lung to which drug is applied) should fall within the range of 0.05 µg-10 µg per mm$^2$ of surface area coated. In another embodiment, chitosan should be applied to a lung surface at a dose of 0.05 µg/mm$^2$-10 µg/mm$^2$ of surface area coated. As specific (polymeric and non-polymeric) drug delivery vehicles and specific pulmonary sealants can release chitosan at differing rates, the above dosing parameters should be utilized in combination with the release rate of the drug from the sealant such that a minimum concentration of 0.01 nM to 1000 µM of chitosan is delivered to the tissue.

Utilizing polylysine as an exemplary fibrosis-inducing agent, the total dose of polylysine delivered from a pulmonary sealant, or coated onto the surface of a lung, should not exceed 100 mg (range of 1 µg to 100 mg). In one embodiment, the total amount of polylysine released from the sealant should be in the range of 10 µg to 50 mg. The dose per unit area (i.e., the dosage of polylysine as a function of the surface area of the lung to which drug is applied) should fall within the range of 0.05 µg-10 µg per mm$^2$ of surface area coated. In another embodiment, polylysine should be applied to a lung surface at a dose of 0.05 µg/mm$^2$-10 µg/mm$^2$ of surface area coated. As specific (polymeric and non-polymeric) drug delivery vehicles and specific pulmonary sealants can release polylysine at differing rates, the above dosing parameters should be utilized in combination with the release rate of the drug from the pulmonary sealant such that a minimum concentration of 0.01 nM to 1000 µM of polylysine is delivered to the tissue.

Utilizing fibronectin as an exemplary fibrosis-inducing agent, the total dose of fibronectin delivered from a pulmonary sealant, or coated onto the surface of a lung, should not exceed 100 mg (range of 1 µg to 100 mg). In one embodiment, the total amount of fibronectin released from the sealant should be in the range of 10 µg to 50 mg. The dose per unit area (i.e., the dosage of fibronectin as a function of the surface area of the lung to which drug is applied) should fall within the range of 0.05 µg-10 µg per mm$^2$ of surface area coated. In another embodiment, fibronectin should be applied to a lung surface at a dose of 0.05 µg/mm$^2$-10 µg/mm$^2$ of surface area coated. As specific (polymeric and non-polymeric) drug delivery vehicles and specific pulmonary sealants can release fibronectin at differing rates, the above dosing parameters should be utilized in combination with the release rate of the drug from the sealant such that a minimum concentration of 0.01 nM to 1000 µM of fibronectin is delivered to the tissue.

Utilizing bleomycin as an exemplary fibrosis-inducing agent, the total dose of bleomycin delivered from a pulmonary sealant, or coated onto the surface of a lung, should not exceed 100 mg (range of 0.01 µg to 100 mg). In one embodiment, the total amount of bleomycin released from the sealant should be in the range of 0.010 µg to 50 mg. The dose per unit area (i.e., the dosage of bleomycin as a function of the surface area of the lung to which drug is applied) should fall within the range of 0.005 µg-10 µg per mm$^2$ of surface area coated. In another embodiment, bleomycin should be applied to a lung surface at a dose of 0.005 µg/mm$^2$-10 µg/mm$^2$ of surface area coated. As specific (polymeric and non-polymeric) drug delivery vehicles and specific pulmonary sealants can release bleomycin at differing rates, the above dosing parameters should be utilized in combination with the release rate of the drug from the sealant such that a minimum concentration of 0.001 nM to 1000 µM of bleomycin is delivered to the tissue.

Utilizing CTGF as an exemplary fibrosis-inducing agent, the total dose of CTGF delivered from a pulmonary sealant, or coated onto the surface of a lung, should not exceed 100 mg (range of 0.01 µg to 100 mg). In one embodiment, the total amount of CTGF released from the sealant should be in the range of 0.10 µg to 50 mg. The dose per unit area (i.e., the dosage of CTGF as a function of the surface area of the lung to which drug is applied) should fall within the range of 0.005 µg-10 µg per mm$^2$ of surface area coated. In another embodiment, CTGF should be applied to a lung surface at a dose of 0.005 µg/mm$^2$-10 µg/mm$^2$ of surface area coated. As specific (polymeric and non-polymeric) drug delivery vehicles and specific pulmonary sealants can release CTGF at differing rates, the above dosing parameters should be utilized in combination with the release rate of the drug from the sealant such that a minimum concentration of 0.001 nM to 1000 µM of CTGF is delivered to the tissue.

The fibrosing agent (e.g., talc, silk, chitosan, polylysine, fibronectin, bleomycin, CTGF) may be released from the pulmonary sealant such that fibrosis in the tissue is promoted for a period ranging from several hours to several months. For example, the fibrosing agent may be released in effective concentrations for a period ranging from 1 hour-30 days. It should be readily evident given the discussions provided herein that analogues and derivatives of the fibrosing agent (e.g., analogues and derivatives of talc, silk, chitosan, polylysine, fibronectin, bleomycin, CTGF, as previously described) with similar functional activity can be utilized for the purposes of this invention; the above dosing parameters are then adjusted according to the relative potency of the analogue or derivative as compared to the parent compound (e.g., a compound twice as potent as the agent is administered at half the above parameters, a compound half as potent as the agent is administered at twice the above parameters, etc.).

Optionally, the sealant may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or an analogue or derivative thereof. Inflammatory cytokines are to be used in formulations at concentrations that range from 0.0001 µg/mL to approximately 20 mg/mL depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1-180 days. The total dose for a single application is typically not to exceed 500 mg (range of 0.0001 µg to 100 mg); preferred 0.001 µg to 50 mg. When used as a device coating, the dose is per unit area of 0.0001 µg-500 µg per mm$^2$; with a preferred dose of 0.001 µg/mm$^2$-200 µg/mm$^2$.

Minimum concentration of $10^{-10}$-$10^{-4}$ g/mL of inflammatory cytokine is to be maintained on the device surface.

Furthermore, the sealant may alone or additionally comprise an agent that stimulates cellular proliferation. Examples include: dexamethasone, isotretinoin (13-cis retinoic acid), 17-β-estradiol, estradiol, 1-α-25 dihydroxyvitamin $D_3$, diethylstibesterol, cyclosporine A, L-NAME, all-trans retinoic acid (ATRA), and analogues and derivatives thereof. Doses used are those concentrations which are demonstrated to stimulate cell proliferation. The proliferative agents are to be used in formulations at concentrations that range from 0.0000001 to 25 mg/mL depending on the specific clinical application, formulation type (e.g., gel, liquid, solid, semi-solid), formulation chemistry, duration of required application, type of medical device interface and formulation volume and or surface area coverage required. Preferably, the proliferative agent is released in effective concentrations for a period ranging from 1-180 days. The total dose for a single application is typically not to exceed 500 mg (range of 0.0001 μg to 200 mg); preferred 0.001 μg to 100 mg. When used as a device coating, the dose is per unit area of 0.00001 μg-500 μg per $mm^2$; with a preferred dose of 0.0001 $μg/mm^2$-200 $μg/mm^2$. Minimum concentration of $10^{-11}$-$10^{-6}$ M of proliferative agent is to be maintained on the device surface.

Biologically Active Agent Delivery

The multifunctional compounds may also be used for localized delivery of various drugs and other biologically active agents. Biologically active agents such as growth factors may be delivered from the composition to a local tissue site in order to facilitate tissue healing and regeneration. Thus, another embodiment of the invention is a method for delivering a biologically active agent, where the composition also includes the biologically active agent to be delivered, and steps (a) and (b) are as described for the method of sealing tissue. Step (c) would involve allowing a three-dimensional matrix to form and delivering the biologically active agent.

The biologically active agent can either be admixed with the compositions of the invention or be chemically coupled to the multifunctional compounds in the composition, e.g., by attachment to one of the reactive groups. For example, processes for covalently binding biologically active agents such as growth factors using functionally activated polyethylene glycols are described in U.S. Pat. No. 5,162,430 to Rhee et al. Such compositions preferably include linkages that can be easily biodegraded, for example as a result of enzymatic degradation, resulting in the release of the active agent into the target tissue, where it will exert its desired therapeutic effect.

In certain aspects, the biologically active agent may be incorporated with a polymeric or non-polymeric carrier to facilitate the incorporation of the agent into the composition. In certain aspects, the carrier may facilitate sustained release of the agent from the composition over a prolonged period of time (e.g., over the course of several days, weeks, or months). For many embodiments, localized delivery as well as localized sustained delivery of the agent may be desired. For example, a therapeutic agent may be admixed with, blended with, conjugated to, or, otherwise modified to contain a polymeric composition (which may be either biodegradable or non-biodegradable) or non-polymeric composition in order to release the therapeutic agent over a period of time.

Representative examples of biodegradable polymers suitable for the delivery of therapeutic agents include albumin, collagen, gelatin, hyaluronic acid, starch, cellulose and cellulose derivatives (e.g., regenerated cellulose, methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextrans, polysaccharides, fibrinogen, poly(ether ester) multiblock copolymers, based on poly(ethylene glycol) and poly(butylene terephthalate), tyrosine-derived polycarbonates (e.g., U.S. Pat. No. 6,120,491), poly (hydroxyl acids), poly(D,L-lactide), poly(D,L-lactide-co-glycolide), poly(glycolide), poly(hydroxybutyrate), polydioxanone, poly(alkylcarbonate) and poly(orthoesters), polyesters, poly(hydroxyvaleric acid), polydioxanone, polyesters, poly(malic acid), poly(tartronic acid), poly(acrylamides), polyanhydrides, polyphosphazenes, poly(amino acids), poly(alkylene oxide)-poly(ester) block copolymers (e.g., X-Y, X-Y-X, Y-X-Y, R-(Y-X)$_n$, or R-(X-Y)$_n$, where X is a polyalkylene oxide (e.g., poly(ethylene glycol, poly(propylene glycol) and block copolymers of poly(ethylene oxide) and poly(propylene oxide) (e.g., PLURONIC® and PLURONIC® R series of polymers from BASF Corporation, Mount Olive, N.J.) and Y is a polyester, where the polyester may comprise the residues of one or more of the monomers selected from lactide, lactic acid, glycolide, glycolic acid, e-caprolactone, gamma-caprolactone, hydroxyvaleric acid, hydroxybutyric acid, beta-butyrolactone, gamma-butyrolactone, gamma-valerolactone, γ-decanolactone, δ-decanolactone, trimethylene carbonate, 1,4-dioxane-2-one or 1,5-dioxepan-2one (e.g., PLGA, PLA, PCL, polydioxanone and copolymers thereof) and R is a multifunctional initiator), and the copolymers as well as blends thereof (see generally, Illum, L., Davids, S. S. (eds.) *Polymers in Controlled Drug Delivery* Wright, Bristol (1987); Arshady, *J. Controlled Release* 17:1-22 (1991); Pitt, *Int. J. Phar.* 59:173-196 (1990); Holland et al., *J. Controlled Release* 4:155-0180 (1986)).

Representative examples of non-degradable polymers suitable for the delivery of therapeutic agents include poly(ethylene-co-vinyl acetate) ("EVA") copolymers, aromatic polyesters, such as poly(ethylene terephthalate), silicone rubber, acrylic polymers (polyacrylate, polyacrylic acid, polymethylacrylic acid, polymethylmethacrylate, poly(butyl methacrylate)), poly(alkylcynoacrylate) (e.g., poly(ethylcyanoacrylate), poly(butylcyanoacrylate) poly(hexylcyanoacrylate) poly(octylcyanoacrylate)), acrylic resin, polyethylene, polypropylene, polyamides (nylon 6,6), polyurethanes (e.g., CHRONOFLEX® AL and CHRONOFLEX AR® (both from CardioTech International, Inc., Woburn, Mass.), TECOFLEX®, and BIONATE® (Polymer Technology Group, Inc., Emeryville, Calif.)), poly(ester urethanes), poly(ether urethanes), poly(ester-urea), polyethers (poly(ethylene oxide), poly(propylene oxide), polyoxyalkylene ether block copolymers based on ethylene oxide and propylene oxide such as the PLURONIC® polymers (e.g., F-127 or F87) from BASF Corporation (Mount Olive, N.J.), and poly(tetramethylene glycol), styrene-based polymers (polystyrene, poly(styrene sulfonic acid), poly(styrene)-block-poly(isobutylene)-block-poly(styrene), poly(styrene)-poly(isoprene) block copolymers), and vinyl polymers (polyvinylpyrrolidone, poly(vinyl alcohol), poly(vinyl acetate phthalate) as well as copolymers and blends thereof. Polymers may also be developed which are either anionic (e.g., alginate, carrageenan, carboxymethyl cellulose, poly(acrylamido-2-methyl propane sulfonic acid) and copolymers thereof, poly(methacrylic acid and copolymers thereof and poly(acrylic acid) and copolymers thereof, as well as blends thereof, or cationic (e.g., chitosan, poly-L-lysine, polyethylenimine, and poly(allyl amine)) and blends thereof (see generally, Dunn et al., *J. Applied Polymer Sci.* 50:353-365 (1993); Cascone et al., *J Materials Sci.: Materials in Medicine* 5:770-774 (1994); Shiraishi et al., *Biol.*

*Pharm. Bull.* 16(11):1164-1168 (1993); Thacharodi and Rao, *Int'l J. Pharm.* 120:115-118 (1995); Miyazaki et al., *Int'l J. Pharm.* 118:257-263 (1995).

Some examples of preferred polymeric carriers for the practice of this invention include poly(ethylene-co-vinyl acetate), polyurethanes, poly (D,L-lactic acid) oligomers and polymers, poly (L-lactic acid) oligomers and polymers, poly (glycolic acid), copolymers of lactic acid and glycolic acid, copolymers of lactide and glycolide, poly (caprolactone), poly (valerolactone), polyanhydrides, copolymers of poly (caprolactone) or poly (lactic acid) with a polyethylene glycol (e.g., MePEG), block copolymers of the form X-Y, X-Y-X, Y-X-Y, R-(Y-X)$_n$, or R-(X-Y)$_n$, [where X is a polyalkylene oxide (e.g., poly(ethylene glycol, poly(propylene glycol) and block copolymers of poly(ethylene oxide) and poly(propylene oxide) (e.g., PLURONIC® and PLURONIC® R series of polymers from BASF Corporation, Mount Olive, N.J.)) and Y is a polyester, where the polyester may comprise the residues of one or more of the monomers selected from lactide, lactic acid, glycolide, glycolic acid, ε-caprolactone, γ-caprolactone, hydroxyvaleric acid, hydroxybutyric acid, ε-butyrolactone, γ-butyrolactone, γ-valerolactone, γ-decanolactone, δ-decanolactone, trimethylene carbonate, 1,4-dioxane-2-one or 1,5-dioxepan-2-one; R is a multifunctional initiator; and n is 2 to 12], silicone rubbers, poly(styrene)block-poly(isobutylene)-block-poly(styrene), poly(acrylate) polymers and blends, admixtures, or co-polymers of any of the above. Other preferred polymers include collagen, poly (alkylene oxide)-based polymers, polysaccharides such as hyaluronic acid, chitosan and fucans, and copolymers of polysaccharides with degradable polymers.

Other representative polymers capable of sustained localized delivery of therapeutic agents described herein include carboxylic polymers, polyacetates, polycarbonates, polyethers, polyethylenes, polyvinylbutyrals, polysilanes, polyureas, polyoxides, polystyrenes, polysulfides, polysulfones, polysulfonides, polyvinylhalides, pyrrolidones, rubbers, thermal-setting polymers, cross-linkable acrylic and methacrylic polymers, ethylene acrylic acid copolymers, styrene acrylic copolymers, vinyl acetate polymers and copolymers, vinyl acetal polymers and copolymers, epoxies, melamines, other amino resins, phenolic polymers, and copolymers thereof, water-insoluble cellulose ester polymers (including cellulose acetate propionate, cellulose acetate, cellulose acetate butyrate, cellulose nitrate, cellulose acetate phthalate, and mixtures thereof), polyvinylpyrrolidone, polyethylene glycols, polyethylene oxide, polyvinyl alcohol, polyethers, polysaccharides, hydrophilic polyurethane, polyhydroxyacrylate, dextran, xanthan, hydroxypropyl cellulose, and homopolymers and copolymers of N-vinylpyrrolidone, N-vinyllactam, N-vinyl butyrolactam, N-vinyl caprolactam, other vinyl compounds having polar pendant groups, acrylate and methacrylate having hydrophilic esterifying groups, hydroxyacrylate, and acrylic acid, and combinations thereof; cellulose esters and ethers, ethyl cellulose, hydroxyethyl cellulose, cellulose nitrate, cellulose acetate, cellulose acetate butyrate, cellulose acetate propionate, natural and synthetic elastomers, rubber, acetal, styrene polybutadiene, acrylic resin, polyvinylidene chloride, polycarbonate, homopolymers and copolymers of vinyl compounds, polyvinylchloride, and polyvinylchloride acetate.

Representative examples of patents relating to drug-delivery polymers and their preparation include PCT Publication Nos. WO 98/19713, WO 01/17575, WO 01/41821, WO 01/41822, and WO 01/15526 (as well as the corresponding U.S. applications), U.S. Pat. Nos. 4,500,676; 4,582,865; 4,629,623; 4,636,524; 4,713,448; 4,795,741; 4,913,743; 5,069,899; 5,099,013; 5,128,326; 5,143,724; 5,153,174; 5,246,698; 5,266,563; 5,399,351; 5,525,348; 5,800,412; 5,837,226; 5,942,555; 5,997,517; 6,007,833; 6,071,447; 6,090,995; 6,106,473; 6,110,483; 6,121,027; 6,156,345; 6,214,901; 6,368,611; 6,630,155; 6,528,080; RE37,950; 6,46,1631; 6,143,314; 5,990,194; 5,792,469; 5,780,044; 5,759,563; 5,744,153; 5,739,176; 5,733,950; 5,681,873; 5,599,552; 5,340,849; 5,278,202; 5,278,201; 6,589,549; 6,287,588; 6,201,072; 6,117,949; 6,004,573; 5,702,717; 6,413,539; 5,714,159; 5,612,052; and U.S. Patent Application Publication Nos. 2003/0068377, 2002/0192286, 2002/0076441, and 2002/0090398.

It should be obvious to one of skill in the art that the polymers as described herein can also be blended or copolymerized in various compositions as required to deliver therapeutic doses of biologically active agents.

Drug delivery vehicles may take a variety of forms. For example, the carrier may be in the form of microspheres (e.g., PLGA, PLLA, PDLLA, PCL, gelatin, polydioxanone, poly (alkylcyanoacrylate)), nanospheres (PLGA, PLLA, PDLLA, PCL, gelatin, polydioxanone, poly(alkylcyanoacrylate)) (see, e.g., Hagan et al., *Proc. Intern. Symp. Control Rel. Bioact. Mater.* 22 (1995); Kwon et al., *Pharm Res.* 12(2):192-195; Kwon et al., *Pharm Res.* 10(7):970-974; Yokoyama et al., *J. Contr. Rel.* 32:269-277 (1994); Gref et al., *Science* 263:1600-1603 (1994): Bazile et al., *J. Pharm. Sci.* 84:493-498 (1994), emulsions (see, e.g., Tarr et al., *Pharm Res.* 4:62-165 (1987), microemulsions, micelles (SDS, block copolymers of the form X-Y, Y-X-Y, R-(Y-X)$_n$, R-(X-Y)$_n$ and X-Y-X (where X in a polyalkylene oxide (e.g., poly(ethylene glycol, poly(propylene glycol) and block copolymers of poly (ethylene oxide) and poly(propylene oxide) (e.g., PLURONIC® and PLURONIC® R series of polymers from BASF Corporation, Mount Olive, N.J.) and Y is a biodegradable polyester, where the polyester may comprise the residues of one or more of the monomers selected from lactide, lactic acid, glycolide, glycolic acid, ε-caprolactone, gamma-caprolactone, hydroxyvaleric acid, hydroxybutyric acid, beta-butyrolactone, gamma-butyrolactone, gamma-valerolactone, γ-decanolactone, δ-decanolactone, trimethylene carbonate, 1,4-dioxane-2-one or 1,5-dioxepan-2one (e.g., PLG-PEG-PLG) and R is a multifunctional initiator), and zeolites.

Other types of carriers that may utilized to contain and deliver therapeutic agents described herein include: cyclodextrins, such as hydroxypropyl cyclodextrin (Cserhati and Hollo, *Int. J. Pharm.* 108:69-75 (1994)), liposomes (see, e.g., Sharma et al., *Cancer Res.* 53:5877-5881, 1993; Sharma and Straubinger, *Pharm. Res.* 11(60):889-896, 1994; WO 93/18751; U.S. Pat. No. 5,242,073), liposome/gel (WO 94/26254), nanocapsules (Bartoli et al., *J. Microencapsulation* 7(2):191-197, 1990), implants (Jampel et al., *Invest. Ophthalm. Vis. Science* 34(11):3076-3083, 1993; Walter et al., *Cancer Res.* 54:22017-2212, 1994), nanoparticles (Violante and Lanzafame PAACR), nanoparticles—modified (U.S. Pat. No. 5,145,684), nanoparticles (surface modified) (U.S. Pat. No. 5,399,363), micelles such as are described in Alkan-Onyuksel et al., *Pharm. Res.* 11(2):206-212, 1994), micelle (surfactant) (U.S. Pat. No. 5,403,858), synthetic phospholipid compounds (U.S. Pat. No. 4,534,899), gas borne dispersion (U.S. Pat. No. 5,301,664), liquid emulsions, foam, spray, gel, lotion, cream, ointment, dispersed vesicles, particles or droplets solid- or liquid-aerosols, microemulsions (U.S. Pat. No. 5,330,756), polymeric shell (nano- and micro-capsule) (U.S. Pat. No. 5,439,686), and implants (U.S. Pat. No. 4,882,168).

Within certain aspects of the present invention, therapeutic agents may be fashioned in the form of microspheres, microparticles, and/or nanoparticles having any size ranging from 50 nm to 500 μm, depending upon the particular use. These compositions can be formed by spray-drying methods, milling methods, coacervation methods, w/o emulsion methods, w/o/w emulsion methods, and solvent evaporation methods. In other aspects, these compositions can include microemulsions, emulsions, liposomes and micelles. Compositions comprising a drug-loaded carrier may also be readily applied as a "spray", which solidifies into a film or coating for use as a device/implant surface coating or to line the tissues of the implantation site. Such sprays may be prepared from microspheres of a wide array of sizes, including for example, from 0.1 rpm to 3 μm, from 10 μm to 30 μm, and from 30 μm to 100 μm.

In one aspect, biologically active agents such as growth factors or fibrosis-inducing agents may be delivered from the composition to a local tissue site in order to facilitate scar formation, tissue healing, and/or regeneration. Thus, in one aspect, a method is provided for delivering a biologically active agent, where the composition also includes the biologically active agent (e.g., a fibrosing agent) to be delivered, and steps (a) and (b) are as described for the method of sealing tissue. Step (c) would involve allowing a three-dimensional matrix to form and delivering the biologically active agent.

As described above, the composition may include an agent that promotes fibrosis. Compositions that include a fibrosis-inducing agent may be used in a variety of applications, including, without limitation, tissue augmentation, bone growth, treatment of aneurysms, filling and blocking of voids in the body, medical devices coatings, and for use in sealant compositions.

In certain embodiments, the fibrosis or adhesion-inducing agent is silk. Silk refers to a fibrous protein, and may be obtained from a number of sources, typically spiders and silkworms. Typical silks contain about 75% of actual fiber, referred to as fibroin, and about 35% sericin, which is a gummy protein that holds the filaments together. Silk filaments are generally very fine and long—as much as 300-900 meters long. There are several species of domesticated silkworm that are used in commercial silk production, however, *Bombyx mori* is the most common, and most silk comes from this source. Other suitable silkworms include *Philosamia cynthia ricini, Antheraea yamamai, Antheraea pernyi*, and *Antheraea mylitta*. Spider silk is relatively more difficult to obtain, however, recombinant techniques hold promise as a means to obtain spider silk at economical prices (see, e.g., U.S. Pat. Nos. 6,268,169; 5,994,099; 5,989,894; and 5,728,810, which are exemplary only). Biotechnology has allowed researchers to develop other sources for silk production, including animals (e.g., goats) and vegetables (e.g., potatoes). Silk from any of these sources may be used in the present invention.

A commercially available silk protein is available from Croda, Inc., of Parsippany, N.J., and is sold under the trade names CROSILK LIQUID (silk amino acids), CROSILK 10,000 (hydrolyzed silk), CROSILK POWDER (powdered silk), and CROSILKQUAT (cocodiammonium hydroxypropyl silk amino acid). Another example of a commercially available silk protein is SERICIN, available from Pentapharm, LTD, a division of Kordia, BV, of the Netherlands. Further details of such silk protein mixtures can be found in U.S. Pat. No. 4,906,460, to Kim, et al., assigned to Sorenco. Silk useful in the present invention includes natural (raw) silk, hydrolyzed silk, and modified silk, i.e., silk that has undergone a chemical, mechanical, or vapor treatment, e.g., acid treatment or acylation (see, e.g., U.S. Pat. No. 5,747,015).

Raw silk is typically twisted into a strand sufficiently strong for weaving or knitting. Four different types of silk thread may be produced by this procedure: organzine, crepe, tram, and thrown singles. Organzine is a thread made by giving the raw silk a preliminary twist in one direction and then twisting two of these threads together in the opposite direction. Crepe is similar to organzine but is twisted to a much greater extent. Twisting in only one direction two or more raw silk threads makes tram. Thrown singles are individual raw silk threads that are twisted in only one direction. Any of these types of silk threads may be used in the present invention.

The silk used in the present invention may be in any suitable form that allows the silk to be joined with the medical implant, e.g., the silk may be in thread or powder-based forms. The silk can be prepared in the powdered form by several different methods. For example the silk can be milled (e.g., cryomill) into a powdered form. Alternatively the silk can be dissolved in a suitable solvent (e.g., HFIP or 9M LiBr) and then sprayed (electrospray, spray dry) or added to a non-solvent to produce a powder. Furthermore, the silk may have any molecular weight, where various molecular weights are typically obtained by the hydrolysis of natural silk, where the extent and harshness of the hydrolysis conditions determines the product molecular weight. For example, the silk may have an average (number or weight) molecular weight of about 200 to 5,000. See, e.g., JP-B-59-29199 (examined Japanese patent publication) for a description of conditions that may be used to hydrolyze silk.

A discussion of silk may be found in the following documents, which are exemplary only: Hinman, M. B. et al. "Synthetic spider silk: a modular fibre" *Trends in Biotechnology* 18(9) 374-379 (2000); Vollrath, F. and Knight, D. P. "Liquid crystalline spinning of spider silk" *Nature* 410(6828) 541-548 (2001); and Hayashi, C. Y. et al. "Hypotheses that correlate the sequence, structure, and mechanical properties of spider silk proteins" *Int. J. Biol. Macromolecules* 24(2-3), 265-270 (1999); and U.S. Pat. No. 6,427,933.

Other representative examples of fibrosis and adhesion-inducing agents include irritants (e.g., talc, talcum powder, copper, metallic beryllium (or its oxides), wool (e.g., animal wool, wood wool, and synthetic wool), quartz dust, silica, crystalline silicates), polymers (e.g., polylysine, polyurethanes, poly(ethylene terephthalate), polytetrafluoroethylene (PTFE), poly(alkylcyanoacrylates), and poly(ethylene-co-vinylacetate)); vinyl chloride and polymers of vinyl chloride; peptides with high lysine content; growth factors and inflammatory cytokines involved in angiogenesis, fibroblast migration, fibroblast proliferation, ECM synthesis and tissue remodeling, such as epidermal growth factor (EGF) family, transforming growth factor-α (TGF.-α), transforming growth factor-β (TGF-β-1, TGF-β-2, TGF-β-3), platelet-derived growth factor (PDGF), fibroblast growth factor (acidic—aFGF; and basic—bFGF), fibroblast stimulating factor-1, activins, vascular endothelial growth factor (including VEGF-2, VEGF-3, VEGF-A, VEGF-B, VEGF-C, placental growth factor —PlGF), angiopoietins, insulin-like growth factors (IGF), hepatocyte growth factor (HGF), connective tissue growth factor (CTGF), myeloid colony-stimulating factors (CSFs), monocyte chemotactic protein, granulocyte-macrophage colony-stimulating factors (GM-CSF), granulocyte colony-stimulating factor (G-CSF), macrophage colony-stimulating factor (M-CSF), erythropoietin, interleukins (particularly IL-1, IL-8, and IL-6), tumor necrosis factor-α (TNF-α), nerve growth factor (NGF), interferon-o interferon-β histamine, endothelin-1, angiotensin II, growth hormone (GH), and synthetic peptides, analogues or derivatives of these factors are also suitable for release from specific implants and devices to be described later. Other examples include CTGF (connective tissue growth factor); inflammatory microcrystals (e.g., crystalline minerals such as crystalline silicates); bromocriptine, methylsergide, methotrexate, chitosan, N-carboxybutyl chitosan, carbon tetrachloride, thioacetamide, fibrosin, ethanol, bleomycin, naturally occurring or synthetic peptides containing the Arg-Gly-Asp (RGD) sequence, generally at one or both termini (see e.g., U.S. Pat. No. 5,997,895), and tissue adhesives, such as cyanoacrylate and crosslinked poly(ethylene glycol)-methylated collagen compositions, such as described below.

Other examples of fibrosis-inducing agents include agents that promote bone growth, such as for example bone morphogenic proteins. Examples of bone morphogenic proteins include the following: BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Of these, BMP-2, BMP-3, BMP-4, BMP-5, BMP-6, and BMP-7. Bone morphogenic proteins are described, for example, in U.S. Pat. Nos. 4,877,864; 5,013,649; 5,661,007; 5,688,678; 6,177,406; 6,432,919; and 6,534,268, and Wozney, J. M. et al., *Science* 242(4885):1528-1534 (1988).

Other representative examples of fibrosis-inducing agents include components of extracellular matrix (e.g., fibronectin, fibrin, fibrinogen, collagen (e.g., bovine collagen), fibrillar and non-fibrillar collagen, adhesive glycoproteins, proteoglycans (e.g., heparin sulfate, chondroitin sulfate, dermatan sulfate), hyaluronan, secreted protein acidic and rich in cysteine (SPARC), thrombospondins, tenacin, and cell adhesion molecules (including integrins, vitronectin, fibronectin, laminin, hyaluronic acid, elastin, bitronectin), proteins found in basement membranes, and fibrosin) and inhibitors of matrix metalloproteinases, such as TIMPs (tissue inhibitors of matrix metalloproteinases) and synthetic TIMPs, e.g., marimistat, batimistat, doxycycline, tetracycline, minocycline, TROCADE, Ro-1130830, CGS 27023A, and BMS-275291.

Within various embodiments of the invention, a composition incorporates a compound which acts to stimulate cellular proliferation. In certain embodiments, a composition may incorporate a compound which acts to stimulate cellular proliferation in addition to a fibrosing agent. Representative examples of agents that stimulate cellular proliferation include, pyruvic acid, naltrexone, leptin, D-glucose, insulin, amlodipine, alginate oligosaccharides, minoxidil, dexamethasone, isotretinoin (13-cis retinoic acid), 17-β-estradiol, estradiol, 1-α-25 dihydroxyvitamin $D_3$, diethylstibesterol, cyclosporine A, L-NAME (L-NG-nitroarginine methyl ester (hydrochloride)), all-trans retinoic acid (ATRA), and analogues and derivatives thereof. Other examples of agents that stimulate cellular proliferation include: sphingosine 1-phosphate receptor agonist (e.g., FTY-720 (1,3-propanediol, 2-amino-2-(2-(4-octylphenyl)ethyl)-,hydrochloride; immunostimulants, such as Imupedone (methanone, [5-amino-2-(4-methyl-1-piperidinyl)phenyl](4-chlorophenyl)-, DIA-PEP227 synthetic peptide (Peptor Ltd., Israel)); and nerve growth factor agonist, e.g., NG-012 (5H,9H,13H,21H,25H,-dibenzo[k,u][1,5,9,15,19]pentaoxacyclotetracosin-5,9,13, 21,25-pentone, 7,8,11,12,15,16,23,24,27,28-decahydro-2,4, 18,20-tetrahydroxy-11-(hydroxymethyl)-7,15,23,27-tetramethyl-, NG-121, SS-701 (2,2':6',2"-terpyridine, 4'-(4-methylphenyl)-, trihydrochloride, AMPAlex (piperidine, 1-(6-quinoxalinylcarbonyl)-, RGH-2716 (8-[4,4-bis(4-fluorophenyl)butyl]-3-(1,1-dimethylethyl)-4-methylene-1-oxa-3,8-diaza-spiro[4.5]decan-2-one, and TDN-345 (1-oxa-3,8-diazaspiro[4.5]decan-2-one, 8-[4,4-bis(4-fluorophenyl) butyl]-3-(1,1-dimethylethyl)-4-methylene-).

Particularly useful biologically active agents for use in the compositions of the present invention are cytokines, which are biologically active molecules including growth factors and active peptides, which aid in healing or regrowth of normal tissue. The function of cytokines is two-fold: 1) they can incite local cells to produce new collagen or tissue, or 2) they can attract cells to the site in need of correction. As such, cytokines, as well as appropriate combinations of cytokines, serve to encourage "biological anchoring" of an implant within the host tissue, by facilitating the regrowth and remodeling of the implant into normal bone tissue. Cytokines may also be used in the treatment of wounds.

Examples of cytokines include, by way of illustration and not limitation, transforming growth factors (TGFs); fibroblast growth factors (FGFs), including both acidic FGF and basic FGF; platelet derived growth factors (PDGFs) such as PDGF-AA, PDGF-AB, and PDGF-BB; epidermal growth factors (EGFs); connective tissue activated peptides (CTAPs); colony stimulating factors (CSFs); erythropoietin (EPO); nerve growth factor (NGF); osteogenic factors; P-thromboglobulin; tumor necrosis factors (TNFs); interleukins; interferons (IFNs); bone morphogenic protein (BMP); and biologically active analogs, fragments, and derivatives of such growth factors. Members of the transforming growth factor (TGF) supergene family, which are multifunctional regulatory proteins, are particularly preferred. Members of the TGF supergene family include TGF-α and the beta transforming growth factors (for example, TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors, e.g., FGFs; EGFs; PDGFs; insulin-like growth factors (IGFs); inhibins such as Inhibin A and Inhibin B; growth differentiating factors, e.g., GDF-1); and activins such as Activin A, Activin B, Activin AB. Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

By varying the relative molar amounts of the different the reactive groups on the multifunctional compounds, it is possible to alter the net charge of the resulting three-dimensional matrix, in order to prepare a matrix for the delivery of a charged compound such as a protein or ionizable drug. As such, the delivery of charged proteins or drugs, which would normally diffuse rapidly out of a neutral carrier matrix, can be controlled.

For example, if a molar excess of nucleophilic groups are used, the resulting matrix has a net positive charge and can be used to ionically bind and deliver negatively charged compounds. Similarly, if a molar excess of electrophilic groups are used, the resulting matrix has a net negative charge and can be used to ionically bind and deliver positively charged compounds. Examples of negatively and positively charged compounds that can be delivered from these matrices include various drugs, cells, proteins, and polysaccharides. Negatively charged collagens, such as succinylated collagen, and glycosaminoglycan derivatives such as sodium hyaluronate, keratan sulfate, keratosulfate, sodium chondroitin sulfate A, sodium dermatan sulfate B, sodium chondroitin sulfate C, heparin, esterified chondroitin sulfate C, and esterified heparin, can also be effectively incorporated into the matrix as described above. Positively charged collagens, such as methylated collagen, and glycosaminoglycan derivatives such as esterified deacetylated hyaluronic acid, esterified deacetylated desulfated chondroitin sulfate A, esterified deacetylated desulfated chondroitin sulfate C, deacetylated desulfated keratan sulfate, deacetylated desulfated keratosulfate, esterified desulfated heparin, and chitosan, can also be similarly incorporated.

In another aspect, biologically active agents such as fibrosis-inhibiting agents may be delivered from the composition to a local tissue site in order to inhibit scar formation, tissue healing, and/or regeneration. Thus, in one aspect, a method is provided for delivering a biologically active agent, where the composition also includes the biologically active agent (e.g., a fibrosis-inhibiting agent) to be delivered, and steps (a) and (b) are as described for the method of sealing tissue. Step (c) would involve allowing a three-dimensional matrix to form to deliver the biologically active agent. Compositions that include a fibrosis-inhibiting agent may be used in a variety of applications, including, without limitation, surgical adhesion prevention and medical devices coatings. Numerous therapeutic compounds have been identified that are of utility in the invention including:

Angiogenesis Inhibitors

In one embodiment, the pharmacologically active compound inhibits angiogenesis (i.e., angiogenesis inhibitor), such as, for example, 2-ME (NSC-659853), PI-88 (D-mannose), O-6-O-phosphono-alpha-D-mannopyranosyl-(1-3)-O-alpha-D-mannopyranosyl-(1-3)-O-alpha-D-mannopyranosyl-(1-3)-O-alpha-D-mannopyranosyl-(1-2)-hydrogen sulphate), thalidomide (1H-isoindole-1,3(2H)-dione, 2-(2,6-dioxo-3-piperidinyl)-), CDC-394, CC-5079, ENMD-0995 (S-3-amino-phthalidoglutarimide), AVE-8062A, vatalanib, SH-268, halofuginone hydrobromide, atiprimod dimaleate (2-azaspivo[4.5]decane-2-propanamine, N,N-diethyl-8,8-dipropyl, dimaleate), ATN-224, CHIR-258, combretastatin A-4 (phenol, 2-methoxy-5-[2-(3,4,5-trimethoxyphenyl)ethenyl]-, (Z)—), GCS-100LE, or an analogue or derivative thereof.

Other examples of angiogenesis inhibitors for use in the compositions of the invention include: 2-methoxyestradiol, A6, ABT-510, ABX-IL8, actimid, Ad5FGF-4, AG3340, alpha5beta1 integrin antibody, AMG001, anecortave acetate, angiocol, angiogenix, angiostatin, angiozyme, antiangiogenic antithrombin 3, anti-VEGF, anti-VEGF Mab, aplidine, aptosyn, ATN-161, avastin, AVE8062A, Bay 12-9566, benefin, BioBypass CAD, MS275291, CAI, carboxymidotriazole, CC 4047, CC 5013, CC7085, CDC801, Celebrex, CEP-7055, CGP-41251/PKC412, cilengitide, CM101, col-3, combretastatin, combretastatin A4P, CP-547, 632, CP-564, 959, Del-1, dexrazoxane, didemnin B, DMXAA, EMD 121974, endostatin, FGF (AGENT 3), flavopiridol, GBC-100, genistein concentrated polysaccharide, green tea extract, HIF-1 alpha, human chorio-gonadotrophin, IM862, INGN 201, interferon alpha-2a, interleukin-12, iressa, ISV-120, LY317615, LY-333531, Mab huJ591-DOTA-90 Yttrium, marimastat, Medi-522, metaret, neoretna, neovastat, NM-3, NPe6, NVIFGF, octreotide, oltipraz, paclitaxel, pegaptanib sodium, penicillamine, pentosan polysulphate, prinomastat, PSK, psorvastat, PTK787/ZK222584, ranibizumab, razoxane, replistatatin, revimid, RhuMab, Ro317453, squalamine, SU101, SU 11248, SU5416, SU6668, tamoxifen, tecogalan sodium, temptostatin, tetrathiomol, tetrathiomolybdate, thalomid, TNP-470, UCN-01, VEGF, VEGF trap, Vioxx, vitaxin, vitaxin-2, ZD6126, ZD6474, angiostatin (plasminogen fragment), a TIMPs, antiangiogenic antithrombin III, pigment epithelial-derived factor (PEDF), canstatin, placental ribonuclease inhibitor, cartilage-derived inhibitor (CDI), plasminogen activator inhibitor, CD59 complement fragment, platelet factor-4, endostatin (collagen XVIII fragment), prolactin 16 kD fragment, fibronectin fragment, proliferin-related protein, gro-beta, a retinoid, a heparinase, tetrahydrocortisol-S, heparin hexasaccharide fragment, thrombospondin-1, human chorionic gonadotropin, transforming growth factor-beta, interferon alpha, interferon beta, or interferon gamma, tumistatin, interferon inducible protein, vasculostatin, interleukin-12, vasostatin (calreticulin fragment), kringle 5 (plasminogen fragment), angioarrestin, or 2-methoxyestradiol. Angiogenesis inhibitors also include antagonists of angiogenin, placental growth factor, angiopoietin-1, platelet-derived endothelial cell growth factor, Del-1, platelet-derived growth factor-BB, aFGF, bFGF, pleiotrophin, follistatin, proliferin, granulocyte colony-stimulating factor, transforming growth factor-alpha, hepatocyte growth factor, transforming growth factor-beta, interleukin-8, tumor necrosis factor-alpha, leptin, vascular endothelial growth factor, midkine, progranulin, 2-methoxyestradiol (PANZEM) (EntreMed), A6, ABT-510, ABX-IL8 (Abgenix), actimid, Ad5FGF-4 (Collateral Therapeutics), AG3340 (Agouron Pharmaceuticals Inc. LaJolla, Calif.), alpha5beta1 integrin antibody, AMG001 (AnGes/Daichi Pharmaceuticals), anecortave acetate (Retaane, Alcon), angiocol, angiogenix (Endovasc Ltd), angiostatin (EntreMed), angiozyme, antiangiogenic antithrombin 3 (Genzyme Molecular Oncology), anti-VEGF (Genentech), anti-VEGF Mab, aplidine, aptosyn, ATN-161, avastin (bevacizumab), AVE8062A, Bay 12-9566 (Bayer Corp. West Haven, Conn.), benefin, BioBypass CAD (VEGF-121) (GenVec), MS275291, CAI (carboxy-amido imidazole), carboxymidotriazole, CC 4047 (Celgene), CC 5013 (Celgene), CC7085, CDC 801 (Celgene), Celebrex (Celecoxib), CEP-7055, CGP-41251/PKC412, cilengitide, CM101 (Carborned Brentwood, Tenn.), col-3 (CollaGenex Pharmaceuticals Inc. Newton, Pa.), combretastatin, combretastatin A4P (Oxigene/Bristol-Myers Squibb), CP-547, 632, CP-564, 959, Del-1 (VLTS-589) (Valentis), dexrazoxane, didemnin B, DMXAA, EMD 121974, endostatin (EntreMed), FGF (AGENT 3) (Berlex (Krannert Institute of Cardiology)), flavopiridol, GBC-100, genistein concentrated polysaccharide, green tea extract, HIF-1 alpha (Genzyme), human choriogonadotrophin, IM862 (Cytran), INGN 201, interferon alpha-2a, interleukin-12, iressa, ISV-120 (Batimastat), LY317615, LY-333531 (Eli Lilly and Company), Mab huJ591-DOTA-90 Yttrium (90Y), marimastat (British Biotech Inc. Annapolis, Md.), Medi-522, metaret (suramin), neo-retna, neovastat (AEterna Laboratories), NM-3, NPe6, NV1FGF (Gencell/Aventis), octreotide, oltipraz, paclitaxel (e.g., taxol, docetaxel, or paxene), pegaptanib sodium (Eyetech), penicillamine, pentosan polysulphate, PI-88, prinomastat (Agouron Pharmaceuticals), PSK, psorvastat, PTK787/ZK222584, ranibizumab (Lucentis, Genentech), razoxane, replistatatin (Platelet factor-4), revimid, RhuMab, Ro317453, squalamine (Magainin Pharmaceuticals, Inc. Plymouth Meeting, Pa.), SUIO1 (Sugen Inc. Redwood City, Calif.), SUI1248, SU5416 (Sugen), SU6668 (Sugen), tamoxifen, tecogalan sodium, temptostatin, tetrathiomol, tetrathiomolybdate, Anti-angiogensis compounds found in vivo may be used in the compositions and methods described including angiostatin (plasminogen fragment), metalloproteinase inhibitors (TIMPs), antiangiogenic antithrombin III (aaATIII), pigment epithelial-derived factor (PEDF), canstatin, placental ribonuclease inhibitor, cartilage-derived inhibitor (CDI), plasminogen activator inhibitor, CD59 complement fragment, platelet factor-4 (PF4), endostatin (collagen XVIII fragment), prolactin 16 kD fragment, fibronectin fragment, proliferin-related protein, gro-beta, retinoids, heparinases, tetrahydrocortisol-S, heparin hexasaccharide fragment, thrombospondin-1, human chorionic gonadotropin (hCG), transforming growth factor-beta, interferon alpha/beta/gamma, tumistatin, interferon inducible protein (IP-10), vasculostatin, interleukin-12 (IL-12), vasostatin (calreticulin fragment), kringle 5 (plasminogen fragment), angioarrestin, and 2-methoxyestradiol.

Compounds that inhibit, block, or antagonize the angiogenic activity of the following species in vivo may be used in the methods and compositions described herein including angiogenin, placental growth factor, angiopoietin-1, platelet-derived endothelial cell growth factor (PD-ECGF), Del-1, platelet-derived growth factor-BB (PDGF-BB), fibroblast growth factors: acidic (aFGF) and basic (bFGF), pleiotrophin (PTN), follistatin, proliferin, granulocyte colony-stimulating factor (G-CSF), transforming growth factor-alpha (TGF-alpha), hepatocyte growth factor (HGF)/scatter factor (SF), transforming growth factor-beta (TGF-beta), interleukin-8 (IL-8), tumor necrosis factor-alpha (TNF-alpha), leptin, vascular endothelial growth factor (VEGF)/vascular permeability factor (VPF), midkine, and progranulin.

Other examples of angiogenesis inhibitors for use in the present compositions include 2-methoxyestradiol, prinomastat, batimastat, BAY 12-9566, carboxyamidotriazole, CC-1088, dextromethorphan acetic, dimethylxanthenone acetic acid, EMD 121974, endostatin, IM-862, marimastat, matrix metalloproteinase, penicillamine, PTK787/ZK 222584, RPI.4610, squalamine, squalamine lactate, SU5416, (.+−.)-thalidomide, S-thalidomide, R-thalidomide, TNP-470, combretastatin, paclitaxel, tamoxifen, COL-3, neovastat, BMS-275291, SU6668, interferon-alpha, anti-VEGF antibody, Medi-522 (Vitaxin II), CAI, celecoxib, Interleukin-12, IM862, Amilloride, Angiostatin, Protein, Angiostatin K1-3, Angiostatin K1-5, Captopril, DL-alpha-Difluoromethylomithine, DL-alpha-Difluoromethylomithine HCl, His-Tag, Endostatin, Protein, Fumagillin, Herbimycin A, 4-Hydroxyphenylretinamide, gamma-interferon, Juglone, Laminin, Laminin Hexapeptide, Laminin Pentapeptide, Lavendustin A, Medroxyprogesterone, Medroxyprogesterone Acetate, Minocycline, Minocycline HCl, Placental Ribonuclease Inhibitor, Suramin, Sodium Salt Suramin, Human Platelet Thrombospondin, Tissue Inhibitor of Metalloproteinase 1, Neutrophil Granulocyte Tissue Inhibitor of Metalloproteinase 1, and Rheumatoid Synovial Fibroblast Tissue Inhibitor of Metalloproteinase 2.

5-Lipoxygenase Inhibitors and Antagonists

In another embodiment, the pharmacologically active compound is a 5-lipoxygenase inhibitor or antagonist (e.g., Wy-50295 (2-naphthaleneacetic acid, alpha-methyl-6-(2-quinolinylmethoxy)-, (S)—), ONO-LP-269 (2,11,14-eicosatrienamide, N-(4-hydroxy-2-(1H-tetrazol-5-yl)-8-quinolinyl)-, (E,Z,Z)—), licofelone (1H-pyrrolizine-5-acetic acid, 6-(4-chlorophenyl)-2,3-dihydro-2,2-dimethyl-7-phenyl-), CMI-568 (urea, N-butyl-N-hydroxy-N'-(4-(3-(methylsulfonyl)-2-propoxy-5-(tetrahydro-5-(3,4,5-trimethoxyphenyl)-2-furanyl)phenoxy)butyl)-,trans-), IP-751 ((3R,4R)-(delta 6)-THC-DMH-11-oic acid), PF-5901 (benzenemethanol, alpha-pentyl-3-(2-quinolinylmethoxy)-), LY-293111 (benzoic acid, 2-(3-(3-((5-ethyl-4'-fluoro-2-hydroxy(1,1'-biphenyl)-4-yl)oxy)propoxy)-2-propylphenoxy)-), RG-5901-A (benzenemethanol, alpha-pentyl-3-(2-quinolinylmethoxy)-, hydrochloride), rilopirox (2(1H)-pyridinone, 6-((4-(4-chlorophenoxy)phenoxy)methyl)-1-hydroxy-4-methyl-), L-674636 (acetic acid, ((4-(4-chlorophenyl)-1-(4-(2-quinolinylmethoxy)phenyl)butyl)thio)-AS)), 7-((3-(4-methoxy-tetrahydro-2H-pyran-4-yl)phenyl)methoxy)-4-phenylnaphtho (2,3-c)furan-1(3H)-one, MK-886 (1H-indole-2-propanoic acid, 1-((4-chlorophenyl)methyl)-3-((1,1-dimethylethyl)thio)-alpha, alpha-dimethyl-5-(1-methylethyl)-), quiflapon (1H-indole-2-propanoic acid, 1-((4-chlorophenyl)methyl)-3-((1,1-dimethylethyl)thio)-alpha, alpha-dimethyl-5-(2-quinolinylmethoxy)-), quiflapon (1H-Indole-2-propanoic acid, 1-((4-chlorophenyl)methyl)-3-((1,1-dimethylethyl)thio)-alpha, alpha-dimethyl-5-(2-quinolinylmethoxy)-), docebenone (2,5-cyclohexadiene-1,4-dione, 2-(12-hydroxy-5,10-dodecadiynyl)-3,5,6-trimethyl-), zileuton (urea, N-(1-benzo(b)thien-2-ylethyl)-N-hydroxy-), or an analogue or derivative thereof).

Chemokine Receptor Antagonists Ccr (1,3, and 5)

In another embodiment, the pharmacologically active compound is a chemokine receptor antagonist which inhibits one or more subtypes of CCR (1, 3, and 5) (e.g., ONO-4128 (1,4,9-triazaspiro(5.5)undecane-2,5-dione, 1-butyl-3-(cyclohexylmethyl)-9-((2,3-dihydro-1,4-benzodioxin-6-yl)methyl-), L-381, CT-112 (L-arginine, L-threonyl-L-threonyl-L-seryl-L-glutaminyl-L-valyl-L-arginyl-L-prolyl-), AS-900004, SCH-C, ZK-811752, PD-172084, UK-427857, SB-380732, vMIP II, SB-265610, DPC-168, TAK-779 (N,N-dimethyl-N-(4-(2-(4-methylphenyl)-6,7-dihydro-5H-benzocyclohepten-8-ylcarboxamido)benzyl)tetrahydro-2H-pyran-4-aminium chloride), TAK-220, KRH-1120), GSK766994, SSR-150106, or an analogue or derivative thereof). Other examples of chemokine receptor antagonists include a-Immunokine-NNS03, BX-471, CCX-282, Sch-350634; Sch-351125; Sch-417690; SCH-C, and analogues and derivatives thereof.

Cell Cycle Inhibitors

In another embodiment, the pharmacologically active compound is a cell cycle inhibitor. Representative examples of such agents include taxanes (e.g., paclitaxel (discussed in more detail below) and docetaxel) (Schiff et al., *Nature* 277: 665-667 (1979); Long and Fairchild, *Cancer Research* 54:4355-4361 (1994); Ringel and Horwitz, *J. Nat'l Cancer Inst.* 83(4):288-291 (1991); Pazdur et al., *Cancer Treat. Rev.* 19(40):351-386, 1993), etanidazole, nimorazole (B. A. Chabner and D. L. Longo. Cancer Chemotherapy and Biotherapy—Principles and Practice. Lippincott-Raven Publishers, New York, 1996, p. 554), perfluorochemicals with hyperbaric oxygen, transfusion, erythropoietin, BW12C, nicotinamide, hydralazine, BSO, WR-2721, ludR, DUdR, etanidazole, WR-2721, BSO, mono-substituted keto-aldehyde compounds (U.S. Pat. No. 4,066,650 to Egyud), nitroimidazole (U.S. Pat. No. 4,462,992 to Agrawal and Sakaguchi), 5-substituted-4-nitroimidazoles (Adams et al., *Int. J. Radiat. Biol. Relat. Stud. Phys., Chem. Med.* 40(2):153-61 (1981)), SR-2508 (Brown et al., *Int. J. Radiat. Oncol., Biol. Phys.* 7(6):695-703 (1981)), 2H-isoindolediones (U.S. Pat. No. 4,494,547 to Myers), chiral (((2-bromoethyl)-amino)methyl)-nitro-1H-imidazole-1-ethanol (U.S. Pat. Nos. 5,543,527; 4,797,397; and 5,342,959 to Beylin et al.), nitroaniline derivatives (U.S. Pat. No. 5,571,845 to Denny et al.), DNA-affinic hypoxia selective cytotoxins (U.S. Pat. No. 5,602,142 to Papadopoulou-Rosenzweig), halogenated DNA ligand (U.S. Pat. No. 5,641,764 to Martin), 1,2,4 benzotriazine oxides (U.S. Pat. Nos. 5,616,584; 5,624,925; and 5,175,287 to Lee et al.), nitric oxide (U.S. Pat. No. 5,650,442 to Mitchell et al.), 2-nitroimidazole derivatives (U.S. Pat. No. 4,797,397 to Suto et al.; U.S. Pat. No. 5,270,330 to T. Suzuki; U.S. Pat. No. 5,270,330 to T. Suzuki et al.; European Patent No. 0 513 351 to Suzuki), fluorine-containing nitroazole derivatives (U.S. Pat. No. 4,927,941 to Kagiya), copper (U.S. Pat. No. 5,100,885 to Abrams), combination modality cancer therapy (U.S. Pat. No. 4,681,091 to Picker et al.), 5-CldC or (d)H$_4$U or 5-halo-2'-halo-2'-deoxy-cytidine or -uridine derivatives (U.S. Pat. No. 4,894,364 to Greer), platinum complexes (U.S. Pat. No. 4,921,963 to Skov; European Publication No. 0 287 317 to Skov), fluorine-containing nitroazole (U.S. Pat. No. 4,927,941 to Kagiya et al.), benzamide (U.S. Pat. No. 5,032,617 to Lee), autobiotics (U.S. Pat. No. 5,147,652 to Egyud), benzamide and nicotinamide (U.S. Pat. No. 5,215,738 to Lee et al.), acridine-intercalator (U.S. Pat. No. 5,294,715 to Papadopoulou-Rosenzweig), fluorine-containing nitroimidazole (U.S. Pat. No. 5,304,654 to Kagiya et al.), hydroxylated texaphyrins (U.S. Pat. No. 5,457,183 to Sessler et al.), hydroxylated compound derivative (Japanese Publication No. 011106775 A to Suzuki et al.; Japanese Publication No. 01139596 A to Suzuki et al.; Japanese Publication No. 63170375 A to Sakaguchi et al.), fluorine containing 3-nitro-1,2,4-triazole (Japanese Publication No. 02076861 A to Kagitani et al.), 5-thiotretrazole derivative or its salt (Japanese Publication No. 61010511 A to Kano et al.), Nitrothiazole (Japanese Publication No. 61167616 A to Kagitani et al.), imidazole derivatives (Japanese Publication Nos. 6203767 A, 62030768 A, and 62030777 A to Inayma et al.), 4-nitro-1,2,3-triazole (Japanese Publication No. 62039525 A to Kagitani et al.), 3-nitro-1,2,4-triazole (Japanesee Publication No. 62138427 A to Kagitani et al.), Carcinostatic action regulator (Japanese Publication No. 63099017 A to Amagase), 4,5-dinitroimidazole derivative (Japanese Publication No. 63310873 A to Inayama), nitrotriazole Compound (Japanese Publication No. 07149737 A to Kagitanil), cisplatin, doxorubin, misonidazole, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide (I. F. Tannock, *Journal of Clinical Oncology* 14(12):3156-3174 (1996)), camptothecin (Ewend M. G. et al., Cancer Research 56(22):5217-5223 (1996) and paclitaxel (Tishler R. B. et al. *International Journal of Radiation Oncology and Biological Physics* 22(3): 613-617 (1992)).

A number of the above-mentioned cell cycle inhibitors also have a wide variety of analogues and derivatives, including, but not limited to, cisplatin, cyclophosphamide, misonidazole, tiripazamine, nitrosourea, mercaptopurine, methotrexate, fluorouracil, epirubicin, doxorubicin, vindesine and etoposide. Analogues and derivatives include (CPA)$_2$Pt (DOLYM) and (DACH)Pt(DOLYM) cisplatin (Choi et al., *Arch. Pharmacal Res.* 22(2): 151-156 (1999), Cis-(PtCl$_2$(4,7-H-5-methyl-7-oxo) 1,2,4(triazolo(1,5-a)pyrimidine)$_2$) (Navarro et al., *J. Med. Chem.* 41(3):332-338 (1998), (Pt(cis-1,4-DACH)(trans-Cl$_2$)(CBDCA))·½MeOH cisplatin (Shamsuddin et al., *Inorg. Chem.* 36(25):5969-5971 (1997), 4-pyridoxate diammine hydroxy platinum (Tokunaga et al., *Pharm. Sci.* 3(7):353-356 (1997), Pt(II)•••Pt(II)(Pt$_2$(NHCHN(C(CH$_2$)(CH$_3$)))$_4$) (Navarro et al., *Inorg. Chem.* 35(26):7829-7835 (1996), 254-S cisplatin analogue (Koga et al., *Neurol. Res.* 18(3):244-247 (1996), o-phenylenediamine ligand bearing cisplatin analogues (Koeckerbauer & Bednarski, *J. Inorg. Biochem.* 62(4):281-298 (1996), trans,cis-(Pt (OAc)$_2$I$_2$(en)) (Kratochwil et al., *J. Med. Chem.* 39(13):2499-2507 (1996), estrogenic 1,2-diarylethylenediamine ligand (with sulfur-containing amino acids and glutathione) bearing cisplatin analogues (Bednarski, *J. Inorg. Biochem.* 62(1):75 (1996), cis-1,4-diaminocyclohexane cisplatin analogues (Shamsuddin et al., *J. Inorg. Biochem.* 61(4):291-301 (1996), 5' orientational isomer of cis-(Pt(NH$_3$)(4-aminoTEMP-O){d (GpG)}) (Dunham & Lippard, *J. Am. Chem. Soc.* 117(43): 10702-12 (1995), chelating diamine-bearing cisplatin analogues (Koeckerbauer & Bednarski, *J. Pharm. Sci.* 84(7): 819-23 (1995), 1,2-diarylethyleneamine ligand-bearing cisplatin analogues (Otto et al., *J. Cancer Res. Clin. Oncol.* 121(1):31-8 (1995), (ethylenediamine)platinum(II) complexes (Pasini et al., *J. Chem. Soc., Dalton Trans.* 4:579-85 (1995), CI-973 cisplatin analogue (Yang et al., *Int. J. Oncol.* 5(3):597-602 (1994), cis-diamminedichloroplatinum(II) and its analogues cis-1,1-cyclobutanedicarbosylato(2R)-2-methyl-1,4-butanediam-mineplatinum(II) and cis-diammine (glycolato)platinum (Claycamp & Zimbrick, J. Inorg. Biochem., 26(4):257-67 (1986); Fan et al., *Cancer Res.* 48(11): 3135-9 (1988); Heiger-Bernays et al., *Biochemistry* 29(36): 8461-6, 1990; Kikkawa et al., *J. Exp. Clin. Cancer Res.* 12(4):233-40 (1993); Murray et al., *Biochemistry* 31(47): 11812-17 (1992); Takahashi et al., *Cancer Chemother. Pharmacol.* 33(1):31-5 (1993)), cis-amine-cyclohexylamine-dichloroplatinum(II) (Yoshida et al., *Biochem. Pharmacol.* 48(4):793-9 (1994)), gem-diphosphonate cisplatin analogues (FR 2683529), (meso-1,2-bis(2,6-dichloro-4-hydroxyphenyl)ethylenediamine)dichloroplatinum(II) (Bednarski et al., *J. Med. Chem.* 35(23):4479-85 (1992)), cisplatin analogues containing a tethered dansyl group (Hartwig et al., *J. Am. Chem. Soc.* 114(21):8292-3 (1992)), platinum(II)polyamines (Siegmann et al., *Inorg. Met.-Containing Polym. Mater.* (*Proc. Am. Chem. Soc. Int. Symp.*) 335-61 (1990)), cis-(3H) dichloro(ethylenediamine)platinum(II) (Eastman, *Anal. Biochem.* 197(2):311-15 (1991)), trans-diamminedichloroplatinum(II) and cis-(Pt(NH$_3$)$_2$(N$_3$-cytosine)Cl) (Bellon & Lippard, *Biophys. Chem.* 35(2-3):179-88 (1990)), 3H-cis-1,2-diaminocyclohexanedichloroplatinum(II) and 3H-cis-1,2-diaminocyclohexanemalonatoplatinum (II) (Oswald et al., *Res. Commun. Chem. Pathol. Pharmacol.* 64(1):41-58 (1989)), diaminocarboxylatoplatinum (EPA 296321), trans-(D,1)-1,2-diaminocyclohexane carrier ligand-bearing platinum analogues (Wyrick & Chaney, *J. Labelled Compd. Radiopharm.* 25(4):349-57, 1988)), aminoalkylaminoanthraquinone-derived cisplatin analogues (Kitov et al., *Eur. J. Med. Chem.* 23(4):381-3 (1988)), spiroplatin, carboplatin, iproplatin and JM40 platinum analogues (Schroyen et al., *Eur. J. Cancer Clin. Oncol.* 24(8):1309-12 (1988)), bidentate tertiary diamine-containing cisplatinum derivatives (Orbell et al., *Inorg. Chim. Acta* 152(2):125-34 (1988)), platinum(II), platinum(IV) (Liu & Wang, *Shandong Yike Daxue Xuebao* 24(1):35-41 (1986)), cis-diammine(1,1-cyclobutanedicarboxylato-)platinum(II) (carboplatin, JM8) and ethylenediammine-malonatoplatinum(II) (JM40) (Begg et al., *Radiother. Oncol.* 9(2):157-65 (1987)), JM8 and JM9 cisplatin analogues (Harstrick et al., *Int. J. Androl.* 10(1); 139-45 (1987)), (NPr4)$_2$((PtCL4).cis-(PtCl2-(NH$_2$Me)$_2$)) (Brammer et al., *J. Chem. Soc., Chem. Commun.* 6:443-5 (1987)), aliphatic tricarboxylic acid platinum complexes (EPA 185225), cis-dichloro(amino acid) (tert-butylamine)platinum(II) complexes (Pasini & Bersanetti, *Inorg. Chim. Acta* 107(4):259-67 (1985)); 4-hydroperoxycylcophosphamide (Ballard et al., *Cancer Chemother. Pharmacol.* 26(6):397-402 (1990)), acyclouridine cyclophosphamide derivatives (Zakerinia et al., *Helv. Chim. Acta* 73(4):912-15 (1990)), 1,3,2-dioxa- and -oxazaphosphorinane cyclophosphamide analogues (Yang et al., *Tetrahedron* 44(20):6305-14 (1988)), C5-substituted cyclophosphamide analogues (Spada, University of Rhode Island Dissertation, 1987), tetrahydrooxazine cyclophosphamide analogues (Valente, University of Rochester Dissertation, 1988), phenyl ketone cyclophosphamide analogues (Hales et al., *Teratology* 39(1):31-7 (1989)), phenylketophosphamide cyclophosphamide analogues (Ludeman et al., *J. Med. Chem.* 29(5):716-27 (1986)), ASTA Z-7557 cyclophosphamide analogues (Evans et al., *Int. J. Cancer* 34(6):883-90 (1984)), 3-(1-oxy-2,2,6,6-tetramethyl-4-piperidinyl)cyclophosphamide (Tsui et al., *J. Med. Chem.* 25(9):1106-10 (1982)), 2-oxobis(2-β-chloroethylamino)-4-,6-dimethyl-1,3,2-oxazaphosphorinane cyclophosphamide (Carpenter et al., *Phosphorus Sulfur* 12(3):287-93 (1982)), 5-fluoro- and 5-chlorocyclophosphamide (Foster et al., *J. Med. Chem.* 24(12):1399-403 (1981)), cis- and trans-4-phenylcyclophosphamide (Boyd et al., *J. Med. Chem.* 23(4):372-5 (1980)), 5-bromocyclophosphamide, 3,5-dehydrocyclophosphamide (Ludeman et al., *J. Med. Chem.* 22(2):151-8 (1979)), 4-ethoxycarbonyl cyclophosphamide analogues (Foster, *J. Pharm. Sci.* 67(5):709-10 (1978)), arylaminotetrahydro-2H-1,3,2-oxazaphosphorine 2-oxide cyclophosphamide analogues (Hamacher, *Arch. Pharm.* (Weinheim, Ger.) 310(5):J, 428-34 (1977)), NSC-26271 cyclophosphamide analogues (Montgomery & Struck, *Cancer Treat. Rep.* 60(4):J381-93 (1976)), benzo annulated cyclophosphamide analogues (Ludeman & Zon, *J. Med. Chem.* 18(12):J1251-3 (1975)), 6-trifluoromethylcyclophosphamide (Farmer & Cox, *J. Med. Chem.* 18(11):J1106-10 (1975)), 4-methylcyclophosphamide and 6-methycyclophosphamide analogues (Cox et al., *Biochem. Pharmacol.* 24(5):J599-606 (1975)); FCE 23762 doxorubicin derivative (Quaglia et al., *J. Liq. Chromatogr.* 17(18):3911-3923 (1994)), annamycin (Zou et al., *J. Pharm. Sci.* 82(11):1151-1154 (1993)), ruboxyl (Rapoport et al., *J. Controlled Release* 58(2):153-162 (1999)), anthracycline disaccharide doxorubicin analogue (Pratesi et al., *Clin. Cancer Res.* 4(11):2833-2839 (1998)), N-(trifluoroacetyl)doxorubicin and 4'-O-acetyl-N-(trifluoroacetyl)doxorubicin (Berube & Lepage, *Synth. Commun.* 28(6):1109-1116 (1998)), 2-pyrrolinodoxorubicin (Nagy et al., *Proc. Nat'l Acad. Sci. U.S.A.* 95(4):1794-1799 (1998)), disaccharide doxorubicin analogues (Arcamone et al., *J. Nat'l Cancer Inst.* 89(16): 1217-1223 (1997)), 4-demethoxy-7-O-(2,6-dideoxy-4-O-(2,3,6-trideoxy-3-amino-α-L-lyxo-hexopyranosyl)-α-L-lyxo-hexopyranosyl)adriamicinone doxorubicin disaccharide analogue (Monteagudo et al., *Carbohydr. Res.* 300(1): 11-16 (1997)), 2-pyrrolinodoxorubicin (Nagy et al., *Proc. Nat'l Acad. Sci. U.S.A.* 94(2):652-656 (1997)), morpholinyl doxorubicin analogues (Duran et al., *Cancer Chemother. Pharmacol.* 38(3):210-216 (1996)), enaminomalonyl-β-alanine doxorubicin derivatives (Seitz et al., *Tetrahedron Lett.* 36(9):1413-16 (1995)), cephalosporin doxorubicin derivatives (Vrudhula et al., *J. Med. Chem.* 38(8):1380-5 (1995)), hydroxyrubicin (Solary et al., *Int. J. Cancer* 58(1):85-94, 1994), methoxymorpholino doxorubicin derivative (Kuhl et al., *Cancer Chemother. Pharmacol.* 33(1):10-16 (1993)), (6-maleimidocaproyl)hydrazone doxorubicin derivative (Willner et al., *Bioconjugate Chem.* 4(6):521-7 (1993)), N-(5, 5-diacetoxypent-1-yl)doxorubicin (Chemf & Farquhar, *J. Med. Chem.* 35(17):3208-14 (1992)), FCE 23762 methoxymorpholinyl doxorubicin derivative (Ripamonti et al., *Br. J. Cancer* 65(5):703-7 (1992)), N-hydroxysuccinimide ester doxorubicin derivatives (Demant et al., *Biochim. Biophys. Acta* 1118(1):83-90 (1991)), polydeoxynucleotide doxorubicin derivatives (Ruggiero et al., *Biochim. Biophys. Acta* 1129 (3):294-302 (1991)), morpholinyl doxorubicin derivatives (EPA 434960), mitoxantrone doxorubicin analogue (Krapcho et al., *J. Med. Chem.* 34(8):2373-80 (1991)), AD198 doxorubicin analogue (Traganos et al., *Cancer Res.* 51(14):3682-9 (1991)), 4-demethoxy-3'-N-trifluoroacetyldoxorubicin (Horton et al., *Drug Des. Delivery* 6(2):123-9 (1990)), 4'-epidoxorubicin (Drzewoski et al., *Pol J. Pharmacol. Pharm.* 40(2):159-65 (1988; Weenen et al., *Eur. J. Cancer Clin. Oncol.* 20(7):919-26 (1984)), alkylating cyanomorpholino doxorubicin derivative (Scudder et al., *J. Nat'l Cancer Inst.* 80(16):1294-8 (1988)), deoxydihydroiodooxorubicin (EPA 275966), adriblastin (Kalishevskaya et al., *Vestn. Mosk. Univ.* (*Biol.* 1) 16:21-7 (1988)), 4'-deoxydoxorubicin (Schoelzel et al., *Leuk. Res.* 10(12):1455-9 (1986)), 4-demethyoxy-4'-o-methyldoxorubicin (Giuliani et al., *Proc. Int. Congr. Chemother.* 16:285-70-285-77 (1983)), 3'-deamino-3'-hydroxydoxorubicin (Horton et al., *J. Antibiot.* 37(8):853-8 (1984)), 4-demethyoxy doxorubicin analogues (Barbieri et al., *Drugs Exp. Clin. Res.* 10(2):85-90 (1984)), N-L-leucyl doxorubicin derivatives (Trouet et al., *Anthracyclines* (Proc. Int. Symp. Tumor Pharmacother.) 179-81 (1983)), 3'-deamino-3'-(4-methoxy-1-piperidinyl) doxorubicin derivatives (U.S. Pat. No. 4,314,054), 3'-deamino-3'-(4-mortholinyl)doxorubicin derivatives (U.S. Pat. No. 4,301, 277), 4'-deoxydoxorubicin and 4'-o-methyldoxorubicin (Giuliani et al., *Int. J. Cancer* 27(1):5-13 (1981)), aglycone doxorubicin derivatives (Chan & Watson, *J. Pharm. Sci.* 67(12):1748-52 (1978)), SM 5887 (*Pharma Japan* 1468:20, (1995)), MX-2 (*Pharma Japan* 1420:19 (1994)), 4'-deoxy-13 (S)-dihydro-4'-iododoxorubicin (EP 275966), morpholinyl doxorubicin derivatives (EPA 434960), 3'-deamino-3'-(4-methoxy-1-piperidinyl)doxorubicin derivatives (U.S. Pat. No. 4,314,054), doxorubicin-14-valerate, morpholinodoxorubicin (U.S. Pat. No. 5,004,606), 3'-deamino-3'-(3"-cyano-4"-morpholinyl doxorubicin; 3'-deamino-3'-(3"-cyano-4"-morpholinyl)-3-dihydroxorubicin; (3'-deamino-3'-(3"-cyano-4"-morpholinyl)daunorubicin; 3'-deamino-3'-(3"-cyano-4"-morpholinyl)-3-dihydrodaunorubicin; and 3'-deamino-3'-(4"-morpholinyl-5-iminodoxorubicin and derivatives (U.S. Pat. No. 4,585,859), 3'-deamino-3'-(4-methoxy-1-piperidinyl)doxorubicin derivatives (U.S. Pat. No. 4,314,054) and 3-deamino-3-(4-morpholinyl)doxorubicin derivatives (U.S. Pat. No. 4,301,277); 4,5-dimethylmisonidazole (Born et al., *Biochem. Pharmacol.* 43(6):1337-44 (1992)), azo and azoxy misonidazole derivatives (Gattavecchia & Tonelli, *Int. J. Radiat. Biol. Relat. Stud. Phys., Chem. Med.* 45(5):469-77 (1984)); RB90740 (Wardman et al., *Br. J. Cancer,* 74 Suppl. 27:S70-S74 (1996)); 6-bromo and 6-chloro-2,3-dihydro-1,4-benzothiazines nitrosourea derivatives (Rai et al., *Heterocycl. Commun.* 2(6):587-592 (1996)), diamino acid nitrosourea derivatives (Dulude et al., *Bioorg. Med. Chem. Lett.* 4(22):2697-700 (1994); Dulude et al., *Bioorg. Med. Chem.* 3(2):151-60 (995), amino acid nitrosourea derivatives (Zheleva et al., *Pharmazie* 50(1):25-6 (1995)), 3',4'-didemethoxy-3',4'-dioxo-4-deoxypodophyllotoxin nitrosourea derivatives (Miyahara et al., *Heterocycles* 39(1):361-9 (1994)), ACNU (Matsunaga et al., *Immunopharmacology* 23(3):199-204 (1992)), tertiary phosphine oxide nitrosourea derivatives (Guguva et al., *Pharmazie* 46(8):603 (1991)), sulfamerizine and sulfamethizole nitrosourea derivatives (Chiang et al., *Zhonghua Yaozue Zazhi* 43(5): 401-6 (1991)), thymidine nitrosourea analogues (Zhang et al., *Cancer Commun.* 3(4):119-26, 1991), 1,3-bis(2-chloroethyl)-1-nitrosourea (August et al., *Cancer Res.* 51(6):1586-90 (1991)), 2,2,6,6-tetramethyl-1-oxopiperidiunium nitrosourea derivatives (U.S.S.R. 1261253), 2- and 4-deoxy sugar nitrosourea derivatives (U.S. Pat. No. 4,902,791), nitroxyl nitrosourea derivatives (U.S.S.R. 1336489), fotemustine (Boutin et al., *Eur. J. Cancer Clin. Oncol.* 25(9): 1311-16 (1989)), pyrimidine (II) nitrosourea derivatives (Wei et al., *Chung-hua Yao Hsueh Tsa Chih* 41(1):19-26 (1989)), CGP 6809 (Schieweck et al., *Cancer Chemother. Pharmacol.* 23(6):341-7 (1989)), B-3839 (Prajda et al., *In Vivo* 2(2): 151-4 (1988)), 5-halogenocytosine nitrosourea derivatives (Chiang & Tseng, *T'ai-wan Yao Hsueh Tsa Chih* 38(1):37-43 (1986)), 1-(2-chloroethyl)-3-isobutyl-3-(β-maltosyl)-1-nitrosourea (Fujimoto & Ogawa, *J. Pharmacobio-Dyn.* 10(7): 341-5 (1987)), sulfur-containing nitrosoureas (Tang et al., *Yaoxue Xuebao* 21(7):502-9, 1986), sucrose, 6-((((2-chloroethyl)nitrosoamino-)carbonyl)amino)-6-deoxysucrose (NS-1C) and 6'-((((2-chloroethyl)nitrosoamino)carbonyl)amino)-

6'-deoxysucrose (NS-1D) nitrosourea derivatives (Tanoh et al., *Chemotherapy* (Tokyo) 33(11):969-77 (1985)), CNCC, RFCNU and chlorozotocin (Mena et al., *Chemotherapy* (Basel) 32(2):131-7 (1986)), CNUA (Edanami et al., *Chemotherapy* (Tokyo) 33(5):455-61 (1985)), 1-(2-chloroethyl)-3-isobutyl-3-(β-maltosyl)-1-nitrosourea (Fujimoto & Ogawa, *Jpn. J. Cancer Res.* (*Gann*) 76(7):651-6 (1985)), choline-like nitrosoalkylureas (Belyaev et al., *Izv. Akad. NA UK SSSR, Ser. Khim.* 3:553-7 (1985)), sucrose nitrosourea derivatives (JP 84219300), sulfa drug nitrosourea analogues (Chiang et al., *Proc. Nat'l Sci. Counc., Repub. China, Part A* 8(1):18-22 (1984)), DONU (Asanuma et al., *J Jpn. Soc. Cancer Ther.* 17(8):2035-43 (1982)), N,N'-bis(N-(2-chloroethyl)-N-nitrosocarbamoyl)cystamine (CNCC) (Blazsek et al., *Toxicol. Appl. Pharmacol.* 74(2):250-7 (1984)), dimethylnitrosourea (Krutova et al., *Izv. Akad. NA UK SSSR, Ser. Biol.* 3:439-45 (1984)), GANU (Sava & Giraldi, *Cancer Chemother. Pharmacol.* 10(3):167-9 (1983)), CCNU (Capelli et al., *Med., Biol., Environ.* 11(1):111-16 (1983)), 5-aminomethyl-2'-deoxyuridine nitrosourea analogues (Shiau, *Shih Ta Hsueh Pao* (Taipei) 27:681-9 (1982)), TA-077 (Fujimoto & Ogawa, *Cancer Chemother. Pharmacol.* 9(3):134-9 (1982)), gentianose nitrosourea derivatives (JP 82 80396), CNCC, RFCNU, RPCNU AND chlorozotocin (CZT) (Marzin et al., *INSERM Symp.* (Nitrosoureas Cancer Treat.) 19:165-74 (1981)), thiocolchicine nitrosourea analogues (George, *Shih Ta Hsueh Pao* (Taipei) 25:355-62 (1980)), 2-chloroethyl-nitrosourea (Zeller & Eisenbrand, *Oncology* 38(1):39-42 (1981)), ACNU, (1-(4-amino-2-methyl-5-pyrimidinyl)methyl-3-(2-chloroethyl)-3-nitrosourea hydrochloride) (Shibuya et al., *Gan To Kagaku Ryoho* 7(8):1393-401 (1980)), N-deacetylmethyl thiocolchicine nitrosourea analogues (Lin et al., *J. Med. Chem.* 23(12):1440-2 (1980)), pyridine and piperidine nitrosourea derivatives (Crider et al., *J. Med. Chem.* 23(8):848-51 (1980)), methyl-CCNU (Zimber & Perk, *Refu. Vet.* 35(1):28 (1978)), phensuzimide nitrosourea derivatives (Crider et al., *J. Med. Chem.* 23(3): 324-6 (1980)), ergoline nitrosourea derivatives (Crider et al., *J. Med. Chem.* 22(1):32-5 (1979)), glucopyranose nitrosourea derivatives (JP 78 95917), 1-(2-chloroethyl)-3-cyclohexyl-1-nitrosourea (Farmer et al., *J. Med. Chem.* 21(6): 514-20 (1978)), 4-(3-(2-chloroethyl)-3-nitrosoureid-o)-cis-cyclohexanecarboxylic acid (Drewinko et al., *Cancer Treat. Rep.* 61(8):J1513-18 (1977)), RPCNU (ICIG 1163) (Larnicol et al., *Biomedicine* 26(3):J176-81 (1977)), IOB-252 (Sorodoc et al., *Rev. Roum. Med., Virol.* 28(1):J55-61 (1977)), 1,3-bis (2-chloroethyl)-1-nitrosourea (BCNU) (Siebert & Eisenbrand, *Mutat. Res.* 42(1):J45-50 (1977)), 1-tetrahydroxycyclopentyl-3-nitroso-3-(2-chloroethyl)-urea (U.S. Pat. No. 4,039,578), d-1-1-(β-chloroethyl)-3-(2-oxo-3-hexahydroazepinyl)-1-nitrosourea (U.S. Pat. No. 3,859,277) and gentianose nitrosourea derivatives (JP 57080396); 6-S-aminoacyloxymethyl mercaptopurine derivatives (Harada et al., *Chem. Pharm. Bull.* 43(10):793-6 (1995)), 6-mercaptopurine (6-MP) (Kashida et al., *Biol. Pharm. Bull.* 18(11):1492-7 (1995)), 7,8-polymethyleneimidazo-1,3,2-diazaphosphorines (Nilov et al., *Mendeleev Commun.* 2:67 (1995)), azathioprine (Chifotides et al., *J. Inorg. Biochem.* 56(4):249-64 (1994)), methyl-D-glucopyranoside mercaptopurine derivatives (Da Silva et al., *Eur. J. Med. Chem.* 29(2): 149-52 (1994)) and s-alkynyl mercaptopurine derivatives (Ratsino et al., *Khim.-Farm. Zh.* 15(8):65-7 (1981)); indoline ring and a modified ornithine or glutamic acid-bearing methotrexate derivatives (Matsuoka et al., *Chem. Pharm. Bull.* 45(7):1146-1150 (1997)), alkyl-substituted benzene ring C bearing methotrexate derivatives (Matsuoka et al., *Chem. Pharm. Bull.* 44(12):2287-2293 (1996)), benzoxazine or benzothiazine moiety-bearing methotrexate derivatives (Matsuoka et al., *J. Med. Chem.* 40(1):105-111 (1997)), 10-deazaminopterin analogues (DeGraw et al., *J. Med. Chem.* 40(3):370-376 (1997)), 5-deazaminopterin and 5,10-dideazaminopterin methotrexate analogues (Piper et al., *J. Med. Chem.* 40(3): 377-384 (1997)), indoline moiety-bearing methotrexate derivatives (Matsuoka et al., *Chem. Pharm. Bull* 44(7):1332-1337 (1996)), lipophilic amide methotrexate derivatives (Pignatello et al., World Meet. Pharm. Biopharm. Pharm. Technol., 563-4, 1995), L-threo-(2S,4S)-4-fluoroglutamic acid and DL-3,3-difluoroglutamic acid-containing methotrexate analogues (Hart et al., *J. Med. Chem.* 39(1):56-65 (1996)), methotrexate tetrahydroquinazoline analogue (Gangjee, et al., *J. Heterocycl. Chem.* 32(1):243-8 (1995)), N-(ca-aminoacyl)methotrexate derivatives (Cheung et al., *Pteridines* 3(1-2):101-2 (1992)), biotin methotrexate derivatives (Fan et al., *Pteridines* 3(1-2):131-2 (1992)), D-glutamic acid or D-erythrou, threo-4-fluoroglutamic acid methotrexate analogues (McGuire et al., *Biochem. Pharmacol.* 42(12):2400-3, 1991), β,γ-μethano methotrexate analogues (Rosowsky et al., *Pteridines* 2(3):133-9, 1991), 10-deazaminopterin (10-EDAM) analogue (Braakhuis et al., *Chem. Biol. Pteridines, Proc. Int. Symp. Pteridines Folic Acid Deriv.* 1027-30 (1989)), γ-tetrazole methotrexate analogue (Kalman et al., *Chem. Biol. Pteridines, Proc. Int. Symp. Pteridines Folic Acid Deriv.* 1154-7 (1989)), N-(L-α-aminoacyl)methotrexate derivatives (Cheung et al., *Heterocycles* 28(2):751-8 (1989)), meta and ortho isomers of aminopterin (Rosowsky et al., *J. Med. Chem.* 32(12):2582 (1989)), hydroxymethylmethotrexate (DE 267495), γ-fluoromethotrexate (McGuire et al., *Cancer Res.* 49(16):4517-25 (1989)), polyglutamyl methotrexate derivatives (Kumar et al., *Cancer Res.* 46(10):5020-3 (1986)), gem-diphosphonate methotrexate analogues (PCT Publication No. WO 88/06158), α- and γ-substituted methotrexate analogues (Tsushima et al., *Tetrahedron* 44(17):5375-87 (1988)), 5-methyl-5-deaza methotrexate analogues (U.S. Pat. No. 4,725,687), Nδ-acyl-Nα-(4-amino-4-deoxypteroyl)-L-ornithine derivatives (Rosowsky et al., *J. Med. Chem.* 31(7):1332-7 (1988)), 8-deaza methotrexate analogues (Kuehl et al., *Cancer Res.* 48(6):1481-8 (1988)), acivicin methotrexate analogue (Rosowsky et al., *J. Med. Chem.* 30(8):1463-9 (1987)), polymeric platinol methotrexate derivative (Carraher et al., *Polym. Sci. Technol.* (*Plenum*) (*Adv. Biomed. Polym.*) 35:311-24 (1987)), methotrexate-γ-dimyristoylphophatidylethanolamine (Kinsky et al., *Biochim. Biophys. Acta* 917(2):211-18 (1987)), methotrexate polyglutamate analogues (Rosowsky et al., *Chem. Biol. Pteridines, Pteridines Folid Acid Deriv., Proc. Int. Symp. Pteridines Folid Acid Deriv.: Chem. Biol. Clin. Aspects* 985-8 1986)), poly-γ-glutamyl methotrexate derivatives (Kisliuk et al., *Chem. Biol. Pteridines, Pteridines Folid Acid Deriv., Proc. Int. Symp. Pteridines Folid Acid Deriv.: Chem., Biol. Clin. Aspects* 989-92 (1986)), deoxyuridylate methotrexate derivatives (Webber et al., *Chem. Biol. Pteridines, Pteridines Folid Acid Deriv., Proc. Int. Symp. Pteridines Folid Acid Deriv.: Chem. Biol. Clin. Aspects* 659-62 (1986)), iodoacetyl lysine methotrexate analogue (Delcamp et al., *Chem. Biol. Pteridines, Pteridines Folid Acid Deriv., Proc. Int. Symp. Pteridines Folid Acid Deriv.: Chem. Biol. Clin. Aspects* 807-9 (1986)), 2, omega.-diaminoalkanoid acid-containing methotrexate analogues (McGuire et al., *Biochem. Pharmacol.* 35(15):2607-13 (1986)), polyglutamate methotrexate derivatives (Kamen & Winick, *Methods Enzymol.* 122:339-46 (1986)), 5-methyl-5-deaza analogues (Piper et al., *J. Med. Chem.* (*Vitam. Coenzymes, Pt. G*) 29(6):1080-7 (1986)), quinazoline methotrexate analogue (Mastropaolo et al., *J. Med. Chem.* 29(1):155-8 (1986)), pyrazine methotrexate analogue (Lever & Vestal, *J. Heterocycl.*

Chem. 22(1):5-6 (1985)), cysteic acid and homocysteic acid methotrexate analogues (U.S. Pat. No. 4,490,529), γ-tert-butyl methotrexate esters (Rosowsky et al., *J. Med. Chem.* 28(5):660-7 (1985)), fluorinated methotrexate analogues (Tsushima et al., *Heterocycles* 23(1):45-9 (1985)), folate methotrexate analogue (Trombe, *J. Bacteriol.* 160(3):849-53 (1984)), phosphonoglutamic acid analogues (Sturtz & Guillamot, *Eur. J. Med. Chem.—Chim. Ther.* 19(3):267-73 (1984)), poly (L-lysine) methotrexate conjugates (Rosowsky et al., *J. Med. Chem.* 27(7):888-93 (1984)), dilysine and trilysine methotrexate derivates (Forsch & Rosowsky, *J. Org. Chem.* 49(7):1305-9 (1984)), 7-hydroxymethotrexate (Fabre et al., *Cancer Res.* 43(10):4648-52 (1983)), poly-γ-glutamyl methotrexate analogues (Piper & Montgomery, *Adv. Exp. Med. Biol. (Folyl Antifolyl Polyglutamates)* 163):95-100 (1983)), 3',5'-dichloromethotrexate (Rosowsky & Yu, *J. Med. Chem.* 26(10):1448-52 (1983)), diazoketone and chloromethylketone methotrexate analogues (Gangjee et al., *J. Pharm. Sci.* 71(6):717-19 (1982)), 10-propargylaminopterin and alkyl methotrexate homologs (Piper et al., *J. Med. Chem.* 25(7):877-80 (1982)), lectin derivatives of methotrexate (Lin et al., *JNCI* 66(3):523-8, 1981), polyglutamate methotrexate derivatives (Galivan, *Mol. Pharmacol.* 17(1):105-10 (1980)), halogentated methotrexate derivatives (Fox, *JNCI* 58(4): J955-8 (1977)), 8-alkyl-7,8-dihydro analogues (Chaykovsky et al., *J. Med. Chem.* 20(10):J1323-7 (1977)), 7-methyl methotrexate derivatives and dichloromethotrexate (Rosowsky & Chen, *J. Med. Chem.* 17(12):J1308-11 (1974)), lipophilic methotrexate derivatives and 3',5'-dichloromethotrexate (Rosowsky, *J. Med. Chem.* 16(10):J1190-3 (1973), deaza amethopterin analogues (Montgomery et al., *Ann. N.Y. Acad. Sci.* 186:J227-34 (1971), MX068 (Pharma Japan, 1658:18 (1999)) and cysteic acid and homocysteic acid methotrexate analogues (EPA 0142220); N3-alkylated analogues of 5-fluorouracil (Kozai et al., *J. Chem. Soc., Perkin Trans.* 1(19): 3145-3146 (1998), 5-fluorouracil derivatives with 1,4-oxaheteroepane moieties (Gomez et al., *Tetrahedron* 54(43): 13295-13312 (1998), 5-fluorouracil and nucleoside analogues (Li, *Anticancer Res.* 17(1A):21-27 (1997), cis- and trans-5-fluoro-5,6-dihydro-6-alkoxyuracil (Van der Wilt et al., *Br. J. Cancer* 68(4):702-7 (1993), cyclopentane 5-fluorouracil analogues (Hronowski & Szarek, *Can. J. Chem.* 70(4):1162-9 (1992), A-OT-fluorouracil (Zhang et al., *Zongguo Yiyao Gongye Zazhi* 20(11):513-15 (1989), N4-trimethoxybenzoyl-5'-deoxy-5-fluorocytidine and 5'-deoxy-5-fluorouridine (Miwa et al., *Chem. Pharm. Bull.* 38(4):998-1003 (1990), 1-hexylcarbamoyl-5-fluorouracil (Hoshi et al., *J. Pharmacobio-Dun.* 3(9):478-81 (1980); Maehara et al., *Chemotherapy* (Basel) 34(6):484-9 (1988)), B-3839 (Prajda et al., In Vivo 2(2):151-4 (1988)), uracil-1-(2-tetrahydrofuryl)-5-fluorouracil (Anai et al., *Oncology* 45(3):144-7 (1988)), 1-(2'-deoxy-2'-fluoro-β-D-arabinofuranosyl)-5-fluorouracil (Suzuko et al., *Mol. Pharmacol.* 31(3):301-6 (1987)), doxifluridine (Matuura et al., *Oyo Yakuri* 29(5):803-31 (1985)), 5'-deoxy-5-fluorouridine (Bollag & Hartmann, *Eur. J. Cancer* 16(4):427-32 (1980)), 1-acetyl-3-O-toluoyl-5-fluorouracil (Okada, *Hiroshima J. Med. Sci.* 28(1):49-66 (1979)), 5-fluorouracil-m-formylbenzene-sulfonate (JP 55059173), N'-(2-furanidyl)-5-fluorouracil (JP 53149985) and 1-(2-tetrahydrofuryl)-5-fluorouracil (JP 52089680); 4'-epidoxorubicin (Lanius, Adv. Chemother. Gastrointest. Cancer, (Int. Symp.), 159-67 (1984)); N-substituted deacetylvinblastine amide (vindesine) sulfates (Conrad et al., *J. Med. Chem.* 22(4):391-400 (1979)); and Cu(II)-VP-16 (etoposide) complex (Tawa et al., *Bioorg. Med. Chem.* 6(7): 1003-1008 (1998)), pyrrolecarboxamidino-bearing etoposide analogues (Ji et al., *Bioorg. Med. Chem. Lett.* 7(5):607-612 (1997)), 4β-amino etoposide analogues (Hu, University of North Carolina Dissertation, 1992), γ-lactone ring-modified arylamino etoposide analogues (Zhou et al., *J. Med. Chem.* 37(2):287-92 (1994)), N-glucosyl etoposide analogue (Allevi et al., *Tetrahedron Lett.* 34(45):7313-16 (1993)), etoposide A-ring analogues (Kadow et al., *Bioorg. Med. Chem. Lett.* 2(1):17-22 (1992)), 4'-deshydroxy-4'-methyl etoposide (Saulnier et al., *Bioorg. Med. Chem. Left.* 2(10):1213-18 (1992)), pendulum ring etoposide analogues (Sinha et al., *Eur. J. Cancer* 26(5):590-3 (1990) and E-ring desoxy etoposide analogues (Saulnier et al., *J. Med. Chem.* 32(7):1418-20 (1989)).

Within one preferred embodiment of the invention, the cell cycle inhibitor is paclitaxel, a compound which disrupts mitosis (M-phase) by binding to tubulin to form abnormal mitotic spindles or an analogue or derivative thereof. Briefly, paclitaxel is a highly derivatized diterpenoid (Wani et al., *J. Am. Chem. Soc.* 93:2325 (1971)) which has been obtained from the harvested and dried bark of *Taxus brevifolia* (Pacific Yew) and *Taxomyces Andreanae* and *Endophytic Fungus* of the Pacific Yew (Stierle et al., *Science* 60:214-216 (1993)). "Paclitaxel" (which should be understood herein to include formulations, prodrugs, analogues and derivatives such as, for example, TAXOL® (Bristol Myers Squibb, New York, N.Y., TAXOTERE® (Aventis Pharmaceuticals, France), docetaxel, 10-desacetyl analogues of paclitaxel and 3'N-desbenzoyl-3'N-t-butoxy carbonyl analogues of paclitaxel) may be readily prepared utilizing techniques known to those skilled in the art (see, e.g., Schiff et al., *Nature* 277:665-667 (1979); Long and Fairchild, Cancer Research 54:4355-4361 (1994); Ringel and Horwitz, *J. Nat'l Cancer Inst.* 83(4):288-291 (1991); Pazdur et al., *Cancer Treat. Rev.* 19(4):351-386 (1993); WO 94/07882; WO 94/07881; WO 94/07880; WO 94/07876; WO 93/23555; WO 93/10076; WO 94/00156; WO 93/24476; EP 590267; WO 94/20089; U.S. Pat. Nos. 5,294, 637; 5,283,253; 5,279,949; 5,274,137; 5,202,448; 5,200,534; 5,229,529; 5,254,580; 5,412,092; 5,395,850; 5,380,751; 5,350,866; 4,857,653; 5,272,171; 5,411,984; 5,248,796; 5,248,796; 5,422,364; 5,300,638; 5,294,637; 5,362,831; 5,440,056; 4,814,470; 5,278,324; 5,352,805; 5,411,984; 5,059,699; 4,942,184; *Tetrahedron Letters* 35(52):9709-9712 (1994); *J. Med. Chem.* 35:4230-4237 (1992); *J. Med. Chem.* 34:992-998 (1991); *J. Natural Prod.* 57(10):1404-1410 (1994); *J. Natural Prod.* 57(11):1580-1583 (1994); *J. Am. Chem. Soc.* 110:6558-6560 (1988)), or obtained from a variety of commercial sources, including for example, Sigma Chemical Co., St. Louis, Mo. (T7402—from *Taxus brevifolia*).

Representative examples of paclitaxel derivatives or analogues include 7-deoxy-docetaxol, 7,8-cyclopropataxanes, N-substituted 2-azetidones, 6,7-epoxy paclitaxels, 6,7-modified paclitaxels, 10-desacetoxytaxol, 10-deacetyltaxol (from 10-deacetylbaccatin III), phosphonooxy and carbonate derivatives of taxol, taxol 2',7-di(sodium 1,2-benzenedicarboxylate, 10-desacetoxy-11,12-dihydrotaxol-10,12(18)-diene derivatives, 10-desacetoxytaxol, Protaxol (2'- and/or 7-O-ester derivatives), (2'- and/or 7-O-carbonate derivatives), asymmetric synthesis of taxol side chain, fluoro taxols, 9-deoxotaxane, (13-acetyl-9-deoxobaccatine III, 9-deoxotaxol, 7-deoxy-9-deoxotaxol, 10-desacetoxy-7-deoxy-9-deoxotaxol, Derivatives containing hydrogen or acetyl group and a hydroxy and tert-butoxycarbonylamino, sulfonated 2'-acryloyltaxol and sulfonated 2'-O-acyl acid taxol derivatives, succinyltaxol, 2'-γ-aminobutyryltaxol formate, 2'-acetyl taxol, 7-acetyl taxol, 7-glycine carbamate taxol, 2'-OH-7-PEG(5000) carbamate taxol, 2'-benzoyl and 2',7-dibenzoyl taxol derivatives, other prodrugs (2'-acetyltaxol;

2',7-diacetyltaxol; 2'succinyltaxol; 2'-(beta-alanyl)-taxol); 2'gamma-aminobutyryltaxol formate; ethylene glycol derivatives of 2'-succinyltaxol; 2'-glutaryltaxol; 2'-(N,N-dimethylglycyl)taxol; 2'-(2-(N,N-dimethylamino)propionyl)taxol; 2'orthocarboxybenzoyl taxol; 2'aliphatic carboxylic acid derivatives of taxol, Prodrugs {2'(N,N-diethylaminopropionyl)taxol, 2'(N,N-dimethylglycyl)taxol, 7(N,N-dimethylglycyl)taxol, 2',7-di-(N,N-dimethylglycyl)taxol, 7(N,N-diethylaminopropionyl)taxol, 2',7-di(N,N-diethylaminopropionyl)taxol, 2'-(L-glycyl)taxol, 7-(L-glycyl)taxol, 2',7-di(L-glycyl) taxol, 2'-(L-alanyl)taxol, 7-(L-alanyl)taxol, 2',7-di(L-alanyl) taxol, 2'-(L-leucyl)taxol, 7-(L-leucyl)taxol, 2',7-di(L-leucyl) taxol, 2'-(L-isoleucyl)taxol, 7-(L-isoleucyl)taxol, 2',7-di(L-isoleucyl)taxol, 2'-(L-valyl)taxol, 7-(L-valyl)taxol, 2'7-di(L-valyl)taxol, 2'-(L-phenylalanyl)taxol, 7-(L-phenylalanyl) taxol, 2',7-di(L-phenylalanyl)taxol, 2'-(L-prolyl)taxol, 7-(L-prolyl)taxol, 2',7-di(L-prolyl)taxol, 2'-(L-lysyl)taxol, 7-(L-lysyl)taxol, 2',7-di(L-lysyl)taxol, 2'-(L-glutamyl)taxol, 7-(L-glutamyl)taxol, 2',7-di(L-glutamyl)taxol, 2'-(L-arginyl) taxol, 7-(L-arginyl)taxol, 2',7-di(L-arginyl)taxol}, taxol analogues with modified phenylisoserine side chains, TAXOTERE®, (N-debenzoyl-N-tert-(butoxycaronyl)-10-deacetyltaxol, and taxanes (e.g., baccatin III, cephalomannine, 10-deacetylbaccatin III, brevifoliol, yunantaxusin and taxusin); and other taxane analogues and derivatives, including 14-beta-hydroxy-10 deacetybaccatin III, debenzoyl-2-acyl paclitaxel derivatives, benzoate paclitaxel derivatives, phosphonooxy and carbonate paclitaxel derivatives, sulfonated 2'-acryloyltaxol; sulfonated 2'-O-acyl acid paclitaxel derivatives, 18-site-substituted paclitaxel derivatives, chlorinated paclitaxel analogues, C4 methoxy ether paclitaxel derivatives, sulfonamide taxane derivatives, brominated paclitaxel analogues, Girard taxane derivatives, nitrophenyl paclitaxel, 10-deacetylated substituted paclitaxel derivatives, 14-beta-hydroxy-10 deacetylbaccatin III taxane derivatives, C7 taxane derivatives, C10 taxane derivatives, 2-debenzoyl-2-acyl taxane derivatives, 2-debenzoyl and -2-acyl paclitaxel derivatives, taxane and baccatin III analogues bearing new C2 and C4 functional groups, n-acyl paclitaxel analogues, 10-deacetylbaccatin III and 7-protected-10-deacetylbaccatin III derivatives from 10-deacetyl taxol A, 10-deacetyl taxol B, and 10-deacetyl taxol, benzoate derivatives of taxol, 2-aroyl-4-acyl paclitaxel analogues, orthro-ester paclitaxel analogues, 2-aroyl-4-acyl paclitaxel analogues and 1-deoxy paclitaxel and 1-deoxy paclitaxel analogues.

In one aspect, the cell cycle inhibitor is a taxane having the structure of formula (IV):

wherein the circled area may be substituted and the non-circled portion is the taxane core. A side-chain (labeled "A" in the diagram) is desirably present in order for the compound to have good activity as a cell cycle inhibitor. Examples of compounds having this structure include paclitaxel (Merck Index entry 7117), docetaxol (TAXOTERE, Merck Index entry 3458), and 3'-desphenyl-3'-(4-ntirophenyl)-N-debenzoyl-N-(t-butoxycarbonyl)-10-deacetyltaxol.

In one aspect, suitable taxanes such as paclitaxel and its analogues and derivatives are disclosed in U.S. Pat. No. 5,440,056 as having the structure of formula (V):

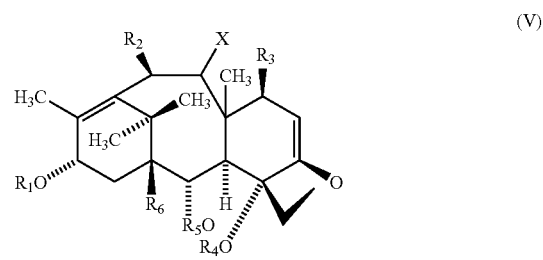

(V)

wherein X may be oxygen (paclitaxel), hydrogen (9-deoxy derivatives), thioacyl, or dihydroxyl precursors; $R_1$ is selected from paclitaxel or TAXOTERE side chains or alkanoyl having the structure of formula (VI)

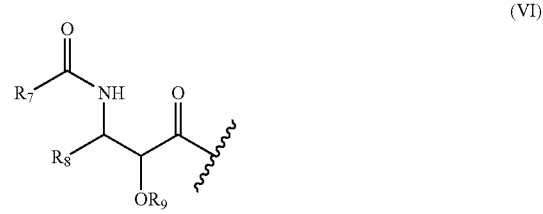

(VI)

wherein $R_7$ is selected from hydrogen, alkyl, phenyl, alkoxy, amino, phenoxy (substituted or unsubstituted); $R_8$ is selected from hydrogen, alkyl, hydroxyalkyl, alkoxyalkyl,

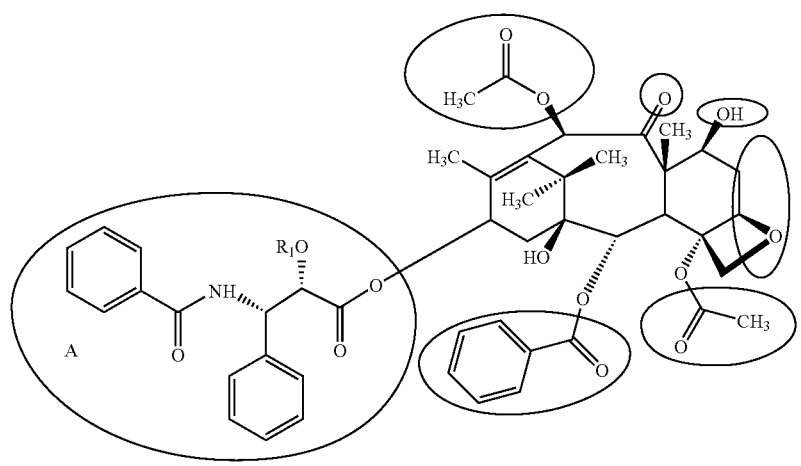

(IV)

aminoalkyl, phenyl (substituted or unsubstituted), alpha or beta-naphthyl; and $R_9$ is selected from hydrogen, alkanoyl, substituted alkanoyl, and aminoalkanoyl; where substitutions refer to hydroxyl, sulfhydryl, allalkoxyl, carboxyl, halogen, thioalkoxyl, N,N-dimethylamino, alkylamino, dialkylamino, nitro, and —$OSO_3H$, and/or may refer to groups containing such substitutions; $I_2$ is selected from hydrogen or oxygen-containing groups, such as hydrogen, hydroxyl, alkoyl, alkanoyloxy, aminoalkanoyloxy, and peptidyalkanoyloxy; $R_3$ is selected from hydrogen or oxygen-containing groups, such as hydrogen, hydroxyl, alkoyl, alkanoyloxy, aminoalkanoyloxy, and peptidyalkanoyloxy, and may further be a silyl containing group or a sulphur containing group; $R_4$ is selected from acyl, alkyl, alkanoyl, aminoalkanoyl, peptidylalkanoyl and aroyl; $R_5$ is selected from acyl, alkyl, alkanoyl, aminoalkanoyl, peptidylalkanoyl and aroyl; $R_6$ is selected from hydrogen or oxygen-containing groups, such as hydrogen, hydroxyl alkoyl, alkanoyloxy, aminoalkanoyloxy, and peptidyalkanoyloxy.

In one aspect, the paclitaxel analogues and derivatives useful as cell cycle inhibitors are disclosed in PCT International Patent Application No. WO 93/10076. As disclosed in this publication, the analogue or derivative should have a side chain attached to the taxane nucleus at $C_{13}$, as shown in the structure of formula VII, in order to confer antitumor activity to the taxane.

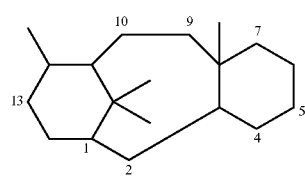

(VII)

WO 93/10076 discloses that the taxane nucleus may be substituted at any position with the exception of the existing methyl groups. The substitutions may include, for example, hydrogen, alkanoyloxy, alkenoyloxy, aryloyloxy. In addition, oxo groups may be attached to carbons labeled 2, 4, 9, and/or 10. As well, an oxetane ring may be attached at carbons 4 and 5. As well, an oxirane ring may be attached to the carbon labeled 4.

In one aspect, the taxane-based cell cycle inhibitor useful in the present invention is disclosed in U.S. Pat. No. 5,440,056, which discloses 9-deoxo taxanes. These are compounds lacking an oxo group at the carbon labeled 9 in the taxane structure shown above (formula VI). The taxane ring may be substituted at the carbons labeled 1, 7 and 10 (independently) with H, OH, O—R, or O—CO—R where R is an alkyl or an aminoalkyl. As well, it may be substituted at carbons labeled 2 and 4 (independently) with aryol, alkanoyl, aminoalkanoyl, or alkyl groups. The side chain of formula (V) may be substituted at $R_7$ and $R_8$ (independently) with phenyl rings, substituted phenyl rings, linear alkanes/alkenes, and groups containing H, O, or N. $R_9$ may be substituted with H, or a substituted or unsubstituted alkanoyl group.

Taxanes in general, and paclitaxel is particular, is considered to function as a cell cycle inhibitor by acting as an anti-microtubule agent, and more specifically as a stabilizer. These compounds have been shown useful in the treatment of proliferative disorders, including: non-small cell (NSC) lung; small cell lung; breast; prostate; cervical; endometrial; head and neck cancers.

In another aspect, the anti-microtuble agent (microtubule inhibitor) is albendazole (carbamic acid, [5-(propylthio)-1H-benzimidazol-2-yl]-, methyl ester), LY-355703 (1,4-dioxa-8,11-diazacyclohexadec-13-ene-2,5,9,12-tetrone, 10-[(3-chloro-4-methoxyphenyl)methyl]-6,6-dimethyl-3-(2-methylpropyl)-16-[(1S)-1-[(2S,3R)-3-phenyloxiranyl]ethyl]-, (3S,10R,13E,16S)—), vindesine (vincaleukoblastine, 3-(aminocarbonyl)-O4-deacetyl-3-de(methoxycarbonyl)-), or WAY-174286

In another aspect, the cell cycle inhibitor is a vinca alkaloid. Vinca alkaloids have the following general structure of formulas (VIII) and (IX). They are indole-dihydroindole dimers.

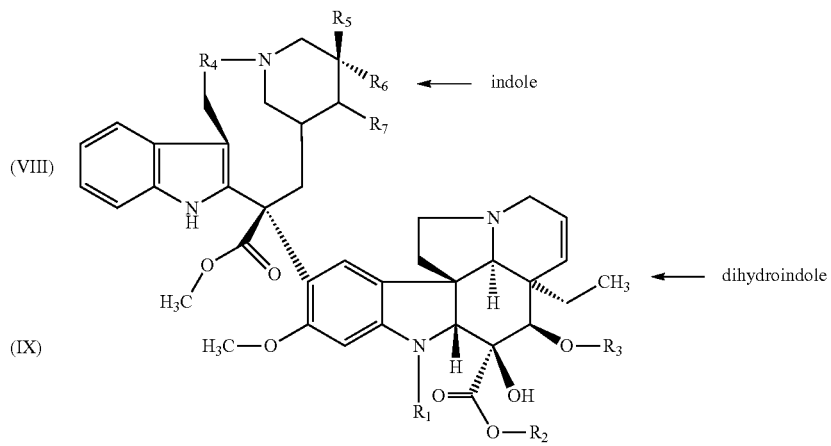

As disclosed in U.S. Pat. Nos. 4,841,045 and 5,030,620, $R_1$ can be a formyl or methyl group or alternately H. $R_1$ can also be an alkyl group or an aldehyde-substituted alkyl (e.g., $CH_2CHO$). $R_2$ is typically a $CH_3$ or $NH_2$ group; however it can be alternately substituted with a lower alkyl ester or the ester linking to the dihydroindole core may be substituted with C(O)—R where R is $NH_2$, an amino acid ester or a peptide ester. $R_3$ is typically $C(O)CH_3$, $CH_3$ or H. Alternately, a protein fragment may be linked by a bifunctional group, such as maleoyl amino acid. $R_3$ can also be substituted to form an alkyl ester which may be further substituted. $R_4$ may be —$CH_2$— or a single bond. $R_5$ and $R_6$ may be H, OH or a lower alkyl, typically —$CH_2CH_3$. Alternatively $R_6$ and $R_7$ may together form an oxetane ring. $R_7$ may alternately be H. Further substitutions include molecules wherein methyl groups are substituted with other alkyl groups, and whereby unsaturated rings may be derivatized by the addition of a side group such as an alkane, alkene, alkyne, halogen, ester, amide, or amino group.

Exemplary vinca alkaloids are vinblastine, vincristine, vincristine sulfate, vindesine, and vinorelbine, having the structures of formula (X):

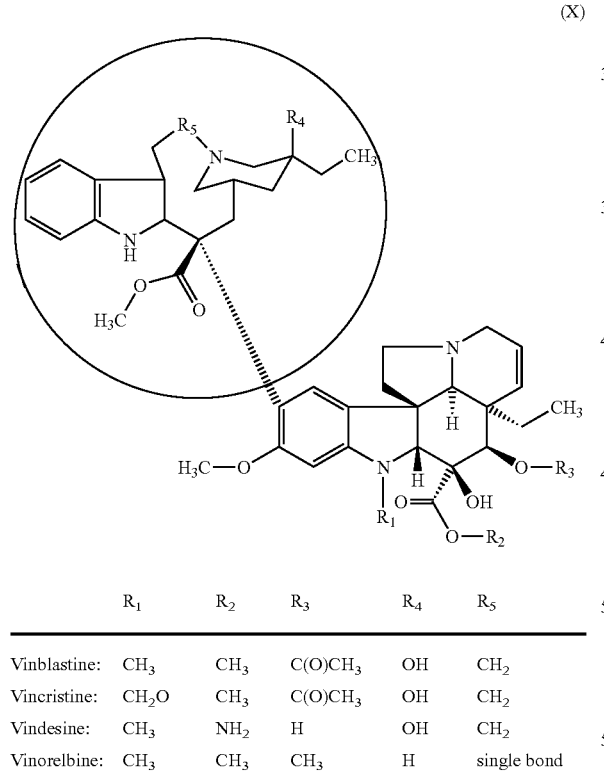

(X)

| | $R_1$ | $R_2$ | $R_3$ | $R_4$ | $R_5$ |
|---|---|---|---|---|---|
| Vinblastine: | $CH_3$ | $CH_3$ | $C(O)CH_3$ | OH | $CH_2$ |
| Vincristine: | $CH_2O$ | $CH_3$ | $C(O)CH_3$ | OH | $CH_2$ |
| Vindesine: | $CH_3$ | $NH_2$ | H | OH | $CH_2$ |
| Vinorelbine: | $CH_3$ | $CH_3$ | $CH_3$ | H | single bond |

Analogues typically require the side group (circled area) in order to have activity. These compounds are thought to act as cell cycle inhibitors by functioning as anti-microtubule agents, and more specifically to inhibit polymerization. These compounds have been shown useful in treating proliferative disorders, including NSC lung; small cell lung; breast; prostate; brain; head and neck; retinoblastoma; bladder; and penile cancers; and soft tissue sarcoma.

In another aspect, the cell cycle inhibitor is a camptothecin, or an analog or derivative thereof. Camptothecins have the following general structure of formula (XI):

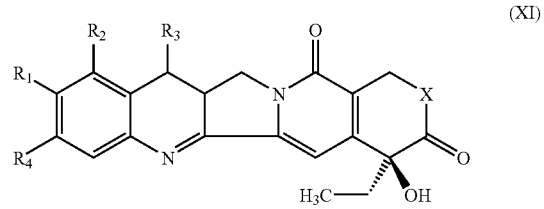

(XI)

In this structure, X is typically O, but can be other groups, e.g., NH in the case of 21-lactam derivatives. $R_1$ is typically H or OH, but may be other groups, e.g., a terminally hydroxylated $C_{1-3}$ alkane. $R_2$ is typically H or an amino containing group such as $(CH_3)_2NHCH_2$, but may be other groups e.g., $NO_2$, $NH_2$, halogen (as disclosed in, e.g., U.S. Pat. No. 5,552,156) or a short alkane containing these groups. $R_3$ is typically H or a short alkyl such as $C_2H_5$. $R_4$ is typically H but may be other groups, e.g., a methylenedioxy group with $R_1$.

Exemplary camptothecin compounds include topotecan, irinotecan (CPT-11), 9-aminocamptothecin, 21-lactam-20 (S)-camptothecin, 10,11-methylenedioxycamptothecin, SN-38, 9-nitrocamptothecin, 10-hydroxycamptothecin. Exemplary compounds have the structures of formula (XII):

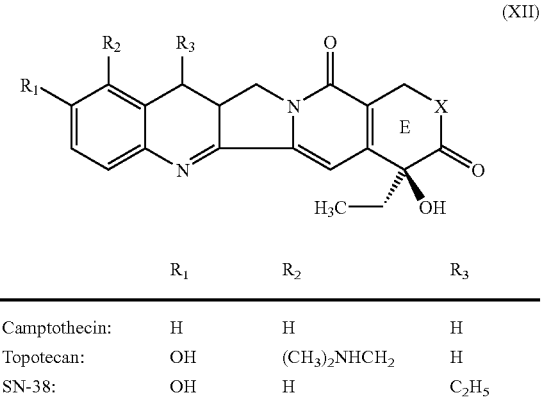

(XII)

| | $R_1$ | $R_2$ | $R_3$ |
|---|---|---|---|
| Camptothecin: | H | H | H |
| Topotecan: | OH | $(CH_3)_2NHCH_2$ | H |
| SN-38: | OH | H | $C_2H_5$ |

X: O for most analogs, NH for 21-lactam analogs

Camptothecins have the five rings shown here. The ring labeled E must be intact (the lactone rather than carboxylate form) for maximum activity and minimum toxicity. These compounds are useful to as cell cycle inhibitors, where they can function as topoisomerase I inhibitors and/or DNA cleavage agents. They have been shown useful in the treatment of proliferative disorders, including, for example, NSC lung; small cell lung; and cervical cancers.

In another aspect, the cell cycle inhibitor is a podophyllotoxin, or a derivative or an analogue thereof. Exemplary compounds of this type are etoposide or teniposide, which have the following structures of formula (XIII):

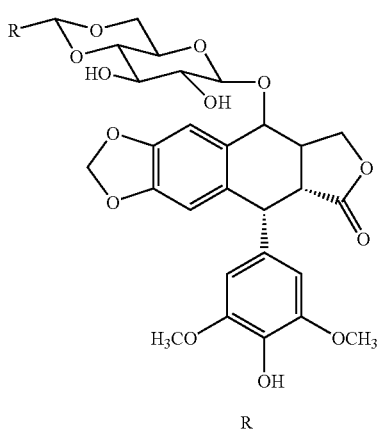

| Etoposide | CH₃ |
| Teniposide | 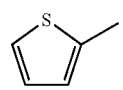 |

These compounds are thought to function as cell cycle inhibitors by being topoisomerase II inhibitors and/or by DNA cleaving agents. They have been shown useful as antiproliferative agents in, e.g., small cell lung, prostate, and brain cancers, and in retinoblastoma.

Another example of a DNA topoisomerase inhibitor is lurtotecan dihydrochloride (11H-1,4-dioxino[2,3-g]pyrano[3',4':6,7]indolizino[1,2-b]quinoline-9,12(8H, 14H)-dione, 8-ethyl-2,3-dihydro-8-hydroxy-15-[(4-methyl-1-piperazinyl)methyl]-, dihydrochloride, (S)—).

In another aspect, the cell cycle inhibitor is an anthracycline. Anthracyclines have the following general structure of formula (XIV), where the R groups may be a variety of organic groups:

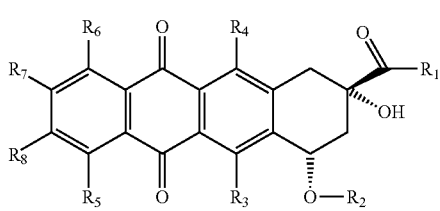

According to U.S. Pat. No. 5,594,158, suitable R groups are: $R_1$ is $CH_3$ or $CH_2OH$; $R_2$ is daunosamine or H; $R_3$ and $R_4$ are independently one of OH, $NO_2$, $NH_2$, F, Cl, Br, I, CN, H or groups derived from these; $R_{5-7}$ are all H or $R_5$ and $R_6$ are H and $R_7$ and R are alkyl or halogen, or vice versa: $R_7$ and $R_8$ are H and $R_5$ and $R_6$ are alkyl or halogen.

According to U.S. Pat. No. 5,843,903, $R_2$ may be a conjugated peptide. According to U.S. Pat. Nos. 4,215,062 and 4,296,105, $R_5$ may be OH or an ether linked alkyl group. $R_1$ may also be linked to the anthracycline ring by a group other than C(O), such as an alkyl or branched alkyl group having the C(O) linking moiety at its end, such as —$CH_2CH(CH_2$—X)C(O)—$R_1$, wherein X is H or an alkyl group (see, e.g., U.S. Pat. No. 4,215,062). $R_2$ may alternately be a group linked by the functional group =N—NHC(O)—Y, where Y is a group such as a phenyl or substituted phenyl ring. Alternately $R_3$ may have the following structure of formula (XV):

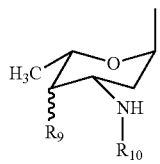

wherein $R_9$ is OH either in or out of the plane of the ring, or is a second sugar moiety such as $R_3$. $R_{10}$ may be H or form a secondary amine with a group such as an aromatic group, saturated or partially saturated 5 or 6 membered heterocyclic having at least one ring nitrogen (see U.S. Pat. No. 5,843,903).

Alternately, $R_{10}$ may be derived from an amino acid, having the structure —C(O)CH(NHR$_{11}$)(R$_{12}$), in which $R_{11}$ is H, or forms a $C_{3-4}$ membered alkylene with $R_{12}$. $R_{12}$ may be H, alkyl, aminoalkyl, amino, hydroxy, mercapto, phenyl, benzyl or methylthio (see U.S. Pat. No. 4,296,105).

Exemplary anthracyclines are doxorubicin, daunorubicin, idarubicin, epirubicin, pirarubicin, zorubicin, and carubicin. Suitable compounds have the structures of formula (XVI):

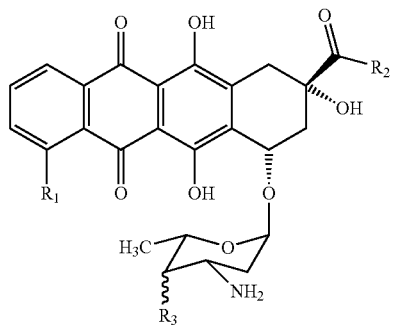

| | $R_1$ | $R_2$ | $R_3$ |
|---|---|---|---|
| Doxorubicin: | OCH₃ | CH₂OH | OH out of ring plane |
| Epirubicin: (4' epimer of doxorubicin) | OCH₃ | CH₂OH | OH in ring plane |
| Daunorubicin: | OCH₃ | CH₃ | OH out of ring plane |
| Idarubicin: | H | CH₃ | OH out of ring plane |
| Pirarubicin | OCH₃ | OH | A |
| Zorubicin | OCH₃ | =N—NHCO(O)C₆H₅ | B |
| Carubicin | OH | CH₃ | B |

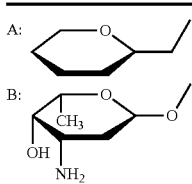

Other suitable anthracyclines are anthramycin, mitoxantrone, menogaril, nogalamycin, aclacinomycin A, olivomycin A, chromomycin A₃, and plicamycin having the structures:

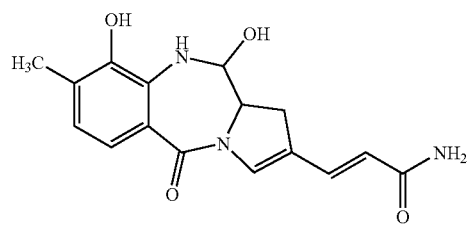
Anthramycin
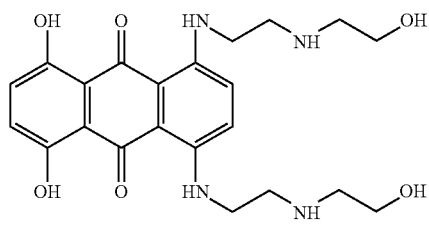
Mitoxantrone
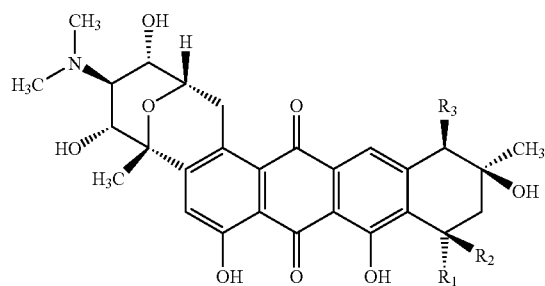
| | $R_1$ | $R_2$ | $R_3$ |
|---|---|---|---|
| Menogaril | H | $OCH_3$ | H |
| Nogalamycin | O-sugar | H | $COOCH_3$ |
sugar: 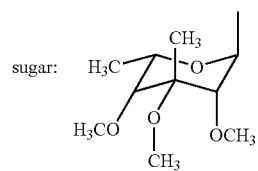
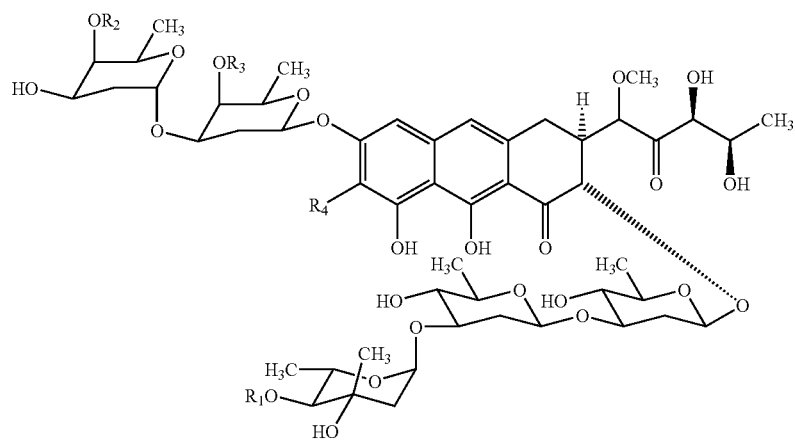

|  | $R_1$ | $R_2$ | $R_3$ | $R_4$ |
|---|---|---|---|---|
| Olivomycin A | COCH(CH$_3$)$_2$ | CH$_3$ | COCH$_3$ | H |
| Chromomycin A$_3$ | COCH$_3$ | CH$_3$ | COCH$_3$ | CH$_3$ |
| Plicamycin | H | H | H | CH$_3$ |

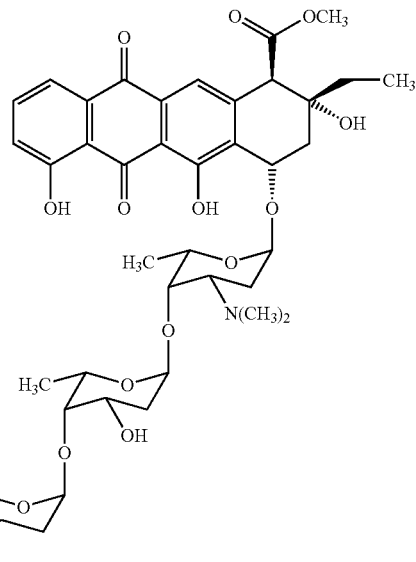

Aclacinomycin A

These compounds are thought to function as cell cycle inhibitors by being topoisomerase inhibitors and/or by DNA cleaving agents. They have been shown useful in the treatment of proliferative disorders, including small cell lung; breast; endometrial; head and neck; retinoblastoma; liver; bile duct; islet cell; and bladder cancers; and soft tissue sarcoma.

In another aspect, the cell cycle inhibitor is a platinum compound. In general, suitable platinum complexes may be of Pt(II) or Pt(IV) and have this basic structure of formula (XVII):

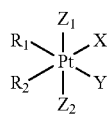

(XVII)

wherein X and Y are anionic leaving groups such as sulfate, phosphate, carboxylate, and halogen; $R_1$ and $R_2$ are alkyl, amine, amino alkyl any may be further substituted, and are basically inert or bridging groups. For Pt(II) complexes $Z_1$ and $Z_2$ are non-existent. For Pt(IV) $Z_1$ and $Z_2$ may be anionic groups such as halogen, hydroxy, carboxylate, ester, sulfate or phosphate. See, e.g., U.S. Pat. Nos. 4,588,831 and 4,250,189.

Suitable platinum complexes may contain multiple Pt atoms. See, e.g., U.S. Pat. Nos. 5,409,915 and 5,380,897. For example bisplatinum and triplatinum complexes of the type:

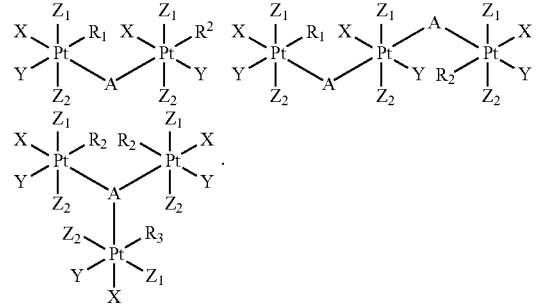

Exemplary platinum compounds are cisplatin, carboplatin, oxaliplatin, and miboplatin having the structures:

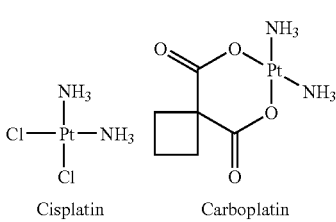

Cisplatin          Carboplatin

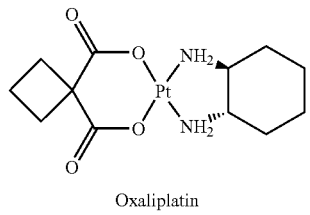

Oxaliplatin

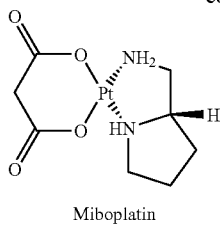

Miboplatin

These compounds are thought to function as cell cycle inhibitors by binding to DNA, i.e., acting as alkylating agents of DNA. These compounds have been shown useful in the treatment of cell proliferative disorders, including, e.g., NSC lung; small cell lung; breast; cervical; brain; head and neck; esophageal; retinoblastom; liver; bile duct; bladder; penile; and vulvar cancers; and soft tissue sarcoma.

In another aspect, the cell cycle inhibitor is a nitrosourea. Nitrosourease have the following general formula (XVIII), where typical R groups are shown below.

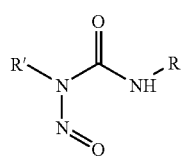

(XVIII)

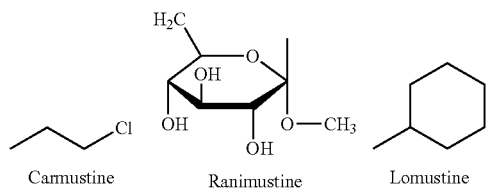

Carmustine    Ranimustine    Lomustine

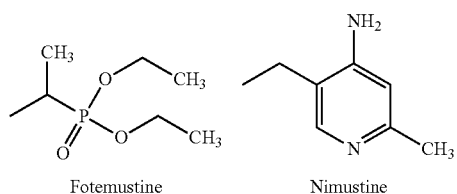

Fotemustine    Nimustine

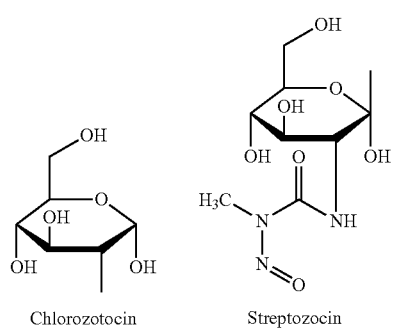

Chlorozotocin    Streptozocin

Other suitable R groups include cyclic alkanes, alkanes, halogen substituted groups, sugars, aryl and heteroaryl groups, phosphonyl and sulfonyl groups. As disclosed in U.S. Pat. No. 4,367,239, R may suitably be $CH_2$—$C(X)(Y)(Z)$, wherein X and Y may be the same or different members of the following groups: phenyl, cyclyhexyl, or a phenyl or cyclohexyl group substituted with groups such as halogen, lower alkyl ($C_{1-4}$), trifluore methyl, cyano, phenyl, cyclohexyl, lower alkyloxy ($C_{1-4}$), Z has the following structure: -alkylene-N—$R_1R_2$, where $R_1$ and $R_2$ may be the same or different members of the following group: lower alkyl ($C_{1-4}$) and benzyl, or together $R_1$ and $R_2$ may form a saturated 5 or 6 membered heterocyclic such as pyrrolidine, piperidine, morfoline, thiomorfoline, N-lower alkyl piperazine, where the heterocyclic may be optionally substituted with lower alkyl groups.

As disclosed in U.S. Pat. No. 6,096,923, R and R' of formula (XVI) may be the same or different, where each may be a substituted or unsubstituted hydrocarbon having 1-10 carbons. Substitutions may include hydrocarbyl, halo, ester, amide, carboxylic acid, ether, thioether, and alcohol groups. As disclosed in U.S. Pat. No. 4,472,379, R of formula (XVI) may be an amide bond and a pyranose structure (e.g., methyl 2'-(N—(N-(2-chloroethyl)-N-nitroso-carbamoyl)-glycyl) amino-2'-deoxy-α-D-glucopyranoside). As disclosed in U.S. Pat. No. 4,150,146, R of formula (XVI) may be an alkyl group of 2 to 6 carbons and may be substituted with an ester, sulfonyl, or hydroxyl group. It may also be substituted with a carboxylic acid or $CONH_2$ group.

Exemplary nitrosoureas are BCNU (carmustine), methyl-CCNU (semustine), CCNU (lomustine), ranimustine, nimustine, chlorozotocin, fotemustine, and streptozocin, having the following structures:

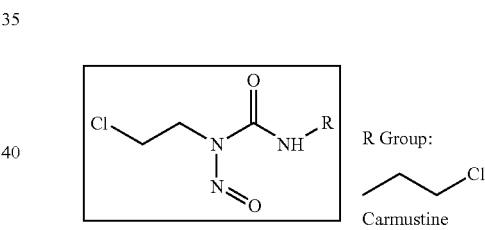

Carmustine

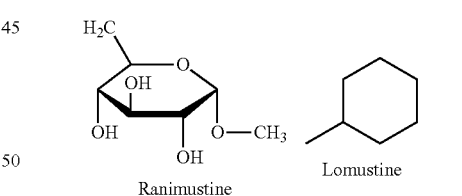

Ranimustine    Lomustine

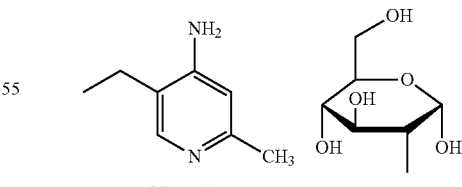

Nimustine    Chlorozotocin

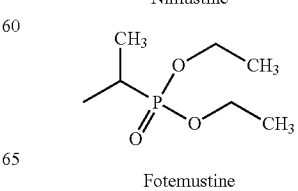

Fotemustine

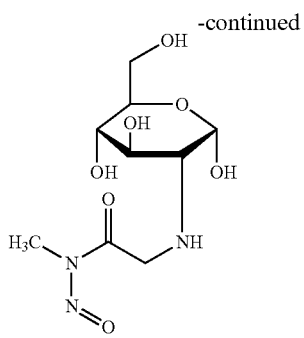

These nitrosourea compounds are thought to function as cell cycle inhibitors by binding to DNA, that is, by functioning as DNA alkylating agents. These cell cycle inhibitors have been shown useful in treating cell proliferative disorders such as, for example, islet cell; small cell lung; melanoma; and brain cancers.

In another aspect, the cell cycle inhibitor is a nitroimidazole, where exemplary nitroimidazoles are metronidazole, benznidazole, etanidazole, and misonidazole, having the structure of formula (XIX):

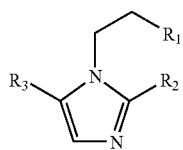

(XIX)

| | $R_1$ | $R_2$ | $R_3$ |
|---|---|---|---|
| Metronidazole | OH | $CH_3$ | $NO_2$ |
| Benznidazole | $C(O)NHCH_2$-benzyl | $NO_2$ | H |
| Etanidazole | $CONHCH_2CH_2OH$ | $NO_2$ | H |

Suitable nitroimidazole compounds are disclosed in, e.g., U.S. Pat. Nos. 4,371,540 and 4,462,992.

In another aspect, the cell cycle inhibitor is a folic acid antagonist, such as methotrexate or derivatives or analogues thereof, including edatrexate, trimetrexate, raltitrexed, piritrexim, denopterin, tomudex, and pteropterin. Methotrexate analogues have the following general structure of formula (XX):

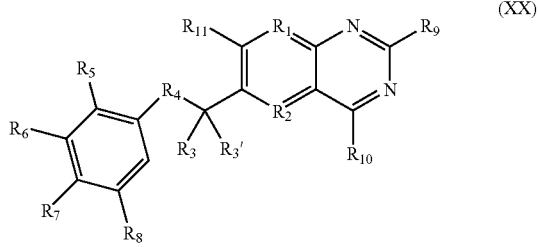

(XX)

The identity of the R group may be selected from organic groups, particularly those groups set forth in U.S. Pat. Nos. 5,166,149 and 5,382,582. For example, $R_1$ may be N, $R_2$ may be N or $C(CH_3)$, $R_3$ and $R_3'$ may H or alkyl, e.g., $CH_3$, $R_4$ may be a single bond or NR, where R is H or alkyl group. $R_{5,6,8}$ may be H, $OCH_3$, or alternately they can be halogens or hydro groups. $R_7$ is a side chain of the general structure of formula (XXI):

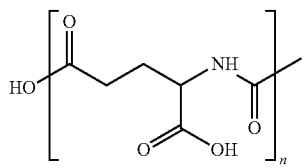

(XXI)

wherein n=1 for methotrexate, n=3 for pteropterin. The carboxyl groups in the side chain may be esterified or form a salt such as a $Zn^{2+}$ salt. $R_9$ and $R_{10}$ can be $NH_2$ or may be alkyl substituted.

Exemplary folic acid antagonist compounds have the structures of formulas (XXII) and (XXIII):

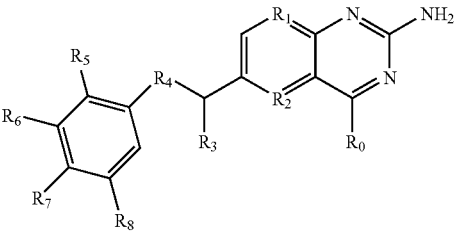

(XXII)

| | $R_0$ | $R_1$ | $R_2$ | $R_3$ | $R_4$ | $R_5$ | $R_6$ | $R_7$ | $R_8$ |
|---|---|---|---|---|---|---|---|---|---|
| Methotrexate | $NH_2$ | N | N | H | $N(CH_3)$ | H | H | A (n = 1) | H |
| Edatrexate | $NH_2$ | N | N | H | $N(CH_2CH_3)$ | H | H | A (n = 1) | H |
| Trimetrexate | $NH_2$ | N | $C(CH_3)$ | H | NH | H | $OCH_3$ | $OCH_3$ | $OCH_3$ |
| Pteropterin | $NH_2$ | N | N | H | $N(CH_3)$ | H | H | A (n = 3) | H |
| Denopterin | OH | N | N | $CH_3$ | $N(CH_3)$ | H | H | A (n = 1) | H |
| Piritrexim | $NH_2$ | N | $C(CH_3)$ | H | single bond | $OCH_3$ | H | H | $OCH_3$ | H |

A:

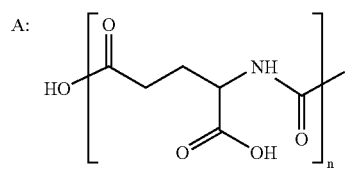

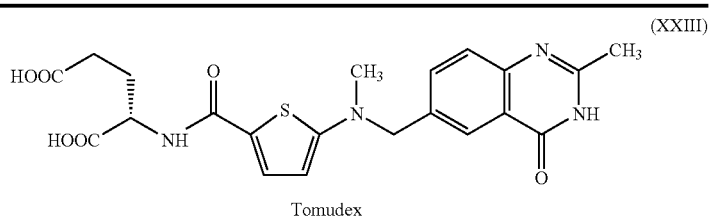

Tomudex

These compounds are thought to function as cell cycle inhibitors by serving as antimetabolites of folic acid. They have been shown useful in the treatment of cell proliferative disorders including, for example, soft tissue sarcoma, small cell lung, breast, brain, head and neck, bladder, and penile cancers.

In another aspect, the cell cycle inhibitor is a cytidine analogue, such as cytarabine or derivatives or analogues thereof, including enocitabine, FMdC ((E(-2'-deoxy-2'-(fluoromethylene)cytidine), gemcitabine, 5-azacitidine, ancitabine, and 6-azauridine. Exemplary compounds have the structure of formula (XXIV):

| | $R_1$ | $R_2$ | $R_3$ | $R_4$ |
|---|---|---|---|---|
| Cytarabine | H | OH | H | CH |
| Enocitabine | $C(O)(CH_2)_{20}CH_3$ | OH | H | CH |
| Gemcitabine | H | F | F | CH |
| Azacitidine | H | H | OH | N |
| FMdC | H | $CH_2F$ | H | CH |

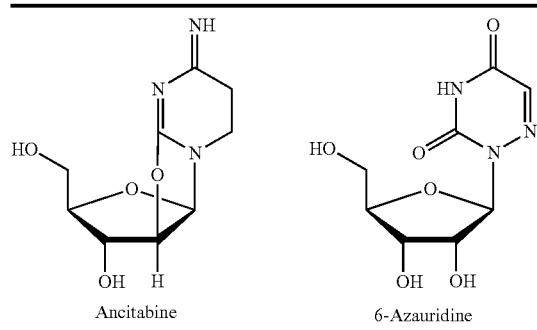

Ancitabine          6-Azauridine

These compounds are thought to function as cell cycle inhibitors as acting as antimetabolites of pyrimidine. These compounds have been shown useful in the treatment of cell proliferative disorders including, for example, pancreatic, breast, cervical, NSC lung, and bile duct cancers.

In another aspect, the cell cycle inhibitor is a pyrimidine analogue. In one aspect, the pyrimidine analogues have the general structure of formula (XXV):

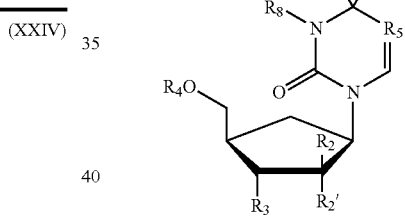

wherein positions 2', 3' and 5' on the sugar ring ($R_2$, $R_3$ and $R_4$, respectively) can be H, hydroxyl, phosphoryl (see, e.g., U.S. Pat. No. 4,086,417) or ester (see, e.g., U.S. Pat. No. 3,894,000). Esters can be of alkyl, cycloalkyl, aryl or heterocyclo/aryl types. The 2' carbon can be hydroxylated at either $R_2$ or $R_2'$, the other group is H. Alternately, the 2' carbon can be substituted with halogens e.g., fluoro or difluoro cytidines such as Gemcytabine. Alternately, the sugar can be substituted for another heterocyclic group such as a furyl group or for an alkane, an alkyl ether or an amide linked alkane such as $C(O)NH(CH_2)_5CH_3$. The 2° amine can be substituted with an aliphatic acyl ($R_1$) linked with an amide (see, e.g., U.S. Pat. No. 3,991,045) or urethane (see, e.g., U.S. Pat. No. 3,894,000) bond. It can also be further substituted to form a quaternary ammonium salt. $R_5$ in the pyrimidine ring may be N or CR, where R is H, halogen-containing groups, or alkyl (see, e.g., U.S. Pat. No. 4,086,417). $R_6$ and $R_7$ can together can form an oxo group or $R_6$=—NH—$R_1$ and $R_7$=H. $R_3$ is H or $R_7$ and $R_8$ together can form a double bond or $R_8$ can be X, where X is a structure of formula (XXVI):

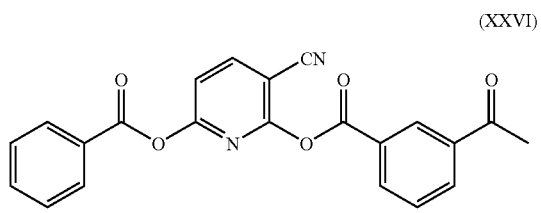

(XXVI)

Specific pyrimidine analogues are disclosed in U.S. Pat. No. 3,894,000 (see, e.g., 2'-O-palmityl-ara-cytidine, 3'-O-benzoyl-ara-cytidine, and more than 10 other examples); U.S. Pat. No. 3,991,045 (see, e.g., N4-acyl-1-β-D-arabinofuranosylcytosine, and numerous acyl groups derivatives as listed therein, such as palmitoyl.

In another aspect, the cell cycle inhibitor is a fluoropyrimidine analogue, such as 5-fluorouracil, or an analogue or derivative thereof, including carmofur, doxifluridine, emitefur, tegafur, and floxuridine. Exemplary compounds have the structures of formulas (XXVII):

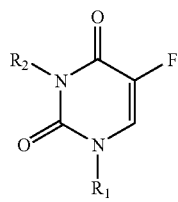

(XXVII)

| | $R_1$ | $R_2$ |
|---|---|---|
| 5-Fluorouracil | H | H |
| Carmofur | C(O)NH(CH$_2$)$_5$CH$_3$ | H |
| Doxifluridine | A$_1$ | H |
| Floxuridine | A$_2$ | H |
| Emitefur | CH$_2$OCH$_2$CH$_3$ | B |
| Tegafur | C | H |

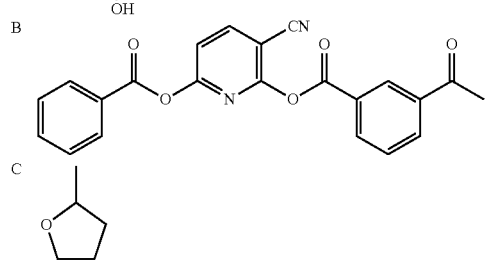

Other suitable fluoropyrimidine analogues include 5-FudR (5-fluoro-deoxyuridine), or an analogue or derivative thereof, including 5-iododeoxyuridine (5-IudR),5-bromodeoxyuridine (5-BudR), fluorouridine triphosphate (5-FUTP), and fluorodeoxyuridine monophosphate (5-dFUMP). Exemplary compounds have the structures of formula (XXVIII):

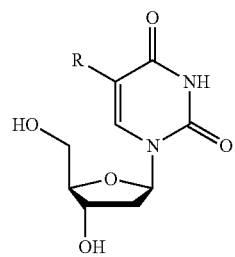

(XXVIII)

5-Fluoro-2'-deoxyuridine: R = F
5-Bromo-2'-deoxyuridine: R = Br
5-Iodoo-2'-deoxyuridine: R = I These compounds are thought to function as cell cycle inhibitors by serving as antimetabolites of pyrimidine. These compounds have been shown useful in the treatment of cell proliferative disorders such as breast, cervical, non-melanoma skin, head and neck, esophageal, bile duct, pancreatic, islet cell, penile, and vulvar cancers.

In another aspect, the cell cycle inhibitor is a purine analogue. Purine analogues have the following general structure of formula (XXIX):

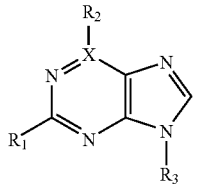

(XXIX)

wherein X is typically carbon; $R_1$ is H, halogen, amine or a substituted phenyl; $R_2$ is H, a primary, secondary or tertiary amine, a sulfur containing group, typically —SH, an alkane, a cyclic alkane, a heterocyclic or a sugar; $R_3$ is H, a sugar (typically a furanose or pyranose structure), a substituted sugar or a cyclic or heterocyclic alkane or aryl group. See, e.g., U.S. Pat. No. 5,602,140 for compounds of this type.

In the case of pentostatin, X—R2 is —CH$_2$CH(OH)—. In this case a second carbon atom is inserted in the ring between X and the adjacent nitrogen atom. The X—N double bond becomes a single bond.

U.S. Pat. No. 5,446,139 describes suitable purine analogues of the type shown in the structure of formula (XXX):

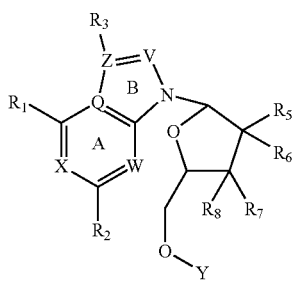

(XXX)

wherein N signifies nitrogen and V, W, X, Z can be either carbon or nitrogen with the following provisos. Ring A may have 0 to 3 nitrogen atoms in its structure. If two nitrogens are present in ring A, one must be in the W position. If only one is present, it must not be in the Q position. V and Q must not be simultaneously nitrogen. Z and Q must not be simultaneously nitrogen. If Z is nitrogen, $R_3$ is not present. Furthermore, $R_{1-3}$ are independently one of H, halogen, $C_{1-7}$ alkyl, $C_{1-7}$ alkenyl, hydroxyl, mercapto, $C_{1-7}$ alkylthio, $C_{1-7}$ alkoxy, $C_{2-7}$ alkenyloxy, aryl oxy, nitro, primary, secondary or tertiary amine containing group. $R_{5-8}$ are H or up to two of the positions may contain independently one of OH, halogen, cyano, azido, substituted amino, $R_5$ and $R_7$ can together form a double bond. Y is H, a $C_{1-7}$ alkylcarbonyl, or a mono- di or tri phosphate.

Exemplary suitable purine analogues include 6-mercaptopurine, thiguanosine, thiamiprine, cladribine, fludarabine, tubercidin, puromycin, pentoxyfilline; where these compounds may optionally be phosphorylated. Exemplary compounds have the structures of formulas (XXXI) and (XXXII):

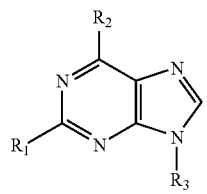

(XXXI)

| | $R_1$ | $R_2$ | $R_3$ |
|---|---|---|---|
| 6-Mercaptopurine | H | SH | H |
| Thioguanosine | $NH_2$ | SH | $B_1$ |
| Thiamiprine | $NH_2$ | A | H |
| Cladribine | Cl | $NH_2$ | $B_2$ |
| Fludarabine | F | $NH_2$ | $B_3$ |
| Puromycin | H | $N(CH_3)_2$ | $B_4$ |
| Tubercidin | H | $NH_2$ | $B_1$ |

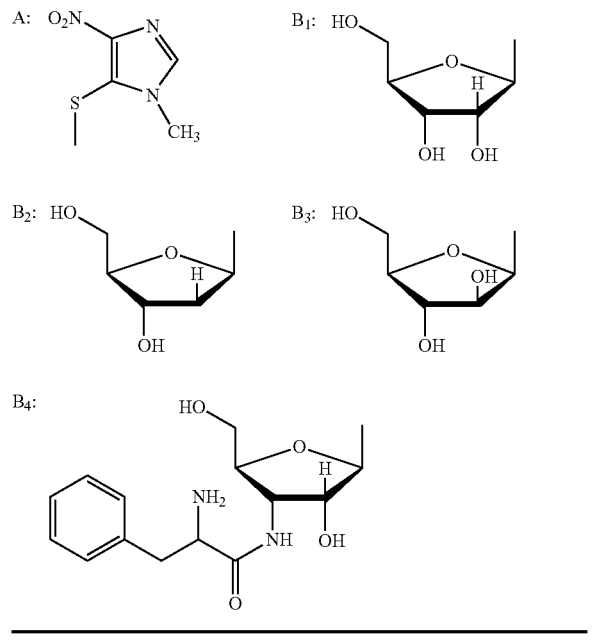

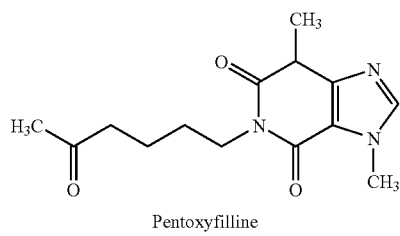

Pentoxyfilline (XXXIII)

These compounds are thought to function as cell cycle inhibitors by serving as antimetabolites of purine.

In another aspect, the cell cycle inhibitor is a nitrogen mustard. Many suitable nitrogen mustards are known and are suitably used as a cell cycle inhibitor in the present invention. Suitable nitrogen mustards are also known as cyclophosphamides.

A preferred nitrogen mustard has the general structure of formula (XXXIV):

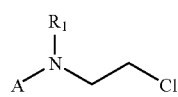

(XXXIV)

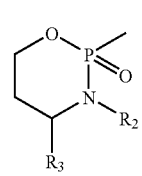

(A)

or —$CH_3$ or other alkane, or chloronated alkane, typically $CH_2CH(CH_3)Cl$, or a polycyclic group such as B, or a substituted phenyl such as C or a heterocyclic group such as D.

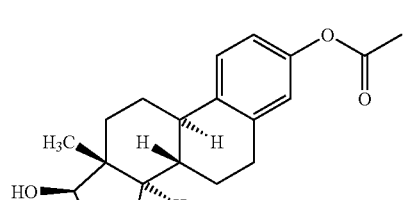

(B)

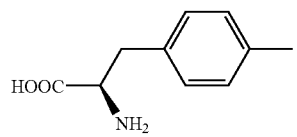

(C)

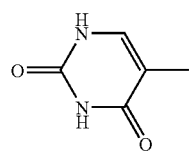

(D)

Examples of suitable nitrogen mustards are disclosed in U.S. Pat. No. 3,808,297, wherein A is:

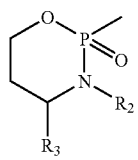
(A)

wherein $R_{1-2}$ are H or $CH_2CH_2Cl$; $R_3$ is H or oxygen-containing groups such as hydroperoxy; and $R_4$ can be alkyl, aryl, heterocyclic. The cyclic moiety need not be intact. See, e.g., U.S. Pat. Nos. 5,472,956, 4,908,356, 4,841,085 that describe the following type of structure of formula (XXXV):

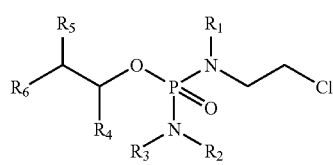
(XXXV)

wherein $R_1$ is H or $CH_2CH_2Cl$, and $R_{2-6}$ are various substituent groups.

Exemplary nitrogen mustards include methylchloroethamine, and analogues or derivatives thereof, including methylchloroethamine oxide hydrohchloride, novembichin, and mannomustine (a halogenated sugar). Exemplary compounds have the following structures:

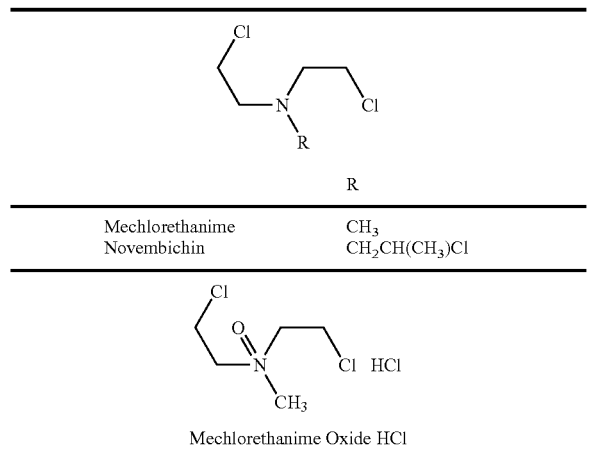

| | R |
|---|---|
| Mechlorethanime | $CH_3$ |
| Novembichin | $CH_2CH(CH_3)Cl$ |

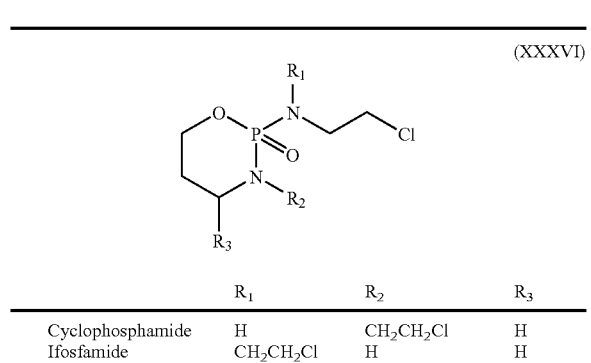

Mechlorethanime Oxide HCl

The nitrogen mustard may be cyclophosphamide, ifosfamide, perfosfamide, or torofosfamide, where these compounds have the structures of formula (XXXVI):

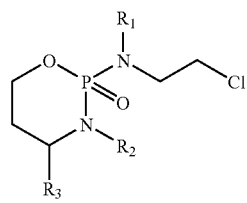
(XXXVI)

| | $R_1$ | $R_2$ | $R_3$ |
|---|---|---|---|
| Cyclophosphamide | H | $CH_2CH_2Cl$ | H |
| Ifosfamide | $CH_2CH_2Cl$ | H | H |
| Perfosfamide | $CH_2CH_2Cl$ | H | OOH |
| Torofosfamide | $CH_2CH_2Cl$ | $CH_2CH_2Cl$ | H |

The nitrogen mustard may be estramustine, or an analogue or derivative thereof, including phenesterine, prednimustine, and estramustine $PO_4$. Thus, suitable nitrogen mustard type cell cycle inhibitors of the present invention have the structures of formulas (XXXVII) and (XXXVIII):

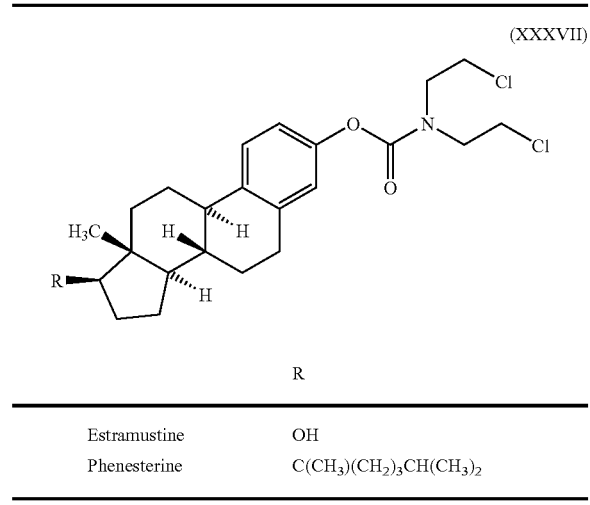
(XXXVII)

| | R |
|---|---|
| Estramustine | OH |
| Phenesterine | $C(CH_3)(CH_2)_3CH(CH_3)_2$ |

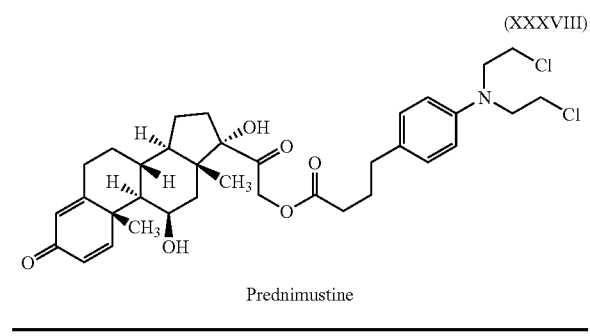
(XXXVIII)

Prednimustine

The nitrogen mustard may be chlorambucil, or an analogue or derivative thereof, including melphalan and chlormaphazine. Thus, suitable nitrogen mustard type cell cycle inhibitors of the present invention have the structures of formula (XXXIX):

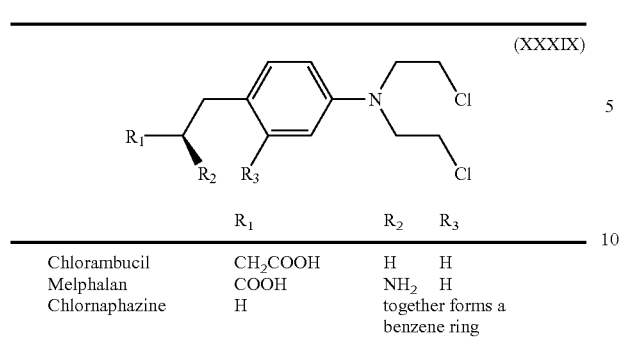

(XXXIX)

| | $R_1$ | $R_2$ | $R_3$ |
|---|---|---|---|
| Chlorambucil | CH$_2$COOH | H | H |
| Melphalan | COOH | NH$_2$ | H |
| Chlornaphazine | H | together forms a benzene ring | |

The nitrogen mustard may be uracil mustard, which has the structure of formula (LX):

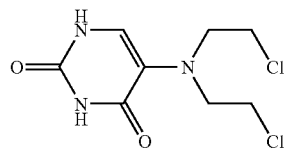

(LX)

The nitrogen mustards are thought to function as cell cycle inhibitors by serving as alkylating agents for DNA. Nitrogen mustards have been shown useful in the treatment of cell proliferative disorders including, for example, small cell lung, breast, cervical, head and neck, prostate, retinoblastoma, and soft tissue sarcoma.

The cell cycle inhibitor of the present invention may be a hydroxyurea. Hydroxyureas have the following general structure of formula (LXI):

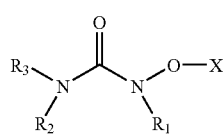

(LXI)

Suitable hydroxyureas are disclosed in, for example, U.S. Pat. No. 6,080,874, wherein $R_1$ is a group represented by the structure of formula (LXII):

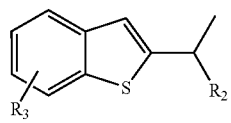

(LXII)

wherein $R_2$ is an alkyl group having 1-4 carbons and $R_3$ is one of H, acyl, methyl, ethyl, and mixtures thereof, such as a methylether.

Other suitable hydroxyureas are disclosed in, e.g., U.S. Pat. No. 5,665,768, wherein $R_1$ is a cycloalkenyl group, for example N-(3-(5-(4-fluorophenylthio)-furyl)-2-cyclopenten-1-yl)N-hydroxyurea; $R_2$ is H or an alkyl group having 1 to 4 carbons and $R_3$ is H; X is H or a cation.

Other suitable hydroxyureas are disclosed in, e.g., U.S. Pat. No. 4,299,778, wherein $R_1$ is a phenyl group substituted with on or more fluorine atoms; $R_2$ is a cyclopropyl group; and $R_3$ and X is H.

Other suitable hydroxyureas are disclosed in, e.g., U.S. Pat. No. 5,066,658, wherein $R_2$ and $R_3$ together with the adjacent nitrogen form which is represented by the structure of formula (XLIII):

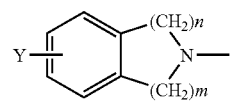

(XLIII)

wherein m is 1 or 2, n is 0-2 and Y is an alkyl group.

In one aspect, the hydroxy urea has the structure of formula (XLIV):

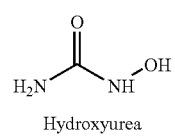

(XLIV)

Hydroxyurea

Hydroxyureas are thought to function as cell cycle inhibitors by serving to inhibit DNA synthesis.

In another aspect, the cell cycle inhibitor is a mytomicin, such as mitomycin C, or an analogue or derivative thereof, such as porphyromycin. Exemplary compounds have the structures of formula (XLV):

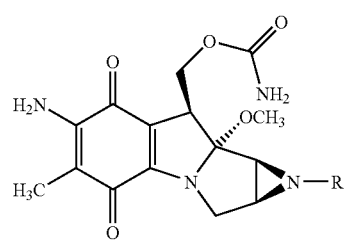

(XLV)

| | R |
|---|---|
| Mitomycin C | H |
| Porphyromycin (N-methyl Mitomycin C) | CH$_3$ |

These compounds are thought to function as cell cycle inhibitors by serving as DNA alkylating agents. Mitomycins have been shown useful in the treatment of cell proliferative disorders such as, for example, esophageal, liver, bladder, and breast cancers.

In another aspect, the cell cycle inhibitor is an alkyl sulfonate, such as busulfan, or an analogue or derivative thereof, such as treosulfan, improsulfan, piposulfan, and pipobroman. Exemplary compounds have the following structures:

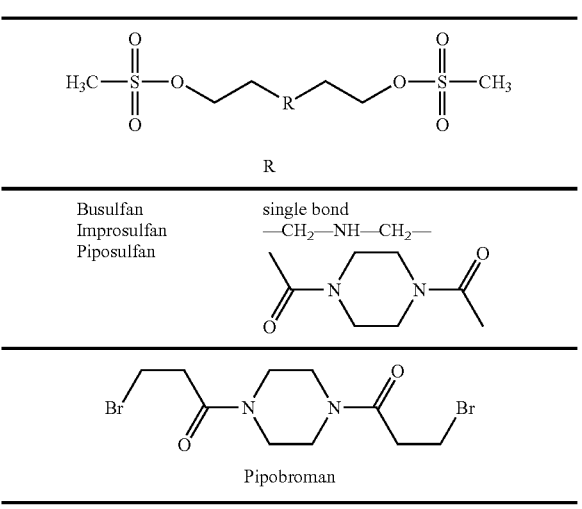

| R | |
|---|---|
| Busulfan | single bond |
| Improsulfan | —CH₂—NH—CH₂— |
| Piposulfan | |

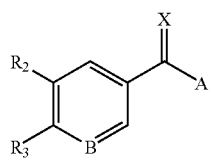

Pipobroman

These compounds are thought to function as cell cycle inhibitors by serving as DNA alkylating agents.

In another aspect, the cell cycle inhibitor is a benzamide. In yet another aspect, the cell cycle inhibitor is a nicotinamide. These compounds have the basic structure of formula (XLIII):

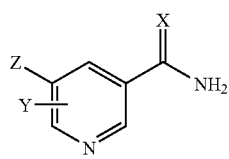

(LXIII)

wherein X is either O or S; A is commonly $NH_2$ or it can be OH or an alkoxy group; B is N or C—$R_4$, where $R_4$ is H or an ether-linked hydroxylated alkane such as $OCH_2CH_2OH$, the alkane may be linear or branched and may contain one or more hydroxyl groups. Alternately, B may be N—$R_5$ in which case the double bond in the ring involving B is a single bond. $R_5$ may be H, and alkyl or an aryl group (see, e.g., U.S. Pat. No. 4,258,052); $R_2$ is H, $OR_6$, $SR_6$, or $NHR_6$, where $R_6$ is an alkyl group; and $R_3$ is H, a lower alkyl, an ether linked lower alkyl such as —O-Me or —O-ethyl (see, e.g., U.S. Pat. No. 5,215,738).

Suitable benzamide compounds have the structures of formula (XLIV):

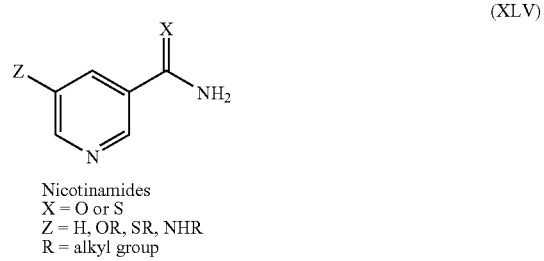

Benzamides
X = O or S
Y = H, OR, $CH_3$, or acetoxy
Z = H, OR, SR, or NHR
R = alkyl group wherein additional compounds are disclosed in U.S. Pat. No. 5,215,738, (listing some 32 compounds).

Suitable nicotinamide compounds have the structures of formula (XLV):

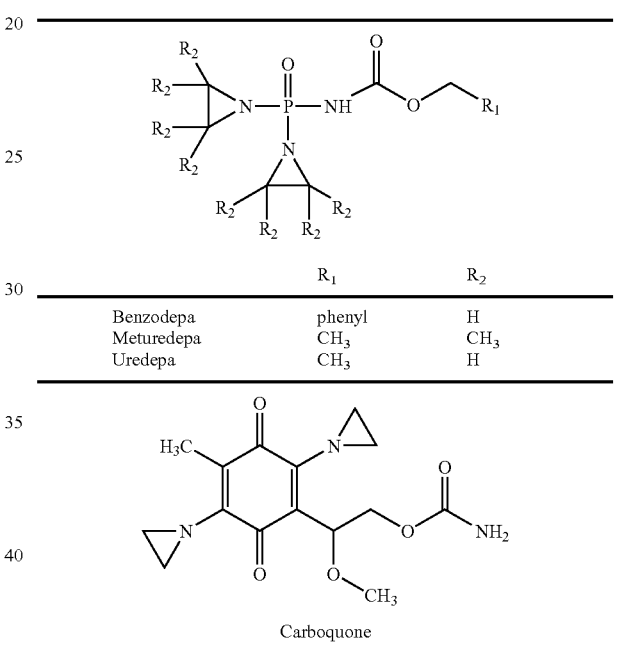

Nicotinamides
X = O or S
Z = H, OR, SR, NHR
R = alkyl group wherein additional compounds are disclosed in U.S. Pat. No. 5,215,738, such as:

| | $R_1$ | $R_2$ |
|---|---|---|
| Benzodepa | phenyl | H |
| Meturedepa | $CH_3$ | $CH_3$ |
| Uredepa | $CH_3$ | H |

Carboquone

In another aspect, the cell cycle inhibitor is a halogenated sugar, such as mitolactol, or an analogue or derivative thereof, including mitobronitol and mannomustine. Exemplary compounds have the structures:

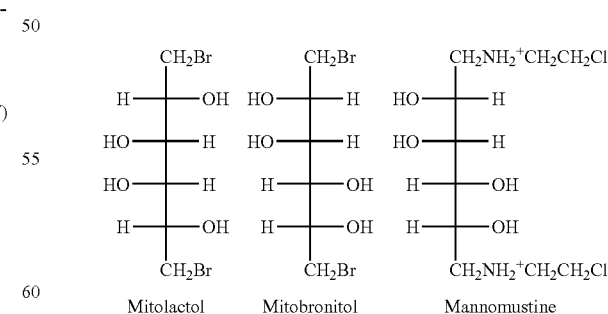

Mitolactol    Mitobronitol    Mannomustine

In another aspect, the cell cycle inhibitor is a diazo compound, such as azaserine, or an analogue or derivative thereof, including 6-diazo-5-oxo-L-norleucine and 5-diazouracil (also a pyrimidine analog). Exemplary compounds have the structures of formula (XLVI):

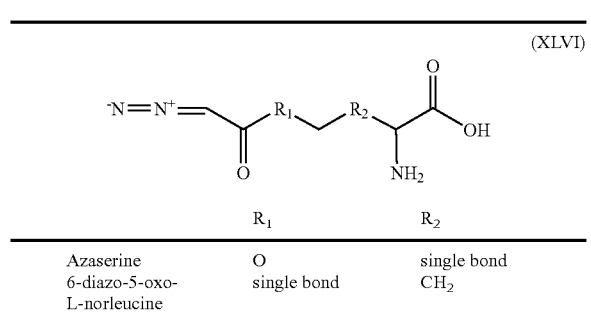

(XLVI)

| | $R_1$ | $R_2$ |
|---|---|---|
| Azaserine | O | single bond |
| 6-diazo-5-oxo-L-norleucine | single bond | $CH_2$ |

Other compounds that may serve as cell cycle inhibitors according to the present invention are pazelliptine; wortmannin; metoclopramide; RSU; buthionine sulfoxime; tumeric; curcumin; AG337, a thymidylate synthase inhibitor; levamisole; lentinan, a polysaccharide; razoxane, an EDTA analogue; indomethacin; chlorpromazine; α and β interferon; MnBOPP; gadolinium texaphyrin; 4-amino-1,8-naphthalimide; staurosporine derivative of CGP; and SR-2508.

Thus, in one aspect, the cell cycle inhibitor is a DNA alylating agent. In another aspect, the cell cycle inhibitor is an anti-microtubule agent. In another aspect, the cell cycle inhibitor is a topoisomerase inhibitor. In another aspect, the cell cycle inhibitor is a DNA cleaving agent. In another aspect, the cell cycle inhibitor is an antimetabolite. In another aspect, the cell cycle inhibitor functions by inhibiting adenosine deaminase (e.g., as a purine analogue). In another aspect, the cell cycle inhibitor functions by inhibiting purine ring synthesis and/or as a nucleotide interconversion inhibitor (e.g., as a purine analogue such as mercaptopurine). In another aspect, the cell cycle inhibitor functions by inhibiting dihydrofolate reduction and/or as a thymidine monophosphate block (e.g., methotrexate). In another aspect, the cell cycle inhibitor functions by causing DNA damage (e.g., bleomycin). In another aspect, the cell cycle inhibitor functions as a DNA intercalation agent and/or RNA synthesis inhibition (e.g., doxorubicin, aclarubicin, or detorubicin (acetic acid, diethoxy-, 2-[4-[(3-amino-2,3,6-trideoxy-alpha-L-lyxo-hexopyranosyl)oxy]-1,2,3,4,6,11-hexahydro-2,5,12-trihydroxy-7-methoxy-6,11-dioxo-2-naphthacenyl]-2-oxoethyl ester, (2S-cis)-)). In another aspect, the cell cycle inhibitor functions by inhibiting pyrimidine synthesis (e.g., N-phosphonoacetyl-L-aspartate). In another aspect, the cell cycle inhibitor functions by inhibiting ribonucleotides (e.g., hydroxyurea). In another aspect, the cell cycle inhibitor functions by inhibiting thymidine monophosphate (e.g., 5-fluorouracil). In another aspect, the cell cycle inhibitor functions by inhibiting DNA synthesis (e.g., cytarabine). In another aspect, the cell cycle inhibitor functions by causing DNA adduct formation (e.g., platinum compounds). In another aspect, the cell cycle inhibitor functions by inhibiting protein synthesis (e.g., L-asparginase). In another aspect, the cell cycle inhibitor functions by inhibiting microtubule function (e.g., taxanes). In another aspect, the cell cycle inhibitor acts at one or more of the steps in the biological pathway shown in FIG. 1.

Additional cell cycle inhibitor s useful in the present invention, as well as a discussion of the mechanisms of action, may be found in Hardman J. G., Limbird L. E. Molinoff R. B., Ruddon R W., Gilman A. G. editors, Chemotherapy of Neoplastic Diseases in Goodman and Gilman's The Pharmacological Basis of Therapeutics Ninth Edition, McGraw-Hill Health Professions Division, New York, 1996, pages 1225-1287. See also U.S. Pat. Nos. 3,387,001; 3,808,297; 3,894,000; 3,991,045; 4,012,390; 4,057,548; 4,086,417; 4,144,237; 4,150,146; 4,210,584; 4,215,062; 4,250,189; 4,258,052; 4,259,242; 4,296,105; 4,299,778; 4,367,239; 4,374,414; 4,375,432; 4,472,379; 4,588,831; 4,639,456; 4,767,855; 4,828,831; 4,841,045; 4,841,085; 4,908,356; 4,923,876; 5,030,620; 5,034,320; 5,047,528; 5,066,658; 5,166,149; 5,190,929; 5,215,738; 5,292,731; 5,380,897; 5,382,582; 5,409,915; 5,440,056; 5,446,139; 5,472,956; 5,527,905; 5,552,156; 5,594,158; 5,602,140; 5,665,768; 5,843,903; 6,080,874; 6,096,923; and RE030561.

In another embodiment, the cell-cycle inhibitor is camptothecin, mitoxantrone, etoposide, 5-fluorouracil, doxorubicin, methotrexate, peloruside A, mitomycin C, or a CDK-2 inhibitor or an analogue or derivative of any member of the class of listed compounds.

In another embodiment, the cell-cycle inhibitor is HTI-286, plicamycin; or mithramycin, or an analogue or derivative thereof.

Other examples of cell cycle inhibitors also include, e.g., 7-hexanoyltaxol (QP-2), cytochalasin A, lantrunculin D, actinomycin-D, Ro-31-7453 (3-(6-nitro-1-methyl-3-indolyl)-4-(1-methyl-3-indolyl)pyrrole-2,5-dione), PNU-151807, brostallicin, C2-ceramide, cytarabine ocfosfate (2(1H)-pyrimidinone, 4-amino-1-(5-O-(hydroxy(octadecyloxy) phosphinyl)-β-D-arabinofuranosyl)-, monosodium salt), paclitaxel (5,20-epoxy-1,2 alpha,4,7β,10β,13 alpha-hexahydroxytax-11-en-9-one-4,10-diacetate-2-benzoate-13-(alpha-phenylhippurate)), doxorubicin (5,12-naphthacenedione, 10-((3-amino-2,3,6-trideoxy-alpha-L-lyxo-hexopyranosyl) oxy)-7,8,9,10-tetrahydro-6,8,11-trihydroxy-8-(hydroxyacetyl)-1-methoxy-, (8S)-cis-), daunorubicin (5,12-naphthacenedione, 8-acetyl-10-((3-amino-2,3,6-trideoxy-alpha-L-lyxo-hexopyranosyl)oxy)-7,8,9,10-tetrahydro-6,8, 11-trihydroxy-1-methoxy-, (8S-cis)-), gemcitabine hydrochloride (cytidine, 2'-deoxy-2',2'-difluoro-,monohydrochloride), nitacrine (1,3-propanediamine, N,N-dimethyl-N'-(1-nitro-9-acridinyl)-), carboplatin (platinum, diammine (1,1-cyclobutanedicarboxylato(2-))-, (SP-4-2)-), altretamine (1,3,5-triazine-2,4,6-triamine, N,N,N',N',N",N"hexamethyl-), teniposide (furo(3',4':6,7)naphtho(2,3-d)-1, 3-dioxol-6(5aH)-one, 5,8,8a,9-tetrahydro-5-(4-hydroxy-3,5-dimethoxyphenyl)-9-((4,6-O-(2-thienylmethylene)-β-D-glucopyranosyl)oxy)-, (5R-(5alpha,5aβ,8aAlpha,9β (R*)))—), eptaplatin (platinum, ((4R,5R)-2-(1-methylethyl)-1,3-dioxolane-4,5-dimethanamine-kappa N4,kappa N5) (propanedioato(2-)-kappa O1, kappa O3)-, (SP-4-2)-), amrubicin hydrochloride (5,12-naphthacenedione, 9-acetyl-9-amino-7-((2-deoxy-β-D-erythro-pentopyranosyl)oxy)-7, 8,9,10-tetrahydro-6,11-dihydroxy-, hydrochloride, (7S-cis)-), ifosfamide(2H-1,3,2-oxazaphosphorin-2-amine, N,3-bis(2-chloroethyl)tetrahydro-,2-oxide), cladribine (adenosine, 2-chloro-2'-deoxy-), mitobronitol (D-mannitol, 1,6-dibromo-1,6-dideoxy-), fludaribine phosphate (9H-purin-6-amine, 2-fluoro-9-(5-O-phosphono-β-D-arabinofuranosyl)-), enocitabine (docosanamide, N-(1-β-D-arabinofuranosyl-1,2-dihydro-2-oxo-4-pyrimidinyl)-), vindesine (vincaleukoblastine, 3-(aminocarbonyl)-O4-deacetyl-3-de (methoxycarbonyl)-), idarubicin (5,12-naphthacenedione, 9-acetyl-7-((3-amino-2,3,6-trideoxy-alpha-L-lyxo-hexopyranosyl)oxy)-7,8,9,10-tetrahydro-6,9,11-trihydroxy-, (7S-cis)-), zinostatin (neocarzinostatin), vincristine (vincaleukoblastine, 22-oxo-), tegafur (2,4(1H,3H)-pyrimidinedione, 5-fluoro-1-(tetrahydro-2-furanyl)-), razoxane (2,6-piperazinedione, 4,4'-(1-methyl-1,2-ethanediyl)bis-), methotrexate (L-glutamic acid, N-(4-(((2,4-diamino-6-pteridinyl)methyl) methylamino)benzoyl)-), raltitrexed (L-glutamic acid, N-((5-(((1,4-dihydro-2-methyl-4-oxo-6-quinazolinyl)methyl)methylamino)-2-thienyl)carbonyl)-), oxaliplatin (platinum, (1,2-cyclohexanediamine-N,N')(ethanedioato(2-)-O,O')-, (SP-4-2-(1R-trans))-), doxifluridine (uridine, 5'-deoxy-5-fluoro-), mitolactol (galactitol, 1,6-dibromo-1,6-dideoxy-), piraubicin (5,12-naphthacenedione, 10-((3-amino-2,3,6-trideoxy-4-O-(tetrahydro-2H-pyran-2-yl)-alpha-L-lyxo-hexopyranosyl)oxy)-7,8,9,10-tetrahydro-6,8,11-trihydroxy-8-(hydroxyacetyl)-1-methoxy-, (8S-(8 alpha, 10 alpha (S*)))—), docetaxel ((2R,3S)—N-carboxy-3-phenylisoserine, N-tert-butyl ester, 13-ester with 5β,20-epoxy-1,2 alpha,4,7β,10β,13 alpha-hexahydroxytax-11-en-9-one 4-acetate 2-benzoate-), capecitabine (cytidine, 5-deoxy-5-fluoro-N-((pentyloxy)carbonyl)-), cytarabine (2(1H)-pyrimidone, 4-amino-1-β-D-arabino furanosyl-), valrubicin (pentanoic acid, 2-(1,2,3,4,6,11-hexahydro-2,5, 12-trihydroxy-7-methoxy-6,11-dioxo-4-((2,3,6-trideoxy-3-((trifluoroacetyl)amino)-alpha-L-lyxo-hexopyranosyl)oxy)-2-naphthacenyl)-2-oxoethyl ester (2S-cis)-), trofosfamide(3-2-(chloroethyl)-2-(bis(2-chloroethyl)amino)tetrahydro-2H-1,3,2-oxazaphosphorin 2-oxide), prednimustine (pregna-1,4-diene-3,20-dione, 21-(4-(4-(bis(2-chloroethyl)amino)phenyl)-1-oxobutoxy)-11,17-dihydroxy-, (11β)-), lomustine (Urea, N-(2-chloroethyl)-N'-cyclohexyl-N-nitroso-), epirubicin (5,12-naphthacenedione, 10-((3-amino-2,3,6-trideoxy-alpha-L-arabino-hexopyranosyl)oxy)-7,8,9,10-tetrahydro-6, 8,11-trihydroxy-8-(hydroxyacetyl)-1-methoxy-, (8S-cis)-), or an analogue or derivative thereof).

Cyclin Dependent Protein Kinase Inhibitors

In another embodiment, the pharmacologically active compound is a cyclin dependent protein kinase inhibitor (e.g., R-roscovitine, CYC-101, CYC-103, CYC-400, MX-7065, alvocidib (4H-1-Benzopyran-4-one, 2-(2-chlorophenyl)-5,7-dihydroxy-8-(3-hydroxy-1-methyl-4-piperidinyl)-, cis-(–)-), SU-9516, AG-12275, PD-0166285, CGP-79807, fascaplysin, GW-8510 (benzenesulfonamide, 4-(((Z)-(6,7-dihydro-7-oxo-8H-pyrrolo[2,3-g]benzothiazol-8-ylidene)methyl) amino)-N-(3-hydroxy-2,2-dimethylpropyl)-), GW-491619, Indirubin 3' monoxime, GW8510, AZD-5438, ZK-CDK or an analogue or derivative thereof).

EGF (Epidermal Growth Factor) Receptor Kinase Inhibitors

In another embodiment, the pharmacologically active compound is an EGF (epidermal growth factor) kinase inhibitor (e.g., erlotinib (4-quinazolinamine, N-(3-ethynylphenyl)-6,7-bis(2-methoxyethoxy)-, monohydrochloride), erbstatin, BIBX-1382, gefitinib (4-quinazolinamine, N-(3-chloro-4-fluorophenyl)-7-methoxy-6-(3-(4-morpholinyl)propoxy)), or an analogue or derivative thereof).

Elastase Inhibitors

In another embodiment, the pharmacologically active compound is an elastase inhibitor (e.g., ONO-6818, sivelestat sodium hydrate (glycine, N-(2-(((4-(2,2-dimethyl-1-oxopropoxy)phenyl)sulfonyl)amino)benzoyl)-), erdosteine (acetic acid, ((2-oxo-2-((tetrahydro-2-oxo-3-thienyl)amino)ethyl) thio)-), MDL-100948A, MDL-104238 (N-(4-(4-morpholinylcarbonyl)benzoyl)-L-valyl-N'-(3,3,4,4,4-pentafluoro-1-(1-methylethyl)-2-oxobutyl)-L-2-azetamide), MDL-27324 (L-prolinamide, N-((5-(dimethylamino)-1-naphthalenyl)sulfonyl)-L-alanyl-L-alanyl-N-(3,3,3-trifluoro-1-(1-methylethyl)-2-oxopropyl)-, (S)—), SR-26831 (thieno(3,2-c)pyridinium, 5-((2-chlorophenyl)methyl)-2-(2,2-dimethyl-1-oxopropoxy)-4,5,6,7-tetrahydro-5-hydroxy-), Win-68794, Win-63110, SSR-69071 (2-(9(2-piperidinoethoxy)-4-oxo-4H-pyrido(1,2-a)pyrimidin-2-yloxymethyl)-4-(1-methylethyl)-6-methyoxy-1,2-benzisothiazol-3(2H)-one-1,1-dioxide), (N(Alpha)-(1-adamantylsulfonyl)N(epsilon)-succinyl-L-lysyl-L-prolyl-L-valinal), Ro-31-3537 (N alpha-(1-adamantanesulphonyl)-N-(4-carboxybenzoyl)-L-lysyl-alanyl-L-valinal), R-665, FCE-28204, ((6R,7R)-2-(benzoyloxy)-7-methoxy-3-methyl-4-pivaloyl-3-cephem 1,1-dioxide), 1,2-benzisothiazol-3(2H)-one, 2-(2,4-dinitrophenyl)-, 1,1-dioxide, L-658758 (L-proline, 1-((3-((acetyloxy)methyl)-7-methoxy-8-oxo-5-thia-1-azabicyclo(4.2.0) oct-2-en-2-yl)carbonyl)-, S,S-dioxide, (6R-cis)-), L-659286 (pyrrolidine, 1-((7-methoxy-8-oxo-3-(((1,2,5,6-tetrahydro-2-methyl-5,6-dioxo-1,2,4-triazin-3-yl)thio)methyl)-5-thia-1-azabicyclo(4.2.0)oct-2-en-2-yl)carbonyl)-, S,S-dioxide, (6R-cis)-), L-680833 (benzeneacetic acid, 4-((3,3-diethyl-1-(((1-(4-methylphenyl)butyl)amino)carbonyl)-4-oxo-2-azetidinyl)oxy)-, (S—(R*,S*))—), FK-706 (L-prolinamide, N-[4[[(carboxymethyl)amino]carbonyl]benzoyl]-L-valyl-N-[3,3,3-trifluoro-1-(1-methylethyl)-2-oxopropyl]-, monosodium salt), Roche R-665, or an analogue or derivative thereof).

Factor Xa Inhibitors

In another embodiment, the pharmacologically active compound is a factor Xa inhibitor (e.g., CY-222, fondaparinux sodium (alpha-D-glucopyranoside, methyl O-2-deoxy-6-O-sulfo-2-(sulfoamino)-alpha-D-glucopyranosyl-(1-4)-O-β-D-glucopyranuronosyl-(1-4)-O-2-deoxy-3,6-di-O-sulfo-2-(sulfoamino)-alpha-D-glucopyranosyl-(1-4)-O-2-O-sulfo-alpha-L-idopyranuronosyl-(1-4)-2-deoxy-2-(sulfoamino)-, 6-(hydrogen sulfate)), danaparoid sodium, or an analogue or derivative thereof).

Farnesyltransferase Inhibitors

In another embodiment, the pharmacologically active compound is a farnesyltransferase inhibitor (e.g., dichlorobenzoprim (2,4-diamino-5-(4-(3,4-dichlorobenzylamino)-3-nitrophenyl)-6-ethylpyrimidine), B-581, B-956 (N-(8(R)-amino-2(S)-benzyl-5(S)-isopropyl-9-sulfanyl-3(Z),6(E)-nonadienoyl)-L-methionine), OSI-754, perillyl alcohol (1-cyclohexene-1-methanol, 4-(1-methylethenyl)-, RPR-114334, lonafarnib (1-piperidinecarboxamide, 4-(2-(4-((11R)-3,10-dibromo-8-chloro-6,11-dihydro-5H-benzo(5,6) cyclohepta(1,2-b)pyridin-11-yl)-1-piperidinyl)-2-oxoethyl)-), Sch-48755, Sch-226374, (7,8-dichloro-5H-dibenzo(b,e)(1,4)diazepin-11-yl)-pyridin-3-ylmethylamine, J-104126, L-639749, L-731734 (pentanamide, 2-((2-((2-amino-3-mercaptopropyl)amino)-3-methylpentyl)amino)-3-methyl-N-(tetrahydro-2-oxo-3-furanyl)-, (3S-(3R*(2R* (2R*(S*),3S*),3R*)))—), L-744832 (butanoic acid, 2-((2-((2-((2-amino-3-mercaptopropyl)amino)-3-methylpentyl) oxy)-1-oxo-3-phenylpropyl)amino)-4-(methylsulfonyl)-, 1-methylethyl ester, (2S-(1(R*(R*)),2R*(S*),3R*))—), L-745631 (1-piperazinepropanethiol, β-amino-2-(2-methoxyethyl)-4-(1-naphthalenylcarbonyl)-, (βR,2S)—), N-acetyl-N-naphthylmethyl-2(S)-((1-(4-cyanobenzyl)-1H-imidazol-5-yl)acetyl)amino-3(S)-methylpentamine, (2alpha)-2-hydroxy-24,25-dihydroxylanost-8-en-3-one, BMS-316810, UCF-1-C (2,4-decadienamide, N-(5-hydroxy-5-(7-((2-hydroxy-5-oxo-1-cyclopenten-1-yl)amino-oxo-1,3,5-heptatrienyl)-2-oxo-7-oxabicyclo(4.1.0)hept-3-en-3-yl)-2,4, 6-trimethyl-, (1S-(1alpha,3(2E,4E,6S*),5 alpha, 5(1E,3E, 5E), 6 alpha))-), UCF-1,6-B, ARGLABIN (3H-oxireno[8,8a] azuleno[4,5-b]furan-8(4aH)-one, 5,6,6a,7,9a,9b-hexahydro-1,4a-dimethyl-7-methylene-, (3aR,4aS,6aS,9aS,9bR)-) from ARGLABIN-Paracure, Inc. (Virginia Beach, Va.), or an analogue or derivative thereof).

Fibrinogen Antagonists

In another embodiment, the pharmacologically active compound is a fibrinogen antagonist (e.g., 2(S)-((p-toluenesulfonyl)amino)-3-(((5,6,7,8,-tetrahydro-4-oxo-5-(2-(piperidin-4-yl)ethyl)-4H-pyrazolo-(1,5-a)(1,4)diazepin-2-yl) carbonyl)-amino)propionic acid, streptokinase (kinase (enzyme-activating), strepto-), urokinase (kinase (enzyme-activating), uro-), plasminogen activator, pamiteplase, monteplase, heberkinase, anistreplase, alteplase, pro-urokinase, picotamide(1,3-benzenedicarboxamide, 4-methoxy-N,N'-bis(3-pyridinylmethyl)-), or an analogue or derivative thereof).

Guanylate Cyclase Stimulants

In another embodiment, the pharmacologically active compound is a guanylate cyclase stimulant (e.g., isosorbide-5-mononitrate (D-glucitol, 1,4:3,6-dianhydro-, 5-nitrate), or an analogue or derivative thereof).

Heat Shock Protein 90 Antagonists

In another embodiment, the pharmacologically active compound is a heat shock protein 90 antagonist (e.g., geldanamycin; NSC-33050 (17-allylaminogeldanamycin; 17-AAG), rifabutin (rifamycin XIV, 1',4-didehydro-1-deoxy-1,4-dihydro-5'-(2-methylpropyl)-1-oxo-), 17-DMAG, or an analogue or derivative thereof).

HMGCoA Reductase Inhibitors

In another embodiment, the pharmacologically active compound is an HMGCoA reductase inhibitor (e.g., BCP-671, BB-476, fluvastatin (6-heptenoic acid, 7-(3-(4-fluorophenyl)-1-(1-methylethyl)-1H-indol-2-yl)-3,5-dihydroxy-, monosodium salt, (R*,S*-(E))-(±)-), dalvastatin (2H-pyran-2-one, 6-(2-(2-(2-(4-fluoro-3-methylphenyl)-4,4,6,6-tetramethyl-1-cyclohexen-1-yl)ethenyl)tetrahydro)-4-hydroxy-, (4-alpha,6β(E))-(+/−)-), glenvastatin (2H-pyran-2-one, 6-(2-(4-(4-fluorophenyl)-2-(1-methylethyl)-6-phenyl-3-pyridinyl)ethenyl)tetrahydro-4-hydroxy-, (4R-(4-alpha,6β(E)))-), S-2468, N-(1-oxododecyl)-4Alpha, 10-dimethyl-8-aza-trans-decal-3β-ol, atorvastatin calcium (1H-Pyrrole-1-heptanoic acid, 2-(4-fluorophenyl)-β,delta-dihydroxy-5-(1-methylethyl)-3-phenyl-4-((phenylamino)carbonyl)-, calcium salt (R—(R*,R*))—), CP-83101 (6,8-nonadienoic acid, 3,5-dihydroxy-9,9-diphenyl-, methyl ester, (R*,S*-(E))-(+/−)-), pravastatin (1-naphthaleneheptanoic acid, 1,2,6,7,8,8a-hexahydro-β,delta,6-trihydroxy-2-methyl-8-(2-methyl-1-oxobutoxy)-, monosodium salt, (1S-(1 alpha(βS*,deltaS*),2 alpha,6 alpha,8β(R*),8a alpha))-), U-20685, pitavastatin (6-heptenoic acid, 7-(2-cyclopropyl-4-(4-fluorophenyl)-3-quinolinyl)-3,5-dihydroxy-, calcium salt (2:1) (S—(R*,S*-(E)))-), N-((1-methylpropyl)carbonyl)-8-(2-(tetrahydro-4-hydroxy-6-oxo-2H-pyran-2-yl)ethyl)-perhydro-isoquinoline, dihydromevinolin (butanoic acid, 2-methyl-, 1,2,3,4,4a,7,8,8a-octahydro-3,7-dimethyl-8-(2-(tetrahydro-4-hydroxy-6-oxo-2H-pyran-2-yl)ethyl)-1-naphthalenyl ester(1 alpha(R*), 3 alpha, 4a alpha,7β,8β(2S*,4S*),8aβ))-), HBS-107, dihydromevinolin (butanoic acid, 2-methyl-, 1,2,3,4,4a,7,8,8a-octahydro-3,7-dimethyl-8-(2-(tetrahydro-4-hydroxy-6-oxo-2H-pyran-2-yl)ethyl)-1-naphthalenyl ester(1 alpha(R*), 3 alpha,4a alpha,7β,8β(2S*,4S*),8aβ))-), L-669262 (butanoic acid, 2,2-dimethyl-, 1,2,6,7,8,8a-hexahydro-3,7-dimethyl-6-oxo-8-(2-(tetrahydro-4-hydroxy-6-oxo-2H-pyran-2-yl)ethyl)-1-naphthalenyl(1S-(1 Alpha,7β,8β(2S*,4S*),8aβ))-), simvastatin (butanoic acid, 2,2-dimethyl-, 1,2,3,7,8,8a-hexahydro-3,7-dimethyl-8-(2-(tetrahydro-4-hydroxy-6-oxo-2H-pyran-2-yl)ethyl)-1-naphthalenyl ester, (1S-(1alpha, 3alpha,7β,8β(2S*,4S*),8aβ))-), rosuvastatin calcium (6-heptenoic acid, 7-(4-(4-fluorophenyl)-6-(1-methylethyl)-2-(methyl(methylsulfonyl)amino)-5-pyrimdinyl)-3,5-dihydroxy-calcium salt (2:1) (S—(R*,S*-(E)))), meglutol (2-hydroxy-2-methyl-1,3-propandicarboxylic acid), lovastatin (butanoic acid, 2-methyl-, 1,2,3,7,8,8a-hexahydro-3,7-dimethyl-8-(2-(tetrahydro-4-hydroxy-6-oxo-2H-pyran-2-yl)ethyl)-1-naphthalenyl ester, (1S-(1 alpha.(R*),3 alpha,7β,8β(2S*,4S*),8aβ))-), or an analogue or derivative thereof).

Hydroorotate Dehydrogenase Inhibitors

In another embodiment, the pharmacologically active compound is a hydroorotate dehydrogenase inhibitor (e.g., leflunomide (4-isoxazolecarboxamide, 5-methyl-N-(4-(trifluoromethyl)phenyl)-), laflunimus (2-propenamide, 2-cyano-3-cyclopropyl-3-hydroxy-N-(3-methyl-4(trifluoromethyl)phenyl)-, (Z)—), or atovaquone (1,4-naphthalenedione, 2-[4-(4-chlorophenyl)cyclohexyl]-3-hydroxy-, trans-, or an analogue or derivative thereof).

IKK2 Inhibitors

In another embodiment, the pharmacologically active compound is an IKK2 inhibitor (e.g., MLN-120B, SPC-839, or an analogue or derivative thereof).

IL-1, ICE and IRAK Antagonists

In another embodiment, the pharmacologically active compound is an IL-1, ICE or an IRAK antagonist (e.g., E-5090 (2-propenoic acid, 3-(5-ethyl-4-hydroxy-3-methoxy-1-naphthalenyl)-2-methyl-, (Z)—), CH-164, CH-172, CH-490, AMG-719, iguratimod (N-(3-(formylamino)-4-oxo-6-phenoxy-4H-chromen-7-yl)methanesulfonamide), AV94-88, pralnacasan (6H-pyridazino(1,2-a)(1,2)diazepine-1-carboxamide, N-((2R,3S)-2-ethoxytetrahydro-5-oxo-3-furanyl)octahydro-9-((1-isoquinolinylcarbonyl)amino)-6,10-dioxo-, (1S,9S)—), (2S-cis)-5-(benzyloxycarbonylamino-1,2,4,5,6,7-hexahydro-4-(oxoazepino(3,2,1-hi)indole-2-carbonyl)-amino)-4-oxobutanoic acid, AVE-9488, esonarimod (benzenebutanoic acid, alpha-((acetylthio)methyl)-4-methyl-gamma-oxo-), pralnacasan (6H-pyridazino(1,2-a)(1,2)diazepine-1-carboxamide, N-((2R,3S)-2-ethoxytetrahydro-5-oxo-3-furanyl)octahydro-9-((1-isoquinolinylcarbonyl)amino)-6,10-dioxo-, (1S,9S)—), tranexamic acid (cyclohexanecarboxylic acid, 4-(aminomethyl)-, trans-), Win-72052, romazarit (Ro-31-3948) (propanoic acid, 2-((2-(4-chlorophenyl)-4-methyl-5-oxazolyl)methoxy)-2-methyl-), PD-163594, SDZ-224-015 (L-alaninamide N-((phenylmethoxy)carbonyl)-L-valyl-N-((1S)-3-((2,6-dichlorobenzoyl)oxy)-1-(2-ethoxy-2-oxoethyl)-2-oxopropyl)-), L-709049 (L-alaninamide, N-acetyl-L-tyrosyl-L-valyl-N-(2-carboxy-1-formylethyl)-, (S)—), TA-383 (1H-imidazole, 2-(4-chlorophenyl)-4,5-dihydro-4,5-dipheny-, monohydrochloride, cis-), EI-1507-1 (6a, 12a-epoxybenz(a)anthracen-1,12(2H,7H)-dione, 3,4-dihydro-3,7-dihydroxy-8-methoxy-3-methyl-), ethyl 4-(3,4-dimethoxyphenyl)-6,7-dimethoxy-2-(1,2,4-triazol-1-yl methyl)quinoline-3-carboxylate, EI-1941-1, TJ-114, anakinra (interleukin 1 receptor antagonist (human isoform x reduced), N2-L-methionyl-), IX-207-887 (acetic acid, (10-methoxy-4H-benzo[4,5]cyclohepta[1,2-b]thien-4-ylidene)-), K-832, or an analogue or derivative thereof).

IL-4 Agonists

In another embodiment, the pharmacologically active compound is an IL-4 μgonist (e.g., glatiramir acetate (L-glutamic acid, polymer with L-alanine, L-lysine and L-tyrosine, acetate (salt)), or an analogue or derivative thereof).

Immunomodulatory Agents

In another embodiment, the pharmacologically active compound is an immunomodulatory agent (e.g., biolimus, ABT-578, methylsulfamic acid 3-(2-methoxyphenoxy)-2-(((methylamino)sulfonyl)oxy)propyl ester, sirolimus (also referred to as rapamycin or RAPAMUNE (American Home Products, Inc., Madison, N.J.)), CCI-779 (rapamycin 42-(3-hydroxy-2-(hydroxymethyl)-2-methylpropanoate)), LF-15-0195, NPC 5669 (L-leucine, N-(((2,7-dimethyl-9H-fluoren-9-yl)methoxy)carbonyl)-), NPC-15670 (L-leucine, N-(((4,5-dimethyl-9H-fluoren-9-yl)methoxy)carbonyl)-), NPC-16570 (4-(2-(fluoren-9-yl)ethyloxy-carbonyl)aminobenzoic acid), sufosfamide(ethanol, 2-((3-(2-chloroethyl) tetrahydro-2H-1,3,2-oxazaphosphorin-2-yl)amino)-, methanesulfonate (ester), P-oxide), tresperimus (2-(N-(4-(3-aminopropylamino)butyl)carbamoyloxy)-N-(6-guanidinohexyl)acetamide), 4-(2-(fluoren-9-yl) ethoxycarbonylamino)-benzo-hydroxamic acid, iaquinimod, PBI-1411, azathioprine (6-((1-Methyl-4-nitro-1H-imidazol-5-yl)thio)-1H-purine), PBI0032, beclometasone, MDL-28842 (9H-purin-6-amine, 9-(5-deoxy-5-fluoro-β-D-threo-pent-4-enofuranosyl)-, (Z)—), FK-788, AVE-1726, ZK-90695, ZK-90695, Ro-54864, didemnin-B, Illinois (didemnin A, N-(1-(2-hydroxy-1-oxopropyl)-L-prolyl)-, (S)—), SDZ-62-826 (ethanaminium, 2-((hydroxy((1-((octadecyloxy)carbonyl)-3-piperidinyl)methoxy)phosphinyl) oxy)-N,N,N-trimethyl-, inner salt), argyrin B ((4S,7S, 13R, 22R)-13-Ethyl-4-(1H-indol-3-ylmethyl)-7-(4-methoxy-1H-indol-3-ylmethyl) 18,22-dimethyl-16-methyl-ene-24-thia-3, 6,9,12,15,18,21,26-octaazabicyclo(21.2.1)-hexacosa-1(25), 23(26)-diene-2,5,8,11,14,17,20-heptaone), everolimus (rapamycin, 42-O-(2-hydroxyethyl)-), SAR-943, L-687795, 6-((4-chlorophenyl)sulfinyl)-2,3-dihydro-2-(4-methoxyphenyl)-5-methyl-3-oxo-4-pyridazinecarbonitrile, 91Y78 (1H-imidazo[4,5-c]pyridin-4-amine, 1-β-D-ribofuranosyl-), auranofin (gold, (1-thio-β-D-glucopyranose 2,3,4,6-tetraacetato-S)(triethylphosphine)-), 27-0-demethylrapamycin, tipredane (androsta-1,4-dien-3-one, 17-(ethylthio)-9-fluoro-11-hydroxy-17-(methylthio)-, (11 β, 17 alpha)-), AI-402, LY-178002 (4-thiazolidinone, 5-((3,5-bis(1,1-dimethylethyl)-4-hydroxyphenyl)methylene)-), SM-8849 (2-thiazolamine, 4-(1-(2-fluoro(1,1'-biphenyl)-4-yl)ethyl)-N-methyl-), piceatannol, resveratrol, triamcinolone acetonide (pregna-1,4-diene-3,20-dione, 9-fluoro-11,21-dihydroxy-16,17-((1-methylethylidene)bis(oxy))-, (11β,16 alpha)-), ciclosporin (cyclosporin A), tacrolimus (15,19-epoxy-3H-pyrido(2,1-c)(1,4)oxaazacyclotricosine-1,7,20,21(4H,23H)-tetrone, 5,6,8,11,12,13,14,15,16,17,18,19,24,25,26,26a-hexadecahydro-5,19-dihydroxy-3-(2-(4-hydroxy-3-methoxycyclohexyl)-1-methylethenyl)-14,16-dimethoxy-4, 10,12,18-tetramethyl-8-(2-propenyl)-, (3S-(3R*(E(1S*,3S*, 4S*)),4S*,5R*,8S*,9E,12R*,14R*,15S*,16R*,18S*,19S*, 26aR*))—), gusperimus (heptanamide, 7-((aminoiminomethyl)amino)-N-(2-((4-((3-aminopropyl) amino)butyl)amino)-1-hydroxy-2-oxoethyl)-, (+/-)-), tixocortol pivalate (pregn-4-ene-3,20-dione, 21-((2,2-dimethyl-1-oxopropyl)thio)-11,17-dihydroxy-, (11β)-), alefacept (1-92 LFA-3 (antigen) (human) fusion protein with immunoglobulin G1 (human hinge-CH2—CH3 gamma1-chain), dimer), halobetasol propionate (pregna-1,4-diene-3,20-dione, 21-chloro-6,9-difluoro-11-hydroxy-16-methyl-17-(1-oxopropoxy)-, (6Alpha, 11β,16β)-), iloprost trometamol (pentanoic acid, 5-(hexahydro-5-hydroxy-4-(3-hydroxy-4-methyl-1-octen-6-ynyl)-2(1H)-pentalenylidene)-), beraprost (1H-cyclopenta(b)benzofuran-5-butanoic acid, 2,3,3a,8b-tetrahydro-2-hydroxy-1-(3-hydroxy-4-methyl-1-octen-6-ynyl)-), rimexolone (androsta-1,4-dien-3-one, 11-hydroxy-16,17-dimethyl-17-(1-oxopropyl)-, (11β,16Alpha, 17β)-), dexamethasone (pregna-1,4-diene-3,20-dione,9-fluoro-11, 17,21-trihydroxy-16-methyl-, (11β,16alpha)-), sulindac (cis-5-fluoro-2-methyl-1-((p-methylsulfinyl)benzylidene)indene-3-acetic acid), proglumetacin (1H-Indole-3-acetic acid, 1-(4-chlorobenzoyl)-5-methoxy-2-methyl-, 2-(4-(3-((4-(benzoylamino)-5-(dipropylamino)-1,5-dioxopentyl)oxy) propyl)-1-piperazinyl)ethylester, (+/-)-), alclometasone dipropionate (pregna-1,4-diene-3,20-dione, 7-chloro-11-hydroxy-16-methyl-17,21-bis(1-oxopropoxy)-, (7alpha, 11β, 16alpha)-), pimecrolimus (15,19-epoxy-3H-pyrido(2,1-c)(1, 4)oxaazacyclotricosine-1,7,20,21 (4H,23H)-tetrone, 3-(2-(4-chloro-3-methoxycyclohexyl)-1-methyletheny)-8-ethyl-5,6, 8,11,12,13,14,15,16,17,18,19,24,25,26,26a-hexadecahydro-5,19-dihydroxy-14,16-dimethoxy-4,10,12,18-tetramethyl-, (3S-(3R*(E(1S*,3S*,4R*)),4S*,5R*,8S*,9E,12R*,14R*, 15S*,16R*,18S*,19S*,26aR*))—), hydrocortisone-17-butyrate (pregn-4-ene-3,20-dione, 11,21-dihydroxy-17-(1-oxobutoxy)-, (11β)-), mitoxantrone (9,10-anthracenedione, 1,4-dihydroxy-5,8-bis((2-((2-hydroxyethyl)amino)ethyl) amino)-), mizoribine (1H-imidazole-4-carboxamide, 5-hydroxy-1-β-D-ribofuranosyl-), prednicarbate (pregna-1,4-diene-3,20-dione, 17-((ethoxycarbonyl)oxy)-11-hydroxy-21-(1-oxopropoxy)-, (11β)-), iobenzarit (benzoic acid, 2-((2-carboxyphenyl)amino)-4-chloro-), glucametacin (D-glucose, 2-(((1-(4-chlorobenzoyl)-5-methoxy-2-methyl-H-indol-3-yl)acetyl)amino)-2-deoxy-), fluocortolone monohydrate ((6 alpha)-fluoro-16alpha-methylpregna-1,4-dien-11β,21-diol-3,20-dione), fluocortin butyl (pregna-1,4-dien-21-oic acid, 6-fluoro-11-hydroxy-16-methyl-3,20-dioxo-, butyl ester, (6alpha,11β,16alpha)-), difluprednate (pregna-1, 4-diene-3,20-dione, 21-(acetyloxy)-6,9-difluoro-11-hydroxy-17-(1-oxobutoxy)-, (6 alpha,11β)-), diflorasone diacetate (pregna-1,4-diene-3,20-dione, 17,21-bis(acetyloxy)-6, 9-difluoro-11-hydroxy-16-methyl-, (6Alpha,11β,16β)-), dexamethasone valerate (pregna-1,4-diene-3,20-dione, 9-fluoro-11,21-dihydroxy-16-methyl-17-((1-oxopentyl) oxy)-, (11β,16Alpha)-), methylprednisolone, deprodone propionate (pregna-1,4-diene-3,20-dione, 11-hydroxy-17-(1-oxopropoxy)-, (11.beta.)-), bucillamine(L-cysteine, N-(2-mercapto-2-methyl-1-oxopropyl)-), amcinonide (benzeneacetic acid, 2-amino-3-benzoyl-, monosodium salt, monohydrate), acemetacin (1H-indole-3-acetic acid, 1-(4-chlorobenzoyl)-5-methoxy-2-methyl-, carboxymethyl ester), or an analogue or derivative thereof).

Further, analogues of rapamycin include tacrolimus and derivatives thereof (e.g., EP0184162B1 and U.S. Pat. No. 6,258,823) everolimus and derivatives thereof (e.g., U.S. Pat. No. 5,665,772). Further representative examples of sirolimus analogues and derivatives can be found in PCT Publication Nos. WO 97/10502, WO 96/41807, WO 96/35423, WO 96/03430, WO 96/00282, WO 95/16691, WO 95/15328, WO 95/07468, WO 95/04738, WO 95/04060, WO 94/25022, WO 94/21644, WO 94/18207, WO 94/10843, WO 94/09010, WO 94/04540, WO 94/02485, WO 94/02137, WO 94/02136, WO 93/25533, WO 93/18043, WO 93/13663, WO 93/11130, WO 93/10122, WO 93/04680, WO 92/14737, and WO 92/05179. Representative U.S. patents include U.S. Pat. Nos. 6,342,507; 5,985,890; 5,604,234; 5,597,715; 5,583,139; 5,563,172; 5,561,228; 5,561,137; 5,541,193; 5,541,189; 5,534,632; 5,527,907; 5,484,799; 5,457,194; 5,457,182; 5,362,735; 5,324,644; 5,318,895; 5,310,903; 5,310,901; 5,258,389; 5,252,732; 5,247,076; 5,225,403; 5,221,625; 5,210,030; 5,208,241; 5,200,411; 5,198,421; 5,147,877; 5,140,018; 5,116,756; 5,109,112; 5,093,338; and 5,091,389.

The structures of sirolimus, everolimus, and tacrolimus are provided below in Table 3:

TABLE 3

| Name | Code Name | Company | Structure |
|---|---|---|---|
| Everolimus | SAR-943 | Novartis | See below |
| Sirolimus | AY-22989 | Wyeth | See below |
| RAPAMUNE ® | NSC-226080 | | |
| Rapamycin | | | |
| Tacrolimus | FK506 | Fujusawa | See below |

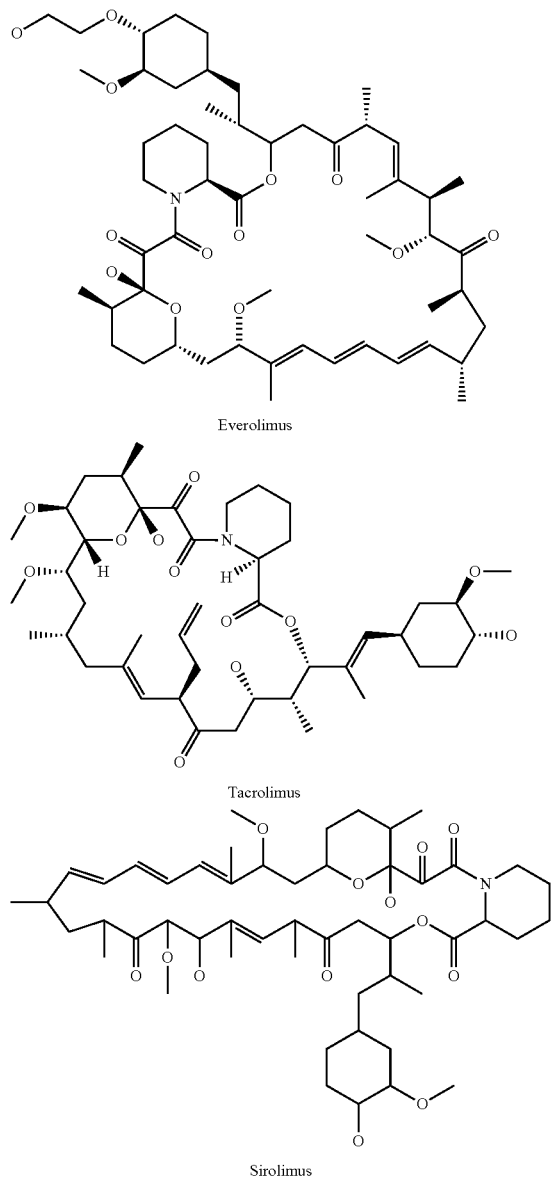

Everolimus

Tacrolimus

Sirolimus

Further sirolimus analogues and derivatives include tacrolimus and derivatives thereof (e.g., EP0184162B1 and U.S. Pat. No. 6,258,823) everolimus and derivatives thereof (e.g., U.S. Pat. No. 5,665,772). Further representative examples of sirolimus analogues and derivatives include ABT-578 and others may be found in PCT Publication Nos. WO 97/10502, WO 96/41807, WO 96/35423, WO 96/03430, WO 9600282, WO 95/16691, WO 9515328, WO 95/07468, WO 95/04738, WO 95/04060, WO 94/25022, WO 94/21644, WO 94/18207, WO 94/10843, WO 94/09010, WO 94/04540, WO 94/02485, WO 94/02137, WO 94/02136, WO 93/25533, WO 93/18043, WO 93/13663, WO 93/11130, WO 93/10122, WO 93/04680, WO 92/14737, and WO 92/05179. Representative U.S. patents include U.S. Pat. Nos. 6,342,507; 5,985,890; 5,604,234; 5,597,715; 5,583,139; 5,563,172; 5,561,228; 5,561,137; 5,541,193; 5,541,189; 5,534,632; 5,527,907; 5,484,799; 5,457,194; 5,457,182; 5,362,735; 5,324,644; 5,318,895; 5,310,903; 5,310,901; 5,258,389; 5,252,732; 5,247,076; 5,225,403; 5,221,625; 5,210,030; 5,208,241; 5,200,411; 5,198,421; 5,147,877; 5,140,018; 5,116,756; 5,109,112; 5,093,338; and 5,091,389.

In one aspect, the fibrosis-inhibiting agent may be, e.g., rapamycin (sirolimus), everolimus, biolimus, tresperimus, auranofin, 27-0-demethylrapamycin, tacrolimus, gusperimus, pimecrolimus, or ABT-578.

Inosine Monophosphate Dehydrogenase Inhibitors

In another embodiment, the pharmacologically active compound is an inosine monophosphate dehydrogenase (IMPDH) inhibitor (e.g., mycophenolic acid, mycophenolate mofetil (4-hexenoic acid, 6-(1,3-dihydro-4-hydroxy-6-methoxy-7-methyl-3-oxo-5-isobenzofuranyl)-4-methyl-, 2-(4-morpholinyl)ethyl ester, (E)-), ribavirin (1H-1,2,4-triazole-3-carboxamide, 1-β-D-ribofuranosyl-), tiazofurin (4-thiazolecarboxamide, 2-β-D-ribofuranosyl-), viramidine, aminothiadiazole, thiophenfurin, tiazofurin) or an analogue or derivative thereof. Additional representative examples are included in U.S. Pat. Nos. 5,536,747, 5,807,876, 5,932,600, 6,054,472, 6,128,582, 6,344,465, 6,395,763, 6,399,773, 6,420,403, 6,479,628, 6,498,178, 6,514,979, 6,518,291, 6,541,496, 6,596,747, 6,617,323, 6,624,184, Patent Application Publication Nos. 2002/0040022A1, 2002/0052513A1, 2002/0055483A1, 2002/0068346A1, 2002/0111378A1, 2002/0111495A1, 2002/0123520A1, 2002/0143176A1, 2002/0147160A1, 2002/0161038A1, 2002/0173491A1, 2002/0183315A1, 2002/0193612A1, 2003/0027845A1, 2003/0068302A1, 2003/0105073A1, 2003/0130254A1, 2003/0143197A1, 2003/0144300A1, 2003/0166201A1, 2003/0181497A1, 2003/0186974A1, 2003/0186989A1, 2003/0195202A1, and PCT Publication Nos. WO 0024725A1, WO 00/25780A1, WO 00/26197A1, WO 00/51615A1, WO 00/56331A1, WO 00/73288A1, WO 01/00622A1, WO 01/66706A1, WO 01/79246A2, WO 01/81340A2, WO 01/85952A2, WO 02/16382A1, WO 02/18369A2, WO 2051814A1, WO 2057287A2, WO2057425A2, WO 2060875A1, WO 2060896A1, WO 2060898A1, WO 2068058A2, WO 3020298A1, WO 3037349A1, WO 3039548A1, WO 3045901A2, WO 3047512A2, WO 3053958A1, WO 3055447A2, WO 3059269A2, WO 3063573A2, WO 3087071A1, WO 90/01545A1, WO 97/40028A1, WO 97/41211A1, WO 98/40381A1, and WO 99/55663A1).

Leukotriene Inhibitors

In another embodiment, the pharmacologically active compound is a leukotriene inhibitor (e.g., ONO-4057(benzenepropanoic acid, 2-(4-carboxybutoxy)-6-((6-(4-methoxyphenyl)-5-hexenyl)oxy)-, (E)-), ONO-LB-448, pirodomast 1,8-naphthyridin-2(1H)-one, 4-hydroxy-1-phenyl-3-(1-pyrrolidinyl)-, Sch-40120 (benzo(b)(1,8)naphthyridin-5(7H)-one, 10-(3-chlorophenyl)-6,8,9,10-tetrahydro-), L-656224

(4-benzofuranol, 7-chloro-2-((4-methoxyphenyl)methyl)-3-methyl-5-propyl-), MAFP (methyl arachidonyl fluorophosphonate), ontazolast (2-benzoxazolamine, N-(2-cyclohexyl-1-(2-pyridinyl)ethyl)-5-methyl-, (S)—), amelubant (carbamic acid, ((4-((3-((4-(1-(4-hydroxyphenyl)-1-methylethyl)phenoxy)methyl)phenyl)methoxy)phenyl)iminomethyl)-ethyl ester), SB-201993 (benzoic acid, 3-(((((6-((1E)-2-carboxyethenyl)-5-((8-(4-methoxyphenyl)octyl)oxy)-2-pyridinyl)methyl)thio)methyl)-), LY-203647 (ethanone, 1-(2-hydroxy-3-propyl-4-(4-(2-(4-(1H-tetrazol-5-yl)butyl)-2H-tetrazol-5-yl)butoxy)phenyl)-), LY-210073, LY-223982 (benzenepropanoic acid, 5-(3-carboxybenzoyl)-2-((6-(4-methoxyphenyl)-5-hexenyl)oxy)-, (E)-), LY-293111 (benzoic acid, 2-(3-(3-((5-ethyl-4'-fluoro-2-hydroxy(1,1'-biphenyl)-4-yl)oxy)propoxy)-2-propylphenoxy)-), SM-9064 (pyrrolidine, 1-(4,11-dihydroxy-13-(4-methoxyphenyl)-1-oxo-5,7,9-tridecatrienyl)-, (E,E,E)-), T-0757 (2,6-octadienamide, N-(4-hydroxy-3,5-dimethylphenyl)-3,7-dimethyl-, (2E)-), or an analogue or derivative thereof).

MCP-1 Antagonists

In another embodiment, the pharmacologically active compound is a MCP-1 antagonist (e.g., nitronaproxen (2-napthaleneacetic acid, 6-methoxy-alpha-methyl 4-(nitrooxy)butyl ester (alpha S)—), bindarit (2-(1-benzylindazol-3-yl)methoxy)-2-methylpropanoic acid), 1-alpha-25 dihydroxy vitamin $D_3$, or an analogue or derivative thereof).

MMP Inhibitors

In another embodiment, the pharmacologically active compound is a matrix metalloproteinase (MMP) inhibitor (e.g., D-9120, doxycycline (2-naphthacenecarboxamide, 4-(dimethylamino)-1,4,4a,5,5a,6,11,12a-octahydro-3,5,10,12,12a-pentahydroxy-6-methyl-1,11-dioxo-(4S-(4 alpha, 4a alpha, 5 lpha, 5a alpha, 6 alpha, 12a alpha))-), BB-2827, BB-1101 (2S-allyl-N-1-hydroxy-3R-isobutyl-N4-(1S-methylcarbamoyl-2-phenylethyl)-succinamide), BB-2983, solimastat (N'-(2,2-dimethyl-1(S)—(N-(2-pyridyl)carbamoyl)propyl)-N4-hydroxy-2(R)-isobutyl-3(S)-methoxysuccinamide), batimastat (butanediamide, N4-hydroxy-N1-(2-(methylamino)-2-oxo-1-(phenylmethyl)ethyl)-2-(2-methylpropyl)-3-((2-thienylthio)methyl)-, (2R-(1(S*),2R*,3S*))-), CH-138, CH-5902, D-1927, D-5410, EF-13 (gamma-linolenic acid lithium salt), CMT-3 (2-naphthacenecarboxamide, 1,4,4a,5,5a,6,11,12a-octahydro-3,10,12,12a-tetrahydroxy-1,11-dioxo-, (4aS,5aR,12aS)—), marimastat (N-(2,2-dimethyl-1(S)—(N-methylcarbamoyl)propyl)-N,3(S)-dihydroxy-2(R)-isobutylsuccinamide), TIMP'S,ONO-4817, rebimastat (L-Valinamide, N-((2S)-2-mercapto-1-oxo-4-(3,4,4-trimethyl-2,5-dioxo-1-imidazolidinyl)butyl)-L-leucyl-N,3-dimethyl-), PS-508, CH-715, nimesulide (methanesulfonamide, N-(4-nitro-2-phenoxyphenyl)-), hexahydro-2-(2(R)-(1 (RS)-(hydroxycarbamoyl)-4-phenylbutyl)nonanoyl)-N-(2,2,6,6-etramethyl-4-piperidinyl)-3(S)-pyridazine carboxamide, Rs-113-080, Ro-1130830, cipemastat (1-piperidinebutanamide, β-(cyclopentylmethyl)-N-hydroxy-gamma-oxo-alpha-((3,4,4-trimethyl-2,5-dioxo-1-imidazolidinyl)methyl)-,(alpha R,βR)—), 5-(4'-biphenyl)-5-(N-(4-nitrophenyl)piperazinyl)barbituric acid, 6-methoxy-1,2,3,4-tetrahydro-norharman-1-carboxylic acid, Ro-31-4724 (L-alanine, N-(2-(2-(hydroxyamino)-2-oxoethyl)-4-methyl-1-oxopentyl)-L-leucyl-, ethyl ester), prinomastat (3-thiomorpholinecarboxamide, N-hydroxy-2,2-dimethyl-4-((4-(4-pyridinyloxy)phenyl)sulfonyl)-, (3R)—), AG-3433 (1H-pyrrole-3-propanic acid, 1-(4'-cyano(1,1'-biphenyl)-4-yl)-b-((((3S)-tetrahydro-4,4-dimethyl-2-oxo-3-furanyl)amino)carbonyl)-, phenylmethyl ester, (bS)—), PNU-142769 (2H-Isoindole-2-butanamide, 1,3-dihydro-N-hydroxy-alpha-((3S)-3-(2-methylpropyl)-2-oxo-1-(2-phenylethyl)-3-pyrrolidinyl)-1,3-dioxo-, (alpha R)—), (S)-1-(2-(((((4,5-dihydro-5-thioxo-1,3,4-thiadiazol-2-yl)amino)-carbonyl)amino)-1-oxo-3-(pentafluorophenyl)propyl)-4-(2-pyridinyl)piperazine, SU-5402 (1H-pyrrole-3-propanoic acid, 2-((1,2-dihydro-2-oxo-3H-indol-3-ylidene)methyl)-4-methyl-), SC-77964, PNU-171829, CGS-27023A, N-hydroxy-2(R)-((4-methoxybenzene-sulfonyl)(4-picolyl) amino)-2-(2-tetrahydrofuranyl)-acetamide, L-758354 ((1,1'-biphenyl)-4-hexanoic acid, alpha-butyl-gamma-(((2,2-dimethyl-1-((methylamino)carbonyl)propyl)amino) carbonyl)-4'-fluoro-, (alpha S-(alpha R*, gammaS*(R*)))—, GI-155704A, CPA-926, TMI-005, XL-784, or an analogue or derivative thereof). Additional representative examples are included in U.S. Pat. Nos. 5,665,777; 5,985,911; 6,288,261; 5,952,320; 6,441,189; 6,235,786; 6,294,573; 6,294,539; 6,563,002; 6,071,903; 6,358,980; 5,852,213; 6,124,502; 6,160,132; 6,197,791; 6,172,057; 6,288,086; 6,342,508; 6,228,869; 5,977,408; 5,929,097; 6,498,167; 6,534,491; 6,548,524; 5,962,481; 6,197,795; 6,162,814; 6,441,023; 6,444,704; 6,462,073; 6,162,821; 6,444,639; 6,262,080; 6,486,193; 6,329,550; 6,544,980; 6,352,976; 5,968,795; 5,789,434; 5,932,763; 6,500,847; 5,925,637; 6,225,314; 5,804,581; 5,863,915; 5,859,047; 5,861,428; 5,886,043; 6,288,063; 5,939,583; 6,166,082; 5,874,473; 5,886,022; 5,932,577; 5,854,277; 5,886,024; 6,495,565; 6,642,255; 6,495,548; 6,479,502; 5,696,082; 5,700,838; 6,444,639; 6,262,080; 6,486,193; 6,329,550; 6,544,980; 6,352,976; 5,968,795; 5,789,434; 5,932,763; 6,500,847; 5,925,637; 6,225,314; 5,804,581; 5,863,915; 5,859,047; 5,861,428; 5,886,043; 6,288,063; 5,939,583; 6,166,082; 5,874,473; 5,886,022; 5,932,577; 5,854,277; 5,886,024; 6,495,565; 6,642,255; 6,495,548; 6,479,502; 5,696,082; 5,700,838; 5,861,436; 5,691,382; 5,763,621; 5,866,717; 5,902,791; 5,962,529; 6,017,889; 6,022,873; 6,022,898; 6,103,739; 6,127,427; 6,258,851; 6,310,084; 6,358,987; 5,872,152; 5,917,090; 6,124,329; 6,329,373; 6,344,457; 5,698,706; 5,872,146; 5,853,623; 6,624,144; 6,462,042; 5,981,491; 5,955,435; 6,090,840; 6,114,372; 6,566,384; 5,994,293; 6,063,786; 6,469,020; 6,118,001; 6,187,924; 6,310,088; 5,994,312; 6,180,611; 6,110,896; 6,380,253; 5,455,262; 5,470,834; 6,147,114; 6,333,324; 6,489,324; 6,362,183; 6,372,758; 6,448,250; 6,492,367; 6,380,258; 6,583,299; 5,239,078; 5,892,112; 5,773,438; 5,696,147; 6,066,662; 6,600,057; 5,990,158; 5,731,293; 6,277,876; 6,521,606; 6,168,807; 6,506,414; 6,620,813; 5,684,152; 6,451,791; 6,476,027; 6,013,649; 6,503,892; 6,420,427; 6,300,514; 6,403,644; 6,177,466; 6,569,899; 5,594,006; 6,417,229; 5,861,510; 6,156,798; 6,387,931; 6,350,907; 6,090,852; 6,458,822; 6,509,337; 6,147,061; 6,114,568; 6,118,016; 5,804,593; 5,847,153; 5,859,061; 6,194,451; 6,482,827; 6,638,952; 5,677,282; 6,365,630; 6,130,254; 6,455,569; 6,057,369; 6,576,628; 6,110,924; 6,472,396; 6,548,667; 5,618,844; 6,495,578; 6,627,411; 5,514,716; 5,256,657; 5,773,428; 6,037,472; 6,579,890; 5,932,595; 6,013,792; 6,420,415; 5,532,265; 5,691,381; 5,639,746; 5,672,598; 5,830,915; 6,630,516; 5,324,634; 6,277,061; 6,140,099; 6,455,570; 5,595,885; 6,093,398; 6,379,667; 5,641,636; 5,698,404; 6,448,058; 6,008,220; 6,265,432; 6,169,103; 6,133,304; 6,541,521; 6,624,196; 6,307,089; 6,239,288; 5,756,545; 6,020,366; 6,117,869; 6,294,674; 6,037,361; 6,399,612; 6,495,568; 6,624,177; 5,948,780; 6,620,835; 6,284,513; 5,977,141; 6,153,612; 6,297,247; 6,559,142; 6,555,535; 6,350,885; 5,627,206; 5,665,764; 5,958,972; 6,420,408; 6,492,422; 6,340,709; 6,022,948; 6,274,703; 6,294,694; 6,531,499; 6,465,508; 6,437,177; 6,376,665; 5,268,384; 5,183,900; 5,189,178; 6,511,993; 6,617,354; 6,331,563; 5,962,466; 5,861,427; 5,830,869; and 6,087,359.

NF Kappa B Inhibitors

In another embodiment, the pharmacologically active compound is a NF kappa B (NFKB) inhibitor (e.g., AVE-0545, Oxi-104 (benzamide, 4-amino-3-chloro-N-(2-(diethylamino)ethyl)-), dexlipotam, R-flurbiprofen ((1,1'-biphenyl)-4-acetic acid, 2-fluoro-alpha-methyl), SP100030 (2-chloro-N-(3,5-di(trifluoromethyl)phenyl)-4-(trifluoromethyl) pyrimidine-5-carboxamide), AVE-0545, Viatris, AVE-0547, Bay 11-7082, Bay 11-7085, 15 deoxy-prostaylandin J2, bortezomib (boronic acid, ((1R)-3-methyl-1-(((2S)-1-oxo-3-phenyl-2-((pyrazinylcarbonyl)amino)propyl)amino)butyl)-, benzamide and nicotinamide derivatives that inhibit NF-kappaB, such as those described in U.S. Pat. Nos. 5,561,161 and 5,340,565 (OxiGene), PG490-88Na, or an analogue or derivative thereof).

NO Agonists

In another embodiment, the pharmacologically active compound is a NO antagonist (e.g., NCX-4016 (benzoic acid, 2-(acetyloxy)-, 3-((nitrooxy)methyl)phenyl ester, NCX-2216, L-arginine or an analogue or derivative thereof).

P38 MAP Kinase Inhibitors

In another embodiment, the pharmacologically active compound is a p38 MAP kinase inhibitor (e.g., GW-2286, CGP-52411, BIRB-798, SB220025, RO-320-1195, RWJ-67657, RWJ-68354, SCIO-469, SCIO-323, AMG-548, CMC-146, SD-31145, CC-8866, Ro-320-1195, PD-98059 (4H-1-benzopyran-4-one, 2-(2-amino-3-methoxyphenyl)-), CGH-2466, doramapimod, SB-203580 (pyridine, 4-(5-(4-fluorophenyl)-2-(4-(methylsulfinyl)phenyl)-1H-imidazol-4-yl)-), SB-220025 ((5-(2-amino-4-pyrimidinyl)-4-(4-fluorophenyl)-1-(4-piperidinyl)imidazole), SB-281832, PD169316, SB202190, GSK-681323, EO-1606, GSK-681323, or an analogue or derivative thereof). Additional representative examples are included in U.S. Pat. Nos. 6,300, 347; 6,316,464; 6,316,466; 6,376,527; 6,444,696; 6,479,507; 6,509,361; 6,579,874; 6,630,485, U.S. Patent Application Publication Nos. 2001/0044538A1; 2002/0013354A1; 2002/0049220A1; 2002/0103245A1; 2002/0151491A1; 2002/0156114A1; 2003/0018051A1; 2003/0073832A1; 2003/0130257A1; 2003/0130273A1; 2003/0130319A1; 2003/0139388A1; 20030139462A1; 2003/0149031A1; 2003/0166647A1; 2003/0181411A1; and PCT Publication Nos. WO 00/63204A2; WO 01/21591A1; WO 01/35959A1; WO 01/74811A2; WO 02/18379A2; WO 2064594A2; WO 2083622A2; WO 2094842A2; WO 2096426A1; WO 2101015A2; WO 2103000A2; WO 3008413A1; WO 3016248A2; WO 3020715A1; WO 3024899A2; WO 3031431A1; WO3040103A1; WO 3053940A1; WO 3053941A2; WO 3063799A2; WO 3079986A2; WO 3080024A2; WO 3082287A1; WO 97/44467A1; WO 99/01449A1; and WO 99/58523A1.

Phosphodiesterase Inhibitors

In another embodiment, the pharmacologically active compound is a phosphodiesterase inhibitor (e.g., CDP-840 (pyridine, 4-((2R)-2-(3-(cyclopentyloxy)-4-methoxyphenyl)-2-phenylethyl)-), CH-3697, CT-2820, D-22888 (imidazo[1,5-a]pyrido(3,2-e)pyrazin-6(5H)-one, 9-ethyl-2-methoxy-7-methyl-5-propyl-), D-4418 (8-methoxyquinoline-5-(N-(2,5-dichloropyridin-3-yl))carboxamide), 1-(3-cyclopentyloxy-4-methoxyphenyl)-2-(2,6-dichloro-4-pyridyl)ethanone oxime, D-4396, ONO-6126, CDC-998, CDC-801, V-11294A (3-(3-(cyclopentyloxy)-4-methoxybenzyl)-6-(ethylamino)-8-isopropyl-3H-purine hydrochloride), S,S'-methylene-bis(2-(8-cyclopropyl-3-propyl-6-(4-pyridylmethylamino)-2-thio-3H-purine))tetrahydrochloride, rolipram (2-pyrrolidinone, 4-(3-(cyclopentyloxy)-4-methoxyphenyl)-), CP-293121, CP-353164 (5-(3-cyclopentyloxy-4-methoxyphenyl)pyridine-2-carboxamide), oxagrelate (6-phthalazinecarboxylic acid, 3,4-dihydro-1-(hydroxymethyl)-5,7-dimethyl-4-oxo-, ethyl ester), PD-168787, ibudilast (1-propanone, 2-methyl-1-(2-(1-methylethyl)pyrazolo(1,5-a)pyridin-3-yl)-), oxagrelate (6-phthalazinecarboxylic acid, 3,4-dihydro-1-(hydroxymethyl)-5, 7-dimethyl-4-oxo-, ethyl ester), griseolic acid (alpha-L-talo-oct-4-enofuranuronic acid, 1-(6-amino-9H-purin-9-yl)-3,6-anhydro-6-C-carboxy-1,5-dideoxy-), KW-4490, KS-506, T-440, roflumilast (benzamide, 3-(cyclopropylmethoxy)-N-(3,5-dichloro-4-pyridinyl)-4-(difluoromethoxy)-), rolipram, milrinone, triflusinal (benzoic acid, 2-(acetyloxy)-4-(trifluoromethyl)-), anagrelide hydrochloride (imidazo[2,1-b]quinazolin-2(3H)-one, 6,7-dichloro-1,5-dihydro-, monohydrochloride), cilostazol (2(1H)-quinolinone, 6-(4-(1-cyclohexyl-1H-tetrazol-5-yl)butoxy)-3,4-dihydro-), propentofylline (1H-purine-2,6-dione, 3,7-dihydro-3-methyl-1-(5-oxohexyl)-7-propyl-), sildenafil citrate (piperazine, 1-((3-(4,7-dihydro-1-methyl-7-oxo-3-propyl-1H-pyrazolo (4,3-d)pyrimidin-5-yl)-4-ethoxyphenyl)sulfonyl)-4-methyl, 2-hydroxy-1,2,3-propanetricarboxylate- (1:1)), tadalafil (pyrazino(1',2':1,6)pyrido(3,4-b)indole 1,4-dione, 6-(1,3-benzodioxol-5-yl)-2,3,6,7,12,12a-hexahydro-2-methyl-, (6R-trans)), vardenafil (piperazine, 1-(3-(1,4-dihydro-5-methyl(-4-oxo-7-propylimidazo(5,1-f)(1,2,4)-triazin-2-yl)-4-ethoxyphenyl)sulfonyl)-4-ethyl-), milrinone ((3,4'-bipyridine)-5-carbonitrile, 1,6-dihydro-2-methyl-6-oxo-), enoximone (2H-imidazol-2-one, 1,3-dihydro-4-methyl-5-(4-(methylthio)benzoyl)-), theophylline (H-purine-2,6-dione, 3,7-dihydro-1,3-dimethyl-), ibudilast (1-propanone, 2-methyl-1-(2-(1-methylethyl)pyrazolo(1,5-a)pyridin-3-yl)-), aminophylline (1H-purine-2,6-dione, 3,7-dihydro-1,3-dimethyl-, compound with 1,2-ethanediamine (2:1)-), acebrophylline (7H-purine-7-acetic acid, 1,2,3,6-tetrahydro-1,3-dimethyl-2,6-dioxo-, compd. with trans-4-(((2-amino-3,5-dibromophenyl)methyl)amino)cyclohexanol (1:1)), plafibride (propanamide, 2-(4-chlorophenoxy)-2-methyl-N-(((4-morpholinylmethyl)amino)carbonyl)-), ioprinone hydrochloride (3-pyridinecarbonitrile, 1,2-dihydro-5-imidazo[1,2-a]pyridin-6-yl-6-methyl-2-oxo-, monohydrochloride-), fosfosal (benzoic acid, 2-(phosphonooxy)-), aminone ((3,4'-bipyridin)-6(1H)-one, 5-amino-, or an analogue or derivative thereof).

Other examples of phosphodiesterase inhibitors include denbufylline (1H-purine-2,6-dione, 1,3-dibutyl-3,7-dihydro-7-(2-oxopropyl)-), propentofylline (1H-purine-2,6-dione, 3,7-dihydro-3-methyl-1-(5-oxohexyl)-7-propyl-) and pelrinone (5-pyrimidinecarbonitrile, 1,4-dihydro-2-methyl-4-oxo-6-[(3-pyridinylmethyl)amino]-).

Other examples of phosphodiesterase III inhibitors include enoximone (2H-imidazol-2-one, 1,3-dihydro-4-methyl-5-[4-(methylthio)benzoyl]-), and saterinone (3-pyridinecarbonitrile, 1,2-dihydro-5-[4-[2-hydroxy-3-[4-(2-methoxyphenyl)-1-piperazinyl]propoxy]phenyl]-6-methyl-2-oxo-).

Other examples of phosphodiesterase IV inhibitors include AWD-12-281, 3-auinolinecarboxylic acid, 1-ethyl-6-fluoro-1,4-dihydro-7-(4-methyl-1-piperazinyl)-4-oxo-), tadalafil (pyrazino(1',2':1,6)pyrido(3,4-b)indole 1,4-dione, 6-(1,3-benzodioxol-5-yl)-2,3,6,7,12,12a-hexahydro-2-methyl-, (6R-trans)), and filaminast (ethanone, 1-[3-(cyclopentyloxy)-4-methoxyphenyl]-, O-(aminocarbonyl)oxime, (1E)-).

Another example of a phosphodiesterase V inhibitor is vardenafil (piperazine, 1-(3-(1,4-dihydro-5-methyl(-4-oxo-7-propylimidazo(5-f)((1,2,4)-triazin-2-yl)-4-ethoxyphenyl) sulfonyl)-4-ethyl-).

TGF Beta Inhibitors

In another embodiment, the pharmacologically active compound is a TGF beta Inhibitor (e.g., mannose-6-phosphate, LF-984, tamoxifen (ethanamine, 2-(4-(1,2-diphenyl-1-butenyl)phenoxy)-N,N-dimethyl-, (Z)—), tranilast, or an analogue or derivative thereof).

Thromboxane A2 Antagonists

In another embodiment, the pharmacologically active compound is a thromboxane A2 antagonist (e.g., CGS-22652 (3-pyridineheptanoic acid, γ-(4-(((4-chlorophenyl)sulfonyl) amino)butyl)-, (+/−)-), ozagrel (2-propenoic acid, 3-(4-(1H-imidazol-1-ylmethyl)phenyl)-, (E)-), argatroban (2-piperidinecarboxylic acid, 1-(5-((aminoiminomethyl)amino)-1-oxo-2-(((1,2,3,4-tetrahydro-3-methyl-8-quinolinyl)sulfonyl) amino)pentyl)-4-methyl-), ramatroban (9H-carbazole-9-propanoic acid, 3-(((4-fluorophenyl)sulfonyl)amino)-1,2,3, 4-tetrahydro-, (R)—), torasemide (3-pyridinesulfonamide, N-(((1-methylethyl)amino)carbonyl)-4-((3-methylphenyl) amino)-), gamma linoleic acid ((Z,Z,Z)-6,9,12-octadecatrienoic acid), seratrodast (benzeneheptanoic acid, zeta-(2,4,5-trimethyl-3,6-dioxo-1,4-cyclohexadien-1-yl)-, (+/−)-, or an analogue or derivative thereof).

TNFa Antagonists and TACE Inhibitors

In another embodiment, the pharmacologically active compound is a TNFa antagonist or TACE inhibitor (e.g., E-5531 (2-deoxy-6-0-(2-deoxy-3-0-(3(R)-(5(Z)-dodecenoyloxy)-decyl)-6-0-methyl-2-(3-oxotetradecanamido)-4-O-phosphono-β-D-glucopyranosyl)-3-0-(3(R)-hydroxydecyl)-2-(3-oxotetradecanamido)-alpha-D-glucopyranose-1-O-phosphate), AZD-4717, glycophosphopeptical, UR-12715 (B=benzoic acid, 2-hydroxy-5-((4-(3-(4-(2-methyl-1H-imidazol(4,5-c)pyridin-1-yl)methyl)-1-piperidinyl)-3-oxo-1-phenyl-1-propenyl)phenyl)azo) (Z)), PMS-601, AM-87, xyloadenosine (9H-purin-6-amine, 9-β-D-xylofuranosyl-), RDP-58, RDP-59, BB2275, benzydamine, E-3330 (undecanoic acid, 2-((4,5-dimethoxy-2-methyl-3,6-dioxo-1,4-cyclohexadien-1-yl)methylene)-, (E)-), N-(D,L-2-(hydroxyaminocarbonyl)methyl-4-methylpentanoyl)-L-3-(2'-naphthyl)alanyl-L-alanine, 2-aminoethyl amide, CP-564959, MLN-608, SPC-839, ENMD-0997, Sch-23863 ((2-(10,11-dihydro-5-ethoxy-5H-dibenzo (a,d) cyclohepten-5-yl)-N,N-dimethyl-ethanamine), SH-636, PKF-241-466, PKF-242-484, TNF-484A, cilomilast (cis-4-cyano-4-(3-(cyclopentyloxy)-4-methoxyphenyl)cyclohexane-1-carboxylic acid), GW-3333, GW-4459, BMS-561392, AM-87, cloricromene (acetic acid, ((8-chloro-3-(2-(diethylamino)ethyl)-4-methyl-2-oxo-2H-1-benzopyran-7-yl) oxy)-, ethyl ester), thalidomide (1H-Isoindole-1,3(2H)-dione, 2-(2,6-dioxo-3-piperidinyl)-), vesnarinone (piperazine, 1-(3,4-dimethoxybenzoyl)-4-(1,2,3,4-tetrahydro-2-oxo-6-quinolinyl)-), infliximab, lentinan, etanercept (1-235-tumor necrosis factor receptor (human) fusion protein with 236-467-immunoglobulin G1 (human gamma1-chain Fc fragment)), diacerein (2-anthracenecarboxylic acid, 4,5-bis(acetyloxy)-9,10-dihydro-9,10-dioxo-, or an analogue or derivative thereof).

Tyrosine Kinase Inhibitors

In another embodiment, the pharmacologically active compound is a tyrosine kinase inhibitor (e.g., SKI-606, ER-068224, SD-208, N-(6-benzothiazolyl)-4-(2-(1-piperazinyl)pyrid-5-yl)-2-pyrimidineamine, celastrol (24,25,26-trinoroleana-1(10),3,5,7-tetraen-29-oic acid, 3-hydroxy-9, 13-dimethyl-2-oxo-, (9 beta.,13alpha,14β,20 alpha)-), CP-127374 (geldanamycin, 17-demethoxy-17-(2-propenylamino)-), CP-564959, PD-171026, CGP-52411 (1H-Isoindole-1,3(2H)-dione, 4,5-bis(phenylamino)-), CGP-53716 (benzamide, N-(4-methyl-3-((4-(3-pyridinyl)-2-pyrimidinyl)amino)phenyl)-), imatinib (4-((methyl-1-piperazinyl) methyl)-N-(4-methyl-3-((4-(3-pyridinyl)-2-pyrimidinyl) amino)-phenyl)benzamide methanesulfonate), NVP-AAK980-NX, KF-250706 (13-chloro,5(R),6(S)-epoxy-14, 16-dihydroxy-11-(hydroyimino)-3(R)-methyl-3,4,5,6,11, 12-hexahydro-1H-2-benzoxacyclotetradecin-1-one), 5-(3-(3-methoxy-4-(2-((E)-2-phenylethenyl)-4-oxazolylmethoxy)phenyl)propyl)-3-(2-((E)-2-phenylethenyl)-4-oxazolylmethyl)-2,4-oxazolidinedione, genistein, NV-06, or an analogue or derivative thereof).

Vitronectin Inhibitors

In another embodiment, the pharmacologically active compound is a vitronectin inhibitor (e.g., O-(9,10-dimethoxy-1,2,3,4,5,6-hexahydro-4-((1,4,5,6-tetrahydro-2-pyrimidinyl)hydrazono)-8-benz(e)azulenyl)-N-((phenylmethoxy)carbonyl)-DL-homoserine 2,3-dihydroxypropyl ester, (2S)-benzoylcarbonylamino-3-(2-((4S)-(3-(4,5-dihydro-1H-imidazol-2-ylamino)-propyl)-2,5-dioxo-imidazolidin-1-yl)-acetylamino)-propionate, Sch-221153, S-836, SC-68448 (β-((2-2-(((3-((aminoiminomethyl)amino)-phenyl)carbonyl)amino)acetyl)amino)-3,5-dichlorobenzenepropanoic acid), SD-7784, S-247, or an analogue or derivative thereof).

Fibroblast Growth Factor Inhibitors

In another embodiment, the pharmacologically active compound is a fibroblast growth factor inhibitor (e.g., CT-052923 (((2H-benzo(d)1,3-dioxalan-5-methyl)amino) (4-(6,7-dimethoxyquinazolin-4-yl)piperazinyl)methane-1-thione), or an analogue or derivative thereof).

Protein Kinase Inhibitors

In another embodiment, the pharmacologically active compound is a protein kinase inhibitor (e.g., KP-0201448, NPC15437 (hexanamide, 2,6-diamino-N-((1-(1-oxotridecyl)-2-piperidinyl)methyl)-), fasudil (1H-1,4-diazepine, hexahydro-1-(5-isoquinolinylsulfonyl)-), midostaurin (benzamide, N-(2,3,10,11,12,13-hexahydro-10-methoxy-9-methyl-1-oxo-9,13-epoxy-1H,9H-diindolo(1,2,3-gh:3',2',1'-1m)pyrrolo(3,4-j)(1,7)benzodiazonin-11-yl)-N-methyl-, (9Alpha,10β,11β,13 Alpha)-),fasudil (1H-1,4-diazepine, hexahydro-1-(5-isoquinolinylsulfonyl)-, dexniguldipine (3,5-pyridinedicarboxylic acid, 1,4-dihydro-2,6-dimethyl-4-(3-nitrophenyl)-, 3-(4,4-diphenyl-1-piperidinyl)propyl methyl ester, monohydrochloride, (R)—), LY-317615 (1H-pyrole-2,5-dione, 3-(1-methyl-1H-indol-3-yl)-4-[1-[1-(2-pyridinylmethyl)-4-piperidinyl]-1H-indol-3-yl]-, monohydrochloride), perifosine (piperidinium, 4-[[hydroxy (octadecyloxy)phosphinyl]oxy]-1,1-dimethyl-, inner salt), LY-333531 (9H,18H-5, 21:12,17-dimethenodibenzo(e,k) pyrrolo(3,4-h)(1,4,13)oxadiazacyclohexadecine-18,20 (19H)-dione,9-((dimethylamino)methyl)-6,7, 10,11-tetrahydro-, (S)—), Kynac; SPC-100270 (1,3-octadecanediol, 2-amino-, [S—(R*,R*)]—), Kynacyte, or an analogue or derivative thereof).

PDGF Receptor Kinase Inhibitors

In another embodiment, the pharmacologically active compound is a PDGF receptor kinase inhibitor (e.g., RPR-127963E, or an analogue or derivative thereof).

Endothelial Growth Factor Receptor Kinase Inhibitors

In another embodiment, the pharmacologically active compound is an endothelial growth factor receptor kinase inhibitor (e.g., CEP-7055, SU-0879 ((E)-3-(3,5-di-tert-butyl-4-hydroxyphenyl)-2-(aminothiocarbonyl)acrylonitrile), BIBF-1000, AG-013736 (CP-868596), AMG-706, AVE-0005, NM-3 (3-(2-methylcarboxymethyl)-6-methoxy-8-hydroxy-isocoumarin), Bay-43-9006, SU-011248, or an analogue or derivative thereof).

Retinoic Acid Receptor Antagonists

In another embodiment, the pharmacologically active compound is a retinoic acid receptor antagonist (e.g., etarotene (Ro-15-1570) (naphthalene, 6-(2-(4-(ethylsulfonyl)phenyl)-1-methylethenyl)-1,2,3,4-tetrahydro-1,1,4,4-tetramethyl-, (E)-), (2E,4E)-3-methyl-5-(2-((E)-2-(2,6,6-trimethyl-1-cyclohexen-1-yl)ethenyl)-1-cyclohexen-1-yl)-2,4-pentadienoic acid, tocoretinate (retinoic acid, 3,4-dihydro-2,5,7,8-tetramethyl-2-(4,8,12-trimethyltridecyl)-2H-1-benzopyran-6-yl ester, (2R*(4R*,8R*))—(±)-), aliretinoin (retinoic acid, cis-9, trans-13-), bexarotene (benzoic acid, 4-(1-(5,6,7,8-tetrahydro-3,5,5,8,8-pentamethyl-2-naphthalenyl)ethenyl)-), tocoretinate (retinoic acid, 3,4-dihydro-2,5,7,8-tetramethyl-2-(4,8,12-trimethyltridecyl)-2H-1-benzopyran-6-yl ester, [2R*(4R*,8R*)]—(±)-, or an analogue or derivative thereof).

Platelet Derived Growth Factor Receptor Kinase Inhibitors

In another embodiment, the pharmacologically active compound is a platelet derived growth factor receptor kinase inhibitor (e.g., leflunomide (4-isoxazolecarboxamide, 5-methyl-N-(4-(trifluoromethyl)phenyl)-, or an analogue or derivative thereof).

Fibrinogen Antagonists

In another embodiment, the pharmacologically active compound is a fibrinogen antagonist (e.g., picotamide (1,3-benzenedicarboxamide, 4-methoxy-N,N'-bis(3-pyridinylmethyl)-, or an analogue or derivative thereof).

Antimycotic Agents

In another embodiment, the pharmacologically active compound is an antimycotic agent (e.g., miconazole, sulconizole, parthenolide, rosconitine, nystatin, isoconazole, fluconazole, ketoconasole, imidazole, itraconazole, terpinafine, elonazole, bifonazole, clotrimazole, conazole, terconazole (piperazine, 1-(4-((2-(2,4-dichlorophenyl)-2-(1H-1,2,4-triazol-1-ylmethyl)-1,3-dioxolan-4-yl)methoxy)phenyl)-4-(1-methylethyl)-, cis-), isoconazole (1-(2-(2-6-dichlorobenzyloxy)-2-(2-,4-dichlorophenyl)ethyl)), griseofulvin (spiro(benzofuran-2(3H), 1'-(2)cyclohexane)-3,4'-dione, 7-chloro-2',4,6-trimeth-oxy-6'methyl-, (1'S-trans)-), bifonazole (1H-imidazole, 1-((1,1'-biphenyl)-4-ylphenylmethyl)-), econazole nitrate (1-(2-((4-chlorophenyl)methoxy)-2-(2,4-dichlorophenyl)ethyl)-1H-imidazole nitrate), croconazole (1H-imidazole, 1-(1-(2-((3-chlorophenyl)methoxy)phenyl)ethenyl)-), sertaconazole (1H-Imidazole, 1-(2-((7-chlorobenzo(b)thien-3-yl)methoxy)-2-(2,4-dichlorophenyl)ethyl)-), omoconazole (1H-imidazole, 1-(2-(2-(4-chlorophenoxy)ethoxy)-2-(2,4-dichlorophenyl)-1-methylethenyl)-, (Z)—), flutrimazole (1H-imidazole, 1-((2-fluorophenyl)(4-fluorophenyl)phenylmethyl)-), fluconazole (1H-1,2,4-triazole-1-ethanol, alpha-(2,4-difluorophenyl)-alpha-(1H-1,2,4-triazol-1-ylmethyl)-), neticonazole (1H-Imidazole, 1-(2-(methylthio)-1-(2-(pentyloxy)phenyl)ethenyl)-, monohydrochloride, (E)-), butoconazole (1H-imidazole, 1-(4-(4-chlorophenyl)-2-((2,6-dichlorophenyl)thio)butyl)-, (+/−)-), clotrimazole (1-((2-chlorophenyl)diphenylmethyl)-1H-imidazole, or an analogue or derivative thereof).

Bisphosphonates

In another embodiment, the pharmacologically active compound is a bisphosphonate (e.g., clodronate, alendronate, pamidronate, zoledronate, or an analogue or derivative thereof).

Phospholipase A1 Inhibitors

In another embodiment, the pharmacologically active compound is a phospholipase A1 inhibitor (e.g., ioteprednol etabonate (androsta-1,4-diene-17-carboxylic acid, 17-((ethoxycarbonyl)oxy)-11-hydroxy-3-oxo-, chloromethyl ester, (11β,17 alpha)-, or an analogue or derivative thereof).

Histamine H1/H2/H3 Receptor Antagonists

In another embodiment, the pharmacologically active compound is a histamine H1, H2, or H3 receptor antagonist (e.g., ranitidine (1,1-ethenediamine, N-(2-(((5-((dimethylamino)methyl)-2-furanyl)methyl)thio)ethyl)-N'-methyl-2-nitro-), niperotidine (N-(2-((5-((dimethylamino)methyl)furfuryl)thio)ethyl)-2-nitro-N'-piperonyl-1,1-ethenediamine), famotidine (propanimidamide, 3-(((2-((aminoiminomethyl)amino)-4-thiazolyl)methyl)thio)-N-(aminosulfonyl)-), roxitadine acetate HCl (acetamide, 2-(acetyloxy)-N-(3-(3-(1-piperidinylmethyl)phenoxy)propyl)-, monohydrochloride), lafutidine (acetamide, 2-((2-furanylmethyl)sulfinyl)-N-(4-((4-(1-piperidinylmethyl)-2-pyridinyl)oxy)-2-butenyl)-, (Z)—), nizatadine (1,1-ethenediamine, N-(2-(((2-((dimethylamino)methyl)-4-thiazolyl)methyl)thio)ethyl)-N'-methyl-2-nitro-), ebrotidine (benzenesulfonamide, N-(((2-(((2-((aminoiminomethyl)amino)-4-thiazoly)methyl)thio)ethyl)amino)methylene)-4-bromo-), rupatadine (5H-benzo(5,6)cyclohepta(1,2-b)pyridine, 8-chloro-6,11-dihydro-11-(1-((5-methyl-3-pyridinyl)methyl)-4-piperidinylidene)-, trihydrochloride-), fexofenadine HCl (benzeneacetic acid, 4-(1-hydroxy-4-(4(hydroxydiphenylmethyl)-1-piperidinyl)butyl)-alpha, alpha-dimethyl-, hydrochloride, or an analogue or derivative thereof).

Macrolide Antibiotics

In another embodiment, the pharmacologically active compound is a macrolide antibiotic (e.g., dirithromycin (erythromycin, 9-deoxo-11-deoxy-9,11-(imino(2-(2-methoxyethoxy)ethyl idene)oxy)-, (9S(R))-), flurithromycin ethylsuccinate (erythromycin, 8-fluoro-mono(ethyl butanedioate) (ester)-), erythromycin stinoprate (erythromycin, 2'-propanoate, compound with N-acetyl-L-cysteine (1:1)), clarithromycin (erythromycin, 6-O-methyl-), azithromycin (9-deoxo-9a-aza-9a-methyl-9a-homoerythromycin-A), telithromycin (3-de((2,6-dideoxy-3-C-methyl-3-O-methyl-alpha-L-ribo-hexopyranosyl)oxy)-11,12-dideoxy-6-O-methyl-3-oxo-12,11-(oxycarbonyl((4-(4-(3-pyridinyl)-1H-imidazol-1-yl)butyl)imino))-), roxithromycin (erythromycin, 9-(O-((2-methoxyethoxy)methyl)oxime)), rokitamycin (leucomycin V, 4B-butanoate 3B-propanoate), RV-11 (erythromycin monopropionate mercaptosuccinate), midecamycin acetate (leucomycin V, 3B,9-diacetate 3,4B-dipropanoate), midecamycin (leucomycin V, 3,4B-dipropanoate), josamycin (leucomycin V, 3-acetate 4B-(3-methylbutanoate), or an analogue or derivative thereof).

GPIIb IIa Receptor Antagonists

In another embodiment, the pharmacologically active compound is a GPIIb IIIa receptor antagonist (e.g., tirofiban hydrochloride (L-tyrosine, N-(butylsulfonyl)-O-(4-(4-piperidinyl)butyl)-, monohydrochloride-), eptifibatide (L-cysteinamide, N6-(aminoiminomethyl)-N2-(3-mercapto-1-oxopropyl)-L-lysylglycyl-L-alpha-aspartyl-L-tryptophyl-L-prolyl-, cyclic(1→6)-disulfide), xemilofiban hydrochloride, or an analogue or derivative thereof).

Endothelin Receptor Antagonists

In another embodiment, the pharmacologically active compound is an endothelin receptor antagonist (e.g., bosentan (benzenesulfonamide, 4-(1,1-dimethylethyl)-N-(6-(2-hydroxyethoxy)-5-(2-methoxyphenoxy)(2,2'-bipyrimidin)-4-yl)-, or an analogue or derivative thereof).

Peroxisome Proliferator-Activated Receptor Agonists

In another embodiment, the pharmacologically active compound is a peroxisome proliferator-activated receptor agonist (e.g., gemfibrozil (pentanoic acid, 5-(2,5-dimethylphenoxy)-2,2-dimethyl-), fenofibrate (propanoic acid, 2-(4-(4-chlorobenzoyl)phenoxy)-2-methyl-, 1-methylethyl ester), ciprofibrate (propanoic acid, 2-(4-(2,2-dichlorocyclopropyl)phenoxy)-2-methyl-), rosiglitazone maleate (2,4-thiazolidinedione, 5-((4-(2-(methyl-2-pyridinylamino) ethoxy)phenyl)methyl]-, (Z)-2-butenedioate (1:1)), pioglitazone hydrochloride (2,4-thiazolidinedione, 5-((4-(2-(5-ethyl-2-pyridinyl)ethoxy)phenyl)methyl]-, monohydrochloride (+/−)-), etofylline clofibrate (propanoic acid, 2-(4-chlorophenoxy)-2-methyl-, 2-(1,2,3,6-tetrahydro-1,3-dimethyl-2,6-dioxo-7H-purin-7-yl)ethyl ester), etofibrate (3-pyridinecarboxylic acid, 2-(2-(4-chlorophenoxy)-2-methyl-1-oxopropoxy)ethyl ester), clinofibrate (butanoic acid, 2,2'-(cyclohexylidenebis(4,1-phenyleneoxy))bis(2-methyl-)), bezafibrate (propanoic acid, 2-(4-(2-((4-chlorobenzoyl)amino)ethyl)phenoxy)-2-methyl-), binifibrate (3-pyridinecarboxylic acid, 2-(2-(4-chlorophenoxy)-2-methyl-1-oxopropoxy)-1,3-propanediyl ester), or an analogue or derivative thereof).

In one aspect, the pharmacologically active compound is a peroxisome proliferator-activated receptor alpha agonist, such as GW-590735, GSK-677954, GSK501516, pioglitazone hydrochloride (2,4-thiazolidinedione, 5-[[4-[2-(5-ethyl-2-pyridinyl)ethoxy]phenyl]methyl]-, monohydrochloride (+/−)-, or an analogue or derivative thereof).

Estrogen Receptor Agents

In another embodiment, the pharmacologically active compound is an estrogen receptor agent (e.g., estradiol, 17-β-estradiol, or an analogue or derivative thereof).

Somatostatin Analogues

In another embodiment, the pharmacologically active compound is a somatostatin analogue (e.g., angiopeptin, or an analogue or derivative thereof).

Neurokinin 1 Antagonists

In another embodiment, the pharmacologically active compound is a neurokinin 1 antagonist (e.g., GW-597599, lanepitant ((1,4'-bipiperidine)-1'-acetamide, N-(2-(acetyl((2-methoxyphenyl)methyl)amino)-1-(1H-indol-3-ylmethyl) ethyl)-(R)—), nolpitantium chloride (1-azoniabicyclo[2.2.2] octane, 1-[2-[3-(3,4-dichlorophenyl)-1-[[3-(1-methylethoxy)phenyl]acetyl]-3-piperidinyl]ethyl]-4-phenyl-, chloride, (S)—), or saredutant (benzamide, N-[4-[4-(acetylamino)-4-phenyl-1-piperidinyl]-2-(3,4-dichlorophenyl)butyl]-N-methyl-, (S)—), or vofopitant (3-piperidinamine, N-[[2-methoxy-5-[5-(trifluoromethyl)-1H-tetrazol-1-yl]phenyl]methyl]-2-phenyl-, (2S,3S)—, or an analogue or derivative thereof).

Neurokinin 3 Antagonist

In another embodiment, the pharmacologically active compound is a neurokinin 3 antagonist (e.g., talnetant (4-quinolinecarboxamide, 3-hydroxy-2-phenyl-N-[(1S)-1-phenylpropyl]-, or an analogue or derivative thereof).

Neurokinin Antagonist

In another embodiment, the pharmacologically active compound is a neurokinin antagonist (e.g., GSK-679769, GSK-823296, SR-489686 (benzamide, N-[4-[4-(acetylamino)-4-phenyl-1-piperidinyl]-2-(3,4-dichlorophenyl)butyl]-N-methyl-, (S)—), SB-223412; SB-235375 (4-quinolinecarboxamide, 3-hydroxy-2-phenyl-N-[(1S)-1-phenylpropyl]-), UK-226471, or an analogue or derivative thereof).

VLA-4 Antagonist

In another embodiment, the pharmacologically active compound is a VLA-4 antagonist (e.g., GSK683699, or an analogue or derivative thereof).

Osteoclast Inhibitor

In another embodiment, the pharmacologically active compound is a osteoclast inhibitor (e.g., ibandronic acid (phosphonic acid, [1-hydroxy-3-(methylpentylamino)propylidene]bis-), alendronate sodium, or an analogue or derivative thereof).

DNA Topoisomerase ATP Hydrolysing Inhibitor

In another embodiment, the pharmacologically active compound is a DNA topoisomerase ATP hydrolysing inhibitor (e.g., enoxacin (1,8-naphthyridine-3-carboxylic acid, 1-ethyl-6-fluoro-1,4-dihydro-4-oxo-7-(1-piperazinyl)-), levofloxacin (7H-Pyrido[1,2,3-de]-1,4-benzoxazine-6-carboxylic acid, 9-fluoro-2,3-dihydro-3-methyl-10-(4-methyl-1-piperazinyl)-7-oxo-, (S)—), ofloxacin (7H-pyrido[1,2,3-de]-1,4-benzoxazine-6-carboxylic acid, 9-fluoro-2,3-dihydro-3-methyl-10-(4-methyl-1-piperazinyl)-7-oxo-, (+/−)-), pefloxacin (3-quinolinecarboxylic acid, 1-ethyl-6-fluoro-1,4-dihydro-7-(4-methyl-1-piperazinyl)-4-oxo-), pipemidic acid (pyrido[2,3-d]pyrimidine-6-carboxylic acid, 8-ethyl-5,8-dihydro-5-oxo-2-(1-piperazinyl)-), pirarubicin (5,12-naphthacenedione, 10-[[3-amino-2,3,6-trideoxy-4-O-(tetrahydro-2H-pyran-2-yl)-alpha-L-lyxo-hexopyranosyl] oxy]-7,8,9,10-tetrahydro-6,8,11-trihydroxy-8-(hydroxyacetyl)-1-methoxy-, [8S-[8 alpha,10 alpha(S*)]]-), sparfloxacin (3-quinolinecarboxylic acid, 5-amino-1-cyclopropyl-7-(3,5-dimethyl-1-piperazinyl)-6,8-difluoro-1,4-dihydro-4-oxo-, cis-), AVE-6971, cinoxacin ([1,3]dioxolo[4,5-g]cinnoline-3-carboxylic acid, 1-ethyl-1,4-dihydro-4-oxo-), or an analogue or derivative thereof).

Angiotensin I Converting Enzyme Inhibitor

In another embodiment, the pharmacologically active compound is an angiotensin I converting enzyme inhibitor (e.g., ramipril (cyclopenta[b]pyrrole-2-carboxylic acid, 1-[2-[[1-(ethoxycarbonyl)-3-phenylpropyl]amino]-1-oxopropyl] octahydro-, [2S—[1[R*(R*)],2 alpha, 3aβ, 6aβ]]-), trandolapril (1H-indole-2-carboxylic acid, 1-[2-[(1-carboxy-3-phenylpropyl)amino]-1-oxopropyl]octahydro-, [2S-[1[R* (R*)],2 alpha,3a alpha,7aβ]]-), fasidotril (L-alanine, N-[(2S)-3-(acetylthio)-2-(1,3-benzodioxol-5-ylmethyl)-1-oxopropyl]-, phenylmethyl ester), cilazapril (6H-pyridazino [1,2-a][1,2]diazepine-1-carboxylic acid, 9-[[1-(ethoxycarbonyl)-3-phenylpropyl]amino]octahydro-10-oxo-, [1S-[1 alpha, 9 alpha(R*)]]-), ramipril (cyclopenta[b] pyrrole-2-carboxylic acid, 1-[2-[[-(ethoxycarbonyl)-3-phenylpropyl]amino]-1-oxopropyl]octahydro-, [2S-[1-[R* (R*)], 2 alpha,3aβ,6aβ]]-, or an analogue or derivative thereof).

Angiotensin II Antagonist

In another embodiment, the pharmacologically active compound is an angiotensin II antagonist (e.g., HR-720 (1H-imidazole-5-carboxylic acid, 2-butyl-4-(methylthio)-1-[[2'-[[[(propylamino)carbonyl]amino]sulfonyl][1,1'-biphenyl]-4-yl]methyl]-, dipotassium salt, or an analogue or derivative thereof).

Enkephalinase Inhibitor

In another embodiment, the pharmacologically active compound is an enkephalinase inhibitor (e.g., Aventis 100240 (pyrido[2,1-a][2]benzazepine-4-carboxylic acid, 7-[[2-(acetylthio)-1-oxo-3-phenylpropyl]amino]-1,2,3,4,6,7,8, 12b-octahydro-6-oxo-, [4S-[4 alpha, 7 alpha(R*),12bβ]]-), AVE-7688, or an analogue or derivative thereof).

Peroxisome Proliferator-Activated Receptor Gamma Agonist Insulin Sensitizer

In another embodiment, the pharmacologically active compound is peroxisome proliferator-activated receptor gamma agonist insulin sensitizer (e.g., rosiglitazone maleate (2,4-thiazolidinedione, 5-((4-(2-(methyl-2-pyridinylamino) ethoxy)phenyl)methyl]-, (Z)-2-butenedioate (1:1), farglitazar (GI-262570, GW-2570, GW-3995, GW-5393, GW-9765), LY-929, LY-519818, LY-674, or LSN-862), or an analogue or derivative thereof).

Protein Kinase C Inhibitor

In another embodiment, the pharmacologically active compound is a protein kinase C inhibitor, such as ruboxistaurin mesylate (9H,18H-5, 21:12,17-dimethenodibenzo(e,k)pyrrolo(3,4-h)(1,4,13)oxadiazacyclohexadecine-18,20(19H)-dione,9-((dimethylamino)methyl)-6,7,10,11-tetrahydro-, (S)—), safingol (1,3-octadecanediol, 2-amino-, [S—(R*,R*)]—), or enzastaurin hydrochloride (1H-pyrole-2,5-dione, 3-(1-methyl-1H-indol-3-yl)-4-[1-[1-(2-pyridinyl-methyl)-4-piperidinyl]-1H-indol-3-yl]-, monohydrochloride), or an analogue or derivative thereof.

ROCK(rho-assoclated kinase) Inhibitors

In another embodiment, the pharmacologically active compound is a ROCK (rho-associated kinase) inhibitor, such as Y-27632, HA-1077, H-11152 and 4-1-(aminoalkyl)-N-(4-pyridyl)cyclohexanecarboxamide or an analogue or derivative thereof.

CXCR3 Inhibitors

In another embodiment, the pharmacologically active compound is a CXCR3 inhibitor such as T-487, T0906487 or analogue or derivative thereof.

Itk Inhibitors

In another embodiment, the pharmacologically active compound is an Itk inhibitor such as BMS-509744 or an analogue or derivative thereof.

Cytosolic Phospholipase $A_2$-Alpha Inhibitors

In another embodiment, the pharmacologically active compound is a cytosolic phospholipase $A_2$-alpha inhibitor such as efipladib (PLA-902) or analogue or derivative thereof.

PPAR Agonist

In another embodiment, the pharmacologically active compound is a PPAR Agonist (e.g., Metabolex ((−)-benzeneacetic acid, 4-chloro-alpha-[3-(trifluoromethyl)-phenoxy]-, 2-(acetylamino)ethyl ester), balaglitazone (5-(4-(3-methyl-4-oxo-3,4-dihydro-quinazolin-2-yl-methoxy)-benzyl)-thiazolidine-2,4-dione), ciglitazone (2,4-thiazolidinedione, 5-[[4-[(1-methylcyclohexyl)methoxy]phenyl]methyl]-), DRF-10945, farglitazar, GSK-677954, GW-409544, GW-501516, GW-590735, GW-590735, K-11, KRP-101, LSN-862, LY-519818, LY-674, LY-929, muraglitazar; BMS-298585 (Glycine, N-[(4-methoxyphenoxy)carbonyl]-N-[[4-[2-(5-methyl-2-phenyl-4-oxazolyl)ethoxy]phenyl]methyl]-), netoglitazone; isaglitazone (2,4-thiazolidinedione, 5-[[6-[(2-fluorophenyl)methoxy]-2-naphthalenyl]methyl]-), Actos AD-4833; U-72107A (2,4-thiazolidinedione, 5-[[4-[2-(5-ethyl-2-pyridinyl)ethoxy]phenyl]methyl]-, monohydrochloride (+/−)-), JTT-501; PNU-182716 (3,5-Isoxazolidinedione, 4-[[4-[2-(5-methyl-2-phenyl-4-oxazolyl)ethoxy]phenyl]methyl]-), AVANDIA (from SB Pharmco Puerto Rico, Inc. (Puerto Rico); BRL-48482; BRL-49653; BRL-49653c; NYRACTA and Venvia (both from (SmithKline Beecham (United Kingdom)); tesaglitazar ((2S)-2-ethoxy-3-[4-[2-[4-[(methylsulfonyl)oxy]phenyl]ethoxy]phenyl]propanoic acid), troglitazone (2,4-Thiazolidinedione, 5-[[4-[(3,4-dihydro-6-hydroxy-2,5,7,8-tetramethyl-2H-1-benzopyran-2-yl)methoxy]phenyl]methyl]-), and analogues and derivatives thereof).

Immunosuppressants

In another embodiment, the pharmacologically active compound is an immunosuppressant (e.g., batebulast (cyclohexanecarboxylic acid, 4-[[(aminoiminomethyl)amino]methyl]-, 4-(1,1-dimethylethyl)phenyl ester, trans-), cyclomunine, exalamide (benzamide, 2-(hexyloxy)-), LYN-001, CCl-779 (rapamycin 42-(3-hydroxy-2-(hydroxymethyl)-2-methylpropanoate)), 1726; 1726-D; AVE-1726, or an analogue or derivative thereof).

Erb Inhibitor

In another embodiment, the pharmacologically active compound is an Erb inhibitor (e.g., canertinib dihydrochloride (N-[4-(3-(chloro-4-fluoro-phenylamino)-7-(3-morpholin-4-yl-propoxy)-quinazolin-6-yl]-acrylamide dihydrochloride), CP-724714, or an analogue or derivative thereof).

Apoptosis Agonist

In another embodiment, the pharmacologically active compound is an apoptosis agonist (e.g., CEFLATONIN® (CGX-635) (from Chemgenex Therapeutics, Inc., Menlo Park, Calif.), CHML, LBH-589, metoclopramide (benzamide, 4-amino-5-chloro-N-[2-(diethylamino)ethyl]-2-methoxy-), patupilone (4,17-dioxabicyclo(14.1.0)heptadecane-5,9-dione, 7,11-dihydroxy-8,8,10,12,16-pentamethyl-3-(1-methyl-2-(2-methyl-4-thiazolyl)ethenyl, (1R,3S,7S,10R,11S,12S,16R)), AN-9; pivanex (butanoic acid, (2,2-dimethyl-1-oxopropoxy)methyl ester), SL-100; SL-102; SL-11093; SL-11098; SL-11099; SL-93; SL-98; SL-99, or an analogue or derivative thereof).

Lipocortin Agonist

In another embodiment, the pharmacologically active compound is an lipocortin agonist (e.g., CGP-13774 (9Alpha-chloro-6Alpha-fluoro-11β,17alpha-dihydroxy-16Alpha-methyl-3-oxo-1,4-androstadiene-17β-carboxylic acid-methylester-17-propionate), or analogue or derivative thereof).

VCAM-1 Antagonist

In another embodiment, the pharmacologically active compound is a VCAM-1 antagonist (e.g., DW-908e, or an analogue or derivative thereof).

Collagen Antagonist

In another embodiment, the pharmacologically active compound is a collagen antagonist (e.g., E-5050 (Benzenepropanamide, 4-(2,6-dimethylheptyl)-N-(2-hydroxyethyl)-β-methyl-), lufironil (2,4-Pyridinedicarboxamide, N,N'-bis(2-methoxyethyl)-), or an analogue or derivative thereof).

Alpha 2 Integrin Antagonist

In another embodiment, the pharmacologically active compound is an alpha 2 integrin antagonist (e.g., E-7820, or an analogue or derivative thereof).

TNF Alpha Inhibitor

In another embodiment, the pharmacologically active compound is a TNF alpha inhibitor (e.g., ethyl pyruvate, Genz-29155, lentinan (Ajinomoto Co., Inc. (Japan)), linomide (3-quinolinecarboxamide, 1,2-dihydro-4-hydroxy-N,1-dimethyl-2-oxo-N-phenyl-), UR-1505, or an analogue or derivative thereof).

Nitric Oxide Inhibitor

In another embodiment, the pharmacologically active compound is a nitric oxide inhibitor (e.g., guanidioethyldisulfide, or an analogue or derivative thereof).

Cathepsin Inhibitor

In another embodiment, the pharmacologically active compound is a cathepsin inhibitor (e.g., SB-462795 or an analogue or derivative thereof).

Delivery of Cells and Genes

The multifunctional compounds of the invention can also be used to deliver various types of living cells or genes to a desired site of administration in order to form new tissue. The term "genes" as used herein is intended to encompass genetic material from natural sources, synthetic nucleic acids, DNA, antisense-DNA and RNA. Thus, this aspect of the invention is a method for delivering living cells or genes, where the composition also includes the cells of genes to be delivered, and steps (a) and (b) are as described for the method of sealing tissue. Step (c) would involve allowing a three-dimensional matrix to form and delivering the cells or genes.

When used to deliver cells, for example, mesenchymal stem cells can be delivered to produce cells of the same type as the tissue into which they are delivered. Mesenchymal stem cells are not differentiated and therefore can differentiate to form various types of new cells due to the presence of an active agent or the effects (chemical, physical, etc.) of the local tissue environment. Examples of mesenchymal stem cells include osteoblasts, chondrocytes, and fibroblasts. Osteoblasts can be delivered to the site of a bone defect to produce new bone; chondrocytes can be delivered to the site of a cartilage defect to produce new cartilage; fibroblasts can be delivered to produce collagen wherever new connective tissue is needed; neurectodermal cells can be delivered to form new nerve tissue; epithelial cells can be delivered to form new epithelial tissues, such as liver, pancreas, etc.

The cells or genes may be either allogeneic or xenogeneic in origin. For example, the multifunctional compounds can be used to deliver cells or genes from other species that have been genetically modified. Because the compounds of the invention are not easily degraded in vivo, cells and genes entrapped within the three-dimensional matrix will be isolated from the patient's own cells and, as such, will not provoke an immune response in the patient. In order to entrap the cells or genes within this matrix, the cells or genes are pre-mixed with the multifunctional compounds in an initial environment. Upon exposure to the modified environment, a three-dimensional matrix is formed, thereby entrapping the cells or genes within the matrix.

As discussed above for biologically active agents, when used to deliver cells or genes, the multifunctional compound may also contain biodegradable groups to aid in controlled release of the cells or genes at the intended site of delivery.

Bioadhesives

As used herein, the terms "bioadhesive," "biological adhesive," and "surgical adhesive" are used interchangeably to refer to biocompatible compositions capable of effecting temporary or permanent attachment between the surfaces of two native tissues, or between a native tissue surface and either a non-native tissue surface or a surface of a synthetic implant.

In a general method for effecting the attachment of a first surface to a second surface, the multifunctional compound is applied to a first surface, which is then contacted with a second surface to effect adhesion therebetween. Preferably, the multifunctional compound is exposed to the modified environment to initiate reaction among the reactive groups and then delivered to the first surface before substantial reaction has occurred. The first surface is then contacted with the second surface, preferably immediately, to effect adhesion. Thus, another embodiment of the invention is a method of bioadhesion between two surfaces, where steps (a) and (b) are as described for the method of sealing tissue, and step (c) involves allowing a three-dimensional matrix to form and adhere the surfaces.

The two surfaces may be held together manually, or using other appropriate means, while the reaction is proceeding to completion. Reaction is typically sufficiently complete for adhesion to occur within about 5 to 60 minutes after exposure of the multifunctional compound to the modified environment. However, the time required for complete reaction to occur is dependent on a number of factors, including the type and molecular weight of each reactive component, the degree of functionalization, and the concentration of the multifunctional compound (i.e., higher concentrations result in faster reaction times).

At least one of the first and second surfaces is preferably a native tissue surface. As used herein, the term "native tissue" refers to biological tissues that are native to the body of the patient being treated. As used herein, the term "native tissue" is intended to include biological tissues that have been elevated or removed from one part of the body of a patient for implantation to another part of the body of the same patient (such as bone autografts, skin flap autografts, etc.). For example, the multifunctional compounds of the invention can be used to adhere a piece of skin from one part of a patient's body to another part of the body, as in the case of a burn victim.

The other surface may be a native tissue surface, a non-native tissue surface, or a surface of a synthetic implant. As used herein, the term "non-native tissue" refers to biological tissues that have been removed from the body of a donor patient (who may be of the same species or of a different species than the recipient patient) for implantation into the body of a recipient patient (e.g., tissue and organ transplants). For example, the multifunctional compounds of the invention can be used to adhere a donor cornea to the eye of a recipient patient. As used herein, the term "synthetic implant" refers to any biocompatible material intended for implantation into the body of a patient not encompassed by the above definitions for native tissue and non-native tissue. Synthetic implants include, for example, artificial blood vessels, heart valves, artificial organs, bone prostheses, implantable lenticules, vascular grafts, stents, and stent/graft combinations, etc.

Ophthalmic Applications

Because of their optical clarity, the multifunctional compounds of the invention are particularly well suited for use in ophthalmic applications. See for example, Margalit et al. "Bioadhesives for Intraocular Use," *Retina* 20:469-477 (2000). For example, a synthetic lenticule for correction of vision can be attached to the Bowman's layer of the cornea of a patient's eye using the methods of the present invention. In a manner similar to that described in U.S. Pat. No. 5,565,519 to Rhee et al., the multifunctional compounds of the invention can be molded into a desired lenticular shape, either during or after formation of the three-dimensional matrix. The resulting collagen lenticule can then be attached to the Bowman's layer of a de-epithelialized cornea of a patient's eye using the methods of the present invention. By applying the multifunctional compounds to the anterior surface of the cornea, then contacting the anterior surface of the cornea with the posterior surface of the lenticule before substantial reaction has occurred, reactive groups (e.g., electrophilic groups) on the compounds will also covalently bind to collagen molecules in both the corneal tissue and the lenticule to firmly anchor the lenticule in place. Alternatively, the multifunctional compounds can be applied first to the posterior surface of the lenticule, which is then contacted with the anterior surface of the cornea.

Thus, another embodiment of the invention is a method of ophthalmic repair of the cornea, where steps (a) and (b) are as described for the method of sealing tissue, and step (c) involves allowing a three-dimensional matrix to form and adhering a lenticule to the cornea.

The compositions of the present invention are also suitable for use in vitreous replacement. In addition, the compositions of the present invention may be used for the delivery of active agents.

Tissue Augmentation

The multifunctional compounds of the invention can also be used for augmentation of soft or hard tissue within the body of a mammalian subject. As such, they may be better than currently marketed collagen-based materials for soft tissue augmentation, because they are less immunogenic and more persistent. Examples of soft tissue augmentation applications include sphincter (e.g., urinary, anal, esophageal) augmentation and the treatment of rhytids and scars. Examples of hard tissue augmentation applications include the repair and/or replacement of bone and/or cartilaginous tissue. Thus, another embodiment of the invention is a method of tissue augmentation for a pre-selected site, where steps (a) and (b) are as described for the method of sealing tissue, and step (c) involves allowing a three-dimensional matrix to form at the pre-selected site.

The multifunctional compounds are particularly suited for use as a replacement material for synovial fluid in osteoarthritic joints, serving to reduce joint pain and improve joint function by restoring a soft hydrogel network in the joint. The compounds can also be used as a replacement material for the nucleus pulposus of a damaged intervertebral disk. The nucleus pulposus of the damaged disk is first removed, and the multifunctional compounds is then injected or otherwise introduced into the center of the disk. The compounds may either be exposed to the modified environment prior to introduction into the disk, or allowed to inter-react in situ.

In a general method for effecting augmentation of tissue within the body of a mammalian subject, the multifunctional compounds are injected simultaneously with exposure to the modified environment, to a tissue site in need of augmentation through a small-gauge (e.g., 25-32 gauge) needle. Once inside the patient's body, the reactive groups on the multifunctional compounds inter-react with each other to form a three-dimensional matrix in situ. In addition, in some embodiments of the invention, the reactive groups on the multifunctional compounds can react with body tissue to further enhance tissue augmentation. For example, when some of the reactive groups are electrophilic groups, such groups may also react with primary amino groups on lysine residues of collagen molecules within the patient's own tissue, providing for "biological anchoring" of the compositions with the host tissue.

Adhesion Prevention

Another use of the multifunctional compounds of the invention is to coat tissues in order to prevent the formation of adhesions following surgery or injury to internal tissues or organs.

Surgical adhesions are abnormal, fibrous bands of scar tissue that can form inside the body as a result of the healing process that follows any open or minimally invasive surgical procedure including abdominal, gynecologic, cardiothoracic, spinal, plastic, vascular, ENT, ophthalmologic, urologic, neuro, or orthopedic surgery. Surgical adhesions are typically connective tissue structures that form between adjacent injured areas within the body. Briefly, localized areas of injury trigger an inflammatory and healing response that culminates in healing and scar tissue formation. If scarring results in the formation of fibrous tissue bands or adherence of adjacent anatomical structures (that should be separate), surgical adhesion formation is said to have occurred. Adhesions can range from flimsy, easily separable structures to dense, tenacious fibrous structures that can only be separated by surgical dissection. While many adhesions are benign, some can cause significant clinical problems and are a leading cause of repeat surgical intervention.

Since interventions involve a certain degree of trauma to the operative tissues, virtually any procedure (no matter how well executed) has the potential to result in the formation of clinically significant adhesion formation. Adhesions can be triggered by surgical trauma such as cutting, manipulation, retraction or suturing, as well as from inflammation, infection (e.g., fungal or mycobacterium), bleeding or the presence of a foreign body. Surgical trauma may also result from tissue drying, ischemia, or thermal injury. Due to the diverse etiology of surgical adhesions, the potential for formation exists regardless of whether the surgery is done in a so-called minimally invasive fashion (e.g., catheter-based therapies, laparoscopy) or in a standard open technique involving one or more relatively large incisions. Although a potential complication of any surgical intervention, surgical adhesions are particularly problematic in GI surgery (causing bowel obstruction), gynecological surgery (causing pain and/or infertility), tendon repairs (causing shortening and flexion deformities), joint capsule procedures (causing capsular contractures), and nerve and muscle repair procedures (causing diminished or lost function).

The placement of medical devices and implants also increases the risk that surgical adhesions will occur. In addition to the above mechanisms, an implanted device can trigger a "foreign body" response where the immune system recognizes the implant as foreign and triggers an inflammatory reaction that ultimately leads to scar tissue formation. A specific form of foreign body reaction in response to medical device placement is complete enclosure ("walling off") of the implant in a capsule of scar tissue (encapsulation). Fibrous encapsulation of implanted devices and implants can complicate any procedure, but breast augmentation and reconstruction surgery, joint replacement surgery, hernia repair surgery, artificial vascular graft surgery, stent placement, and neurosurgery are particularly prone to this complication. In each case, the implant becomes encapsulated by a fibrous connective tissue capsule which compromises or impairs the function of the surgical implant (e.g., breast implant, artificial joint, surgical mesh, vascular graft, stent or dural patch).

Adhesions generally begin to form within the first several days after surgery. Generally, adhesion formation is an inflammatory reaction in which factors are released, increasing vascular permeability and resulting in fibrinogen influx and fibrin deposition. This deposition forms a protein matrix that bridges the abutting tissues. Fibroblasts accumulate, attach to the protein matrix, deposit collagen and induce angiogenesis. If this cascade of events can be prevented within 4 to 5 days following surgery, then adhesion formation may be inhibited.

The compositions of the invention may be used to prevent adhesion formation in a wide variety of surgical procedures including spinal and neurosurgical procedures (e.g., open surgical resection of a ruptured lumbar disc or entrapped spinal nerve root (laminectomy); disectomies; and microlumbar disc excision (microdiscectomy)); gynecological surgical procedures (e.g., hysterectomy, myomectomy, endometriosis, infertility, birth control (e.g., tubal ligation), reversal of sterilization, pain, dysmennorrhea, dysfunctional uterine bleeding, ectopic pregnancy, ovarian cysts, and gynecologic malignancies); abdominal surgical procedures (e.g., hernia repair (abdominal, ventral, inguinal, incisional), bowel obstruction, inflammatory bowel disease (ulcerative colitis, Crohn's disease), appendectomy, trauma (penetrating wounds, blunt trauma), tumor resection, infections (abscesses, peritonitis), cholecystectomy, gastroplasty (bariatric surgery), esophageal and pyloric strictures, colostomy, diversion iliostomy, anal-rectal fistulas, hemorrhoidectomies, splenectomy, hepatic tumor resection, pancreatitis, bowel perforation, upper and lower GI bleeding, and ischemic bowel); cardiac surgical procedure (e.g., transplant surgery, vascular repair, coronary artery bypass grafting (CABG), congenital heart defects, and valve replacements, staged procedures and reoperations (particularly repeat CABG surgery)); orthopedic surgical procedures (e.g., surgical interventions performed as a result of injury or trauma (e.g., fractures (open and closed), sprains, joint dislocations, crush injuries, ligament and muscle tears, tendon injuries, nerve injuries, congenital deformities and malformations, total joint or partial joint replacement, and cartilage injuries); and cosmetic or reconstructive surgical procedure (e.g., breast augmentation, breast reconstruction after cancer surgery, craniofacial procedures, reconstruction after trauma, congenital craniofacial reconstruction and oculoplastic surgical procedures).

For certain applications compositions may be include and/or release a therapeutic agent able to reduce scarring (i.e., a fibrosis-inhibiting agent) at a surgical site, such as to prevent or inhibit the formation of post-operative adhesions. Within one embodiment of the invention, compositions for the prevention of surgical adhesions may include or be adapted to release an agent that inhibits one or more of the five general components of the process of fibrosis (or scarring), including: inflammatory response and inflammation, migration and proliferation of connective tissue cells (such as fibroblasts or smooth muscle cells), formation of new blood vessels (angiogenesis), deposition of extracellular matrix (ECM), and remodeling (maturation and organization of the fibrous tissue). By inhibiting one or more of the components of fibrosis (or scarring), the overgrowth of scar tissue at a surgical site may be inhibited or reduced.

Examples of fibrosis-inhibiting agents that may be combined with the present compositions to prevent the formation of adhesions include the following: cell cycle inhibitors including (A) anthracyclines (e.g., doxorubicin and mitoxantrone), (B) taxanes (e.g., paclitaxel, TAXOTERE® and docetaxel), and (C) podophyllotoxins (e.g., etoposide); (D) immunomodulators (e.g., sirolimus, everolimus, tacrolimus); (E) heat shock protein 90 antagonists (e.g., geldanamycin, 17-AAG, 17-DMAG); (F) HMGCoA reductase inhibitors (e.g., simvastatin); (G) inosine monophosphate dehydrogenase inhibitors (e.g., mycophenolic acid, 1-alpha-25 dihydroxy vitamin $D_3$); (H)NF kappa B inhibitors (e.g., Bay 11-7082); (I) antimycotic agents (e.g., sulconizole) and (J) p38 MAP kinase inhibitors (e.g., SB202190), as well as analogues and derivatives of the aforementioned.

The drug dose administered from the present compositions for surgical adhesion prevention will depend on a variety of factors, including the type of formulation, the location of the treatment site, and the type of condition being treated; however, certain principles can be applied in the application of this art. Drug dose can be calculated as a function of dose per unit area (of the treatment site), total drug dose administered can be measured, and appropriate surface concentrations of active drug can be determined. Drugs are to be used at concentrations that range from several times more than to 50%, 20%, 10%, 5%, or even less than 1% of the concentration typically used in a single systemic dose application. In certain aspects, the anti-scarring agent is released from the polymer composition in effective concentrations in a time period that may be measured from the time of infiltration into tissue adjacent to the device, which ranges from about less than 1 day to about 180 days. Generally, the release time may also be from about less than 1 day to about 180 days; from about 7 days to about 14 days; from about 14 days to about 28 days; from about 28 days to about 56 days; from about 56 days to about 90 days; from about 90 days to about 180 days. In one aspect, the drug is released in effective concentrations for a period ranging from 1-90 days.

The exemplary anti-fibrosing agents, used alone or in combination, should be administered under the following dosing guidelines. The total amount (dose) of anti-scarring agent in the composition can be in the range of about 0.01 µg-10 µg, or 10 µg-10 mg, or 10 mg-250 mg, or 250 mg-1000 mg, or 1000 mg-2500 mg. The dose (amount) of anti-scarring agent per unit area of surface to which the agent is applied may be in the range of about 0.01 µg/mm$^2$-1 µg/mm$^2$, or 1 µg/mm$^2$-10 µg/mm$^2$, or 10 µg/mm$^2$-250 µg/mm$^2$, 250 µg/mm$^2$-1000 µg/mm$^2$, or 1000 µg/mm$^2$-2500 µg/mm$^2$.

Provided below are exemplary dosage ranges for various anti-scarring agents that can be used in conjunction with compositions for treating or preventing surgical adhesions in accordance with the invention. (A) Cell cycle inhibitors including doxorubicin and mitoxantrone. Doxorubicin analogues and derivatives thereof: total dose not to exceed 25 mg (range of 0.1 µg to 25 mg); preferred 1 µg to 5 mg. Dose per unit area of 0.01 µg-100 µg per mm$^2$; preferred dose of 0.1 µg/mm$^2$-10 µg/mm$^2$. Mitoxantrone and analogues and derivatives thereof: total dose not to exceed 5 mg (range of 0.01 µg to 5 mg); preferred 0.1 µg to 1 mg. Dose per unit area of 0.01 µg-20 µg per mm$^2$; preferred dose of 0.05 µg/mm$^2$-3 µg/mm$^2$. (B) Cell cycle inhibitors including paclitaxel and analogues and derivatives (e.g., docetaxel) thereof: total dose not to exceed 10 mg (range of 0.1 µg to 10 mg); preferred 1 µg to 3 mg. Dose per unit area of 0.1 µg-10 µg per mm$^2$; preferred dose of 0.25 µg/mm$^2$-5 µg/mm$^2$. (C) Cell cycle inhibitors such as podophyllotoxins (e.g., etoposide): total dose not to exceed 10 mg (range of 0.1 µg to mg); preferred 1 µg to 3 mg. Dose per unit area of 0.1 µg-10 µg per mm$^2$; preferred dose of 0.25 µg/mm$^2$-5 µg/mm$^2$. (D) Immunomodulators including sirolimus and everolimus. Sirolimus (i.e., rapamycin, RAPAMUNE®): total dose not to exceed 10 mg (range of 0.1 µg to 10 mg); preferred 10 µg to 1 mg. Dose per unit area of 0.1 g-100 µg per mm$^2$; preferred dose of 0.5 µg/mm$^2$-10 µg/mm$^2$. Everolimus and derivatives and analogues thereof: total dose should not exceed 10 mg (range of 0.1 µg to 10 mg); preferred 10 µg to 1 mg. Dose per unit area of 0.1 µg-100 µg per mm$^2$ of surface area; preferred dose of 0.3 µg/mm$^2$-10 µg/mm$^2$. (E) Heat shock protein 90 antagonists (e.g., geldanamycin) and analogues and derivatives thereof: total dose not to exceed 20 mg (range of 0.1 µg to 20 mg); preferred 1 µg to 5 mg. Dose per unit area of 0.1 µg-10 µg per mm$^2$; preferred dose of 0.25 µg/mm$^2$-5 µg/mm$^2$. (F) HMGCoA reductase inhibitors (e.g., simvastatin) and analogues and derivatives thereof: total dose not to exceed 2000 mg (range of 10.0 µg to 2000 mg); preferred 10 µg to 300 mg. Dose per unit area of 1.0 µg-1000 µg per mm$^2$; preferred dose of 2.5 µg/mm$^2$-500 µg/mm$^2$. (G) Inosine monophosphate dehydrogenase inhibitors (e.g., mycophenolic acid, 1-alpha-25 dihydroxy vitamin $D_3$) and analogues and derivatives thereof: total dose not to exceed 2000 mg (range of 10.0 µg to 2000 mg); preferred 10 µg to 300 mg. Dose per unit area of 1.0 µg-1000 µg per mm$^2$; preferred dose of 2.5 g/mm$^2$-500 µg/mm$^2$. (H)NF kappa B inhibitors (e.g., Bay 11-7082) and analogues and derivatives thereof: total dose not to exceed 200 mg (range of 1.0 g to 200 mg); preferred 1 µg to 50 mg. Dose per unit area of 1.0 µg-100 µg per mm$^2$; preferred dose of 2.5 µg/mm$^2$-50 µg/mm$^2$. (I) Antimycotic agents (e.g., sulconizole) and analogues and derivatives thereof: total dose not to exceed 2000 mg (range of 10.0 µg to 2000 mg); preferred 10 µg to 300 mg. Dose per unit area of 1.0 g-1000 µg per mm$^2$; preferred dose of 2.5 µg/mm$^2$-500 µg/mm$^2$ and (J) p38 MAP kinase inhibitors (e.g., SB202190)

and analogues and derivatives thereof: total dose not to exceed 2000 mg (range of 10.0 μg to 2000 mg); preferred 10 μg to 300 mg. Dose per unit area of 1.0 μg-1000 μg per mm$^2$; preferred dose of 2.5 μg/mm$^2$-500 μg/mm$^2$.

In a general method for coating tissues to prevent the formation of adhesions following surgery, the multifunctional compounds are exposed to the modified environment and a thin layer of the composition is then applied to the tissues comprising, surrounding, and/or adjacent to the surgical site before substantial reaction has occurred. Application of the multifunctional compounds to the tissue site may be by extrusion, brushing, spraying (as described above), or by any other convenient means. Thus, the invention also relates to a method of preventing adhesions between tissues of a patient, where steps (a) and (b) are as described for the method of sealing tissue, and step (c) involves allowing a three-dimensional matrix to form on the tissue, and thus prevent tissue adhesion.

Following application of the compounds to the surgical site, inter-reaction is allowed to continue in situ prior to closure of the surgical incision. Once the reaction has reached equilibrium, tissues that are brought into contact with the coated tissues will not adhere thereto. The surgical site can then be closed using conventional means such as by sutures, and so forth.

In general, compounds that achieve complete inter-reaction within a relatively short period of time (i.e., 5-15 minutes following exposure of the multifunctional compounds to the modified environment) are preferred for use in the prevention of surgical adhesions, so that the surgical site may be closed relatively soon after completion of the surgical procedure.

Certain surgical procedures may involve placement of a medical device or implant at the surgical site, in which case it may be desirable to apply the composition (with or without a therapeutic agent) to the surface of the implant, to the implant-tissue interface, and/or to tissue in the vicinity of the implanted device to minimize the formation of post-operative surgical adhesions, unwanted scarring in the vicinity of the implant, and encapsulation of the implant by a fibrous connective tissue capsule.

For the prevention of adhesions in spinal and neurosurgical procedures, the compositions alone or loaded with a therapeutic agent (e.g., a fibrosis-inhibiting agent) may be applied to the tissue surface at a spinal or neurosurgical site or to the surface of an implanted device (e.g., dural patches, spinal prostheses, artificial disc, rods, bone fixation devices (e.g., anchoring plates and bone screws), injectable filling or bulking agents for discs, spinal grafts, spinal nucleus implants, intervertebral disc spacers, fusion cages, or to implants placed in the brain, such as drains, shunts, drug-delivery pumps, or neurostimulation devices) and/or the tissue surrounding the implant before, during, or after the surgical procedure.

For the prevention of adhesions associated with gynecological procedures, the compositions alone or loaded with a therapeutic agent (e.g., a fibrosis-inhibiting agent) may be applied during open or endoscopic gynecological surgery to the tissue surface of the pelvic side wall, adnexa, uterus and any adjacent affected tissues during the surgical procedure or to the surface of an implanted device or implant (e.g., genitalurinary stents, bulking agents, sterilization devices (e.g., valves, clips and clamps), and tubal occlusion implants and plugs) and/or the tissue surrounding the implant before, during, or after the surgical procedure.

For the prevention of adhesions associated with abdominal surgical procedures, the compositions alone or loaded with a therapeutic agent (e.g., a fibrosis-inhibiting agent) may be applied during open, endoscopic, or laparoscopic abdominal surgery to the tissue surface of the peritoneal cavity, visceral peritoneum, abdominal organs, abdominal wall and any adjacent affected tissues during the surgical procedure or to the surface of an implanted device or implant and/or the tissue surrounding the implant before, during, or after the surgical procedure. Representative examples of implants for use in abdominal procedures includes, without limitation, hernia meshes, restriction devices for obesity, implantable sensors, implantable pumps, peritoneal dialysis catheters, peritoneal drug-delivery catheters, GI tubes for drainage or feeding, portosystemic shunts, shunts for ascites, gastrostomy or percutaneous feeding tubes, jejunostomy endoscopic tubes, colostomy devices, drainage tubes, biliary T-tubes, hemostatic implants, enteral feeding devices, colonic and biliary stents, low profile devices, gastric banding implants, capsule endoscopes, anti-reflux devices, and esophageal stents.

For the prevention of adhesions associated with cardiac surgical procedures, the compositions alone or loaded with a therapeutic agent (e.g., a fibrosis-inhibiting agent) may be applied during open or endoscopic heart surgery to the tissue surface of the pericardium (or infiltrated into the pericardial sac), heart, great vessels, pleura, lungs, chest wall and any adjacent affected tissues during the surgical procedure or to the surface of an implanted device or implant and/or the tissue surrounding the implant before, during, or after the surgical procedure. Representative examples of implants for use in cardiac procedures includes, without limitation, heart valves (porcine, artificial), ventricular assist devices, cardiac pumps, artificial hearts, stents, bypass grafts (artificial and endogenous), patches, cardiac electrical leads, defibrillators and pacemakers.

For the prevention of adhesions associated with orthopedic surgical procedures, the compositions alone or loaded with a therapeutic agent (e.g., a fibrosis-inhibiting agent) may be applied during open or arthroscopic orthopedic surgery to the tissue surface of the bone, joint, muscle, tendon, ligament, cartilage and any adjacent affected tissues during the surgical procedure or to the surface of an implanted orthopedic device or implant and/or the tissue surrounding the implant before, during, or after the surgical procedure. Representative examples of implants for use in orthopedic procedures include plates, rods, screws, pins, wires, total and partial joint prostheses (artificial hips, knees, shoulders, phalangeal joints), reinforcement patches, tissue fillers, synthetic bone fillers, bone cement, synthetic graft material, allograft material, autograft material, artificial discs, spinal cages, and intermedulary rods.

For the prevention of adhesions associated with cosmetic or reconstructive surgical procedures, the compositions alone or loaded with a therapeutic agent (e.g., a fibrosis-inhibiting agent) may be applied during open or endoscopic cosmetic surgery to the soft tissue implant surface before, during, or after the implantation procedure or to the surface of the tissue of the implantation pocket immediately prior to, or during implantation of the soft tissue implant. Representative examples of soft tissue implants for use in cosmetic, plastic, and reconstructive surgical procedures include face, nose, breast, chin, buttocks, chest, lip and cheek implants) or to the surface of the soft tissue implant and/or the tissue surrounding the implant before, during, or after implantation of the soft tissue implant.

Implants and Coating Material for Implants

The multifunctional compounds of the invention can also be formed as solid implants, a term that is used herein to refer to any solid object which is designed for insertion and use within the body, and includes bone and cartilage implants (e.g., artificial joints, retaining pins, cranial plates, and the like, of metal, plastic and/or other materials), breast implants (e.g., silicone gel envelopes, foam forms, and the like), catheters and cannulas intended for long-term use (beyond about three days) in place, artificial organs and vessels (e.g., artificial hearts, pancreases, kidneys, blood vessels, and the like), drug delivery devices (including monolithic implants, pumps and controlled release devices such as ALZET® minipumps (Durect Corporation, Cupertino, Calif.), steroid pellets for anabolic growth or contraception, and the like), sutures for dermal or internal use, periodontal membranes, ophthalmic shields, corneal lenticules, and the like.

Another use of the compounds is as a coating material for synthetic implants. In a general method for coating a surface of a synthetic implant, the multifunctional compounds are exposed to the modified environment, and a thin layer of the composition is then applied to a surface of the implant before substantial inter-reaction has occurred. In one embodiment, in order to minimize cellular and fibrous reaction to the coated implant, the compounds are selected so as to result in a matrix that has a net neutral charge. Application of the compounds to the implant surface may be by extrusion, brushing, spraying, or by any other convenient means. Following application of the compounds to the implant surface, inter-reaction is allowed to continue until complete and the three-dimensional matrix is formed.

Although this method can be used to coat the surface of any type of synthetic implant, it is particularly useful for implants where reduced thrombogenicity is an important consideration, such as artificial blood vessels and heart valves, vascular grafts, vascular stents, and stent/graft combinations. The method may also be used to coat implantable surgical membranes (e.g., monofilament polypropylene) or meshes (e.g., for use in hernia repair). Breast implants may also be coated using the above method in order to minimize capsular contracture.

The compounds can also be coated on a suitable fibrous material, which can then be wrapped around a bone to provide structural integrity to the bone. The term "suitable fibrous material" as used herein, refers to a fibrous material which is substantially insoluble in water, non-immunogenic, biocompatible, and immiscible with the crosslinkable compositions of the invention. The fibrous material may comprise any of a variety of materials having these characteristics and may be combined with crosslinkable compositions herein in order to form and/or provide structural integrity to various implants or devices used in connection with medical and pharmaceutical uses.

The compounds of the present invention may also be used to coat lenticules, which are made from either naturally occurring or synthetic polymers.

Medical Implants Combined with Fibrosing Agents

In one aspect, medical implants may contain and/or are adapted to release an agent which induces or promotes adhesion between the implant and tissue or a fibrotic reaction. The clinical performance of numerous medical devices may be improved by anchoring the device effectively into the surrounding tissue to provide either structural support or to facilitate scarring and healing. Effective attachment of the device into the surrounding tissue, however, is not always readily achieved. One reason for ineffective attachment is that implantable medical devices generally are composed of materials that are highly biocompatible and designed to reduce the host tissue response. These materials (e.g., stainless steel, titanium based alloys, fluoropolymers, and ceramics) typically do not provide a good substrate for host tissue attachment and ingrowth during the scarring process. As a result of poor attachment between the device and the host tissue, devices can have a tendency to migrate within the vessel or tissue in which they are implanted. The extent to which a particular type of medical device can move or migrate after implantation depends on a variety of factors including the type and design of the device, the material(s) from which the device is formed, the mechanical attributes (e.g., flexibility and ability to conform to the surrounding geometry at the implantation site), the surface properties, and the porosity of the device or device surface. The tendency of a device to loosen after implantation also depends on the type of tissue and the geometry at the treatment site, where the ability of the tissue to conform around the device generally can help to secure the device in the implantation site. Device migration can result in device failure and, depending on the type and location of the device, can lead to leakage, vessel occlusion, and/or damage to the surrounding tissue. Incorporation of a fibrosis-inducing agent with the compositions of the invention can provide an effective, long-lasting and biocompatible approach for anchoring implantable medical devices into or onto biological tissue.

In certain embodiments, the medical implant, when placed in to a tissue, releases an agent that induces or promotes adhesion between the implant and the tissue or a fibrotic reaction. In other embodiments, the medical implant contains or is made of a fibrosing agent, but does not release the fibrosing agent. In such embodiments, the fibrosing agent contained in the medical implant induces or promotes by direct contact of the agent to the tissue where the implant is placed.

Alternatively, or in addition, the tissue cavity into which the device or implant is placed can be treated with a fibrosis-inducing agent prior to, during, or after the implantation procedure. This can be accomplished, for example, by topical application of the composition comprising a fibrosing agent or by spraying the composition into the anatomical space where the device can be placed or at the interface between the implant and the tissue surface.

Representative examples of medical implants of particular utility for use in combination with a fibrosis-inducing agent include, but are not restricted to, orthopaedic implants (artificial joints, ligaments and tendons, screws, plates, and other implantable hardware), dental implants, intravascular implants (particularly arterial and venous occlusion devices and implants; vascular destructive implants), male and female contraceptive or sterilization devices and implants, soft palate implants, embolization devices, surgical meshes (e.g., hernia repair meshes, tissue scaffolds), fistula treatments, and spinal implants (e.g., artificial intervertebral discs, stent grafts, spinal fusion devices, etc.).

As medical implants are made in a variety of configurations and sizes, the exact dose administered can vary with the amount injected or with the device size, surface area and design; however, certain principles can be applied in the application of this art. Drug dose can be calculated as a function of dose per unit area (of the portion of the device being coated), total drug dose administered can be measured, and appropriate surface concentrations of active drug can be determined. It should be readily evident to one of skill in the art that any of the previously described fibrosis inducing agents or derivatives or analogues thereof can be utilized with the present compositions without deviating from the spirit and scope of the invention.

Regardless of the method of application of the drug to the implant, the exemplary fibrosing agents, used alone or in combination, should be administered under the following dosing guidelines:

Utilizing talc as an exemplary fibrosis-inducing agent, the total amount of talc delivered from an implant or coated onto the surface of an implant should not exceed 100 mg (range of 1 µg to 100 mg). In one embodiment, the total amount of talc released from the implant should be in the range of 10 µg to 50 mg. The dose per unit area of the device (i.e., the dosage of talc as a function of the surface area of the portion of the device to which drug is applied and/or incorporated) should fall within the range of 0.05 µg-10 µg per mm$^2$ of surface area coated. In another embodiment, talc should be applied to an implant surface at a dose of 0.05 µg/mm$^2$-10 µg/mm$^2$ of surface area coated.

Utilizing silk as an exemplary fibrosis-inducing agent, the total amount of silk delivered from an implant or coated onto the surface of an implant should not exceed 100 mg (range of 1 µg to 100 mg). In one embodiment, the total amount of silk released from the prosthesis should be in the range of 10 µg to 50 mg. The dose per unit area of the device (i.e., the dosage of silk as a function of the surface area of the portion of the device to which drug is applied and/or incorporated) should fall within the range of 0.05 µg-10 µg per mm$^2$ of surface area coated. In another embodiment, silk should be applied to an implant at a dose of 0.05 µg/mm$^2$-10 µg/mm$^2$ of surface area coated.

Utilizing chitosan as an exemplary fibrosis-inducing agent, the total amount of chitosan delivered from an implant or coated onto the surface of an implant, should not exceed 100 mg (range of 1 µg to 100 mg). In one embodiment, the total amount of chitosan released from the implant should be in the range of 10 µg to 50 mg. The dose per unit area of the device (i.e., the dosage of chitosan as a function of the surface area of the portion of the device to which drug is applied and/or incorporated) should fall within the range of 0.05 µg-10 µg per mm$^2$ of surface area coated. In another embodiment, chitosan should be applied to an implant surface at a dose of 0.05 µg/mm$^2$-10 µg/mm$^2$ of surface area coated.

Utilizing polylysine as an exemplary fibrosis-inducing agent, the total amount polylysine delivered from an implant or coated onto the surface of an implant should not exceed 100 mg (range of 1 µg to 100 mg). In one embodiment, the total amount of polylysine released from the implant should be in the range of 10 µg to 50 mg. The dose per unit area of the device (i.e., the dosage of polylysine as a function of the surface area of the portion of the device to which drug is applied and/or incorporated) should fall within the range of 0.05 µg-10 µg per mm$^2$ of surface area coated. In another embodiment, polylysine should be applied to an implantsurface at a dose of 0.05 µg/mm$^2$-10 µg/mm$^2$ of surface area coated.

Utilizing fibronectin as an exemplary fibrosis-inducing agent, the total amount of fibronectin delivered from an implant or coated onto the surface of an implant, should not exceed 100 mg (range of 1 µg to 100 mg). In one embodiment, the total amount of fibronectin released from the prosthesis should be in the range of 10 µg to 50 mg. The dose per unit area of the device (i.e., the dosage of fibronectin as a function of the surface area of the portion of the device to which drug is applied and/or incorporated) should fall within the range of 0.05 µg-10 µg per mm$^2$ of surface area coated. In another embodiment, talc should be applied to an implant surface at a dose of 0.05 µg/mm$^2$-10 µg/mm$^2$ of surface area coated.

Utilizing bleomycin as an exemplary fibrosis-inducing agent, the total amount of bleomycin delivered from an implant, or coated onto the surface of an implant, should not exceed 100 mg (range of 0.01 µg to 100 mg). In one embodiment, the total amount of bleomycin released from the implant should be in the range of 0.10 µg to 50 mg. The dose per unit area of the device (i.e., the dosage of bleomycin as a function of the surface area of the portion of the device to which drug is applied and/or incorporated) should fall within the range of 0.005 µg-10 µg per mm$^2$ of surface area coated. In another embodiment, bleomycin should be applied to an implant surface at a dose of 0.005 µg/mm$^2$-10 µg/mm$^2$ of surface area coated. In one embodiment, bleomycin is released from the surface of an implant such that fibrosis in the tissue is promoted for a period ranging from several hours to several months.

Utilizing CTGF as an exemplary fibrosis-inducing agent, the total amount of CTGF delivered from an implant or coated onto the surface of an implant should not exceed 100 mg (range of 0.01 µg to 100 mg). In one embodiment, the total amount of CTGF released from the implant should be in the range of 0.10 µg to 50 mg. The dose per unit area of the device (i.e., the dosage of CTGF as a function of the surface area of the portion of the device to which drug is applied and/or incorporated) should fall within the range of 0.005 µg-10 µg per mm$^2$ of surface area coated. In another embodiment, CTGF should be applied to an implant surface at a dose of 0.005 µg/mm$^2$-10 µg/mm$^2$ of surface area coated.

The fibrosing agent (e.g., talc, silk, chitosan, polylysine, fibronectin, bleomycin, CTGF) may be released from the surface of the implant such that fibrosis in the tissue is promoted for a period ranging from several hours to several months. For example, the fibrosing agent may be released in effective concentrations for a period ranging from 1 hour-30 days. It should be readily evident given the discussions provided herein that analogues and derivatives of the fibrosing agent (e.g., analogues and derivatives of talc, silk, chitosan, polylysine, fibronectin, bleomycin, CTGF, as previously described) with similar functional activity can be utilized for the purposes of this invention; the above dosing parameters are then adjusted according to the relative potency of the analogue or derivative as compared to the parent compound (e.g., a compound twice as potent as the agent is administered at half the above parameters, a compound half as potent as the agent is administered at twice the above parameters, etc.).

As described above, the device may additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) and/or a bone morphogenic protein (BMP) (e.g., BMP-2, BMP-3, BMP-4, BMP-5, BMP-6, or BMP-7 or an analogue or derivative thereof).

Bone morphogenic protein(s) (e.g., BMP-2, BMP-3, BMP-4, BMP-5, BMP-6, or BMP-7 or an analogue or derivative thereof) are to be used in formulations at concentrations that range from 0.001 µg/mL to approximately 20 mg/mL depending on the specific clinical application, formulation type (e.g., gel, liquid, solid, semi-solid), formulation chemistry, duration of required application, type of medical device interface and formulation volume and or surface area coverage required. Preferably, the bone morphogenic protein is released in effective concentrations for a period ranging from 1-180 days. The total dose for a single application is typically not to exceed 500 mg (range of 0.001 µg to 500 mg); preferred 1 µg to 250 mg. When used as a device coating, the dose is per unit area of 0.001 µg-1000 µg per mm$^2$; with a preferred dose of 0.01 µg/mm$^2$-200 µg/mm$^2$. Minimum concentration of $10^{-9}$-$10^{-4}$ M of bone morphogenic protein is to be maintained on the device surface.

Inflammatory cytokines are to be used in formulations at concentrations that range from 0.0001 µg/mL to approximately 20 mg/mL depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1-180 days. The total dose for a single application is typically not to exceed 500 mg (range of 0.0001 µg to 100 mg); preferred 0.001 µg to 50 mg. When used as a device coating, the dose is per unit area of 0.0001 µg-500 µg per mm$^2$; with a preferred dose of 0.001 µg/mm$^2$-200 µg/mm$^2$. Minimum concentration of $10^{-10}$-$10^{-4}$ g/mL of inflammatory cytokine is to be maintained on the device surface.

Furthermore, the device may alone or additionally comprise an agent that stimulates cellular proliferation. Examples include: dexamethasone, isotretinoin (13-cis retinoic acid), 17-β-estradiol, estradiol, 1-α-25 dihydroxyvitamin D$_3$, diethylstibesterol, cyclosporine A, L-NAME, all-trans retinoic acid (ATRA), and analogues and derivatives thereof. Doses used are those concentrations which are demonstrated to stimulate cell proliferation. The proliferative agents are to be used in formulations at concentrations that range from 0.1 ng/mL to 25 mg/mL depending on the specific clinical application, formulation type, formulation chemistry, duration of required application, type of medical device interface and formulation volume and or surface area coverage required. Preferably, the proliferative agent is released in effective concentrations for a period ranging from 1-180 days. The total dose for a single application is typically not to exceed 500 mg (range of 0.0001 µg to 200 mg); preferred 0.001 µg to 100 mg. When used as a device coating, the dose is per unit area of 0.00001 µg-500 µg per mm$^2$; with a preferred dose of 0.0001 µg/mm$^2$-200 µg/mm$^2$. Minimum concentration of 10–11-$10^{-6}$ M of proliferative agent is to be maintained on the device surface.

Medical Implants Combined with Fibrosis-Inhibiting Agents

In another aspect, medical implants may be coated with, or otherwise adapted to release or incorporate an agent which inhibits the formation of reactive scar tissue on, or around, the surface of the device or implant. Compositions that include a fibrosis-inhibiting agent may be used in combination with a variety of medical implants to make them resistant to overgrowth by inflammatory and fibrous scar tissue upon implantation. Compositions and methods are described for coating medical devices and implants with drug-delivery compositions such that the pharmaceutical agent is delivered in therapeutic levels over a period sufficient to allow normal healing to occur.

Upon implantation, excessive scar tissue growth can occur around the all or parts of the implant, which can lead to a reduction in the performance of these devices. In certain cases, an implanted device may be combined with a therapeutic agent (e.g., an anti-fibrotic agent) to minimize the formation of post-operative surgical adhesions, unwanted scarring in the vicinity of the implant, and encapsulation of the implant by a fibrous connective tissue capsule.

Examples of medical devices of particular utility for use in combination with a fibrosis-inhibiting agent include, but are not restricted to, vascular stents, gastrointestinal stents, tracheal/bronchial stents, genital-urinary stents, ENT stents, intraocular lenses, implants for hypertrophic scars and keloids, vascular grafts, anastomotic connector devices, surgical adhesion barriers, glaucoma drainage devices, film or mesh, prosthetic heart valves, tympanostomy tubes, penile implants, endotracheal and tracheostomy tubes, peritoneal dialysis catheters, intracranial pressure monitors, vena cava filters, central venous catheters, ventricular assist devices (e.g., LVAD's), spinal prostheses, and gastrointestinal drainage tubes.

In one aspect, the medical device may be an electrical device (e.g., a device having electrical components that can be placed in contact with tissue in an animal host and can provide electrical excitation to nervous or muscular tissue). Electrical devices can generate electrical impulses and may be used to treat many bodily dysfunctions and disorders by blocking, masking, or stimulating electrical signals within the body. Electrical medical devices of particular utility in the present invention include, but are not restricted to, devices used in the treatment of cardiac rhythm abnormalities, pain relief, epilepsy, Parkinson's Disease, movement disorders, obesity, depression, anxiety and hearing loss. Other examples of electrical devices include neurostimulator and neurostimulation devices (e.g., electrical devices for electrical excitation of the central, autonomic, or peripheral nervous system), cardiac stimulation device such as cardiac rhythm management devices, cardiac pacemakers, implantable cardiac defibrillators (ICD) and other electrical devices for electrical excitation of cardiac muscle tissue (including the specialized cardiac muscle cells that make up the conductive pathways of the heart). Electrical devices also include electrical leads which are used as a conductor to carry electrical signals from the generator to the tissues. The electrical lead may be a wire or other material that transmits electrical impulses from a generator (e.g., pacemaker, defibrillator, or other neurostimulator). Electrical leads may be unipolar, in which they are adapted to provide effective therapy with only one electrode. Multi-polar leads are also available, including bipolar, tripolar and quadripolar leads.

In another aspect, the medical device may be an implantable sensor (i.e., a medical device that is implanted in the body to detect blood or tissue levels of a particular chemical (e.g., glucose, electrolytes, drugs, hormones) and/or changes in body chemistry, metabolites, function, pressure, flow, physical structure, electrical activity or other variable parameter). Representative examples of implantable sensors include, blood/tissue glucose monitors, electrolyte sensors, blood constituent sensors, temperature sensors, pH sensors, optical sensors, amperometric sensors, pressure sensors, biosensors, sensing transponders, strain sensors, activity sensors and magnetoresistive sensors.

In another aspect, the medical device may be a drug-delivery pump (i.e., a medical device that includes a pump which is configured to deliver a biologically active agent (e.g., a drug) at a regulated dose). These devices are implanted within the body and may include an external transmitter for programming the controlled release of drug, or alternatively, may include an implantable sensor that provides the trigger for the drug delivery pump to release drug as physiologically required. Drug-delivery pumps may be used to deliver virtually any agent, but specific examples include insulin for the treatment of diabetes, medication for the relief of pain, chemotherapy for the treatment of cancer, anti-spastic agents for the treatment of movement and muscular disorders, or antibiotics for the treatment of infections. Representative examples of drug delivery pumps for use in the practice of the invention include, without limitation, constant flow drug delivery pumps, programmable drug delivery pumps, intrathecal pumps, implantable insulin delivery pumps, implantable osmotic pumps, ocular drug delivery pumps and implants, metering systems, peristaltic (roller) pumps, electronically driven pumps, elastomeric pumps, spring-contraction pumps, gas-driven pumps (e.g., induced by electrolytic cell or chemical reaction), hydraulic pumps, piston-dependent pumps and non-piston-dependent pumps, dispensing chambers, infusion pumps, passive pumps, infusate pumps and osmotically-driven fluid dispensers.

In yet another aspect, the medical device may be a soft tissue implant. Soft tissue implants are medical devices that may includes a volume replacement material for augmentation or reconstruction to replace a whole or part of a living structure. Soft tissue implants are used for the reconstruction of surgically or traumatically created tissue voids, augmentation of tissues or organs, contouring of tissues, the restoration of bulk to aging tissues, and to correct soft tissue folds or wrinkles (rhytides). Soft tissue implants may be used for the augmentation of tissue for cosmetic (aesthetic) enhancement or in association with reconstructive surgery following disease or surgical resection. Representative examples of soft tissue implants include breast implants, chin implants, calf implants, cheek implants and other facial implants, buttocks implants, and nasal implants.

Soft tissue implants that release a therapeutic agent for reducing scarring at the implant-tissue interface can be used to enhance the appearance, increase the longevity, reduce the need for corrective surgery or repeat procedures, decrease the incidence of pain and other symptoms, and improve the clinical function of implant. Accordingly, the present invention provides soft tissue implants that are coated or otherwise incorporate an anti-scarring agent or a composition that includes an anti-scarring agent.

According to the present invention, any fibrosis-inhibiting agent described above can be utilized in the practice of this embodiment. Within one embodiment of the invention, medical implants may be adapted to release an agent that inhibits one or more of the four general components of the process of fibrosis (or scarring), including: formation of new blood vessels (angiogenesis), migration and proliferation of connective tissue cells (such as fibroblasts or smooth muscle cells), deposition of extracellular matrix (ECM), and remodeling (maturation and organization of the fibrous tissue). By inhibiting one or more of the components of fibrosis (or scarring), the overgrowth of granulation tissue may be inhibited or reduced.

Several examples of agents for use with medical implants include the following: cell cycle inhibitors including (A) anthracyclines (e.g., doxorubicin and mitoxantrone), (B) taxanes (e.g., paclitaxel, TAXOTERE® and docetaxel), and (C) podophyllotoxins (e.g., etoposide); (D) immunomodulators (e.g., sirolimus, everolimus, tacrolimus); (E) heat shock protein 90 antagonists (e.g., geldanamycin); (F) HMGCoA reductase inhibitors (e.g., simvastatin); (G) inosine monophosphate dehydrogenase inhibitors (e.g., mycophenolic acid, 1-alpha-25 dihydroxy vitamin $D_3$); (H)NF kappa B inhibitors (e.g., Bay 11-7082); (I) antimycotic agents (e.g., sulconizole), (J) p38 MAP kinase inhibitors (e.g., SB202190), and (K) angiogenesis inhibitors (e.g., halofuginone bromide), as well as analogues and derivatives of the aforementioned.

Regardless of the method of application of the drug to the device, the exemplary anti-fibrosing agents, used alone or in combination, should be administered under the following dosing guidelines. The total amount (dose) of anti-scarring agent in or on the device may be in the range of about 0.01 µg-10 µg, or 10 µg-10 mg, or 10 mg-250 mg, or 250 mg-1000 mg, or 1000 mg-2500 mg. The dose (amount) of anti-scarring agent per unit area of device surface to which the agent is applied may be in the range of about 0.01 µg/mm²-1 µg/mm², or 1 µg/mm²-10 µg/mm², or 10 µg/mm²-250 µg/mm², 250 µg/mm²-1000 µg/mm², or 1000 µg/mm²-2500 µg/mm².

As medical implants are made in a variety of configurations and sizes, the exact dose administered will vary with device size, surface area and design; however, certain principles can be applied in the application of this art. Drug dose can be calculated as a function of dose per unit area (of the portion of the device being coated), total drug dose administered, and appropriate surface concentrations of active drug can be determined. Drugs are to be used at concentrations that range from several times more than to 10%, 5%, or even less than 1% of the concentration typically used in a single chemotherapeutic systemic dose application. Preferably, the drug is released in effective concentrations for a period ranging from 1-90 days.

Provided below are exemplary dosage ranges for various anti-scarring agents that can be used in conjunction with medical implants in accordance with the invention. A) Cell cycle inhibitors including doxorubicin and mitoxantrone. Doxorubicin analogues and derivatives thereof: total dose not to exceed 25 mg (range of 0.1 µg to 25 mg); preferred 1 µg to 5 mg. The dose per unit area of 0.01 g-100 µg per mm²; preferred dose of 0.1 µg/mm²-10 µg/mm². Mitoxantrone and analogues and derivatives thereof: total dose not to exceed 5 mg (range of 0.01 µg to 5 mg); preferred 0.1 µg to 1 mg. The dose per unit area of the device of 0.01 µg-20 µg per mm²; preferred dose of 0.05 µg/mm²-3 µg/mm². B) Cell cycle inhibitors including paclitaxel and analogues and derivatives (e.g., docetaxel) thereof: total dose not to exceed 10 mg (range of 0.1 µg to 10 mg); preferred 1 µg to 3 mg. The dose per unit area of the device of 0.1 µg-10 µg per mm²; preferred dose of 0.25 µg/mm²-5 µg/mm². (C) Cell cycle inhibitors such as podophyllotoxins (e.g., etoposide): total dose not to exceed 10 mg (range of 0.1 µg to 10 mg); preferred 1 µg to 3 mg. The dose per unit area of the device of 0.1 µg-10 µg per mm²; preferred dose of 0.25 µg/mm²-5 µg/mm². (D) Immunomodulators including sirolimus and everolimus. Sirolimus (i.e., rapamycin, RAPAMUNE®): Total dose not to exceed 10 mg (range of 0.1 µg to 10 mg); preferred 10 µg to 1 mg. The dose per unit area of 0.1 g-100 µg per mm²; preferred dose of 0.5 µg/mm²-10 µg/mm². Everolimus and derivatives and analogues thereof: Total dose should not exceed 10 mg (range of 0.1 µg to 10 mg); preferred 10 µg to 1 mg. The dose per unit area of 0.1 µg-100 µg per mm² of surface area; preferred dose of 0.3 µg/mm²-10 µg/mm². (E) Heat shock protein 90 antagonists (e.g., geldanamycin) and analogues and derivatives thereof: total dose not to exceed 20 mg (range of 0.1 µg to 20 mg); preferred 1 µg to 5 mg. The dose per unit area of the device of 0.1 µg-10 µg per mm²; preferred dose of 0.25 g/mm²-5 µg/mm². (F) HMGCoA reductase inhibitors (e.g., simvastatin) and analogues and derivatives thereof: total dose not to exceed 2000 mg (range of 10.0 µg to 2000 mg); preferred 10 µg to 300 mg. The dose per unit area of the device of 1.0 g-1000 µg per mm²; preferred dose of 2.5 µg/mm²-500 µg/mm². (G) Inosine monophosphate dehydrogenase inhibitors (e.g., mycophenolic acid, 1-alpha-dihydroxy vitamin $D_3$) and analogues and derivatives thereof: total dose not to exceed 2000 mg (range of 10.0 µg to 2000 mg); preferred 10 µg to 300 mg. The dose per unit area of the device of 1.0 µg-1000 µg per mm²; preferred dose of 2.5 µg/mm²-500 µg/mm². (H) NF kappa B inhibitors (e.g., Bay 11-7082) and analogues and derivatives thereof: total dose not to exceed 200 mg (range of 1.0 µg to 200 mg); preferred 1 µg to 50 mg. The dose per unit area of the device of 1.0 µg-100 µg per mm²; preferred dose of 2.5 µg/mm²-50 µg/mm². (I) Antimycotic agents (e.g., sulconizole) and analogues and derivatives thereof: total dose not to exceed 2000 mg (range of 10.0 µg to 2000 mg); preferred 10 µg to 300 mg. The dose per unit area of the device of 1.0 µg-1000 µg per mm²; preferred dose of 2.5 µg/mm²-500 µg/mm². (J) p38 MAP Kinase Inhibitors (e.g., SB202190) and analogues and derivatives thereof: total dose not to exceed 2000 mg (range of 10.0 µg to 2000 mg); preferred 10 μg to 300 mg. The dose per unit area of the device of 1.0 μg-1000 μg per mm$^2$; preferred dose of 2.5 μg/mm$^2$-500 μg/mm$^2$. (K) anti-angiogenic agents (e.g., halofuginone bromide) and analogues and derivatives thereof: total dose not to exceed 10 mg (range of 0.1 μg to 10 mg); preferred 1 μg to 3 mg. The dose per unit area of the device of 0.1 μg-10 μg per mm$^2$; preferred dose of 0.25 μg/mm$^2$-5 μg/mm$^2$.

In addition to those described above (e.g., sirolimus, everolimus, and tacrolimus), several other examples of immunomodulators and appropriate dosages ranges for use with medical implants include the following: (A) Biolimus and derivatives and analogues thereof: Total dose should not exceed 10 mg (range of 0.1 μg to 10 mg); preferred 10 μg to 1 mg. The dose per unit area of 0.1 μg-100 μg per mm$^2$ of surface area; preferred dose of 0.3 μg/mm$^2$-10 μg/mm$^2$. (B) Tresperimus and derivatives and analogues thereof: Total dose should not exceed 10 mg (range of 0.1 μg to 10 mg); preferred 10 μg to 1 mg. The dose per unit area of 0.1 μg-100 μg per mm$^2$ of surface area; preferred dose of 0.3 μg/mm$^2$-10 μg/mm$^2$. (C) Auranofin and derivatives and analogues thereof: Total dose should not exceed 10 mg (range of 0.1 μg to 10 mg); preferred 10 μg to 1 mg. The dose per unit area of 0.1 μg-100 μg per mm2 of surface area; preferred dose of 0.3 μg/mm$^2$-10 μg/mm$^2$. (D) 27-0-Demethylrapamycin and derivatives and analogues thereof: Total dose should not exceed 10 mg (range of 0.1 μg to 10 mg); preferred 10 μg to 1 mg. The dose per unit area of 0.1 μg-100 μg per mm$^2$ of surface area; preferred dose of 0.3 μg/mm$^2$-10 μg/mm$^2$. (E) Gusperimus and derivatives and analogues thereof: Total dose should not exceed 10 mg (range of 0.1 μg to 10 mg); preferred 10 μg to 1 mg. The dose per unit area of 0.1 μg-100 μg per mm$^2$ of surface area; preferred dose of 0.3 μg/mm$^2$-10 μg/mm$^2$. (F) Pimecrolimus and derivatives and analogues thereof: Total dose should not exceed 10 mg (range of 0.1 μg to 10 mg); preferred 10 μg to 1 mg. The dose per unit area of 0.1 μg-100 μg per mm$^2$ of surface area; preferred dose of 0.3 μg/mm$^2$-10 μg/mm$^2$, and (G) ABT-578 and analogues and derivatives thereof: Total dose should not exceed 10 mg (range of 0.1 μg to 10 mg); preferred 10 μg to 1 mg. The dose per unit area of 0.1 μg-100 μg per mm$^2$ of surface area; preferred dose of 0.3 μg/mm$^2$-10 μg/mm$^2$.

In a general method for coating a surface of a synthetic implant, the composition is exposed to the aqueous environment, and a thin layer of the composition is then applied to a surface of the implant before substantial inter-reaction has occurred. In one embodiment, in order to minimize cellular and fibrous reaction to the coated implant, the components are selected so as to result in a matrix that has a net neutral charge. Application of the composition to the implant surface may be by extrusion, brushing, spraying (as described above), or by any other convenient means. Following application of the composition to the implant surface, inter-reaction is allowed to continue until complete and the three-dimensional matrix is formed.

Although this method can be used to coat the surface of any type of synthetic implant, it is particularly useful for implants where reduced thrombogenicity is an important consideration, such as artificial blood vessels and heart valves, vascular grafts, vascular stents, and stent/graft combinations. The method may also be used to coat implantable surgical membranes (e.g., monofilament polypropylene) or meshes (e.g., for use in hernia repair). Breast implants may also be coated using the above method in order to minimize capsular contracture.

The compositions of the invention can also be coated on a suitable fibrous material, which can then be wrapped around a bone to provide structural integrity to the bone. The term "suitable fibrous material" as used herein, refers to a fibrous material which is substantially insoluble in water, non-immunogenic, biocompatible, and immiscible with the crosslinkable compositions of the invention. The fibrous material may comprise any of a variety of materials having these characteristics and may be combined with crosslinkable compositions herein in order to form and/or provide structural integrity to various implants or devices used in connection with medical and pharmaceutical uses.

The compositions of the present invention may also be used to coat lenticules, which are made from either naturally occurring or synthetic polymers.

Treatment of Aneurysm

The multifunctional compounds can be extruded or molded in the shape of a string or coil, then dehydrated. The resulting dehydrated string or coil can be delivered via catheter to the site of a vascular malformation, such as an aneurysm, for the purpose of vascular occlusion and, ultimately, repair of the malformation. The dehydrated string or coil can be delivered in a compact size and will rehydrate inside the blood vessel, swelling several times in size compared to its dehydrated state, while maintaining its original shape.

Thus, another embodiment of the invention is a method for treating an aneurysm, where steps (a) and (b) are as described for the method of sealing tissue, and step (c) involves allowing a three-dimensional matrix to form in the desired shape, delivering it to the site of interest, and allowing the matrix to rehydrate in situ.

Other Uses

As discussed in U.S. Pat. No. 5,752,974 to Rhee et al., the multifunctional compounds can be used to block or fill various lumens and voids in the body of a mammalian subject. The compounds can also be used as biosealants to seal fissures or crevices within a tissue or structure (such as a vessel), or junctures between adjacent tissues or structures, to prevent leakage of blood or other biological fluids. The compositions may also be used to seal or close a fistula, where a scar-promoting agent or sclerosing agent, e.g., silk, may be included in the composition to promote tissue closure.

The multifunctional compounds can also be used as a large space-filling device for organ displacement in a body cavity during surgical or radiation procedures, for example, to protect the intestines during a planned course of radiation to the pelvis.

The compounds can also be coated onto the interior surface of a physiological lumen, such as a blood vessel or Fallopian tube, thereby serving as a sealant to prevent restenosis of the lumen following medical treatment, such as, for example, balloon catheterization to remove arterial plaque deposits from the interior surface of a blood vessel, or removal of scar tissue or endometrial tissue from the interior of a Fallopian tube. A thin layer of the compounds is preferably applied to the interior surface of the vessel (for example, via catheter) immediately following exposure to the modified environment. Because the compounds of the invention are not readily degradable in vivo, the potential for restenosis due to degradation of the coating is minimized. The use of a three-dimensional matrix having a net neutral charge further minimizes the potential for restenosis.

It is to be understood that while the invention has been described in conjunction with the preferred specific embodiments thereof, the foregoing description, as well as the examples that are presented above, are intended to illustrate and not limit the scope of the invention. Other aspects, advantages, and modifications will be apparent to those skilled in the art to which the invention pertains. All patents, patent applications, journal articles, and other references cited herein are incorporated by reference in their entireties.

EXPERIMENTAL

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

Example 1

Preparation of a Multifunctional Compound 0.1 g (~2 eq) of NaOH is added to a solution of methanol (25 mL) and 10 g of tetra-functional HS-PEG (Mw 10,000). The solution is stirred until all of the NaOH is dissolved. The solution is then evaporated and the residue is dissolved into methylene chloride (20 mL). The methylene chloride solution is then dried with $MgSO_4$. After the polymer solution has been filtered it is slowly dropped into a solution of methylene chloride with a 10 times excess of acrolyl chloride. The material is stirred at room temperature for a few hours and then filtered to remove the NaCl before it is precipitated into diethyl ether. The di-functional HS-di-functional acrolyl PEG final product is then isolated as a white powder after filtration. This powder can then be dissolved in a 0.1 M HCl aqueous solution at a 40% concentration, which then can be co-extruded with a 0.3 M pH 9.6 buffer prepared from a mixture of sodium carbonate and sodium phosphate. The material will gel immediately upon coextrusion.

Example 2

Gellation of a Multifinctional Compound

The multifunctional compound from Example 1 is dissolved in a 0.1 M HCl aqueous solution at a 40% (w/v) concentration, which is then co-extruded with a 0.3 M pH 9.6 buffer, prepared from a mixture of sodium carbonate and sodium phosphate. The material gels immediately upon coextrusion.

Example 3

Preparation of Drug Loaded Microspheres by Spray Drying 3.6 grams of methoxy poly(ethylene glycol 5000))-block-(poly (DL-lactide) (65:35 MePEG:PDLLA weight ratio) was dissolved in 200 mL methylene chloride. 400 mg of a drug (mycophenolic acid (MPA), chlorpromazine (CPZ) or paclitaxel (PTX)) was added and the resulting solution was spray dried (Buchi spray drier model B191). Inlet temperature 50° C., outlet temperature<39° C., aspirator 100%, flow rate 7001/hr. The collected microspheres were dried under vacuum at room temperature overnight to produce uniform, spherical particles having size ranges of less than about 10 microns (typically about 0.5 to about 2 microns).

Example 4

MPA Loaded Microspheres (<10 Micron)

100 mL of freshly prepared 10% polyvinyl alcohol (PVA) solution and 10 mL of pH 3 acetic acid solution saturated with MPA was added into a 600 mL beaker. The acidified PVA solution was stirred at 2000 rpm for 30 minutes. Meanwhile, a solution of 400 mg MPA and 800 mg MePEG5000-PDLLA (65:35) in 20 mL dichloromethane was prepared. The polymer/dichloromethane solution was added dropwise to the PVA solution while stirring at 2000 rpm with a Fisher DYNA-MIX stirrer. After addition was complete, the solution was allowed to stir for an additional 45 minutes. The microsphere solution was transferred to several disposable graduated polypropylene conical centrifuge tubes, washed with pH 3 acetic acid solution saturated with MPA, and centrifuged at 2600 rpm for 10 minutes. The aqueous layer was decanted and the washing, centrifuging and decanting was repeated 3 times. The combined, washed microspheres were freeze-dried and vacuum dried to remove any excess water.

Example 5

MPA Containing Microspheres (50-100 Micron)

Microspheres having an average size of about 50-100 microns were prepared using a 1% PVA solution and 500 rpm stirring rate using the same procedure described in Example 4.

Example 6

CPZ and PTX Containing Microspheres

Paclitaxel (PTX) and chlorpromazine (CPZ) containing microspheres were prepared using the procedure described in Example 4 with the exception that the PVA solution and the washing solution does not have to be acidified and saturated with the drug.

Example 7

Paclitaxel Containing Micelles

MePEG2000 (41 g) and MePEG2000-PDLLA (60:40) (410 g) were combined in a vessel and heated to 75° C. with stirring. After the polymers were completely melted and mixed, the temperature was decreased to 55° C. Meanwhile, a PTX solution in tetrahydrofuran (46 g/200 mL) was prepared and poured into the polymer solution under constant stirring. Stirring was continued for and additional hour. The PTX containing micelles were dried at 50° C. under vacuum to remove solvent and were ground on a 2 mm mesh screen after cooling.

Example 8

Surgical Adhesions Model to Assess Fibrosis Inhibiting Agents in Rats

The rat caecal sidewall model is used to as to assess the anti-fibrotic capacity of formulations in vivo. Sprague Dawley rats are anesthetized with halothane. Using aseptic precautions, the abdomen is opened via a midline incision. The caecum is exposed and lifted out of the abdominal cavity. Dorsal and ventral aspects of the caecum are successively scraped a total of 45 times over the terminal 1.5 cm using a No. 10 scalpel blade. Blade angle and pressure are controlled to produce punctate bleeding while avoiding severe tissue damage. The left side of the abdomen is retracted and everted to expose a section of the peritoneal wall that lies proximal to the caecum. The superficial layer of muscle (transverses abdominis) is excised over an area of 1×2 $cm^2$, leaving behind torn fibers from the second layer of muscle (internal oblique muscle). Abraded surfaces are tamponaded until bleeding stops. The abraded caecum is then positioned over the sidewall wound and attached by two sutures. The formulation is applied over both sides of the abraded caecum and over the abraded peritoneal sidewall. A further two sutures are placed to attach the caecum to the injured sidewall by a total of 4 sutures and the abdominal incision is closed in two layers. After 7 days, animals are evaluated post mortem with the extent and severity of adhesions being scored both quantitatively and qualitatively.

Example 9

Surgical Adhesions Model to Assess Fibrosis Inhibiting Agents in Rabbits

The rabbit uterine horn model is used to assess the anti-fibrotic capacity of formulations in vivo. Mature New Zealand White (NZW) female rabbits are placed under general anesthetic. Using aseptic precautions, the abdomen is opened in two layers at the midline to expose the uterus. Both uterine horns are lifted out of the abdominal cavity and assessed for size on the French Scale of catheters. Horns between Nos. 8 and 14 on the French Scale (2.5-4.5 mm diameter) are deemed suitable for this model. Both uterine horns and the opposing peritoneal wall are abraded with a #10 scalpel blade at a 45° angle over an area 2.5 cm in length and 0.4 cm in width until punctuate bleeding is observed. Abraded surfaces are tamponaded until bleeding stops. The individual horns are then opposed to the peritoneal wall and secured by two sutures placed 2 mm beyond the edges of the abraded area. The formulation is applied and the abdomen is closed in three layers. After 14 days, animals are evaluated post mortem with the extent and severity of adhesions being scored both quantitatively and qualitatively.

Example 10

Spinal Surgical Adhesions Model to Assess Fibrosis Inhibiting Agents in Rabbits

Extensive scar formation and adhesions often occur after lumbar spine surgery involving the vertebrae. The dense and thick fibrous tissue adherent to the spine and adjacent muscles must be removed by surgery. Unfortunately, fibrous adhesions usually reform after the secondary surgery. Adhesions are formed by proliferation and migration of fibroblasts from the surrounding tissue at the site of surgery. These cells are responsible for the healing response after tissue injury. Once they have migrated to the wound they lay down proteins such as collagen to repair the injured tissue. Overproliferation and secretion by these cells induce local obstruction, compression, and contraction of the surrounding tissues with accompanying side effects.

The rabbit laminectomy spinal adhesion model described herein is used to investigate spinal adhesion prevention by local slow release of antifibrotic drugs.

Five to six animals are included in each experimental group to allow for meaningful statistical analysis. Formulations with various concentrations of antifibrotic drugs are tested against control animals to assess inhibition of adhesion formation.

Rabbits are anesthetized with an IM injection of ketamine/zylazine. An endotracheal tube is inserted for maintenance of anesthesia with halothane. The animal is placed prone on the operating table on top of a heating pad and the skin over the lower half of the back is shaved and prepared for sterile surgery. A longitudinal midline skin incision is made from L-1 to L-5 and down the lumbosacral fascia. The fascia is incised to expose the tips of the spinous processes. The paraspinous muscles are dissected and retracted from the spinous process and lamina of L-4. A laminectomy is performed at L-4 by removal of the spinal process with careful bilateral excision of the laminae, thus creating a small 5×100 mm laminectomy defect. Hemostasis is obtained with Gelfoam. The test formulations are applied to the injury site and the wound is closed in layers with Vicryl sutures. The animals are placed in an incubator until recovery from anesthesia and then returned to their cage.

Two weeks after surgery, the animals are anesthetized using procedures similar to those described above. The animals are euthanized with Euthanyl. After a skin incision, the laminectomy site is analyzed by dissection and the amount of adhesion is scored using scoring systems published in the scientific literature for this type of injury.

Example 11

Tendon Surgical Adhesions Model to Assess Fibrosis Inhibiting Agents in Rabbits

This model is used to investigate whether adhesion of the tendons can be prevented by local slow release of drugs known to inhibit fibrosis. Polymeric formulations are loaded with drugs and implanted around injured tendons in rabbits. In animals without fibrosis-inhibiting formulations, adhesions develop within 3 weeks of flexor tendon injury if immobilization of the tendon is maintained during that period. An advantage of rabbits is that their tendon anatomy and cellular behaviour during tendon healing are similar to those in man except for the rate of healing that is much faster in rabbits.

Rabbits are anesthetized and the skin over the right hindlimb is shaved and prepared for sterile surgery. Sterile surgery is performed aided by an operating microscope. A longitudinal midline skin incision is made on the volvar aspect of the proximal phalange in digits 2 and 4. The synovial sheath of the tendons is carefully exposed and incised transversally to access the flexor digitorum profundus distal to the flexor digitorum superficialis bifurcation. Tendon injury is performed by gently lifting the flexor digitorum profundus with curved forceps and incising transversally through half of its substance. The formulation containing the test drug formulation is applied around the tendons in the sheath of one of the two digits randomly selected. The other digit is left untreated and is used as a control. The sheath is then repaired with 6-0 nylon suture. An immobilizing 6-0 nylon suture is inserted through the transverse metacarpal ligament into the tendon/sheath complex to immobilize the tendon and the sheath as a single unit to encourage adhesion formation. The wound is closed with 4-0 interrupted sutures. A bandage is applied around the hindpaw to further augment immobilization of the digits and ensure comfort and ambulation of the animals. The animals are recovered and returned to their cage.

Three weeks after surgery, the animals are anesthetized. After a skin incision, the tissue plane around the synovial sheath is dissected and the tendon—sheath complex harvested en block and transferred in 10% phosphate buffered formaldehyde for histopathology analysis. The animals are then euthanized. After paraffin embedding, serial 5-um thin cross-sections are cut every 2 mm through the sheath and tendon complex. Sections are stained with H&E and Movat's stains to evaluate adhesion growth. Each slide is digitized using a computer connected to a digital microscope camera (Nikon Micropublisher cooled camera). Morphometry analysis is then performed using image analysis software (ImagePro). Thickness and area of adhesion defined as the substance obliterating the synovial space are measured and compared between formulation-treated and control animals.

Example 12

Mycophenolic Acid in Multifunctional Compound

A 1 mL syringe (syringe 1) equipped with a luer-lock mixing connector is filled with a multifunctional compound (Example 1) (100 mg), and MPA (60 mg, sifted<100 micron). A 1 mL capped syringe (syringe 2) is filled with 0.25 mL of 6.3 mM HCl solution (pH 2.1). A 1 mL capped syringe (syringe 3) is filled with 0.35 mL 0.24 M monobasic sodium phosphate and 0.4 M sodium carbonate (pH 10.0) buffer. The solid contents of syringe 1 and the acidic solution of syringe 2 are mixed through a mixing connector by repeatedly transferring the contents from one syringe to the other. After complete mixing, the entire mixture is pushed into one of the syringes. The syringe containing the mixture then is attached to one inlet of an applicator (MICROMEDICS® air assisted spray-applicator (Model SA-6105)). Syringe 3 containing the pH 9.7 solution is attached onto the other inlet of the applicator. The formulation is applied to a tissue surface as specified by the applicator manufacturer.

Example 13

Mycophenolic Acid and Disodium Salt of Mpa (Na$_2$MPA) in Multifunctional Compound A 1 mL syringe (syringe 1) equipped with a luer-lock mixing connector is filled with a multifunctional compound (Example 1) (100 mg). A 1 mL capped syringe (syringe 2) is filled with 0.25 mL of 6.3 mM HCl solution (pH 2.1). A 1 mL capped syringe (syringe 3) is filled with 0.25 mL 0.12 M monobasic sodium phosphate and 0.2 M sodium carbonate (pH 9.7) buffer. A 1 mL syringe (syringe 4) equipped with luer-lock mixing connector is filled with MPA (5 mg) and Na$_2$MPA (95 mg), both sifted<100 micron. The contents of syringe 4 and syringe 2 are mixed through a mixing connector by repeatedly transferring the contents from one syringe to the other. This solution is then used to reconstitute the solids in syringe 1. After complete mixing, all of the formulation is pushed into one of the syringes, which is then attached to one inlet of an applicator (MICROMEDICS® air assisted spray-applicator (Model SA-6105)). Syringe 3 containing the pH 9.7 solution is attached onto the other inlet of the applicator. The formulation is applied to a tissue surface as specified by the applicator manufacturer.

Example 14

Chlorpromazine in Multifunctional Compound

A 1 mL syringe (syringe 1) equipped with a luer-lock mixing connector is filled with a multifunctional compound (Example 1) (100 mg), and CPZ (5 or 10 mg). A 1 mL capped syringe (syringe 2) is filled with 0.25 mL of 6.3 mM HCl solution (pH 2.1). A 1 mL capped syringe (syringe 3) is filled 0.25 mL 0.12 M monobasic sodium phosphate and 0.2 M sodium carbonate (pH 9.7) buffer. The components are mixed and applied to a tissue surface using the procedure described in Example 12.

Example 15

Paclitaxel-Loaded Microspheres in Multifunctional Compound

A 1 mL syringe (syringe 1) equipped with a luer-lock mixing connector is filled with a multifunctional compound (Example 1) (100 mg), and 10% PTX loaded MePEG5000-PDLLA (65:35) microspheres prepared by spray drying (0.5 or 2 mg) (prepared using the procedure described in Example 12). A 1 mL capped syringe (syringe 2) is filled with 0.25 mL of 6.3 mM HCl solution (pH 2.1). A 1 mL capped syringe (syringe 3) is filled 0.25 mL 0.12 M monobasic sodium phosphate and 0.2 M sodium carbonate (pH 9.7) buffer. The components are mixed and applied to a tissue surface using the procedure described in Example 12.

Example 16

CPZ-Loaded Microspheres in Multifunctional Compound

A 1 mL syringe (syringe 1) equipped with a luer-lock mixing connector is filled with a multifunctional compound (Example 1) (100 mg), and 10% CPZ loaded MePEG5000-PDLLA (65:35) microspheres prepared by spray drying (50 or 100 mg) (prepared using the procedure described in Example 12). A 1 mL capped syringe (syringe 2) is filled with 0.25 mL of 6.3 mM HCl solution (pH 2.1). A 1 mL capped syringe (syringe 3) is filled 0.25 mL 0.12 M monobasic sodium phosphate and 0.2 M sodium carbonate (pH 9.7) buffer. The components are mixed and applied to a tissue surface using the procedure described in Example 12.

Example 17

MPA-Loaded Microspheres in Multifunctional Compound

A 1 mL syringe (syringe 1) equipped with a luer-lock mixing connector is filled with a multifunctional compound (Example 1) (100 mg), and 10% MPA loaded MePEG5000-PDLLA 65:35 microspheres prepared by spray drying (25 or 75 mg) (prepared using the procedure described in Example 13). A 1 mL capped syringe (syringe 2) is filled with 0.25 mL 6.3 mM HCl solution (pH 2.1). A 1 mL capped syringe (syringe 3) is filled 0.35 mL 0.24 M monobasic sodium phosphate and 0.4 M sodium carbonate (pH 10.0) buffer. The components are mixed and applied to a tissue surface using the procedure described in Example 12.

Example 18

Incorporation of PTX Loaded Micelles into a Multifunctional Compound

A 1 mL syringe (syringe 1) equipped with a luer-lock mixing connector is filled with a multifunctional compound (Example 1) (100 mg). A 2 mL serum vial is filled with 1.5 mL of 6.3 mM HCl solution (pH 2.1). A 1 mL capped syringe (syringe 2) is filled with 0.25 mL 0.12 M monobasic sodium phosphate and 0.2 M sodium carbonate (pH 9.7) buffer. A 2 mL serum vial is filled with 10% PTX loaded micelles (2 mg or 8 mg) (prepared as in Example 7) and reconstituted with 1 mL of the pH 2.1 solution. 0.25 mL of the micelle solution is removed with a 1 mL syringe; the syringe is attached to syringe 1 containing the solids PEG-SG4 and PEG-SH4; and the components are mixed through the mixing connector by repeatedly transferring the contents from one syringe to the other. After complete mixing, the entire mixture is pushed into one of the syringes, which is then attached to one inlet of an applicator (MICROMEDICS® air assisted spray-applicator (Model SA-6105)). Syringe 3 containing the pH 9.7 solution is attached onto the other inlet of the applicator. The formulation is applied to a tissue surface as specified by the applicator manufacturer.

Example 19

MPA Loaded Microspheres in a Multifunctional Compound

A 1 mL syringe (syringe 1) equipped with a luer-lock mixing connector is filled with a multifunctional compound (Example 1) (100 mg) and 10% PTX loaded MePEG5000-PDLLA (65:35) microspheres (0.5 or 2 mg) (prepared using the procedure described in Example 3 and 4). A 1 mL capped syringe (syringe 2) is filled with 0.25 mL of 6.3 mM HCl solution (pH 2.1). A 1 mL capped syringe (syringe 3) is filled 0.25 mL 0.12 M monobasic sodium phosphate and 0.2 M sodium carbonate (pH 9.7) buffer. The components are mixed and applied to a tissue surface using the procedure described in Example 12.

Example 20

Preparation of Silk Powder (Hydrolysis)

Several pieces of silk braid (Ethicon 4-0, 638) are cut into lengths of approx 0.4 cm. These cut pieces are placed in a 100 ml round bottom flask that contains 50 ml 2M NaOH. The sample is stirred using a magnetic stirrer at room temperature for 24 h. The sample is neutralized using concentrated HCl. The neutralized contents are then dialyzed against deionized water using Spectrum cellulose-based dialysis tubing (WMCO approx 3000). The sample is dialyzed for 48 hours with 5 water changes. The dialyzed sample is then poured into a 100 ml round bottom flask. The sample is frozen and freeze-dried to yield a fluffy powdered material.

Example 21

Preparation of Silk Powder Using a Cryomill

Fibers of degummed silk were cut into pieces approximately 1-2 cm in length. The material was then milled to a powder using a cryomill (Spex Certiprep Freezer/Mill—Model 6850). A portion of the milled powder was then sieved through a series of different sized metal sieves to obtain silk powder of different size ranges.

Example 22

Silk in a Multifunctional Compound

A 1 mL syringe (syringe 1) equipped with a luer-lock mixing connector is filled with a multifunctional compound (Example 1) (100 mg) and 10% silk powder (Example 34 and Example 35). A 1 mL capped syringe (syringe 2) is filled with 0.25 mL of 6.3 mM HCl solution (pH 2.1). A 1 mL capped syringe (syringe 3) is filled 0.25 mL 0.12 M monobasic sodium phosphate and 0.2 M sodium carbonate (pH 9.7) buffer. The components are mixed and applied to a tissue surface using the procedure described in Example 12.

Example 23

In Vivo Evaluation of Perivascular Silk Powder to Assess Scarring

A rat carotid artery model is described for determining whether a substance stimulates fibrosis. Wistar rats weighing 300 g to 400 g are anesthetized with halothane. The skin over the neck region is shaved and the skin is sterilized. A vertical incision is made over the trachea and the left carotid artery is exposed. Silk powder formulation (Example 36 and Example 46) is applied on the exposed artery that is then wrapped with a PU film. Carotids wrapped with PU films only are used as a control group. The wound is closed and the animal is recovered. After 28 days, the rats are sacrificed with carbon dioxide and pressure-perfused at 100 mmHg with 10% buffered formaldehyde. Both carotid arteries are harvested and processed for histology. Serial cross-sections will be cut every 2 mm in the treated left carotid artery and at corresponding levels in the untreated right carotid artery. Sections are stained with H&E and Movat's stains to evaluate tissue growth around the carotid artery. Area of tunica intima, tunica media, and perivascular granulation tissue is quantified by computer-assisted morphometric analysis.

Example 24

Mycophenolic Acid in Multifunctional Compound/Premix Composition

A 1 mL syringe (syringe 1) equipped with a luer-lock mixing connector is filled with a multifunctional compound (Example 1) (50 mg), a mixture of PEG-SG4 (25 mg) and PEG-SH4 (25 mg), and MPA (60 mg, sifted<100 micron). A 1 mL capped syringe (syringe 2) is filled with 0.25 mL of 6.3 mM HCl solution (pH 2.1). A 1 mL capped syringe (syringe 3) is filled with 0.35 mL 0.24 M monobasic sodium phosphate and 0.4 M sodium carbonate (pH 10.0) buffer. The solid contents of syringe 1 and the acidic solution of syringe 2 are mixed through a mixing connector by repeatedly transferring the contents from one syringe to the other. After complete mixing, the entire mixture is pushed into one of the syringes. The syringe containing the mixture then is attached to one inlet of an applicator (MICROMEDICS® air assisted spray-applicator (Model SA-6105)). Syringe 3 containing the pH 9.7 solution is attached onto the other inlet of the applicator. The formulation is applied to a tissue surface as specified by the applicator manufacturer.

Example 25

Mycophenolic acid and disodium salt of MPA (Na$_2$MPA) in Multifunctional Compound/Premix Composition A 1 mL syringe (syringe 1) equipped with a luer-lock mixing connector is filled with a multifunctional compound (Example 1) (50 mg), a mixture of PEG-SG4 (25 mg) and PEG-SH4 (25 mg). A 1 mL capped syringe (syringe 2) is filled with 0.25 mL of 6.3 mM HCl solution (pH 2.1). A 1 mL capped syringe (syringe 3) is filled with 0.25 mL 0.12 M monobasic sodium phosphate and 0.2 M sodium carbonate (pH 9.7) buffer. A 1 mL syringe (syringe 4) equipped with luer-lock mixing connector is filled with MPA (5 mg) and Na$_2$MPA (95 mg), both sifted<100 micron. The contents of syringe 4 and syringe 2 are mixed through a mixing connector by repeatedly transferring the contents from one syringe to the other. This solution is then used to reconstitute the solids in syringe 1. After complete mixing, all of the formulation is pushed into one of the syringes, which is then attached to one inlet of an applicator (MICROMEDICS® air assisted spray-applicator (Model SA-6105)). Syringe 3 containing the pH 9.7 solution is attached onto the other inlet of the applicator. The formulation is applied to a tissue surface as specified by the applicator manufacturer.

Example 26

Chlorpromazine in Multifunctional Compound/Premix Composition

A 1 mL syringe (syringe 1) equipped with a luer-lock mixing connector is filled with a multifunctional compound (Example 1) (50 mg), a mixture of PEG-SG4 (25 mg) and PEG-SH4 (25 mg), and CPZ (5 or 10 mg). A 1 mL capped syringe (syringe 2) is filled with 0.25 mL of 6.3 mM HCl solution (pH 2.1). A 1 mL capped syringe (syringe 3) is filled 0.25 mL 0.12 M monobasic sodium phosphate and 0.2 M sodium carbonate (pH 9.7) buffer. The components are mixed and applied to a tissue surface using the procedure described in Example 12.

Example 27

Paclitaxel-Loaded Microspheres in Multifunctional Compound/Premix Composition A 1 mL syringe (syringe 1) equipped with a luer-lock mixing connector is filled with a multifunctional compound (Example 1) (50 mg), a mixture of PEG-SG4 (25 mg) and PEG-SH4 (25 mg), and 10% PTX loaded MePEG5000-PDLLA (65:35) microspheres prepared by spray drying (0.5 or 2 mg) (prepared using the procedure described in Example 3). A 1 mL capped syringe (syringe 2) is filled with 0.25 mL of 6.3 mM HCl solution (pH 2.1). A 1 mL capped syringe (syringe 3) is filled 0.25 mL 0.12 M monobasic sodium phosphate and 0.2 M sodium carbonate (pH 9.7) buffer. The components are mixed and applied to a tissue surface using the procedure described in Example 12.

Example 28

CPZ-Loaded Microspheres in Multifunctional Compound/Premix Composition

A 1 mL syringe (syringe 1) equipped with a luer-lock mixing connector is filled with a multifunctional compound (Example 1) (50 mg), a mixture of PEG-SG4 (25 mg) and PEG-SH4 (25 mg), and 10% CPZ loaded MePEG5000-PDLLA (65:35) microspheres prepared by spray drying (50 or 100 mg) (prepared using the procedure described in Example 3). A 1 mL capped syringe (syringe 2) is filled with 0.25 mL of 6.3 mM HCl solution (pH 2.1). A 1 mL capped syringe (syringe 3) is filled 0.25 mL 0.12 M monobasic sodium phosphate and 0.2 M sodium carbonate (pH 9.7) buffer. The components are mixed and applied to a tissue surface using the procedure described in Example 12.

Example 29

MPA-Loaded Microspheres in Multifunctional Compound/Premix Composition

A 1 mL syringe (syringe 1) equipped with a luer-lock mixing connector is filled with a multifunctional compound (Example 1) (50 mg), a mixture of PEG-SG4 (25 mg) and PEG-SH4 (25 mg), and 10% MPA loaded MePEG5000-PDLLA 65:35 microspheres prepared by spray drying (25 or 75 mg) (prepared using the procedure described in Example 3). A 1 mL capped syringe (syringe 2) is filled with 0.25 mL 6.3 mM HCl solution (pH 2.1). A 1 mL capped syringe (syringe 3) is filled 0.35 mL 0.24 M monobasic sodium phosphate and 0.4 M sodium carbonate (pH 10.0) buffer. The components are mixed and applied to a tissue surface using the procedure described in Example 12.

Example 30

Incorporation of PTX Loaded Micelles into a Multifunctional Compound/Premix Composition A 1 mL syringe (syringe 1) equipped with a luer-lock mixing connector is filled with a multifunctional compound (Example 1) (50 mg), a mixture of PEG-SG4 (25 mg) and PEG-SH4 (25 mg). A 2 mL serum vial is filled with 1.5 mL of 6.3 mM HCl solution (pH 2.1). A 1 mL capped syringe (syringe 2) is filled with 0.25 mL 0.12 M monobasic sodium phosphate and 0.2 M sodium carbonate (pH 9.7) buffer. A 2 mL serum vial is filled with 10% PTX loaded micelles (2 mg or 8 mg) (prepared as in Example 7) and reconstituted with 1 mL of the pH 2.1 solution. 0.25 mL of the micelle solution iss removed with a 1 mL syringe; the syringe is attached to syringe 1 containing the solids PEG-SG4 and PEG-SH4; and the components are mixed through the mixing connector by repeatedly transferring the contents from one syringe to the other. After complete mixing, the entire mixture is pushed into one of the syringes, which is then attached to one inlet of an applicator (MICROMEDICS® air assisted spray-applicator (Model SA-6105)). Syringe 3 containing the pH 9.7 solution is attached onto the other inlet of the applicator. The formulation is applied to a tissue surface as specified by the applicator manufacturer.

Example 31

Silk in a Multifunctional Compound/Premix Composition

A 1 mL syringe (syringe 1) equipped with a luer-lock mixing connector is filled with a multifunctional compound (Example 1) (50 mg), a mixture of PEG-SG4 (25 mg) and PEG-SH4 (25 mg) and 10% silk powder (Example 20 and Example 21). A 1 mL capped syringe (syringe 2) is filled with 0.25 mL of 6.3 mM HCl solution (pH 2.1). A 1 mL capped syringe (syringe 3) is filled 0.25 mL 0.12 M monobasic sodium phosphate and 0.2 M sodium carbonate (pH 9.7) buffer. The components are mixed and applied to a tissue surface using the procedure described in Example 12.

We claim:

1. A multifunctional compound having the structure of formula (I):

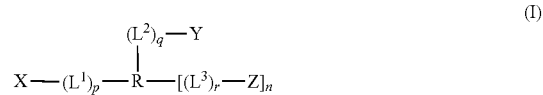

wherein:
n is an integer from 1-12, and when n is 2-12, each Z component may be different;
R is selected from hydrophilic polymers, hydrophobic polymers, amphiphilic polymers, $C_{2-14}$ hydrocarbyls, and heteroatom-containing $C_{2-14}$ hydrocarbyls;
X is a nucleophilic group, Y is an electrophilic group, and Z is an electrophilic or a nucleophilic group;
$L^1$, $L^2$, and $L^3$ are linking groups; and
p, q, and r are integers from 0-1;
wherein the compound is essentially non-reactive in an initial environment but is rendered reactive upon exposure to a modification in the initial environment that provides a modified environment such that a plurality of the multifunctional compounds inter-react in the modified environment to form a three-dimensional matrix.

2. The multifunctional compound of claim 1, wherein the nucleophilic groups are selected from —$NH_2$, —$NHR^1$, —$N(R^1)_2$, —SH, —OH, —COOH, —$C_6H_4$—OH, —H, —$PH_2$, —$PHR^1$, —$P(R^1)_2$, —NH—$NH_2$, —CO—NH—$NH_2$, and —$C_5H_4N$, where $R^1$ is a hydrocarbyl group, and each $R^1$ may be the same or different.

3. The multifunctional compound of claim 1, wherein the electrophilic groups are selected from —CO—Cl, —(CO)—O—(CO)—$R^a$ (where $R^a$ is an alkyl group), —CH=CH—CH=O, —CH=CH—C($CH_3$)=O, halo, —N=C=O, —N=C=S, —$SO_2$CH=$CH_2$, —O(CO)—C=$CH_2$, —O(CO)—C($CH_3$)=$CH_2$, —S—S—($C_5H_4N$), —O(CO)—C($CH_2CH_3$)=$CH_2$, —CH=CH—C=NH, —COOH, —(CO)O—N(COC$H_2$)$_2$, —CHO, —(CO)O—N(COC$H_2$)$_2$ —S(O)$_2$OH, and —N(COCH)$_2$.

4. The multifunctional compound of claim 1, wherein the nucleophilic groups are sulfhydryl groups and the electrophilic groups are sulfhydryl-reactive groups.

5. The multifunctional compound of claim 4 wherein the sulfhydryl-reactive groups are selected from mixed anhydrides; ester derivatives of phosphorus; ester derivatives of p-nitrophenol, p-nitrothiophenol and pentafluorophenol; esters of substituted hydroxylamines, including N-hydroxyphthalimide esters, N-hydroxysuccinimide esters, N-hydroxysulfosuccinimide esters, and N-hydroxyglutarimide esters; esters of 1-hydroxybenzotriazole; 3-hydroxy-3,4-dihydro-benzotriazin-4-one; 3-hydroxy-3,4-dihydro-quinazoline-4-one; carbonylimidazole derivatives; acid chlorides; ketenes; and isocyanates.

6. The multifunctional compound of claim 4, wherein the sulfhydryl-reactive groups are selected so as to form a thioester, imido-thioester, thioether, or disulfide linkage upon reaction with the sulfhydryl groups.

7. The multifunctional compound of claim 1, wherein R is a hydrophilic polymer.

8. The multifunctional compound of claim 7, wherein the hydrophilic polymer is a linear, branched, dendrimeric, hyperbranched, or star polymer.

9. The multifunctional compound of claim 8, wherein the hydrophilic polymer is selected from polyalkylene oxides; polyols; poly(oxyalkylene)-substituted diols and polyols; polyoxyethylated sorbitol; polyoxyethylated glucose; poly(acrylic acids) and analogs and copolymers thereof; polymaleic acids; polyacrylamides; poly(olefinic alcohols); poly(N-vinyl lactams); polyoxazolines; polyvinylamines; and copolymers thereof.

10. The multifunctional compound of claim 9, wherein the hydrophilic polymer is a poly(oxyalkylene)-substituted polyol selected from mono-, di- and tri-polyoxyethylated glycerol, mono- and di-polyoxyethylated propylene glycol, and mono- and di-polyoxyethylated trimethylene glycol, and tetra(oxyethylene)pentaerythritol.

11. A kit for use in medical applications, comprising:
(a) a plurality of a multifunctional compound;
(b) a first buffer solution having a pH within the range of about 1.0 to 5.5; and
(c) a second buffer solution having a pH within the range of about 6.0 to 11.0,
wherein the multifunctional compound has the structure of formula (I):

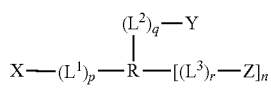

(I)

wherein:
n is an integer from 1-12, and when n is 2-12, each Z component may be different;
R is selected from hydrophilic polymers, hydrophobic polymers, amphiphilic polymers, $C_{2-14}$ hydrocarbyls, and heteroatom-containing $C_{2-14}$ hydrocarbyls;
X is a nucleophilic group, Y is an electrophilic group, and Z is an electrophilic or a nucleophilic group;
$L^1$, $L^2$, and $L^3$ are linking groups; and
p, q, and r are integers from 0-1;
wherein the nucleophilic and electrophilic groups are non-reactive in a dry environment but are rendered reactive upon exposure to an aqueous environment such that the components inter-react in the aqueous environment to form a three-dimensional matrix, and further wherein each component is packaged separately and admixed immediately prior to use.

12. The kit of claim 11 further comprising a biologically active agent.

13. The kit of claim 12 wherein the biologically active agent is packaged with the multifunctional compound.

14. The kit of claim 12, wherein the biologically active agent is packaged as a solution with the first buffer, or packaged as a solution with the second buffer.

15. The kit of claim 12 wherein the biologically active agent is an anti-fibrotic agent.

16. The kit of claim 15 wherein the anti-fibrotic agent is a cell cycle inhibitor selected from the group consisting of taxanes, vinca alkoid, camptothecin, anthracycline, nitrosourea, folic acid antagonist, cytidine analogue, pyrimidine analogues, purine analogue, nitrogen mustard, mytomycin, alkyl sulfonate, benzamide, halogenated sugar, azaserine, or a derivative thereof.

17. The kit of claim 16 wherein the cell cycle inhibitor is paclitaxel or an analogue or derivative thereof.

18. A method of forming a three-dimensional matrix comprising the steps of:
(a) providing a plurality of a multifunctional compound; and
(b) rendering the nucleophilic and electrophilic groups reactive by exposing the multifunctional compound to an aqueous environment to effect inter-reaction; wherein said exposure comprises:
(i) dissolving the multifunctional compound in a first buffer solution having a pH within the range of about 1.0 to 5.5 to form a homogeneous solution, and
(ii) adding a second buffer solution having a pH within the range of about 6.0 to 11.0 to the homogeneous solution; and
(c) allowing a three-dimensional matrix to form;
wherein, the multifunctional compound has the structure of formula (I):

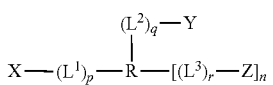

(I)

wherein:
n is an integer from 1-12, and when n is 2-12, each Z component may be different;
R is selected from hydrophilic polymers, hydrophobic polymers, amphiphilic polymers, $C_{2-14}$ hydrocarbyls, and heteroatom-containing $C_{2-14}$ hydrocarbyls;
X is a nucleophilic group, Y is an electrophilic group, and Z is an electrophilic or a nucleophilic group;
$L^1$, $L^2$, and $L^3$ are linking groups; and
p, q, and r are integers from 0-1;
wherein the nucleophilic and electrophilic groups are non-reactive in a dry environment but are rendered reactive upon exposure to an aqueous environment such that the components inter-react in the aqueous environment to form a three-dimensional matrix, and further wherein each component is packaged separately and admixed immediately prior to use.

* * * * *